US 9,238,657 B2

(12) United States Patent
Nishitani et al.

(10) Patent No.: US 9,238,657 B2
(45) Date of Patent: Jan. 19, 2016

(54) CEPHALOSPORIN HAVING CATECHOL GROUP

(75) Inventors: Yasuhiro Nishitani, Osaka (JP); Kenji Yamawaki, Osaka (JP); Yusuke Takeoka, Sapporo (JP); Hideki Sugimoto, Osaka (JP); Shinya Hisakawa, Osaka (JP); Toshiaki Aoki, Osaka (JP)

(73) Assignee: SHIONOGI & CO., LTD., Osaka (JP)

( * ) Notice: Subject to any disclaimer, the term of this patent is extended or adjusted under 35 U.S.C. 154(b) by 753 days.

(21) Appl. No.: 13/063,878

(22) PCT Filed: Oct. 27, 2009

(86) PCT No.: PCT/JP2009/068400
§ 371 (c)(1),
(2), (4) Date: Apr. 25, 2011

(87) PCT Pub. No.: WO2010/050468
PCT Pub. Date: May 6, 2010

(65) Prior Publication Data
US 2011/0190254 A1 Aug. 4, 2011

(30) Foreign Application Priority Data
Oct. 31, 2008 (JP) ................. 2008-280828

(51) Int. Cl.
C07D 501/46 (2006.01)
C07D 505/24 (2006.01)
C07D 519/06 (2006.01)
A61K 31/546 (2006.01)

(52) U.S. Cl.
CPC ............ *C07D 501/46* (2013.01); *C07D 505/24* (2013.01); *C07D 519/06* (2013.01)

(58) Field of Classification Search
CPC ... C07D 501/46; C07D 519/06; C07D 505/24
USPC ....................................................... 514/202
See application file for complete search history.

(56) References Cited

U.S. PATENT DOCUMENTS

| | | | |
|---|---|---|---|
| 4,647,556 A | | 3/1987 | Lattrell et al. |
| 4,906,623 A | * | 3/1990 | Matsumura et al. .......... 514/202 |
| 5,055,462 A | | 10/1991 | Davies et al. |
| 5,095,012 A | | 3/1992 | Okita et al. |
| 5,104,866 A | | 4/1992 | Sakane et al. |
| 5,126,336 A | | 6/1992 | Imae et al. |
| 5,143,910 A | | 9/1992 | Onoue et al. |
| 5,149,803 A | | 9/1992 | Davies et al. |
| 5,234,920 A | | 8/1993 | Okita et al. |
| 5,244,890 A | | 9/1993 | Yamanaka et al. |
| 2005/0153950 A1 | | 7/2005 | Nishitani et al. |
| 2013/0079319 A1 | | 3/2013 | Yamawaki et al. |
| 2013/0096299 A1 | | 4/2013 | Kusano et al. |
| 2013/0102583 A1 | | 4/2013 | Hisakawa et al. |

FOREIGN PATENT DOCUMENTS

| | | |
|---|---|---|
| AU | 676218 | 3/1997 |
| DE | 25 19 400 | 3/1976 |

(Continued)

OTHER PUBLICATIONS

Bryskier, A.,"New concepts in the field of cephalosporins: C-3' quaternary ammonium cephems (Group IV)." Clinical Microbiology and Infection 3.s1 (1997): s1-s6.*
Silley, P., et al. "Mode of action of GR69153, a novel catechol-substituted cephalosporin, and its interaction with the tonB-dependent iron transport system." Antimicrobial agents and chemotherapy 34.9 (1990): 1806-1808.*
Takeda et al. "In Vitro Antibacterial Activity of New Cephalosporin, FR295389, against IMP-type Metallo-β-lactamase-producers". *Journal of Antibiotics* vol. 61, No. 1, pp. 36-39 (2008).

(Continued)

*Primary Examiner* — Samantha Shterengarts
*Assistant Examiner* — Matt Mauro
(74) *Attorney, Agent, or Firm* — Hamre, Schumann, Mueller & Larson, P.C.

(57) ABSTRACT

The present disclosure describes Cephem compounds of the formula:

[Formula 1]

(I)

wherein,
X is N, CH or C—Cl;
T is S or the like;
A and G are lower alkylene or the like;
B is a single bond or the like;
D is optionally present, and when present is, $-NR^7-$, $-CO-$, $-CO-NR^7-$, $-NR^7-CO-$, $-NR^7-CO-NR^7-$, or the like;
F is optionally present, and when present is or phenylene;
$R^3$ and $R^4$ are $-OR^8$;
$R^5$ and $R^6$ each is independently hydrogen, halogen, nitrile, or $-OR^8$;
or an ester at the carboxyl at the 7-position side chain or at the 4-position, a compound protected at the amino on the ring in the 7-side chain, a pharmaceutically acceptable salt, or a solvate thereof, which have a wide antimicrobial spectrum and have potent antimicrobial activity against beta-lactamase producing Gram negative bacteria.

21 Claims, No Drawings

(56) References Cited

FOREIGN PATENT DOCUMENTS

| | | |
|---|---|---|
| EP | 0 114 752 | 8/1984 |
| EP | 0 168 177 | 1/1986 |
| EP | 0 211 656 | 2/1987 |
| EP | 0 241 901 | 10/1987 |
| EP | 0 305 111 | 3/1989 |
| EP | 0 345 671 | 12/1989 |
| EP | 0 346 465 | 12/1989 |
| EP | 0 376 724 | 7/1990 |
| EP | 0 474 049 | 3/1992 |
| EP | 0 485 808 | 5/1992 |
| EP | 1 489 084 | 12/2004 |
| EP | 2 341 053 | 7/2011 |
| JP | 57-118588 | 7/1982 |
| JP | 58-162592 | 9/1983 |
| JP | 62-30788 | 2/1987 |
| JP | 62-158291 | 7/1987 |
| JP | 2-15090 | 1/1990 |
| JP | 2-28185 | 1/1990 |
| JP | 2-28187 | 1/1990 |
| JP | 2-117678 | 5/1990 |
| JP | 2-275886 | 11/1990 |
| JP | 4-364189 | 12/1992 |
| JP | 5-213971 | 8/1993 |
| JP | 6-345776 | 12/1994 |
| JP | 5498393 | 3/2014 |
| WO | WO 86/05183 | 9/1986 |
| WO | WO 92/21683 | 12/1992 |
| WO | WO 99/33839 | 7/1999 |
| WO | WO 03/099826 | 12/2003 |
| WO | WO 2006/104141 | 10/2006 |
| WO | WO 2007/096740 | 8/2007 |
| WO | WO 2007/119511 | 10/2007 |

OTHER PUBLICATIONS

Hashizume et al. "Comparison of Transport Pathways of Catechol-Substituted Cephalosporins, BO-1236 and BO-1341, through the Outer Membrane of *Escherichia coli*". *The Journal of Antibiotics*, vol. 43 No. 12, pp. 1617-1620 (1990).

Weissberger et al. "L-658,310 A New Injectable Cephalosporin". *The Journal of Antibiotics*, vol. 42, No. 5, pp. 795-806 (1989).

Okita et al. "Synthesis and Antibacterial Activity of Cephalosporins having a Catechol in the C3 Side Chain". *The Journal of Antibiotics*, vol. 46, No. 5, pp. 833-839 (1993).

Imae et al. "Cephalosporins having a Heterocyclic Catechol in the C3 Side Chain-Enhancement of Efficacy against Gram-Negative Bacteria". *The Journal of Antibiotics*, vol. 46, pp. 840-849 (1993).

Imura et al. "Cephalosports having a Heterocyclic Catechol in the C3 Side Chain-Improvement of Pharmacokinetic Profile". *The Journal of Antibiotics*, vol. 46, pp. 850-857 (1993).

Baudart et al. "Synthesis and Biological Activity of C-3' Ortho Dihydroxyphthalimido Cephalosporins". *The Journal of Antibiotics*, vol. 46, pp. 1458-1470 (1993).

Choi et al. "Studies on New Catechol Containing Cephalosporins-Synthesis and Structure-activity Relationships of Cephalosporins having a Catechol Moiety at the C-3 Position". *The Journal of Antibiotics*, vol. 48, No. 11, pp. 1371-1374 (1995).

Arnould et al. "Synthesis and Structure-Activity Relationships of Cephalosporins with C-3' Catechol-Containing Residues". *Journal of Medicinal Chemistry*, vol. 35, pp. 2631-2642 (1992).

Bird et al. "Pharmacokinetics of Catechol Cephalosporins, The Effect of Incorporating Substituents into the Catechol Moiety of Pharmacokinetics in a Marmoset Model". *Journal of Medicinal Chemistry*, vol. 35, pp. 2643-2651 (1992).

Tsuji et al. "Synthesis and Antibacterial Activity of Cephalosporins having C-3 Catechol-Containing (Pyridinium-4'-Thio) Methyl Groups". *Bioorganic and Medicinal Chemistry Letters*, vol. 5, No. 9, pp. 963-966 (1995).

Adams et al. "Structure-activity Relationships within a Series of C(7)-Substituedoxyiminocephalosporins Containing the C(3)-Methylaminopyridiniumthiomethyl Substituent". *The Journal of Antibiotics*, vol. 48, No. 5, pp. 417-424 (1995).

Mochizuki et al. "Antibacterial and Pharmacokinetic Properties of M14659, A New Injectable Semisynthetic Cephalosporin". *The Journal of Antibiotics*, vol. 41, No. 3, pp. 377-391 (1988).

Kim et al. "Synthesis and Antibacterial Activities of Novel C(7)-Catechol-susbtituted Cephalosporins (I)". *The Journal of Antibiotics*, vol. 49, pp. 496-498 (1996).

Guest et al. "Sythesis and Biological Activity of 3-(N-Substituted Pyridinium-4-Thiomethy1-7α-Formamido Cephalosporins". *The Journal of Antibiotics*, vol. 46, No. 8, pp. 1279-1288 (1993).

Yamano et al. Ferric iron transport system of *Pseudomonas aeruginosa* PAO1 that functions as the uptake pathway of a novel catechol-substituted cephalosporin, S-9096. *Applied Microbiology and Biotechnology*, vol. 40 , pp. 892-897 (1994).

Yamawaki et al. "A novel series of parenteral cephalosporins exhibiting potent activities against *Pseudomonas aeruginosa* and other Gram-negative pathogens: Synthesis and structure-activity relationships". *Bioorganic of Medicinal Chemistry*, vol. 15, pp. 6716-6732 (2007).

Almeida et al. "Synthesis of N-(2-chloro-3,4-dimethoxybenzylideneamino)guanidinium acetate [α-$^{14}$C]". *Journal of Labelled Compounds and Radiopharmaceuticals*, vol. 45, pp. 371-377 (2002).

Obi et al. "Novel Cephalosporins having a Benzothiopyran Group-Synthesis and Biological Activity of Catecholic Benzothiopyrain Group at the C-3 Side Chain", *The Journal of Antibiotics*, vol. 48, pp. 278-281 (1995).

Yamano et al.. "Ferric iron transport system of *Pseudomonas aeruginosa* PA01 that functions as the uptake pathway of a novel catechol-substituted cephalosporin, S-9096". *Appl. Microbiol. Biotechnol.*, vol. 40, pp. 892-897 (1994).

Takeda et al. "In Vitro Antibacterial Activity of a New Cephalosporin, FR295389, against IMP-type Metallo-β- lactamase-producers". *J. Antibio.*, vol. 61, No. 1., pp. 36-39 (2008).

Hashizume et al. "Comparison of Transport Pathways of Catechol-Substituted Cephalosporins, BO-1236 and BO-1341, Through the Outer Membrane of *Escherichia coli*". *The Journal of Antibiotics*, vol. 43, No. 12, pp. 1617-1620 (1990).

Weissberger et al. "L-658,310, A New Injectable Cephalosporin". *The Journal of Antibiotics*, vol. 42, No. 5, pp. 795-806 (1989).

Branch et al. "Studies on Semi-Synthetic 7 α-Formamidocephalosporins". *The Journal of Antibiotics*, vol. 40, pp. 646-651 (1987).

Wermuth, Camille G., "Molecular Variations Based on Isosteric Replacements." The Practice of Medicinal Chemistry, Academic Press, 1996, pp. 203-237.

Tashiro, Tatsuo. Macromol. Mater. Eng. 2001, 286, pp. 63-87.

* cited by examiner

CEPHALOSPORIN HAVING CATECHOL GROUP

TECHNICAL FIELD

The compounds of the present invention are related to cephem compounds, which have a wide antimicrobial spectrum, and in particular exhibit potent antimicrobial activity against beta-lactamase producing Gram negative bacteria, and pharmaceutical composition comprising the same.

BACKGROUND ART

To date, a variety of beta-lactam drugs have been developed and beta-lactam drugs have become clinically extremely important antimicrobial drugs. However, there are increasing number of bacterial types which have obtained resistancy against beta-lactama drugs by producing beta-lactamase, which degrade beta-lactam drugs.

According to the Ambler molecular classification, beta-lactamase are largely classified into four classes. Specifically, those are Class A (TEM type, SHV type, CTX-M type and the like), Class B (IMP type, VIM type, L-1 type and the like), Class C (AmpC type) and Class D (OXA type and the like). Amongst these, Classes A, C and D types are largely classified into serine-beta-lactamase, and on the other hand, Class B type is classified in to metallo-beta-lactamase. It has been known that both have respectively different mechanisms to each other in terms of hydrolysis of beta-lactam drugs.

Recently, clinical problem has been occurring due to the existence of Gram negative bacteria which have become highly resistant to beta-lactam drugs including Cephems and Carbapenems by production of Class A or D types serine-beta-lactamase and Class B type metallo-beta-lactamase which have extended their substrate spectrum. Particularly, metallo-beta-lactamase is known to be one of the causes of obtaining multi-resistancy in Gram negative bacteria. Cephem compounds which exhibit intermediate activity against metallo-beta-lactamase producing Gram negative bacteria are known (e.g., Patent Literature 1 and Non-Patent Literature 1). However, there is a demand for development of Cephem compounds which exhibit more potent antimicrobial activity, in particular effectivity against a variety of beta-lactamase producing Gram negative bacteria.

One of known antimicrobials having high anti-Gram negative bactericidal activity is Cephem compounds having a catechol group intramolecularly (e.g., Non-Patent Literatures 2-4). The action thereof is that the catechol group forms a chelate with $Fe^{3+}$, thereby the compound is efficiently incorporated into the bacterial body by means of Fe3+ transportation system on the cellular membrane (tonB-dependent iron transport system). Therefore, research has been conducted on compounds having catechol or similar structure thereto, on the 3-position side chain or 7-position side chain on the Cephem backbone.

Patent Literatures 2-8 and Non-patent Literatures 2-11 and 16 disclose compounds having a catechol or a structure similar thereto on the 3-position side chain of the Cephem backbone.

Patent Literature 9 and Non-patent Literatures 12-15 disclose compounds having a catechol or a structure similar thereto on the 7-position side chain of the Cephem backbone.

Non-patent Literatures 7, 9, 10 and 12-15 describe Cephem compounds which have been stabilized against beta-lactamase.

However, these references do not disclose the compounds of the present invention. Furthermore, these references, which describe Cephem compounds having catechol group intramolecularly, have no specific description regarding met-allo-beta-lactamase of Class B type, or antibacterial activity against wide spectrum of Gram negative bacteria including Class B type.

Patent Literatures 10 and 11 do not specifically disclose Cephem compounds having catechol type substituents.

PRIOR ART REFERENCES

Patent Literature

[Patent Literature 1] International Publication No. 2007/119511 pamphlet
[Patent Literature 2] Japanese Laid-Open Publication No. H3-173893
[Patent Literature 3] Japanese Laid-Open Publication No. H2-15090
[Patent Literature 4] Japanese Laid-Open Publication No. H2-28187
[Patent Literature 5] Japanese Laid-Open Publication No. H2-117678
[Patent Literature 6] Japanese PCT National Phase Laid-Open Publication No. H6-510523
[Patent Literature 7] Japanese Laid-Open Publication No. H5-213971
[Patent Literature 8] Japanese Laid-Open Publication No. H2-28185
[Patent Literature 9] Japanese Laid-Open Publication No. H6-345776
[Patent Literature 10] International Publication No. 2007/096740 pamphlet
[Patent Literature 11] International Publication No. 2003/078440 pamphlet

Non-Patent Literature

[Non-Patent Literature 1] The Journal of Antibiotics, Vol 61, pp. 36-39 (2008)
[Non-Patent Literature 2] The Journal of Antibiotics, Vol. 43, pp. 1617-1620 (1990)
[Non-Patent Literature 3] The Journal of Antibiotics, Vol. 42, pp. 795-806 (1989)
[Non-Patent Literature 4] The Journal of Antibiotics, Vol. 46, pp. 833-839 (1993)
[Non-Patent Literature 5] The Journal of Antibiotics, Vol. 46, pp. 840-849 (1993)
[Non-Patent Literature 6] The Journal of Antibiotics, Vol. 46, pp. 850-857 (1993)
[Non-Patent Literature 7] The Journal of Antibiotics, Vol. 46, pp. 1458-1470 (1993)
[Non-Patent Literature 8] The Journal of Antibiotics, Vol. 48, pp. 1371-1374 (1995)
[Non-Patent Literature 9] The Journal of Medicinal Chemistry, Vol. 35, pp. 2631-2642 (1992)
[Non-Patent Literature 10] The Journal of Medicinal Chemistry, Vol. 35, pp. 2643-2651 (1992)
[Non-Patent Literature 11] Bioorganic & Medicinal Chemistry Letters, Vol. 5, pp. 963-966 (1995)
[Non-Patent Literature 12] The Journal of Antibiotics, Vol. 48, pp. 417-424 (1995)
[Non-Patent Literature 13] The Journal of Antibiotics, Vol. 41, pp. 377-391 (1988)
[Non-Patent Literature 14] The Journal of Antibiotics, Vol. 49, pp. 496-498 (1996)
[Non-Patent Literature 15] The Journal of Antibiotics, Vol. 46, pp. 1279-1288 (1993)
[Non-Patent Literature 16] Applied Microbiology and Biotechnology, Vol. 40, pp. 892-897 (1994)

ABSTRACT OF INVENTION

Problems to be Solved by the Invention

The present invention provides Cephem compounds which exhibit potent antimicrobial spectrum against a variety of bacteria including Gram negative bacteria and/or Gram positive bacteria.

Preferably, the present invention provides Cephem compounds which exhibit potent antimicrobial activity against beta-lactamase producing Gram negative bacteria.

More preferably, the present invention provides Cephem compounds which exhibit potent antimicrobial activity against multi-drug resistant microbials, in particular, Glass B type metallo-beta-lactamase producing Gram negative bacteria.

Still preferably, the present invention provides Cephem compounds which do not exhibit cross-resistance against known Cephem drug or Carbapenem drugs.

Means for Solving the Problems

The present invention provides Cephem compounds which have solved the above-mentioned problems having at least following structural features:

1) The compounds of the present invention have cyclic quarterly ammonium group on the 3-position side chain, and a catechol type substituent on the extreme thereof, preferably, have a chloride atom on the benzene ring of the catechol group;

2) The compounds of the present invention have a spacer moiety (-G-B-D) between the quarterly ammonium group and the catechol type substituent;

3) The compounds of the present invention have an aminothiadiazol ring or aminothiazol ring on the 7-position side chain, and a carboxylic group on the extreme of the oxime moiety.

Specifically, the present invention provides the following inventions:

1) A compound of the formula:

(I)

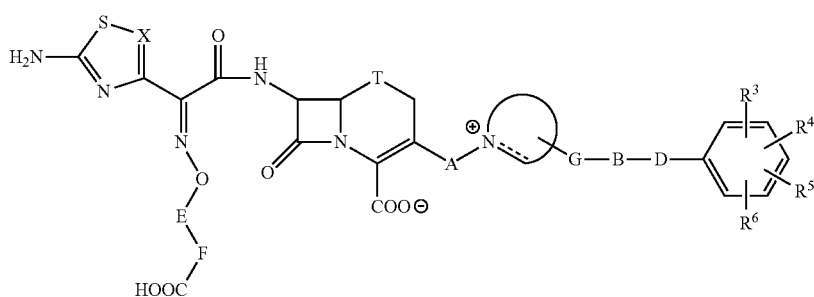

wherein,
X is N, CH or C—Cl;
T is S, S=O, CH₂ or O;
A is lower alkylene, lower alkenylene or lower alkynylene;
G is a single bond, optionally substituted lower alkylene, optionally substituted lower alkenylene, or optionally substituted lower alkynylene;
B is a single bond or 5- or 6-membered heterocyclic group containing at least 1 to 3 N atom(s);
D is a single bond, —CO—, —O—CO—, —CO—O—, —NR⁷—, —NR⁷—CO—, —CO—NR⁷—, —NR⁷—CO—NR⁷—, —O—, —S—, —SO—, —SO₂—NR⁷—, —NR⁷—SO₂—, —CH₂—NR⁷—CO— or —SO₂—;
E is optionally substituted lower alkylene;
F is a single bond or optionally substituted phenylene;
R³, R⁴, R⁵ and R⁶ each is independently hydrogen, halogene, nitrile, or —OR⁸;
R⁷ each is independently hydrogen or optionally substituted lower alkyl;
R⁸ each is independently hydrogen, lower alkyl, halo(lower)alkyl, lower alkylcarbonyl or carbamoyl;
A group of the formula:

[Formula 2]

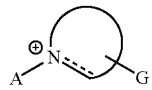

is an optionally substituted, saturated or unsaturated, monocyclic or fused cyclic quarternary ammonium group containing at least one or more N atom(s);
the broken line shows a bond in the ring;
provided that when G bonds to a cationic N atom, the broken line is absent, and when G does not bond to a cationic N atom, the broken line shows a single bond between the cationic N atom and a neighboring atom or shows lower alkylene between the cationic N atom and a ring-forming atom other than the neighboring atom; and when G is a single bond, B is a single bond and D is —NH—CO— or —S—, a group of the formula:

[Formula 3]

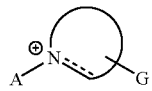

is not a group of the formula:

[Formula 4]

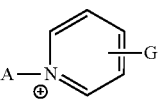

wherein, a hydrogen atom(s) may be substituted;

an ester, a protected compound at the amino on the ring in the 7-side chain, a pharmaceutically acceptable salt, or a solvate thereof.

2) The compound, or an ester, a protected compound at the amino on the ring in the 7-side chain, a pharmaceutically acceptable salt, or a solvate thereof according to item 1), wherein
said formula

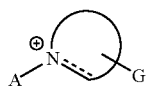

[Formula 5]

is the following formula:

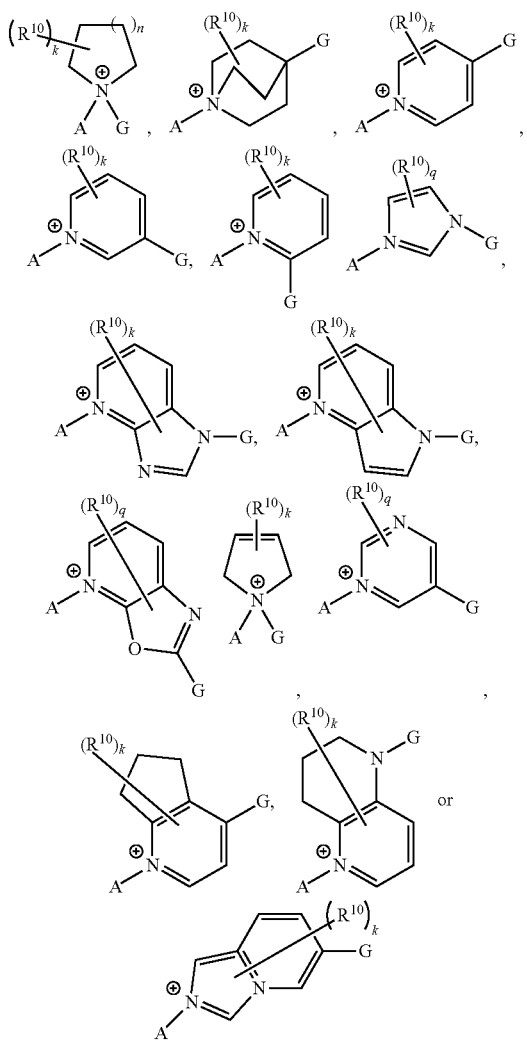

[Formula 6]

wherein n is an integer from 0 to 5, k is an integer from 0 to 5, q is an integer from 0 to 3, $R^{10}$ is halogen, hydroxy, lower alkyl, halo(lower)alkyl, lower alkoxy, or halo(lower)alkoxy, provided that $R^{10}$ may be identical or different at k or q occurrences, and A and G are as defined in item 1).

3) The compound, or an ester, a protected compound at the amino on the ring in the 7-side chain, a pharmaceutically acceptable salt, or a solvate thereof according to item 1), wherein said formula

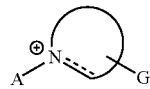

[Formula 7]

Is the formula:

[Formula 8]

Wherein n, k g and $R^{10}$ are as defined in item 2), and A and G are as defined in item 1).

4) The compound, or an ester, a protected compound at the amino on the ring in the 7-side chain, a pharmaceutically acceptable salt, or a solvate thereof according to any one of items 1)-3), wherein $R^3$ and $R^4$ are —$OR^8$, wherein R8 is as defined in item 1).

5) The compound, or an ester, a protected compound at the amino on the ring in the 7-side chain, a pharmaceutically acceptable salt, or a solvate thereof according to any one of items 1)-3), wherein the formula

[Formula 9]

is the formula:

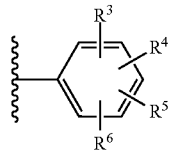

[Formula 10]

wherein $R^3$, $R^4$, $R^5$, $R^6$ and $R^8$ are as defined in item 1).

6) The compound, or an ester, a protected compound at the amino on the ring in the 7-side chain, a pharmaceutically acceptable salt, or a solvate thereof according to any one of items 1)-3), wherein the formula:

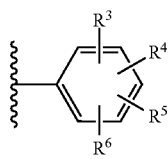
[Formula 11]

is the formula

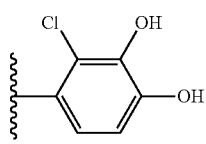
[Formula 12]

wherein $R^3$, $R^4$, $R^5$ and $R^6$ are as defined in item 1).

7) The compound, or an ester, a protected compound at the amino on the ring in the 7-side chain, a pharmaceutically acceptable salt, or a solvate thereof according to any one of items 1)-6), wherein A is —$CH_2$—, —$CH_2$—$CH_2$—, —$CH_2$—$CH_2$—$CH_2$—, —CH=CH—, —CH=CH—$CH_2$— or —$CH_2$—CH=CH—.

8) The compound, or an ester, a protected compound at the amino on the ring in the 7-side chain, a pharmaceutically acceptable salt, or a solvate thereof according to any one of items 1)-7), wherein G is a single bond, —$CH_2$—, —$CH_2$—$CH_2$—, —$CH_2$—$CH_2$—$CH_2$—, —CH=CH—, —CH=CH—$CH_2$—, —$CH_2$—CH=CH—, —$CH_2$—CH($CH_3$)—, —$CH_2$—CH ($^iPr$)— or —$CH_2$—CH(Ph)-, wherein $^iPr$ refers to isopropyl group, and Ph refers to a phenyl group.

9) The compound, or an ester, a protected compound at the amino on the ring in the 7-side chain, a pharmaceutically acceptable salt, or a solvate thereof according to any one of items 1)-8), wherein B is a single bond or the formula:

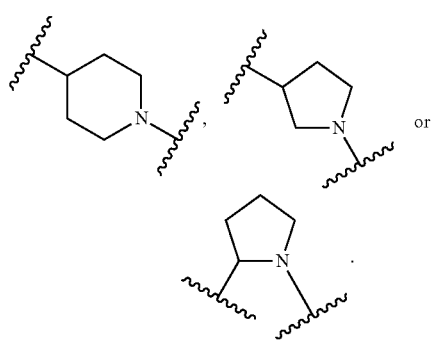
[Formula 13]

10) The compound, or an ester, a protected compound at the amino on the ring in the 7-side chain, a pharmaceutically acceptable salt, or a solvate thereof according to any one of claims 1-9, wherein D is a single bond, —CO—, —O—CO—, —CO—O—, —$NR^7$—, —$NR^7$—CO—$NR^7$—$NR^7$—CO— or —CO—$NR^7$ wherein R is as defined in item 1).

11) The compound, or an ester, a protected compound at the amino on the ring in the 7-side chain, a pharmaceutically acceptable salt, or a solvate thereof according to any one of items 1)-9), wherein D is a single bond, —CO—, —$NR^7$—CO—$NR^7$—, —$NR^7$—CO— or —CO—$NR^7$—, wherein $R^7$ is as defined in item 1).

12) The compound, or an ester, a protected compound at the amino on the ring in the 7-side chain, a pharmaceutically acceptable salt, or a solvate thereof according to any one of items 1)-11), wherein E is the formula:

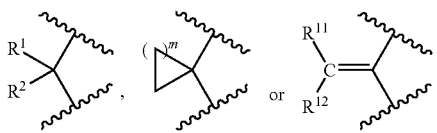
[Formula 14]

wherein $R^1$ and $R^2$ are each independently hydrogen, halogen, an optionally substituted lower alkyl, an optionally substituted lower alkylthio, or an optionally substituted phenyl, $R^{11}$ and $R^{12}$ are each independently hydrogen, an optionally substituted lower alkyl, an optionally substituted carboxyl, or a carbamoyl, and m refers to an integer of 1 to 5.

13) The compound, or an ester, a protected compound at the amino on the ring in the 7-side chain, a pharmaceutically acceptable salt, or a solvate thereof according to any one of items 1)-12), wherein $R^7$ and $R^8$ are each independently hydrogen or a lower alkyl.

14) The compound, or an ester, a protected compound at the amino on the ring in the 7-side chain, a pharmaceutically acceptable salt, or a solvate thereof according to any one of items 1)-13), wherein X is N.

15) The compound, or an ester, a protected compound at the amino on the ring in the 7-side chain, a pharmaceutically acceptable salt, or a solvate thereof according to any one of items 1)-13), wherein X is CH or C—Cl.

16) The compound, or an ester, a protected compound at the amino on the ring in the 7-side chain, a pharmaceutically acceptable salt, or a solvate thereof according to any one of items 1)-15), wherein T is S.

17) The compound, or an ester, a protected compound at the amino on the ring in the 7-side chain, a pharmaceutically acceptable salt, or a solvate thereof according to item 1, wherein X is N, CH or C—Cl;

T is S;

A is a lower alkylene;

G is a single bond or a lower alkylene;

the formula:

[Formula 15]

is the formula:

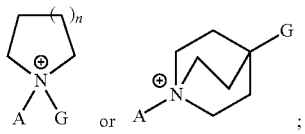
[Formula 16]

B is a single bond;
n is an integer of 0-3;
D is —NH—CO— or —CO—NH—;
E is the formula:

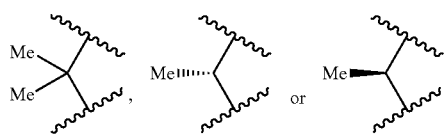
[Formula 17]

wherein Me refers to a methyl group;
F is a single bond;
$R^3$ and $R^4$ are —OH, and $R^5$ is hydrogen or Cl, and $R^6$ is hydrogen.
18) A pharmaceutical composition comprising the compound, or an ester, a protected compound at the amino on the ring in the 7-side chain, a pharmaceutically acceptable salt, or a solvate thereof according to any one of items 1-17.
19) The pharmaceutical composition according to item 18), which has an antimicrobial activity.
20) A method for treating an infectious disease, characterized in the step of administering the compound, or an ester, a protected compound at the amino on the ring in the 7-side chain, a pharmaceutically acceptable salt, or a solvate thereof according to any one of items 1)-17).
21) The compound, or an ester, a protected compound at the amino on the ring in the 7-side chain, a pharmaceutically acceptable salt, or a solvate thereof according to any one of items 1-17, which is for treating an infectious disease.
22) Use of the compound, or an ester, a protected compound at the amino on the ring in the 7-side chain, a pharmaceutically acceptable salt, or a solvate thereof according to any one of items 1)-17), for manufacturing an infectious disease therapeutic agent.

The present invention provides the following inventions as alternative embodiments:
1') A compound of the formula:

[Formula 18]

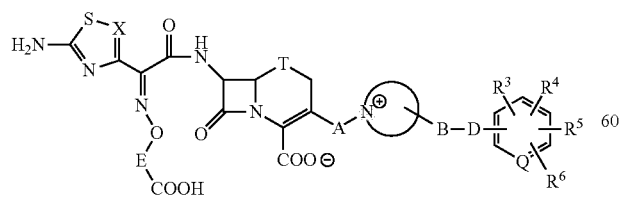
(I')

wherein
X is N, CH or C—Cl;
T is S, S=O, $CH_2$ or O;

A is lower alkylene, lower alkenylene or lower alkynylene;
B is lower alkylene, lower alkenylene, lower alkynylene or 5- or 6-membered heterocyclic group containing at least 1 to 3 N atom(s);
D is a single bond, a lower alkylene, —CO—, —O—CO—, —CO—O—, —$NR^7$—, —$NR^7$—CO—, —CO—$NR^7$—, —$NR^7$—CO—$NR^7$—, —O—, —S—, —SO—, —$SO_2$—$NR^7$—, —$NR^7$—$SO_2$— or —$SO_2$—;
E is an optionally substituted lower alkylene;
Q is N or $CR^9$,
$R^3$, $R^4$, $R^5$, $R^6$ and $R^9$ each is independently hydrogen, halogene, nitrile, or —$OR^8$;
$R^7$ each is independently hydrogen or optionally substituted lower alkyl;
$R^8$ each is independently hydrogen, lower alkyl, halo(lower)alkyl, lower alkylcarbonyl or carbamoyl; and
a group of the formula

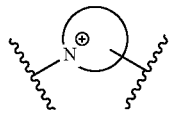
[Formula 19]

is an optionally substituted, saturated or unsaturated, monocyclic or fused cyclic quarternary ammonium group containing at least one or more N atom(s);
or an ester, a protected compound at the amino on the ring in the 7-side chain, a pharmaceutically acceptable salt, or a solvate thereof, provided that the following is excluded:

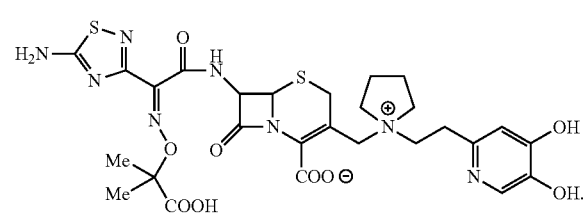
[Formula 20]

2') The compound, or an ester, a protected compound at the amino on the ring in the 7-side chain, a pharmaceutically acceptable salt, or a solvate thereof according to item 1'), wherein said formula

[Formula 21]

is the following formula:

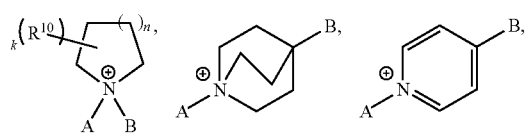
[Formula 22]

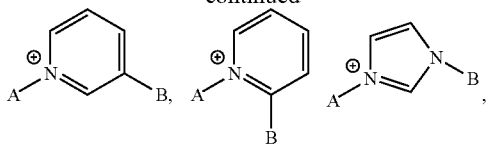

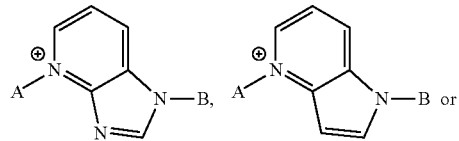

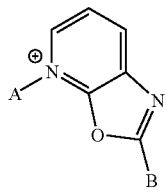

wherein n is an integer from 0 to 5, R10 is halogen, hydroxy, or a lower alkyl, k is an integer from 0 to 4, and A and B are as defined in item 1').

3') The compound, or an ester, a protected compound at the amino on the ring in the 7-side chain, a pharmaceutically acceptable salt, or a solvate thereof according to claim 1, wherein
said formula

[Formula 23]

is the formula:

[Formula 24]

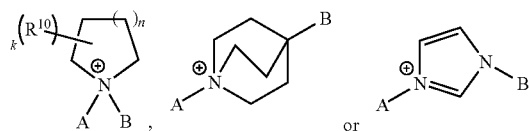

wherein n, $R^{10}$ and k are as defined in item 2'), and A and B are as defined in item 1').

4') The compound, or an ester, a protected compound at the amino on the ring in the 7-side chain, a pharmaceutically acceptable salt, or a solvate thereof according to any one of items 1')-3'), wherein $R^3$ and $R^4$ are —$OR^8$, wherein $R^8$ is as defined in item 1').

5') The compound, or an ester, a protected compound at the amino on the ring in the 7-side chain, a pharmaceutically acceptable salt, or a solvate thereof according to any one of claims 1-3, wherein
the formula:

[Formula 25]

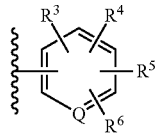

is the formula:

[Formula 26]

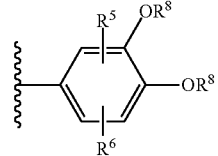

wherein $R^5$, $R^6$ and $R^8$ are as defined in item 1').

6') The compound, or an ester, a protected compound at the amino on the ring in the 7-side chain, a pharmaceutically acceptable salt, or a solvate thereof according to any one of items 1')-5'), wherein A is —$CH_2$—, —$CH_2$—$CH_2$—, —$CH_2$—$CH_2$—$CH_2$—, —CH=CH—, —CH=CH—$CH_2$— or —$CH_2$—CH=CH—.

7') The compound, or an ester, a protected compound at the amino on the ring in the 7-side chain, a pharmaceutically acceptable salt, or a solvate thereof according to any one of item 1')-6'), wherein B is —$CH_2$—, —$CH_2$—$CH_2$—, —$CH_2$—$CH_2$—$CH_2$—, —CH=CH—, —CH=CH—$CH_2$—, —$CH_2$—CH=CH— or the formula:

[Formula 27]

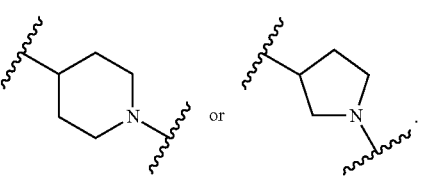

8') The compound, or an ester, a protected compound at the amino on the ring in the 7-side chain, a pharmaceutically acceptable salt, or a solvate thereof according to any one of items 1')-7'), wherein D is a single bond, —CO—, —O—CO—, —CO—O—, —$NR^7$—, —$NR^7$—CO—$NR^7$—, —$NR^7$—CO— or —CO—$NR^7$—, wherein $R^7$ is as defined in item 1').

9') The compound, or an ester, a protected compound at the amino on the ring in the 7-side chain, a pharmaceutically acceptable salt, or a solvate thereof according to any one of items 1')-7'), wherein D is —CO—, —$NR^7$—CO—$NR^7$—, —$NR^7$—CO— or —CO—$NR^7$—, wherein $R^7$ is as defined in item 1').

10') The compound, or an ester, a protected compound at the amino on the ring in the 7-side chain, a pharmaceutically acceptable salt, or a solvate thereof according to any one of claims 1')-9'), wherein E is the formula:

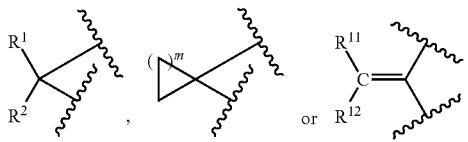
, or 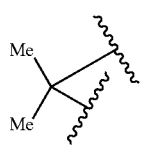

wherein $R^1$ and $R^2$ are each independently hydrogen, halogen, an optionally substituted lower alkyl, a lower alkylthio, or an optionally substituted phenyl, $R^{11}$ and $R^{12}$ are each independently hydrogen, an optionally substituted lower alkyl, an optionally substituted carboxyl, or a carbamoyl, and m refers to an integer of 1 to 5.

11') The compound, or an ester, a protected compound at the amino on the ring in the 7-side chain, a pharmaceutically acceptable salt, or a solvate thereof according to any one of items 1')-10'), wherein $R^7$ and $R^8$ are each independently hydrogen or a lower alkyl.

12') The compound, or an ester, a protected compound at the amino on the ring in the 7-side chain, a pharmaceutically acceptable salt, or a solvate thereof according to any one of items 1')-11'), wherein X is N.

13') The compound, or an ester, a protected compound at the amino on the ring in the 7-side chain, a pharmaceutically acceptable salt, or a solvate thereof according to any one of items 1')-11'), wherein X is CH or C—Cl.

14') The compound, or an ester, a protected compound at the amino on the ring in the 7-side chain, a pharmaceutically acceptable salt, or a solvate thereof according to any one of items 1')-13'), wherein T is S.

15') The compound, or an ester, a protected compound at the amino on the ring in the 7-side chain, a pharmaceutically acceptable salt, or a solvate thereof according to item 1'), wherein X is N, CH or C—Cl;

T is S;

the formula:

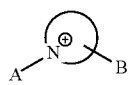

is the formula:

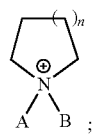

A is a lower alkylene;

B is a lower alkylene;

n is an integer of 0-3;

D is —NH—CO— or —CO—NH—;

E is the formula:

[Formula 31]

wherein Me refers to a methyl group;

Q is CH;

$R^3$ and $R^4$ are —OH, and $R^5$ is hydrogen or Cl, and $R^6$ is hydrogen.

16') A pharmaceutical composition comprising the compound, or an ester, a protected compound at the amino on the ring in the 7-side chain, a pharmaceutically acceptable salt, or a solvate thereof according to any one of items 1')-15').

17') The pharmaceutical composition according to item 16'), which has an antimicrobial activity.

Effects of the Invention

The compounds of the present invention are useful as a pharmaceutical product in that the compounds have at least one of the following features:

1) The compound exhibits potent antimicrobial spectrum against a variety of bacteria including Gram negative bacteria and/or Gram negative bacteria;

2) the compounds exhibit potent antimicrobial activity against beta-lactamase producing Gram negative bacteria;

3) the compounds exhibit potent antimicrobial activity against multi drug resistant bacteria, in particular, Class B type, metallo-beta-lactamase producing Gram negative bacteria;

4) the compounds do not exhibit cross resistance with known Cephem drugs and/or Carbapenem drugs;

5) the compounds do not exhibit side effects such as fever after administration into the body.

BEST MODE OF CARRYING OUT THE INVENTION

The respective terms used herein are as defined alone or in combination with other terms as follows:

"Halogen" includes fluorine, chlorine, bromine and iodine. Preferably, halogen is fluorine, chlorine or bromine, and more preferably halogen is chlorine.

"Lower alkyl" includes linear or branched alkyl having 1-8 carbons, preferably 1-6 carbons, and more preferably 1-3 carbons, and include for example, methyl, ethyl, n-propyl, isopropyl, n-butyl, isobutyl, sec-butyl, tert-butyl, n-pentyl, isopentyl, neopentyl, hexyl, isohexyl, n-heptyl, isoheptyl, n-octyl and the like.

The lower alkyl moiety in halo(lower)alkyl", "lower alkylcarbonyl", "lower alkylthio", "lower alkoxy", "hydroxy(lower)alkoxy", "lower alkoxy(lower)alkoxy", "hydroxy(lower)alkoxy", "lower alkoxy(lower)alkoxy", "lower alkylamino", "lower alkylimino", "lower alkylcarbamoyl", "hydroxy(lower)alkylcarbamoyl", "lower alkylsulfamoyl", "lower alkylsulfinyl", "lower alkylthio", and the like is as above in "lower alkyl".

Substituents in "an optionally substituted lower alkyl" is at least one of those groups selected from "Substituents group alpha".

"Substituents group alpha" is a group consisting of halogen, hydroxy, lower alkoxy, hydroxy(lower)alkoxy, lower alkoxy(lower)alkoxy, carboxy, hydroxy(lower)alkoxy, lower alkoxy(lower)alkoxy, amino, acylamino, lower alkylamino, imino, hydroxyimino, lower alkoxyimino, lower alkylthio, carbamoyl, lower alkylcarbamoyl, hydroxy(lower)alkylcarbamoyl, sulfamoyl, lower alkylsulfamoyl, lower alkylsulfinyl, cyano, nitro, carbocyclic group, and heterocyclic group.

"Halo(lower)alkyl" refers to a group in which at least one position of a lower alkyl is substituted with the above "halogen", and include, for example, monofluoromethyl, difluoromethyl, trifluoromethyl, monochloromethyl, monobromomethyl, monofluoromethyl, monochloroethyl, and the like.

"Lower alkylene" includes linear alkylene having 1-8 carbons, preferably 1-6 carbons, and more preferably 1-3 carbons. and include, for example, methylene, ethylene, n-propylene, n-butylene, n-pentylene, n-hexylene and the like.

"Lower alkenylene" includes linear alkenyl having 2-8 carbons, preferably 2-6 carbons, more preferably 2-4 carbons having at least one double bond at any position, and include, for example, vinylene, allylene, propenylene, butenylene, prenylene, butadienylene, pentenylene, pentadienylene, hexenylene, hexadienylene, and the like.

"Lower alkynylene" includes a linear alkynylene having 2-8 carbons, preferably 2-6 carbons, more preferably 2-4 carbons, having at least one triple bond at any position, and include, for example, ethynylene, propynylene, butynylene, pentynylene, hexynylene and the like.

Substituents of "an optionally substituted lower alkylene", "an optionally substituted lower alkenylene", and "an optionally substituted lower alkynylene" include at least one group selected from Substituent Group Alpha.

"An optionally substituted lower alkylene" is a group in which the —CH$_2$— moiety of "lower alkylene" includes the cases where as described in the formula:

[Formula 32]

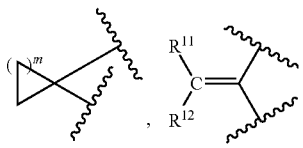

$R^{11}$ and $R^{12}$ are each independently hydrogen, an optionally substituted lower alkyl, an optionally substituted carboxyl, or a carbamoyl, and m refers to an integer of 1 to 5, the cases where the substituents are taken together to form a ring, and cases where the substituents are taken together to form a bond with an adjacent carbon atom.

Substituents of "an optionally substituted phenylene" and "an optionally substituted phenyl" include at least one group selected from the Substituent Group Alpha.

"Carbocyclic group" includes cycloalkyl, cycloalkenyl, aryl and non-aromatic fused carbocyclic groups and the like.

"Cycloalkyl" is a carbocyclic group having 3-10 carbons, preferably 3-8 carbons, more preferably 4-8 carbons, and includes, for example, cyclopropyl, cyclobutyl, cyclopentyl, cyclohexyl, cycloheptyl, cyclooctyl, cyclononyl and cyclodecyl, and the like.

"Cycloalkenyl" includes those in which at least one double bond is included in the ring of the cycloalkyl at any position, and specifically include, for example, cyclopropenyl, cyclobutenyl, cyclopentenyl, cyclohexenyl, cycloheptynyl, cyclooctynyl, and cyclohexadienyl and the like.

"Aryl" includes phenyl, naphtyl, anthryl and phenanthryl and the like, and in particular, phenyl is preferable.

"Non-aromatic fused carbocyclic group" includes group in which two or more cyclic groups selected from the "cycloalkyl", "cycloalkenyl" and "aryl" are fused, and specifically, includes, for example, indanyl, indenyl, tetrahydronaphtyl, and fluorenyl and the like.

"Heterocyclic group" includes heterocyclic groups having at least one hetero atom arbitrarily selected from O, S and N, in the ring thereof, and specifically includes, for example, 5-membered or 6-membered heteroaryl such as pyrrolyl, imidazolyl, pyrazolyl, pyridyl, pyridazinyl, pyrimidinyl, pyrazinyl, triazolyl, triazinyl, tetrazolyl, isoxazolyl, oxazolyl, oxadiazolyl, isothiazolyl, thiazolyl, thiadiazolyl, furyl and thienyl and the like; bicyclic fused heterocyclic groups such as indolyl, isoindolyl, indazolyl, indolylizinyl, indolynyl, isoindolinyl, quinolyl, isoquinolyl, cinnoninyl, phthalazinyl, quinazolinyl, naphtylizinyl, quinoxanilyl, purinyl, pteridinyl, benzopyranyl, benzimidazolyl, benzotriazolyl, benzisoxazolyl, benzoxazolyl, benzoxadiazoyl, benzisothiazolyl, benzothiazolyl, benzothiadiazolyl, benzofuryl, isobenzofuryl, benzothienyl, benzotriazolyl, imidazopyridyl, pyrazolopyridine, quinazolinyl, quinolyl, isoquinolyl, naphtylidinyl, dihydrobenzofuryl, tetrahydroquinolyl, tetrahydroisoquinolyl, dihydrobenzoxazine, tetrahydrobenzothienyl, and the like; tricyclic fused heterocyclic group such as carbazolyl, acridinyl, xanthenyl, phenothiadinyl, phenoxathiinyl, phenoxazinyl, dibenzofuryl, imidazoquinolyl and the like; non-aromatic heterocyclic group such as dioxanyl, thiiranyl, oxiranyl, oxathioranyl, azetidinyl, thianyl, thiazolidine, pyrrolidinyl, pyrrolinyl, imidazolidinyl, imidazolinyl, pyrazolidinyl, pyrazolinyl, pyperadinyl, morpholinyl, morpholino, thiomorpholinyl, thiomorpholino, dihydropyridyl, dihyrobenzimidazolyl, tetrahydropyridyl, tetrahydrofuryl, tetrahydropyranyl, tetrahydrothiazolyl, tetrahydroisothiazolyl, dihydrooxazinyl, hexahydroazepinyl, tetrandydrodiazepinyl, and the like.

"5- or 6-membered heterocyclic group containing at least 1 to 3 N atom(s)" includes, for example, any of those groups as follows:

[Formula 33]

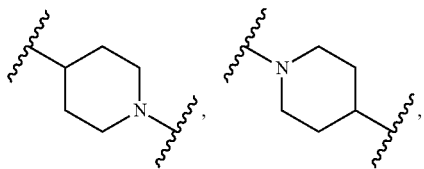

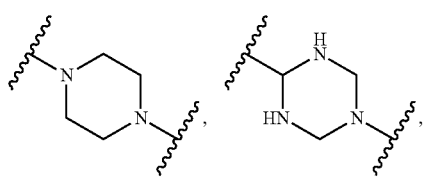

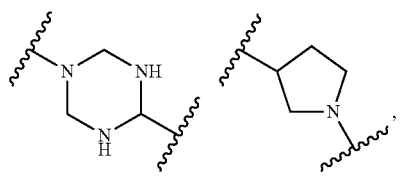

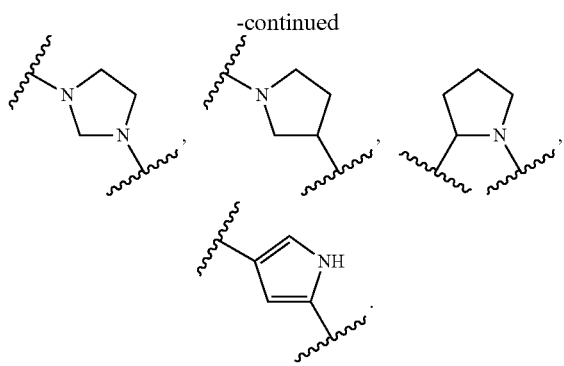

Preferably, it includes any group as follows:

[Formula 34]

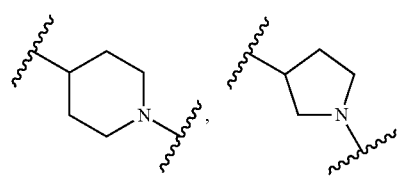

wherein a quarternary ammonium group as shown in Formula:

[Formula 35]

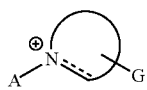

is a saturated or unsaturated, monocyclic or fused cyclic quarternary ammonium group preferably including 1-4 N atoms, more preferably 1-3 N atoms, and still more preferably 1-2 N atoms, and including 1-4, preferably 1-2 substituents, and said ring may include an additional one or more O and/or S atoms.

Hetero rings which form the quaternary ammonium group is as follows:

Saturated hetero ring containing N atom includes, for example, azetidine, pyrrolidine, pyrazolidine, thiazolidine, oxazolidine, imidazolidine, piperidine, piperazine, morpholine, thiomorpholine, azepane, azocane, quinuclidine, and fused ring containing the same, and preferably pyrrolidine, piperazine, azepane, or quinuclidine.

Unsaturated N-atom containing hetero ring includes, for example, monocycle (for example, pyrrol, pirazol, imidazol, oxazol, isoxazol, thiazol, isothiazol, pyridine, pyridazine, pyridimine, pyrazine, triazine, triazol, 2,3-dihydro-1H-pyrrol, 2,5-dihydro-1H-pyrrol, and fused bicyclic ring containing these monocycle in the ring (for example, indole, benzimidazole, benzopyrazole, indolydine, quinoline, isoquinoline, quinoline, phtalazine, quinazoline, benzoisoxazole, benzoxazole, benzoxadiazole, benzoisothiazole, benzthiazole, benzoxadiazole, benzisothiazole, benzthiazole, benzotriazole, purine, indoline, 1H-pyrrolo[3,2-b]pyridine, 1H-pyrrazolo[4,3-b]pyridine, 1H-pyrazolo[4,3-b]pyridine, thiazolo[4,5-c]pyridine, 1,4-dihydro-pyrido[3,4-b]pyrazine, 1,3-dihydro-imidazo[4,5-c]pyridine and the like), and preferably, pyrrol, imidazole, pyridine, benzimidazole, 2,5-dihydro-1H-pyrrole.

Specifically, for example, heterocyclic groups which optionally have a plurality of substituents at an appropriate position, for example, as described below are included. Substituents include at least one selected from an optionally substituted lower alkyl or a Substituted Group Alpha:

[Formula 36]

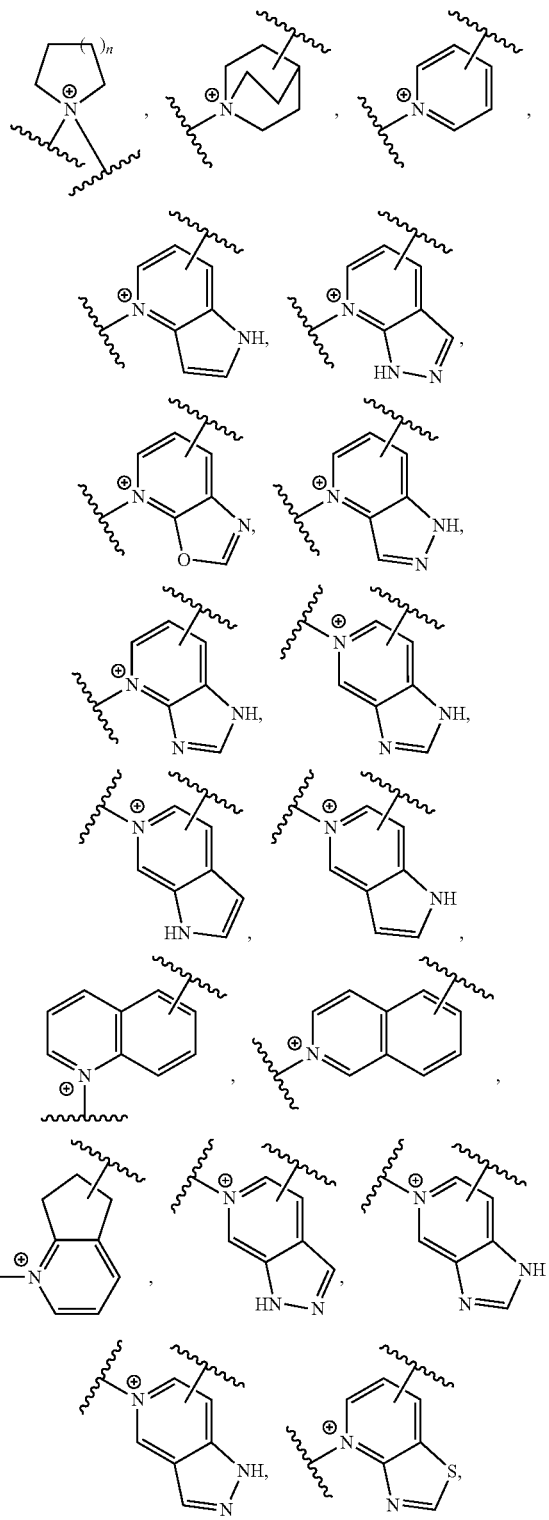

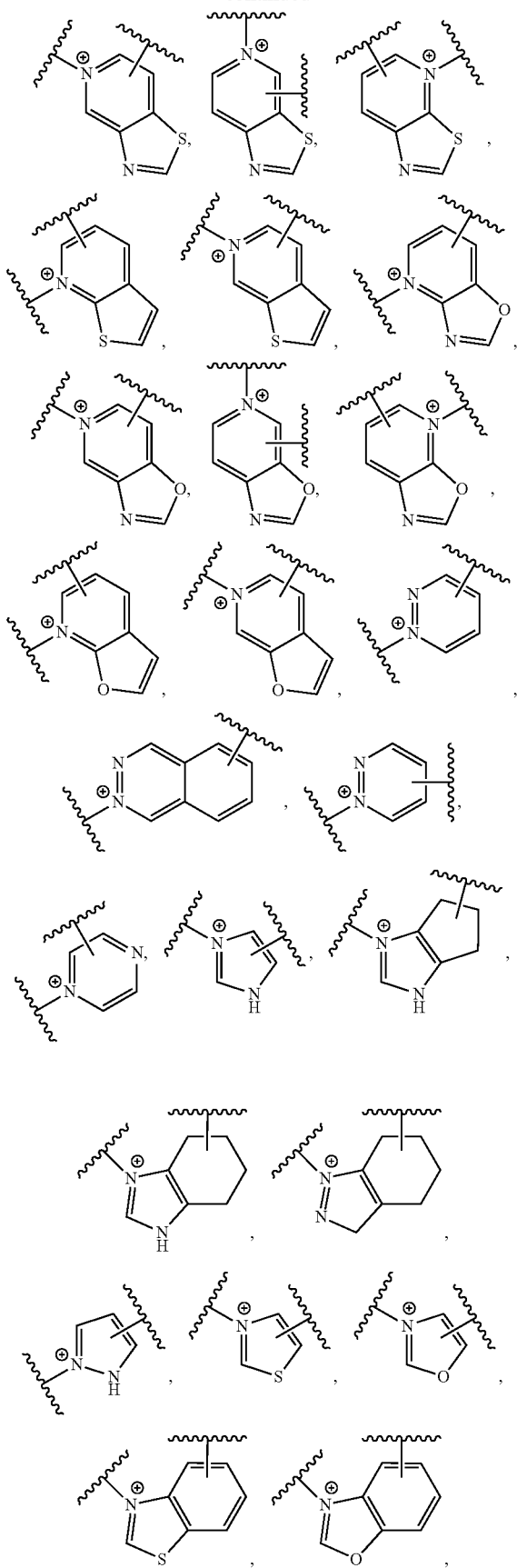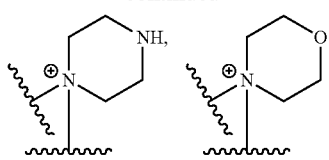
wherein n is an integer from 0 to 5, k is an integer from 0 to 4, $R^{10}$ is halogen, hydroxy, lower alkyl, halo(lower)alkyl, lower alkoxy, or halo(lower)alkoxy, provided that $R^{10}$ may be identical or different at k occurrences.
More preferably, the following heterocyclic groups are included as follows:
[Formula 37]
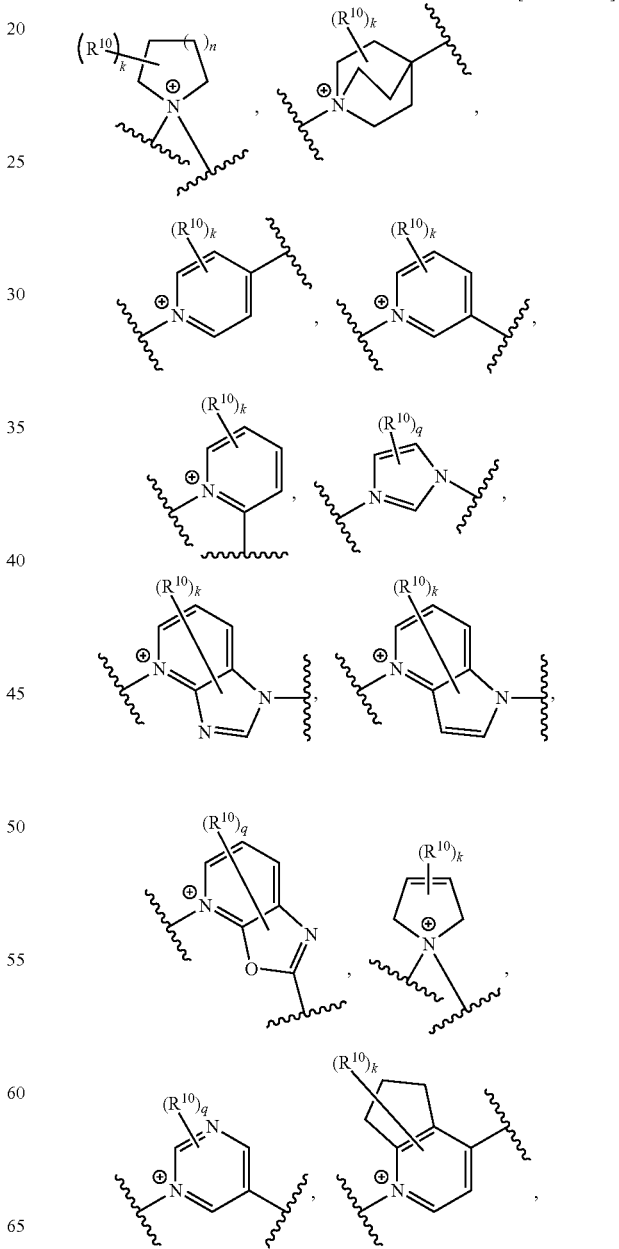

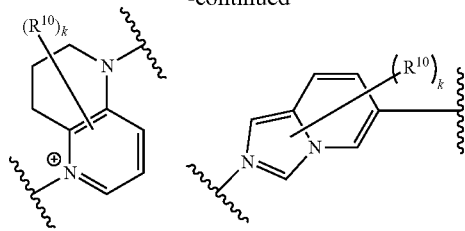

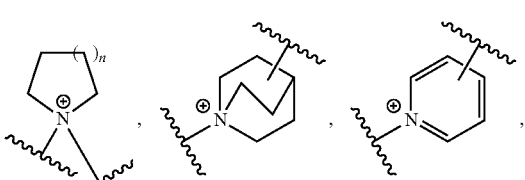

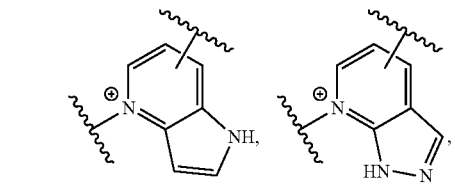

wherein n is an integer from 0 to 5, k is an integer from 0 to 4, q is an integer from 0 to 3, $R^{10}$ is halogen, hydroxy, lower alkyl, halo(lower)alkyl, lower alkoxy, or halo(lower)alkoxy, provided that $R^{10}$ may be identical or different at k or q occurrences Still more preferably, the heterocyclic groups are included as follows:

[Formula 38]

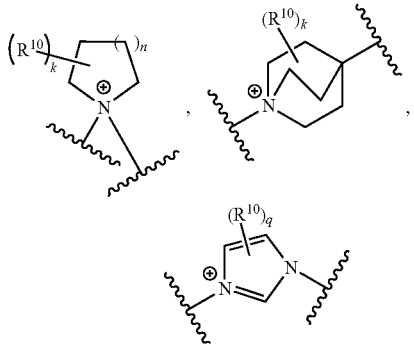

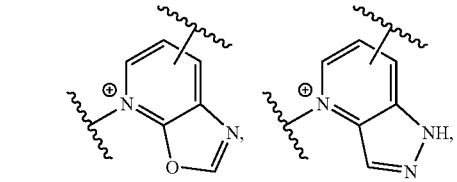

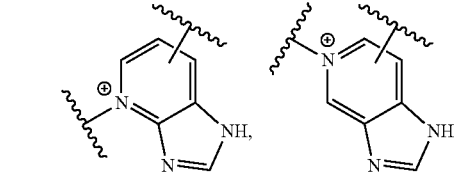

n, k, g and $R^{10}$ are as defined above.

The heterocyclic group as shown as follows is most preferable.

[Formula 39]

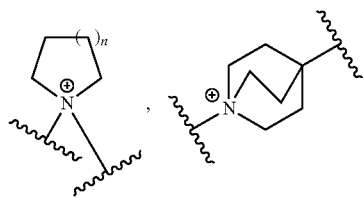

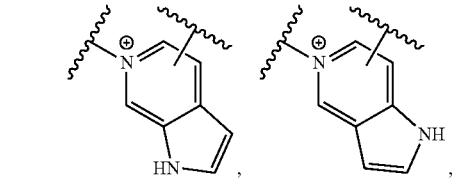

wherein n is as defined above.

"A saturated or unsaturated, monocyclic or fused cyclic quaternary ammonium group including at least one N atoms" is a saturated or unsaturated, monocyclic or fused cyclic quaternary ammonium group preferably including 1-4 N atoms, more preferably 1-3 N atoms, and still more preferably 1-2 N atoms, and including 1-4, preferably 1-2 substituents, and said ring may include additional one or more O and/or S atoms.

Specifically, the heterocyclic groups which may have a plurality of substituents at an appropriate position are included as follows, for example. Substituents include a group selected from an optionally substituted lower alkyl or Substituents Group Alpha:

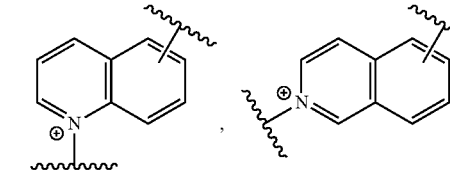

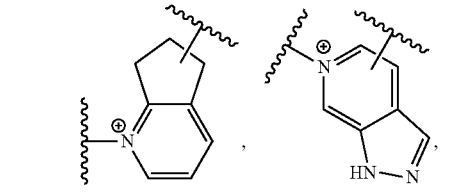

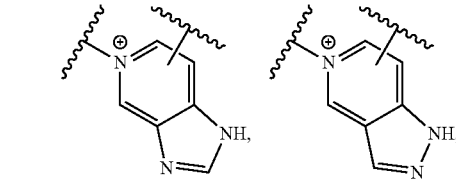

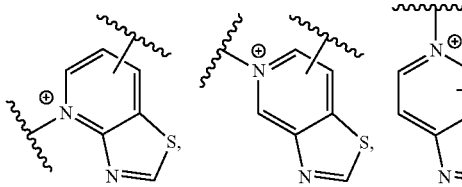

wherein n is an integer from 0 to 5, $R^{13}$ is halogen, hydroxy, lower alkyl, k is an integer of 0 to 4, Rx is an optionally substituted lower alkyl, and furthermore, hydrogen atom in NH may be substituted with a group selected from an optionally substituted lower alkyl or Substituents Group Alpha.

More preferably, the heterocyclic group which may be substituted at an appropriate position is as follows. Substituents include those groups selected from an optionally substituted lower alkyl or Substituted Group Alpha.

[Formula 41]

wherein n, $R^{13}$ and k are as defined above.

More preferably, the heterocyclic groups are included as follows:

[Formula 42]

wherein n, $R^{13}$ and k are as defined above.

The nomenclature of the substitution position on the Cephem backbone of Compounds (I) and (I') are as follows.

7-position side chain and 3-position side chain as used herein refers to a group which binds to the 7-position or 3-position of the Cephem backbone as shown below.

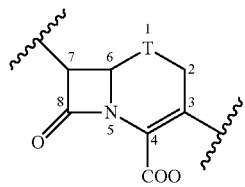
[Formula 43]

Esters of Compounds (I) and (I') preferably include, those esters at the carboxyl at the 7-position side chain or at the 4-position. Esters at the carboxyl at the 7-position side chain refers to a compound which has an esterified structure as shown in the formula as follows:

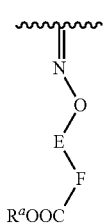
[Formula 44]

wherein E and F is as defined in item 1), and R1 is an ester residue of the carboxyl protecting group and the like. The esters include those esters which are readily metabolized in the body to form a carboxy state.

Esters at the 4-position of Compounds (I) and (I') refer to compounds which have an esterified structure at the 4-position moiety as shown in the formula as follows:

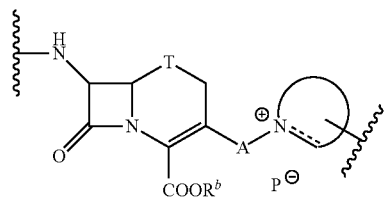
[Formula 45]

wherein A and T is as defined in item 1), and Rb is an ester residue such as a carboxylic protecting group and the like, and P— is a counterion such as halogen. Such esters include those esters which are readily metabolized to form a carboxylic state.

The above mentioned carboxylic protecting groups include lower alkyl (for example, methyl, ethyl, t-butyl), optionally substituted aralkyl (for example, benzyl, benzhydryl, phenethyl, p-methoxybenzyl, p-nitrobenzyl), silyl group (t-butyldimethylsilyl, diphenyl t-butylsilyl) and the like.

Compounds protected at the amino of the thiazol or thiadiazole ring of the 7-position side chain of Compounds (I) or (I') refer to compounds in which the thiazol or thiadiazol rings are a ring as shown in the formula:

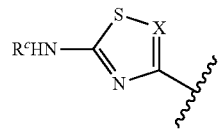
[Formula 46]

wherein X is as defined in item 1, and $R^c$ refers to an amino protecting group. Such amino protecting groups include groups which are readily metabolized in the body to form amino. Such amino protecting groups include lower alkoxycarbonyl (for example, t-butoxycarbonyl, benzyloxycarbonyl, p-nitrobenzyloxycarbonyl), optionally substituted aralkanoyl (for example, p-nitrobenzoyl), acyl (for example, formyl, chloroacetyl) and the like.

Pharmaceutically acceptable salts of Compounds (I) and (I') include, for example, salts or intramolecular salts formed with inorganic base, ammonia, organic base, inorganic acid, organic acid, basic amino acid, halogen ions and the like. Such inorganic base include alkali metal (Na, K and the like), alkali earth metal (Mg and the like), organic base includes procaine, 2-phenylethylbenzyl amine, dibenzylethylene diamine, ethanolamine, diethanolamine, trishydroxymethyl aminomethane, polyhydroxalkylamine, N-methyl glucosamine and the like. Inorganic acids include, for example, hydrochloric acid, hydrobromic acid, sulfuric acid, nitric acid, phosphoric acid and the like. Organic acids include, for example, p-toluene sulfonic acid, methane sulfonic acid, formic acid, acetic acid, trifluoroacetic acid, maleic acid and the like. Basic amino acids include, for example, lysine, arginine (アルギン), ornithine, histidine and the like.

As used herein, "solvate" refers to a solvate with water or organic solvent (for example, methanol, ethanol, isopropyl alcohol, acetone), and preferably hydrate.

The Compounds (I) and (I') of the present invention are not limited to particular isomers but include any possible isomers and racemates as exemplified as follows:

In Compounds (I) and (I'):

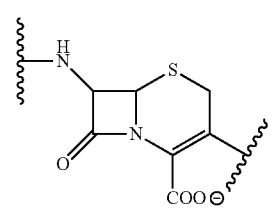
[Formula 47]

includes

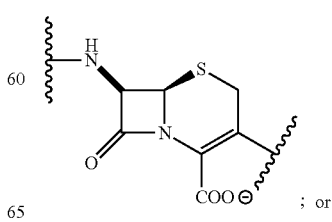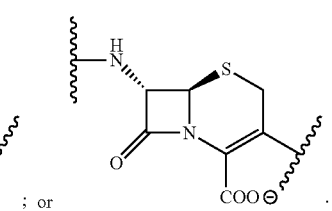
[Formula 48]

; or

In E of Compounds (I) and (I'),

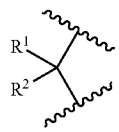

[Formula 49]

includes

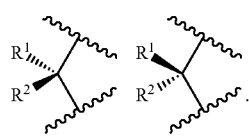

[Formula 50]

Furthermore, Formula (I') includes the following isomers:

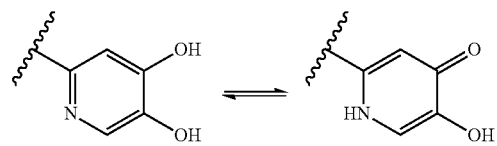

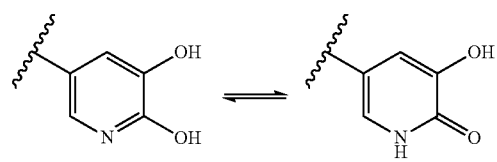

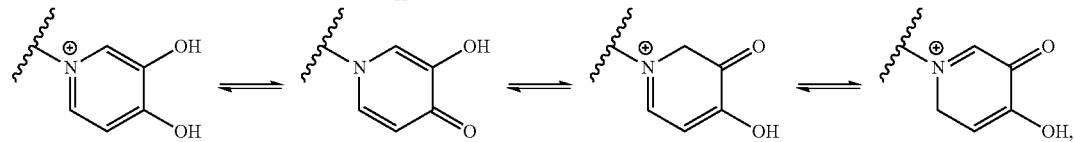

[Formula 51]

wherein —OH group may form a salt with a counter cation (for example, $Na^+$, $K^+$, $Li^+$ and the like).

The compounds of the present invention are preferably those compounds as specifically shown as follows:
Formula (I):

[Formula 52]

Preferable embodiments of Formula (I) are as follows:
1) Compounds wherein T is S (hereinafter T is s1)
2) Compounds wherein A is a lower alkylene or a lower alkenylene (hereinafter A is a1);
compounds wherein A is —$CH_2$— (hereinafter A is a2);
compounds wherein A is —$CH_2$—$CH_2$—, —$CH_2$—$CH_2$—$CH_2$— or —CH=CH—$CH_2$— (hereinafter A is a3);
Preferably, A is a2 as described above.
3) Compounds wherein B is a single bond (hereinafter B is b1)
compounds wherein B is

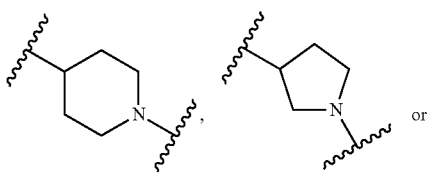

[Formula 53]

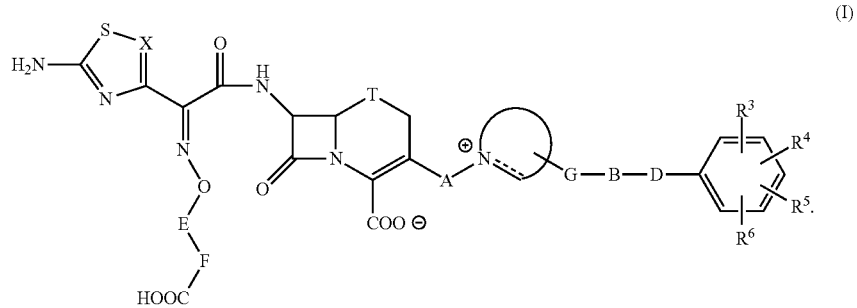

(I)

[Formula - pyrrolidine structure]

(hereinafter B is b2)
Preferably, B is b1.
4) Compounds wherein D is a single bond or —CO— (hereinafter D is d1);
compounds wherein D is —NH—CO—, —N(CH$_3$)—CO—, —CO—NH—, —CO—N(CH$_3$)— or —NH—CO—NH— (hereinafter D is d2)
more preferably, D is d2 as described above.
5) Compounds wherein E is —CH$_2$— (hereinafter E is e1);
compounds wherein E is —CH(CH$_3$)— (hereinafter E is e2);
compounds wherein E is —C(CH$_3$)$_3$— (hereinafter E is e3);
compounds wherein E is as follows:

[Formula 54]

More preferably, E is e2 or e3 as described above.
6) Compounds wherein F is a single bond or phenylene (hereinafter F is f1)
7) Compounds wherein G is a lower alkylene or lower alkenylene (hereinafter G is g1);
compounds wherein G is —CH$_2$—, —CH$_2$—CH$_2$—, or —CH$_2$—CH$_2$—CH$_2$— (hereinafter G is g2);
Compounds wherein G is —CH=CH— or —CH=CH—CH$_2$— (hereinafter G is g3);
Compounds wherein G is a single bond (hereinafter G is g4)
compounds wherein G is —CH$_2$—CH(CH$_3$)—, —CH$_2$—CH($^i$Pr)— or —CH$_2$—CH(Ph)- (wherein iPr refers to isopropyl group, PH refers to a phenyl group) (hereinafter G is g5).
More preferably, G is g2 above.
8) Compounds wherein X i CH, C—Cl or X (hereinafter X is x1).
9) Compounds wherein the formula:

[Formula 55]

is the formula:

[Formula 56]

(wherein n is an integer of 1 to 5, and A and G is as defined above) (hereinafter h1);

compounds wherein the formula:

[Formula 57]

is the formula:

[Formula 58]:

wherein A and G are as defined above (hereinafter h2).
10) Compounds wherein R$^3$ and R$^4$ are —OH, and R$^5$ and R$^6$ are hydrogen, hereinafter i1);
compounds wherein R$^3$ and R$^4$ are —OH, and R$^5$ is hydrogen and R$^6$ is halogen (hereinafter i2);
compounds wherein R$^3$ and R$^4$ are —OH, and R$^5$ and R$^6$ are halogen (hereinafter i3);
More preferably, R$^3$, R$^4$, R$^5$ and R$^6$ are i2 mentioned above.
Further preferable embodiments of Compound (I) are those in which the combination of T, A, B, D, E, F G, X and the formula:

[Formula 59]

and R$^3$, R$^4$, R$^5$ and R$^6$ are as follows:
(s1, a1, b1, d1, e1, f1, g1, x1, h1, i1), (s1, a1, b1, d1, e1, f1, g1, x1, h1, i2), (s1, a1, b1, d1, e1, f1, g1, x1, h1, i3), (s1, a1, b1, d1, e1, f1, g1, x1, h2, i1), (s1, a1, b1, d1, e1, f1, g1, x1, h2, i2), (s1, a1, b1, d1, e1, f1, g1, x1, h2, i3), (s1, a1, b1, d1, e1, f1, g2, x1, h1, i1), (s1, a1, b1, d1, e1, f1, g2, x1, h1, i2), (s1, a1, b1, d1, e1, f1, g2, x1, h1, i3), (s1, a1, b1, d1, e1, f1, g2, x1, h2, i1), (s1, a1, b1, d1, e1, f1, g2, x1, h2, i2), (s1, a1, b1, d1, e1, f1, g2, x1, h2, i3), (s1, a1, b1, d1, e1, f1, g3, x1, h1, i1), (s1, a1, b1, d1, e1, f1, g3, x1, h1, i2), (s1, a1, b1, d1, e1, f1, g3, x1, h1, i3), (s1, a1, b1, d1, e1, f1, g3, x1, h2, i1), (s1, a1, b1, d1, e1, f1, g3, x1, h2, i2), (s1, a1, b1, d1, e1, f1, g3, x1, h2, i3), (s1, a1, b1, d1, e1, f1, g4, x1, h1, i1), (s1, a1, b1, d1, e1, f1, g4, x1, h1, i2), (s1, a1, b1, d1, e1, f1, g4, x1, h1, i3), (s1, a1, b1, d1, e1, f1, g4, x1, h2, i1), (s1, a1, b1, d1, e1, f1, g4, x1, h2, i2), (s1, a1, b1, d1, e1, f1, g4, x1, h2, i3), (s1, a1, b1, d1, e1, f1, g5, x1, h1, i1), (s1, a1, b1, d1, e1, f1, g5, x1, h1, i2), (s1, a1, b1, d1, e1, f1, g5, x1, h1, i3), (s1, a1, b1, d1, e1, f1, g5, x1, h2, i1), (s1, a1, b1, d1, e1, f1, g5, x1, h2, i2), (s1, a1, b1, d1, e1, f1, g5, x1, h2, i3), (s1, a1, b1, d1, e2, f1, g1, x1, h1, i1), (s1, a1, b1, d1, e2, f1, g1, x1, h1, i2), (s1, a1, b1, d1, e2, f1, g1, x1, h1, i3), (s1, a1, b1, d1, e2, f1, g1, x1, h2, i1), (s1, a1, b1, d1, e2, f1, g1, x1, h2, i2), (s1, a1, b1, d1, e2, f1, g1, x1, h2, i3), (s1, a1, b1, d1, e2, f1, g2, x1, h1, i1), (s1, a1, b1, d1, e2, f1, g2, x1, h1, i2), (s1, a1, b1, d1, e2, f1, g2, x1, h1, i3), (s1, a1, b1, d1, e2, f1, g2, x1, h2, i1), (s1, a1, b1, d1, e2, f1, g2, x1, h2, i2), (s1, a1, b1, d1, e2, f1, g2, x1, h2, i3), (s1, a1, b1, d1, e2, f1, g3, x1, h1, i1), (s1, a1, b1, d1, e2, f1, g3, x1, h1, i2), (s1, a1, b1, d1, e2, f1, g3, x1, h1, i3), (s1, a1, b1, d1, e2, f1, g3, x1, h2, i1), (s1, a1, b1, d1, e2, f1, g3, x1, h2, i2), (s1, a1, b1, d1, e2, f1, g3, x1, h2, i3), (s1, a1, b1, d1, e2, f1, g4, x1, h1, i1), (s1, a1, b1, d1, e2, f1, g4, x1, h1, i2), (s1, a1, b1, d1, e2, f1, g4, x1, h1, i3), (s1, a1, b1, d1, e2, f1, g4, x1, h2, i1), (s1, a1, b1, d1, e2, f1, g4, x1, h2, i2), (s1, a1, b1, d1, e2, f1, g4, x1, h2, i3), (s1, a1, b1, d1, e2, f1, g5, x1, h1, i1), (s1, a1, b1, d1, e2, f1, g5, x1, h1, i2), (s1, a1, b1, d1, e2, f1, g5, x1, h1, i3), (s1, a1, b1, d1, e2, f1, g5, x1, h2, i1), (s1, a1, b1, d1, e2, f1, g5, x1, h2, i2), (s1, a1, b1, d1, e2, f1, g5, x1, h2, i3), (s1, a1, b1, d1, e3, f1, g1, x1, h1, i1), (s1, a1, b1, d1, e3, f1, g1, x1, h1, i2), (s1, a1, b1, d1, e3, f1, g1, x1, h1, i3), (s1, a1, b1, d1, e3, f1, g1, x1, h2, i1), (s1, a1, b1, d1, e3, f1, g1, x1, h2, i2), (s1, a1, b1, d1, e3, f1, g1, x1, h2, i3), (s1, a1, b1, d1, e3, f1, g2, x1, h1, i1), (s1, a1, b1, d1, e3, f1, g2, x1, h1, i2), (s1, a1, b1, d1, e3, f1, g2, x1, h1, i3), (s1, a1, b1, d1, e3, f1, g2, x1, h2, i1), (s1, a1, b1, d1, e3, f1, g2, x1, h2, i2), (s1, a1, b1, d1, e3, f1, g2, x1, h2, i3), (s1, a1, b1, d1, e3, f1, g3, x1, h1, i1), (s1, a1, b1, d1, e3, f1, g3, x1, h1, i2), (s1, a1, b1, d1, e3, f1, g3, x1, h1, i3), (s1, a1, b1, d1, e3, f1, g3, x1, h2, i1), (s1, a1, b1, d1, e3, f1, g3, x1, h2, i2), (s1, a1, b1, d1, e3, f1, g3, x1, h2, i3), (s1, a1, b1, d1, e3, f1, g4, x1, h1, i1), (s1, a1, b1, d1, e3, f1, g4, x1, h1, i2), (s1, a1, b1, d1, e3, f1, g4, x1, h1, i3), (s1, a1, b1, d1, e3, f1, g4, x1, h2, i1), (s1, a1, b1, d1, e3, f1, g4, x1, h2, i2), (s1, a1, b1, d1, e3, f1, g4, x1, h2, i3), (s1, a1, b1, d1, e3, f1, g5, x1, h1, i1), (s1, a1, b1, d1, e3, f1, g5, x1, h1, i2), (s1, a1, b1, d1, e3, f1, g5, x1, h1, i3), (s1, a1, b1, d1, e3, f1, g5, x1, h2, i1), (s1, a1, b1, d1, e3, f1, g5, x1, h2, i2), (s1, a1, b1, d1, e3, f1, g5, x1, h2, i3), (s1, a1, b1, d1, e4, f1, g1, x1, h1, i1), (s1, a1, b1, d1, e4, f1, g1, x1, h1, i2), (s1, a1, b1, d1, e4, f1, g1, x1, h1, i3), (s1, a1, b1, d1, e4, f1, g1, x1, h2, i1), (s1, a1, b1, d1, e4, f1, g1, x1, h2, i2), (s1, a1, b1, d1, e4, f1, g1, x1, h2, i3), (s1, a1, b1, d1, e4, f1, g2, x1, h1, i1), (s1, a1, b1, d1, e4, f1, g2, x1, h1, i2), (s1, a1, b1, d1, e4, f1, g2, x1, h1, i3), (s1, a1, b1, d1, e4, f1, g2, x1, h2, i1), (s1, a1, b1, d1, e4, f1, g2, x1, h2, i2), (s1, a1, b1, d1, e4, f1, g2, x1, h2, i3), (s1, a1, b1, d1, e4, f1, g3, x1, h1, i1), (s1, a1, b1, d1, e4, f1, g3, x1, h1, i2), (s1, a1, b1, d1, e4, f1, g3, x1, h1, i3), (s1, a1, b1, d1, e4, f1, g3, x1, h2, i1), (s1, a1, b1, d1, e4, f1, g3, x1, h2, i2), (s1, a1, b1, d1, e4, f1, g3, x1, h2, i3), (s1, a1, b1, d1, e4, f1, g4, x1, h1, i1), (s1, a1, b1, d1, e4, f1, g4, x1, h1, i2), (s1, a1, b1, d1, e4, f1, g4, x1, h1, i3), (s1, a1, b1, d1, e4, f1, g4, x1, h2, i1), (s1, a1, b1, d1, e4, f1, g4, x1, h2, i2), (s1, a1, b1, d1, e4, f1, g4, x1, h2, i3), (s1, a1, b1, d1, e4, f1, g5, x1, h1, i1), (s1, a1, b1, d1, e4, f1, g5, x1, h1, i2), (s1, a1, b1, d1, e4, f1, g5, x1, h1, i3), (s1, a1, b1, d1, e4, f1, g5, x1, h2, i1), (s1, a1, b1, d1, e4, f1, g5, x1, h2, i2), (s1, a1, b1, d1, e4, f1, g5, x1, h2, i3), (s1, a1, b1, d2, e1, f1, g1, x1, h1, i1), (s1, a1, b1, d2, e1, f1, g1, x1, h1, i2), (s1, a1, b1, d2, e1, f1, g1, x1, h1, i3), (s1, a1, b1, d2, e1, f1, g1, x1, h2, i1), (s1, a1, b1, d2, e1, f1, g1, x1, h2, i2), (s1, a1, b1, d2, e1, f1, g1, x1, h2, i3), (s1, a1, b1, d2, e1, f1, g2, x1, h1, i1), (s1, a1, b1, d2, e1, f1, g2, x1, h1, i2), (s1, a1, b1, d2, e1, f1, g2, x1, h1, i3), (s1, a1, b1, d2, e1, f1, g2, x1, h2, i1), (s1, a1, b1, d2, e1, f1, g2, x1, h2, i2), (s1, a1, b1, d2, e1, f1, g2, x1, h2, i3), (s1, a1, b1, d2, e1, f1, g3, x1, h1, i1), (s1, a1, b1, d2, e1, f1, g3, x1, h1, i2), (s1, a1, b1, d2, e1, f1, g3, x1, h1, i3), (s1, a1, b1, d2, e1, f1, g3, x1, h2, i1), (s1, a1, b1, d2, e1, f1, g3, x1, h2, i2), (s1, a1, b1, d2, e1, f1, g3, x1, h2, i3), (s1, a1, b1, d2, e1, f1, g4, x1, h1, i1), (s1, a1, b1, d2, e1, f1, g4, x1, h1, i2), (s1, a1, b1, d2, e1, f1, g4, x1, h1, i3), (s1, a1, b1, d2, e1, f1, g4, x1, h2, i1), (s1, a1, b1, d2, e1, f1, g4, x1, h2, i2), (s1, a1, b1, d2, e1, f1, g4, x1, h2, i3), (s1, a1, b1, d2, e1, f1, g5, x1, h1, i1), (s1, a1, b1, d2, e1, f1, g5, x1, h1, i2), (s1, a1, b1, d2, e1, f1, g5, x1, h1, i3), (s1, a1, b1, d2, e1, f1, g5, x1, h2, i1), (s1, a1, b1, d2, e1, f1, g5, x1, h2, i2), (s1, a1, b1, d2, e1, f1, g5, x1, h2, i3), (s1, a1, b1, d2, e2, f1, g1, x1, h1, i1), (s1, a1, b1, d2, e2, f1, g1, x1, h1, i2), (s1, a1, b1, d2, e2, f1, g1, x1, h1, i3), (s1, a1, b1, d2, e2, f1, g1, x1, h2, i1), (s1, a1, b1, d2, e2, f1, g1, x1, h2, i2), (s1, a1, b1, d2, e2, f1, g1, x1, h2, i3), (s1, a1, b1, d2, e2, f1, g2, x1, h1, i1), (s1, a1, b1, d2, e2, f1, g2, x1, h1, i2), (s1, a1, b1, d2, e2, f1, g2, x1, h1, i3), (s1, a1, b1, d2, e2, f1, g2, x1, h2, i1), (s1, a1, b1, d2, e2, f1, g2, x1, h2, i2), (s1, a1, b1, d2, e2, f1, g2, x1, h2, i3), (s1, a1, b1, d2, e2, f1, g3, x1, h1, i1), (s1, a1, b1, d2, e2, f1, g3, x1, h1, i2), (s1, a1, b1, d2, e2, f1, g3, x1, h1, i3), (s1, a1, b1, d2, e2, f1, g3, x1, h2, i1), (s1, a1, b1, d2, e2, f1, g3, x1, h2, i2), (s1, a1, b1, d2, e2, f1, g3, x1, h2, i3), (s1, a1, b1, d2, e2, f1, g4, x1, h1, i1), (s1, a1, b1, d2, e2, f1, g4, x1, h1, i2), (s1, a1, b1, d2, e2, f1, g4, x1, h1, i3), (s1, a1, b1, d2, e2, f1, g4, x1, h2, i1), (s1, a1, b1, d2, e2, f1, g4, x1, h2, i2), (s1, a1, b1, d2, e2, f1, g4, x1, h2, i3), (s1, a1, b1, d2, e2, f1, g5, x1, h1, i1), (s1, a1, b1, d2, e2, f1, g5, x1, h1, i2), (s1, a1, b1, d2, e2, f1, g5, x1, h1, i3), (s1, a1, b1, d2, e2, f1, g5, x1, h2, i1), (s1, a1, b1, d2, e2, f1, g5, x1, h2, i2), (s1, a1, b1, d2, e2, f1, g5, x1, h2, i3), (s1, a1, b1, d2, e3, f1, g1, x1, h1, i1), (s1, a1, b1, d2, e3, f1, g1, x1, h1, i2), (s1, a1, b1, d2, e3, f1, g1, x1, h1, i3), (s1, a1, b1, d2, e3, f1, g1, x1, h2, i1), (s1, a1, b1, d2, e3, f1, g1, x1, h2, i2), (s1, a1, b1, d2, e3, f1, g1, x1, h2, i3), (s1, a1, b1, d2, e3, f1, g2, x1, h1, i1), (s1, a1, b1, d2, e3, f1, g2, x1, h1, i2), (s1, a1, b1, d2, e3, f1, g2, x1, h1, i3), (s1, a1, b1, d2, e3, f1, g2, x1, h2, i1), (s1, a1, b1, d2, e3, f1, g2, x1, h2, i2), (s1, a1, b1, d2, e3, f1, g2, x1, h2, i3), (s1, a1, b1, d2, e3, f1, g3, x1, h1, i1), (s1, a1, b1, d2, e3, f1, g3, x1, h1, i2), (s1, a1, b1, d2, e3, f1, g3, x1, h1, i3), (s1, a1, b1, d2, e3, f1, g3, x1, h2, i1), (s1, a1, b1, d2, e3, f1, g3, x1, h2, i2), (s1, a1, b1, d2, e3, f1, g3, x1, h2, i3), (s1, a1, b1, d2, e3, f1, g4, x1, h1, i1), (s1, a1, b1, d2, e3, f1, g4, x1, h1, i2), (s1, a1, b1, d2, e3, f1, g4, x1, h1, i3), (s1, a1, b1, d2, e3, f1, g4, x1, h2, i1), (s1, a1, b1, d2, e3, f1, g4, x1, h2, i2), (s1, a1, b1, d2, e3, f1, g4, x1, h2, i3), (s1, a1, b1, d2, e3, f1, g5, x1, h1, i1), (s1, a1, b1, d2, e3, f1, g5, x1, h1, i2), (s1, a1, b1, d2, e3, f1, g5, x1, h1, i3), (s1, a1, b1, d2, e3, f1, g5, x1, h2, i1), (s1, a1, b1, d2, e3, f1, g5, x1, h2, i2), (s1, a1, b1, d2, e3, f1, g5, x1, h2, i3), (s1, a1, b1, d2, e4, f1, g1, x1, h1, i1), (s1, a1, b1, d2, e4, f1, g1, x1, h1, i2), (s1, a1, b1, d2, e4, f1, g1, x1, h1, i3), (s1, a1, b1, d2, e4, f1, g1, x1, h2, i1), (s1, a1, b1, d2, e4, f1, g1, x1, h2, i2), (s1, a1, b1, d2, e4, f1, g1, x1, h2, i3), (s1, a1, b1, d2, e4, f1, g2, x1, h1, i1), (s1, a1, b1, d2, e4, f1, g2, x1, h1, i2), (s1, a1, b1, d2, e4, f1, g2, x1, h1, i3), (s1, a1, b1, d2, e4, f1, g2, x1, h2, i1), (s1, a1, b1, d2, e4, f1, g2, x1, h2, i2), (s1, a1, b1, d2, e4, f1, g2, x1, h2, i3), (s1, a1, b1, d2, e4, f1, g3, x1, h1, i1), (s1, a1, b1, d2, e4, f1, g3, x1, h1, i2), (s1, a1, b1, d2, e4, f1, g3, x1, h1, i3), (s1, a1, b1, d2, e4, f1, g3, x1, h2, i1), (s1, a1, b1, d2, e4, f1, g3, x1, h2, i2), (s1, a1, b1, d2, e4, f1, g3, x1, h2, i3), (s1, a1, b1, d2, e4, f1, g4, x1, h1, i1), (s1, a1, b1, d2, e4, f1, g4, x1, h1, i2), (s1, a1, b1, d2, e4, f1, g4, x1, h1, i3), (s1, a1, b1, d2, e4, f1, g4, x1, h2, i1), (s1, a1, b1, d2, e4, f1, g4, x1, h2, i2), (s1, a1, b1, d2, e4, f1, g4, x1, h2, i3), (s1, a1, b1, d2, e4, f1, g5, x1, h1, i1), (s1, a1, b1, d2, e4, f1, g5, x1, h1, i2), (s1, a1, b1, d2, e4, f1, g5, x1, h1, i3), (s1, a1, b1, d2, e4, f1, g5, x1, h2, i1), (s1, a1, b1, d2, e4, f1, g5, x1, h2, i2), (s1, a1, b1, d2, e4, f1, g5, x1, h2, i3), (s1, a1, b2, d1, e1, f1, g1, x1, h1, i1), (s1, a1, b2, d1, e1, f1, g1, x1, h1, i2), (s1, a1, b2, d1, e1, f1, g1, x1, h1, i3), (s1, a1, b2, d1, e1, f1, g1, x1, h2, i1), (s1, a1, b2, d1, e1, f1, g1, x1, h2, i2), (s1, a1, b2, d1, e1, f1, g1, x1, h2, i3), (s1, a1, b2, d1, e1, f1, g2, x1, h1, i1), (s1, a1, b2, d1, e1, f1, g2, x1, h1, i2), (s1, a1, b2, d1, e1, f1, g2, x1, h1, i3), (s1, a1, b2, d1, e1, f1, g2, x1, h2, i1), (s1, a1, b2, d1, e1, f1, g2, x1, h2, i2), (s1, a1, b2, d1, e1, f1, g2, x1, h2, i3), (s1, a1, b2, d1, e1, f1, g3, x1, h1, i1), (s1, a1, b2, d1, e1, f1, g3, x1, h1, i2), (s1, a1, b2, d1, e1, f1, g3, x1, h1, i3), (s1, a1, b2, d1, e1, f1, g3, x1, h2, i1), (s1, a1, b2, d1, e1, f1, g3, x1, h2, i2), (s1, a1, b2, d1, e1, f1, g3, x1, h2, i3), (s1, a1, b2, d1, e1, f1, g4, x1, h1, i1), (s1, a1, b2, d1, e1, f1, g4, x1, h1, i2), (s1, a1, b2, d1, e1, f1, g4, x1, h1, i3), (s1, a1, b2, d1, e1, f1, g4, x1, h2, i1), (s1, a1, b2, d1, e1, f1, g4, x1, h2, i2), (s1, a1, b2, d1, e1, f1, g4, x1, h2, i3), (s1, a1, b2, d1, e1, f1, g5, x1, h1, i1), (s1, a1, b2, d1, e1, f1, g5, x1, h1, i2), (s1, a1, b2, d1, e1, f1, g5, x1, h1, i3), (s1, a1, b2, d1, e1, f1, g5, x1, h2, i1), (s1, a1, b2, d1, e1, f1, g5, x1, h2, i2), (s1, a1, b2, d1, e1, f1, g5, x1, h2, i3)

(s1, a1, b2, d1, e2, f1, g1, x1, h1, i1), (s1, a1, b2, d1, e2, f1, g1, x1, h1, i2), (s1, a1, b2, d1, e2, f1, g1, x1, h1, i3), (s1, a1, b2, d1, e2, f1, g1, x1, h2, i1), (s1, a1, b2, d1, e2, f1, g1, x1, h2, i2), (s1, a1, b2, d1, e2, f1, g1, x1, h2, i3), (s1, a1, b2, d1, e2, f1, g2, x1, h1, i1), (s1, a1, b2, d1, e2, f1, g2, x1, h1, i2), (s1, a1, b2, d1, e2, f1, g2, x1, h1, i3), (s1, a1, b2, d1, e2, f1, g2, x1, h2, i1), (s1, a1, b2, d1, e2, f1, g2, x1, h2, i2), (s1, a1, b2, d1, e2, f1, g2, x1, h2, i3), (s1, a1, b2, d1, e2, f1, g3, x1, h1, i1), (s1, a1, b2, d1, e2, f1, g3, x1, h1, i2), (s1, a1, b2, d1, e2, f1, g3, x1, h1, i3), (s1, a1, b2, d1, e2, f1, g3, x1, h2, i1), (s1, a1, b2, d1, e2, f1, g3, x1, h2, i2), (s1, a1, b2, d1, e2, f1, g3, x1, h2, i3), (s1, a1, b2, d1, e2, f1, g4, x1, h1, i1), (s1, a1, b2, d1, e2, f1, g4, x1, h1, i2), (s1, a1, b2, d1, e2, f1, g4, x1, h1, i3), (s1, a1, b2, d1, e2, f1, g4, x1, h2, i1), (s1, a1, b2, d1, e2, f1, g4, x1, h2, i2), (s1, a1, b2, d1, e2, f1, g4, x1, h2, i3), (s1, a1, b2, d1, e2, f1, g5, x1, h1, i1), (s1, a1, b2, d1, e2, f1, g5, x1, h1, i2), (s1, a1, b2, d1, e2, f1, g5, x1, h1, i3), (s1, a1, b2, d1, e2, f1, g5, x1, h2, i1), (s1, a1, b2, d1, e2, f1, g5, x1, h2, i2), (s1, a1, b2, d1, e2, f1, g5, x1, h2, i3), (s1, a1, b2, d1, e3, f1, g1, x1, h1, i1), (s1, a1, b2, d1, e3, f1, g1, x1, h1, i2), (s1, a1, b2, d1, e3, f1, g1, x1, h1, i3), (s1, a1, b2, d1, e3, f1, g1, x1, h2, i1), (s1, a1, b2, d1, e3, f1, g1, x1, h2, i2), (s1, a1, b2, d1, e3, f1, g1, x1, h2, i3), (s1, a1, b2, d1, e3, f1, g2, x1, h1, i1), (s1, a1, b2, d1, e3, f1, g2, x1, h1, i2), (s1, a1, b2, d1, e3, f1, g2, x1, h1, i3), (s1, a1, b2, d1, e3, f1, g2, x1, h2, i1), (s1, a1, b2, d1, e3, f1, g2, x1, h2, i2), (s1, a1, b2, d1, e3, f1, g2, x1, h2, i3), (s1, a1, b2, d1, e3, f1, g3, x1, h1, i1), (s1, a1, b2, d1, e3, f1, g3, x1, h1, i2), (s1, a1, b2, d1, e3, f1, g3, x1, h1, i3), (s1, a1, b2, d1, e3, f1, g3, x1, h2, 1.1), (s1, a1, b2, d1, e3, f1, g3, x1, h2, i2), (s1, a1, b2, d1, e3, f1, g3, x1, h2, i3), (s1, a1, b2, d1, e3, f1, g4, x1, h1, i1), (s1, a1, b2, d1, e3, f1, g4, x1, h1, i2), (s1, a1, b2, d1, e3, f1, g4, x1, h1, i3), (s1, a1, b2, d1, e3, f1, g4, x1, h2, i1), (s1, a1, b2, d1, e3, f1, g4, x1, h2, i2), (s1, a1, b2, d1, e3, f1, g4, x1, h2, i3), (s1, a1, b2, d1, e3, f1, g5, x1, h1, i1), (s1, a1, b2, d1, e3, f1, g5, x1, h1, i2), (s1, a1, b2, d1, e3, f1, g5, x1, h1, i3), (s1, a1, b2, d1, e3, f1, g5, x1, h2, i1), (s1, a1, b2, d1, e3, f1, g5, x1, h2, i2), (s1, a1, b2, d1, e3, f1, g5, x1, h2, i3), (s1, a1, b2, d1, e4, f1, g1, x1, h1, i1), (s1, a1, b2, d1, e4, f1, g1, x1, h1, i2), (s1, a1, b2, d1, e4, f1, g1, x1, h1, i3), (s1, a1, b2, d1, e4, f1, g1, x1, h2, (s1, a1, b2, d1, e4, f1, g1, x1, h2, i2), (s1, a1, b2, d1, e4, f1, g1, x1, h2, i3), (s1, a1, b2, d1, e4, f1, g2, x1, h1, i1), (s1, a1, b2, d1, e4, f1, g2, x1, h1, i2), (s1, a1, b2, d1, e4, f1, g2, x1, h1, i3), (s1, a1, b2, d1, e4, f1, g2, x1, h2, i1), (s1, a1, b2, d1, e4, f1, g2, x1, h2, i2), (s1, a1, b2, d1, e4, f1, g2, x1, h2, i3), (s1, a1, b2, d1, e4, f1, g3, x1, h1, i1), (s1, a1, b2, d1, e4, f1, g3, x1, h1, i2), (s1, a1, b2, d1, e4, f$_1$, g3, x1, h1, i3), (s1, a1, b2, d1, e4, f1, g3, x1, h2, i1), (s1, a1, b2, d1, e4, f1, g3, x1, h2, i2), (s1, a1, b2, d1, e4, f1, g3, x1, h2, i3), (s1, a1, b2, d1, e4, f1, g4, x1, h1, i1), (s1, a1, b2, d1, e4, f1, g4, x1, h1, i2), (s1, a1, b2, d1, e4, f1, g4, x1, h1, i3), (s1, a1, b2, d1, e4, f1, g4, x1, h2, i1), (s1, a1, b2, d1, e4, f1, g4, x1, h2, i2), (s1, a1, b2, d1, e4, f1, g4, x1, h2, i3), (s1, a1, b2, d1, e4, f1, g5, x1, h1, i1), (s1, a1, b2, d1, e4, f1, g5, x1, h1, i2), (s1, a1, b2, d1, e4, f1, g5, x1, h1, i3), (s1, a1, b2, d1, e4, f1, g5, x1, h2, i1), (s1, a1, b2, d1, e4, f1, g5, x1, h2, i2), (s1, a1, b2, d1, e4, f1, g5, x1, h2, i3), (s1, a1, b2, d2, e1, f1, g1, x1, h1, i1), (s1, a1, b2, d2, e1, f1, g1, x1, h1, i2), (s1, a1, b2, d2, e1, f1, g1, x1, h1, i3), (s1, a1, b2, d2, e1, f1, g1, x1, h2, i1), (s1, a1, b2, d2, e1, f1, g1, x1, h2, i2), (s1, a1, b2, d2, e1, f1, g1, x1, h2, i3), (s1, a1, b2, d2, e1, f1, g2, x1, h1, i1), (s1, a1, b2, d2, e1, f1, g2, x1, h1, i2), (s1, a1, b2, d2, e1, f1, g2, x1, h1, i3), (s1, a1, b2, d2, e1, f1, g2, x1, h2, i1), (s1, a1, b2, d2, e1, f1, g2, x1, h2, i2), (s1, a1, b2, d2, e1, f1, g2, x1, h2, i3), (s1, a1, b2, d2, e1, f1, g3, x1, h1, i1), (s1, a1, b2, d2, e1, f1, g3, x1, h1, i2), (s1, a1, b2, d2, e1, f1, g3, x1, h1, i3), (s1, a1, b2, d2, e1, f1, g3, x1, h2, i1), (s1, a1, b2, d2, e1, f1, g3, x1, h2, i2), (s1, a1, b2, d2, e1, f1, g3, x1, h2, i3), (s1, a1, b2, d2, e1, f1, g4, x1, h1, i1), (s1, a1, b2, d2, e1, f1, g4, x1, h1, i2), (s1, a1, b2, d2, e1, f1, g4, x1, h1, i3), (s1, a1, b2, d2, e1, f1, g4, x1, h2, i1), (s1, a1, b2, d2, e1, f1, g4, x1, h2, i2), (s1, a1, b2, d2, e1, f1, g4, x1, h2, i3), (s1, a1, b2, d2, e1, f1, g5, x1, h1, i1), (s1, a1, b2, d2, e1, f1, g5, x1, h1, i2), (s1, a1, b2, d2, e1, f1, g5, x1, h1, i3), (s1, a1, b2, d2, e1, f1, g5, x1, h2, i1), (s1, a1, b2, d2, e1, f1, g5, x1, h2, i2), (s1, a1, b2, d2, e1, f1, g5, x1, h2, i3), (s1, a1, b2, d2, e2, f1, g1, x1, h1, i1), (s1, a1, b2, d2, e2, f1, g1, x1, h1, i2), (s1, a1, b2, d2, e2, f1, g1, x1, h1, i3), (s1, a1, b2, d2, e2, f1, g1, x1, h2, i1), (s1, a1, b2, d2, e2, f1, g1, x1, h2, i2), (s1, a1, b2, d2, e2, f1, g1, x1, h2, i3), (s1, a1, b2, d2, e2, f1, g2, x1, h1, i1), (s1, a1, b2, d2, e2, f1, g2, x1, h1, i2), (s1, a1, b2, d2, e2, f1, g2, x1, h1, i3), (s1, a1, b2, d2, e2, f1, g2, x1, h2, i1), (s1, a1, b2, d2, e2, f1, g2, x1, h2, i2), (s1, a1, b2, d2, e2, f1, g2, x1, h2, i3), (s1, a1, b2, d2, e2, f1, g3, x1, h1, i1), (s1, a1, b2, d2, e2, f1, g3, x1, h1, i2), (s1, a1, b2, d2, e2, f1, g3, x1, h1, i3), (s1, a1, b2, d2, e2, f1, g3, x1, h2, i1), (s1, a1, b2, d2, e2, f1, g3, x1, h2, i2), (s1, a1, b2, d2, e2, f1, g3, x1, h2, i3), (s1, a1, b2, d2, e2, f1, g4, x1, h1, i1), (s1, a1, b2, d2, e2, f1, g4, x1, h1, i2), (s1, a1, b2, d2, e2, f1, g4, x1, h1, i3), (s1, a1, b2, d2, e2, f1, g4, x1, h2, i1), (s1, a1, b2, d2, e2, f1, g4, x1, h2, i2), (s1, a1, b2, d2, e2, f1, g4, x1, h2, i3), (s1, a1, b2, d2, e2, f1, g5, x1, h1, i1), (s1, a1, b2, d2, e2, f1, g5, x1, h1, i2), (s1, a1, b2, d2, e2, f1, g5, x1, h1, i3), (s1, a1, b2, d2, e2, f1, g5, x1, h2, i1), (s1, a1, b2, d2, e2, f1, g5, x1, h2, i2), (s1, a1, b2, d2, e2, f1, g5, x1, h2, i3), (s1, a1, b2, d2, e3, f1, g1, x1, h1, i2), (s1, a1, b2, d2, e3, f1, g1, x1, h1, i2), (s1, a1, b2, d2, e3, f1, g1, x1, h1, i3), (s1, a1, b2, d2, e3, f1, g1, x1, h2, i1), (s1, a1, b2, d2, e3, f1, g1, x1, h2, i2), (s1, a1, b2, d2, e3, f1, g1, x1, h2, i3), (s1, a1, b2, d2, e3, f1, g2, x1, h1, i1), (s1, a1, b2, d2, e3, f1, g2, x1, h1, i2), (s1, a1, b2, d2, e3, f1, g2, x1, h1, i3), (s1, a1, b2, d2, e3, f1, g2, x1, h2, i1), (s1, a1, b2, d2, e3, f1, g2, x1, h2, i2), (s1, a1, b2, d2, e3, f1, g2, x1, h2, i3), (s1, a1, b2, d2, e3, f1, g3, x1, h1, i1), (s1, a1, b2, d2, e3, f1, g3, x1, h1, i2), (s1, a1, b2, d2, e3, f1, g3, x1, h1, i3), (s1, a1, b2, d2, e3, f1, g3, x1, h2, i1), (s1, a1, b2, d2, e3, f1, g3, x1, h2, i2), (s1, a1, b2, d2, e3, f1, g3, x1, h2, i3), (s1, a1, b2, d2, e3, f1, g4, x1, h1, i1), (s1, a1, b2, d2, e3, f1, g4, x1, h1, i2), (s1, a1, b2, d2, e3, f1, g4, x1, h1, i3), (s1, a1, b2, d2, e3, f1, g4, x1, h2, i1), (s1, a1, b2, d2, e3, f1, g4, x1, h2, i2), (s1, a1, b2, d2, e3, f1, g4, x1, h2, i3), (s1, a1, b2, d2, e3, f1, g5, x1, h1, i1), (s1, a1, b2, d2, e3, f1, g5, x1, h1, i2), (s1, a1, b2, d2, e3, f1, g5, x1, h1, i3), (s1, a1, b2, d2, e3, f1, g5, x1, h2, i1), (s1, a1, b2, d2, e3, f1, g5, x1, h2, i2), (s1, a1, b2, d2, e3, f1, g5, x1, h2, i3), (s1, a1, b2, d2, e4, f1, g1, x1, h1, i1), (s1, a1, b2, d2, e4, f1, g1, x1, h1, i2), (s1, a1, b2, d2, e4, f1, g1, x1, h1, i3), (s1, a1, b2, d2, e4, f1, g1, x1, h2, i1), (s1, a1, b2, d2, e4, f1, g1, x1, h2, i2), (s1, a1, b2, d2, e4, f1, g1, x1, h2, i3), (s1, a1, b2, d2, e4, f1, g2, x1, h1, i1), (s1, a1, b2, d2, e4, f1, g2, x1, h1, i2), (s1, a1, b2, d2, e4, f1, g2, x1, h1, i3), (s1, a1, b2, d2, e4, f1, g2, x1, h2, i1), (s1, a1, b2, d2, e4, f1, g2, x1, h2, i2), (s1, a1, b2, d2, e4, f1, g2, x1, h2, i3), (s1, a1, b2, d2, e4, f1, g3, x1, h1, i1), (s1, a1, b2, d2, e4, f1, g3, x1, h1, i2), (s1, a1, b2, d2, e4, f1, g3, x1, h1, i3), (s1, a1, b2, d2, e4, f1, g3, x1, h2, i1), (s1, a1, b2, d2, e4, f1, g3, x1, h2, i2), (s1, a1, b2, d2, e4, f1, g3, x1, h2, i3), (s1, a1, b2, d2, e4, f1, g4, x1, h1, i1), (s1, a1, b2, d2, e4, f1, g4, x1, h1, i2), (s1, a1, b2, d2, e4, f1, g4, x1, h1, i3), (s1, a1, b2, d2, e4, f1, g4, x1, h2, i1), (s1, a1, b2, d2, e4, f1, g4, x1, h2, i2), (s1, a1, b2, d2, e4, f1, g4, x1, h2, i3), (s1, a1, b2, d2, e4, f1, g5, x1, h1, i1), (s1, a1, b2, d2, e4, f1, g5, x1, h1, i2), (s1, a1, b2, d2, e4, f1, g5, x1, h1, i3), (s1, a1, b2, d2, e4, f1, g5, x1, h2, i1), (s1, a1, b2, d2, e4, f1, g5, x1, h2, i2), (s1, a1, b2, d2, e4, f1, g5, x1, h2, i3), (s1, a2, b1, d1, e1, f1, g1, x1, h1, i1), (s1, a2, b1, d1, e1, f1, g1, x1, h1, i2), (s1, a2, b1, d1, e1, f1, g1, x1, h1, i3), (s1, a2, b1, d1, e1, f1, g1, x1, h2, i1), (s1, a2, b1, d1, e1, f1, g1, x1, h2, i2), (s1, a2, b1, d1, e1, f1, g1, x1, h2, i3), (s1, a2, b1, d1, e1, f1, g2, x1, h1, i1), (s1, a2, b1, d1, e1, f1, g2, x1, h1, i2), (s1, a2, b1, d1, e1, f1, g2, x1, h1, i3), (s1, a2, b1, d1, e1, f1, g2, x1, h2, i1), (s1, a2, b1, d1, e1, f1, g2, x1, h2, i2), (s1, a2, b1, d1, e1, f1, g2, x1, h2, i3), (s1, a2, b1, d1, e1, f1, g3, x1, h1, i1), (s1, a2, b1, d1, e1, f1, g3, x1, h1, i2), (s1, a2, b1, d1, e1, f1, g3, x1, h1, i3), (s1, a2, b1, d1, e1, f1, g3, x1, h2, i1), (s1, a2, b1, d1, e1, f1, g3, x1, h2, i2), (s1, a2, b1, d1, e1, f1, g3, x1, h2, i3), (s1, a2, b1, d1, e1, f1, g4, x1, h1, i1), (s1, a2, b1, d1, e1, f1, g4, x1, h1, i2), (s1, a2, b1, d1, e1, f1, g4, x1, h1, i3), (s1, a2, b1, d1, e1, f1, g4, x1, h2, i1), (s1, a2, b1, d1, e1, f1, g4, x1, h2, i2), (s1, a2, b1, d1, e1, f1, g4, x1, h2, i3), (s1, a2, b1, d1, e1, f1, g5, x1, h1, i1), (s1, a2, b1, d1, e1, f1, g5, x1, h1, i2), (s1, a2, b1, d1, e1, f1, g5, x1, h1, i3), (s1, a2, b1, d1, e1, f1, g5, x1, h2, i1), (s1, a2, b1, d1, e1, f1, g5, x1, h2, i2), (s1, a2, b1, d1, e1, f1, g5, x1, h2, i3), (s1, a2, b1, d1, e2, f1, g1, x1, h1, i1), (s1, a2, b1, d1, e2, f1, g1, x1, h1, i2), (s1, a2, b1, d1, e2, f1, g1, x1, h1, i3), (s1, a2, b1, d1, e2, f1, g1, x1, h2, i1), (s1, a2, b1, d1, e2, f1, g1, x1, h2, i2), (s1, a2, b1, d1, e2, f1, g1, x1, h2, i3), (s1, a2, b1, d1, e2, f1, g2, x1, h1, i1), (s1, a2, b1, d1, e2, f1, g2, x1, h1, i2), (s1, a2, b1, d1, e2, f1, g2, x1, h1, i3), (s1, a2, b1, d1, e2, f1, g2, x1, h2, i1), (s1, a2, b1, d1, e2, f1, g2, x1, h2, i2), (s1, a2, b1, d1, e2, f1, g2, x1, h2, i3), (s1, a2, b1, d1, e2, f1, g3, x1, h1, i1), (s1, a2, b1, d1, e2, f1, g3, x1, h1, i2), (s1, a2, b1, d1, e2, f1, g3, x1, h1, i3), (s1, a2, b1, d1, e2, f1, g3, x1, h2, i1), (s1, a2, b1, d1, e2, f1, g3, x1, h2, i2), (s1, a2, b1, d1, e2, f1, g3, x1, h2, i3), (s1, a2, b1, d1, e2, f1, g4, x1, h1, i1), (s1, a2, b1, d1, e2, f1, g4, x1, h1, i2), (s1, a2, b1, d1, e2, f1, g4, x1, h1, i3), (s1, a2, b1, d1, e2, f1, g4, x1, h2, i1), (s1, a2, b1, d1, e2, f1, g4, x1, h2, i2), (s1, a2, b1, d1, e2, f1, g4, x1, h2, i3), (s1, a2, b1, d1, e2, f1, g5, x1, h1, i1), (s1, a2, b1, d1, e2, f1, g5, x1, h1, i2), (s1, a2, b1, d1, e2, f1, g5, x1, h1, i3), (s1, a2, b1, d1, e2, f1, g5, x1, h2, i1), (s1, a2, b1, d1, e2, f1, g5, x1, h2, i2), (s1, a2, b1, d1, e2, f1, g5, x1, h2, i3), (s1, a2, b1, d1, e3, f1, g1, x1, h1, i1), (s1, a2, b1, d1, e3, f1, g1, x1, h1, i2), (s1, a2, b1, d1, e3, f1, g1, x1, h1, i3), (s1, a2, b1, d1, e3, f1, g1, x1, h2, i1), (s1, a2, b1, d1, e3, f1, g1, x1, h2, i2), (s1, a2, b1, d1, e3, f1, g1, x1, h2, i3), (s1, a2, b1, d1, e3, f1, g2, x1, h1, i1), (s1, a2, b1, d1, e3, f1, g2, x1, h1, i2), (s1, a2, b1, d1, e3, f1, g2, x1, h1, i3), (s1, a2, b1, d1, e3, f1, g2, x1, h2, i1), (s1, a2, b1, d1, e3, f1, g2, x1, h2, i2), (s1, a2, b1, d1, e3, f1, g2, x1, h2, i3), (s1, a2, b1, d1, e3, f1, g3, x1, h1, i1), (s1, a2, b1, d1, e3, f1, g3, x1, h1, i2), (s1, a2, b1, d1, e3, f1, g3, x1, h1, i3), (s1, a2, b1, d1, e3, f1, g3, x1, h2, i1), (s1, a2, b1, d1, e3, f1, g3, x1, h2, i2), (s1, a2, b1, d1, e3, f1, g3, x1, h2, i3), (s1, a2, b1, d1, e3, f1, g4, x1, h1, i1), (s1, a2, b1, d1, e3, f1, g4, x1, h1, i2), (s1, a2, b1, d1, e3, f1, g4, x1, h1, i3), (s1, a2, b1, d1, e3, f1, g4, x1, h2, i1), (s1, a2, b1, d1, e3, f1, g4, x1, h2, i2), (s1, a2, b1, d1, e3, f1, g4, x1, h2, i3), (s1, a2, b1, d1, e3, f1, g5, x1, h1, i1), (s1, a2, b1, d1, e3, f1, g5, x1, h1, i2), (s1, a2, b1, d1, e3, f1, g5, x1, h1, i3), (s1, a2, b1, d1, e3, f1, g5, x1, h2, i1), (s1, a2, b1, d1, e3, f1, g5, x1, h2, i2), (31, a2, b1, d1, e3, f1, g5, x1, h2, i3), (s1, a2, b1, d1, e4, f1, g1, x1, h1, i1), (s1, a2, b1, d1, e4, f1, g1, x1, h1, i2), (s1, a2, b1, d1, e4, f1, g1, x1, h1, i3), (s1, a2, b1, d1, e4, f1, g1, x1, h2, i1), (s1, a2, b1, d1, e4, f1, g1, x1, h2, i2), (s1, a2, b1, d1, e4, f1, g1, x1, h2, i3), (s1, a2, b1, d1, e4, f1, g2, x1, h1, i1), (s1, a2, b1, d1, e4, f1, g2, x1, h1, i2), (s1, a2, b1, d1, e4, f1, g2, x1, h1, i3), (s1, a2, b1, d1, e4, f1, g2, x1, h2, i1), (s1, a2, b1, d1, e4, f1, g2, x1, h2, i2), (s1, a2, b1, d1, e4, f1, g2, x1, h2, i3), (s1, a2, b1, d1, e4, f1, g3, x1, h1, i1), (s1, a2, b1, d1, e4, f1, g3, x1, h1, i2), (s1, a2, b1, d1, e4, f1, g3, x1, h1, i3), (s1, a2, b1, d1, e4, f1, g3, x1, h2, i1), (s1, a2, b1, d1, e4, f1, g3, x1, h2, i2), (s1, a2, b1, d1, e4, f1, g3, x1, h2, i3), (s1, a2, b1, d1, e4, f1, g4, x1, h1, i1), (s1, a2, b1, d1, e4, f1, g4, x1, h1, i2), (s1, a2, b1, d1, e4, f1, g4, x1, h1, i3), (s1, a2, b1, d1, e4, f1, g4, x1, h2, i1), (s1, a2, b1, d1, e4, f1, g4, x1, h2, i2), (s1, a2, b1, d1, e4, f1, g4, x1, h2, i3), (s1, a2, b1, d1, e4, f1, g5, x1, h1, i1), (s1, a2, b1, d1, e4, f1, g5, x1, h1, i2), (s1, a2, b1, d1, e4, f1, g5, x1, h1, i3), (s1, a2, b1, d1, e4, f1, g5, x1, h2, i1), (s1, a2, b1, d1, e4, f1, g5, x1, h2, i2), (s1, a2, b1, d1, e4, f1, g5, x1, h2, i3), (s1, a2, b1, d2, e1, f1, g1, x1, h1, i1), (s1, a2, b1, d2, e1, f1, g1, x1, h1, i2), (s1, a2, b1, d2, e1, f1, g1, x1, h1, i3), (s1, a2, b1, d2, e1, f1, g1, x1, h2, i1), (s1, a2, b1, d2, e1, f1, g1, x1, h2, i2), (s1, a2, b1, d2, e1, f1, g1, x1, h2, i3), (s1, a2, b1, d2, e1, f1, g2, x1, h1, i1), (s1, a2, b1, d2, e1, f1, g2, x1, h1, i2), (s1, a2, b1, d2, e1, f1, g2, x1, h1, i3), (s1, a2, b1, d2, e1, f1, g2, x1, h2, i1), (s1, a2, b1, d2, e1, f1, g2, x1, h2, i2), (s1, a2, b1, d2, e1, f1, g2, x1, h2, i3), (s1, a2, b1, d2, e1, f1, g3, x1, h1, i1), (s1, a2, b1, d2, e1, f1, g3, x1, h1, i2), (s1, a2, b1, d2, e1, f1, g3, x1, h1, i3), (s1, a2, b1, d2, e1, f1, g3, x1, h2, i1), (s1, a2, b1, d2, e1, f1, g3, x1, h2, i2), (s1, a2, b1, d2, e1, f1, g3, x1, h2, i3), (s1, a2, b1, d2, e1, f1, g4, x1, h1, i1), (s1, a2, b1, d2, e1, f1, g4, x1, h1, i2), (s1, a2, b1, d2, e1, f1, g4, x1, h1, i3), (s1, a2, b1, d2, e1, f1, g4, x1, h2, i1), (s1, a2, b1, d2, e1, f1, g4, x1, h2, i2), (s1, a2, b1, d2, e1, f1, g4, x1, h2, i3), (s1, a2, b1, d2, e1, f1, g5, x1, h1, i1), (s1, a2, b1, d2, e1, f1, g5, x1, h1, i2), (s1, a2, b1, d2, e1, f1, g5, x1, h1, i3), (s1, a2, b1, d2, e1, f1, g5, x1, h2, i1), (s1, a2, b1, d2, e1, f1, g5, x1, h2, i2), (s1, a2, b1, d2, e1, f1, g5, x1, h2, i3), (s1, a2, b1, d2, e2, f1, g1, x1, h1, i1), (s1, a2, b1, d2, e2, f1, g1, x1, h1, i2), (s1, a2, b1, d2, e2, f1, g1, x1, h1, i3), (s1, a2, b1, d2, e2, f1, g1, x1, h2, i1), (s1, a2, b1, d2, e2, f1, g1, x1, h2, i2), (s1, a2, b1, d2, e2, f1, g1, x1, h2, i3), (s1, a2, b1, d2, e2, f1, g2, x1, h1, i1), (s1, a2, b1, d2, e2, f1, g2, x1, h1, i2), (s1, a2, b1, d2, e2, f1, g2, x1, h1, i3), (s1, a2, b1, d2, e2, f1, g2, x1, h2, i1), (s1, a2, b1, d2, e2, f1, g2, x1, h2, i2), (s1, a2, b1, d2, e2, f1, g2, x1, h2, i3), (s1, a2, b1, d2, e2, f1, g3, x1, h1, i1), (s1, a2, b1, d2, e2, f1, g3, x1, h1, i2), (s1, a2, b1, d2, e2, f1, g3, x1, h1, i3), (s1, a2, b1, d2, e2, f1, g3, x1, h2, i1), (s1, a2, b1, d2, e2, f1, g3, x1, h2, i2), (s1, a2, b1, d2, e2, f1, g3, x1, h2, i3), (s1, a2, b1, d2, e2, f1, g4, x1, h1, i1), (s1, a2, b1, d2, e2, f1, g4, x1, h1, i2), (s1, a2, b1, d2, e2, f1, g4, x1, h1, i3), (s1, a2, b1, d2, e2, f1, g4, x1, h2, i1), (s1, a2, b1, d2, e2, f1, g4, x1, h2, i2), (s1, a2, b1, d2, e2, f1, g4, x1, h2, i3), (s1, a2, b1, d2, e2, f1, g5, x1, h1, i1), (s1, a2, b1, d2, e2, f1, g5, x1, h1, i2), (s1, a2, b1, d2, e2, f1, g5, x1, h1, i3), (s1, a2, b1, d2, e2, f1, g5, x1, h2, i1), (s1, a2, b1, d2, e2, f1, g5, x1, h2, i2), (s1, a2, b1, d2, e2, f1, g5, x1, h2, i3), (s1, a2, b1, d2, e3, f1, g1, x1, h1, i1), (s1, a2, b1, d2, e3, f1, g1, x1, h1, i2), (s1, a2, b1, d2, e3, f1, g1, x1, h1, i3), (s1, a2, b1, d2, e3, f1, g1, x1, h2, i1), (s1, a2, b1, d2, e3, f1, g1, x1, h2, i2), (s1, a2, b1, d2, e3, f1, g1, x1, h2, i3), (s1, a2, b1, d2, e3, f1, g2, x1, h1, i1), (s1, a2, b1, d2, e3, f1, g2, x1, h1, i2), (s1, a2, b1, d2, e3, f1, g2, x1, h1, i3), (s1, a2, b1, d2, e3, f1, g2, x1, h2, i1), (s1, a2, b1, d2, e3, f1, g2, x1, h2, i2), (s1, a2, b1, d2, e3, f1, g2, x1, h2, i3), (s1, a2, b1, d2, e3, f1, g3, x1, h1, i1), (s1, a2, b1, d2, e3, f1, g3, x1, h1, i2), (s1, a2, b1, d2, e3, f1, g3, x1, h1, i3), (s1, a2, b1, d2, e3, f1, g3, x1, h2, i1), (s1, a2, b1, d2, e3, f1, g3, x1, h2, i2), (s1, a2, b1, d2, e3, f1, g3, x1, h2, i3), (s1, a2, b1, d2, e3, f1, g4, x1, h1, i1), (s1, a2, b1, d2, e3, f1, g4, x1, h1, i2), (s1, a2, b1, d2, e3, f1, g4, x1, h1, i3), (s1, a2, b1, d2, e3, f1, g4, x1, h2, i1), (s1, a2, b1, d2, e3, f1, g4, x1, h2, i2), (s1, a2, b1, d2, e3, f1, g4, x1, h2, i3), (s1, a2, b1, d2, e3, f1, g5, x1, h1, i1), (s1, a2, b1, d2, e3, f1, g5, x1, h1, i2), (s1, a2, b1, d2, e3, f1, g5, x1, h1, i3), (s1, a2, b1, d2, e3, f1, g5, x1, h2, i1), (s1, a2, b1, d2, e3, f1, g5, x1, h2, i2), (s1, a2, b1, d2, e3, f1, g5, x1, h2, i3), (s1, a2, b1, d2, e4, f1, g1, x1, h1, i1), (s1, a2, b1, d2, e4, f1, g1, x1, h1, i2), (s1, a2, b1, d2, e4, f1, g1, x1, h1, i3), (s1, a2, b1, d2, e4, f1, g1, x1, h2, i1), (s1, a2, b1, d2, e4, f1, g1, x1, h2, i2), (s1, a2, b1, d2, e4, f1, g1, x1, h2, i3), (s1, a2, b1, d2, e4, f1, g2, x1, h1, i1), (s1, a2, b1, d2, e4, f1, g2, x1, h1, i2), (s1, a2, b1, d2, e4, f1, g2, x1, h1, i3), (s1, a2, b1, d2, e4, f1, g2, x1, h2, i1), (s1, a2, b1, d2, e4, f1, g2, x1, h2, i2), (s1, a2, b1, d2, e4, f1, g2, x1, h2, i3), (s1, a2, b1, d2, e4, f1, g3, x1, h1, i1), (s1, a2, b1, d2, e4, f1, g3, x1, h1, i2), (s1, a2, b1, d2, e4, f1, g3, x1, h1, i3), (s1, a2, b1, d2, e4, f1, g3, x1, h2, i1), (s1, a2, b1, d2, e4, f1, g3, x1, h2, i2), (s1, a2, b1, d2, e4, f1, g3, x1, h2, i3), (s1, a2, b1, d2, e4, f1, g4, x1, h1, i1), (s1, a2, b1, d2, e4, f1, g4, x1, h1, i2), (s1, a2, b1, d2, e4, f1, g4, x1, h1, i3), (s1, a2, b1, d2, e4, f1, g4, x1, h2, i1), (s1, a2, b1, d2, e4, f1, g4, x1, h2, i2), (s1, a2, b1, d2, e4, f1, g4, x1, h2, i3), (s1, a2, b1, d2, e4, f1, g5, x1, h1, i1), (s1, a2, b1, d2, e4, f1, g5, x1, h1, i2), (s1, a2, b1, d2, e4, f1, g5, x1, h1, i3), (s1, a2, b1, d2, e4, f1, g5, x1, h2, i1), (s1, a2, b1, d2, e4, f1, g5, x1, h2, i2), (s1, a2, b1, d2, e4, f1, g5, x1, h2, i3), (s1, a2, b2, d1, e1, f1, g1, x1, h1, i1), (s1, a2, b2, d1, e1, f1, g1, x1, h1, i2), (s1, a2, b2, d1, e1, f1, g1, x1, h1, i3), (s1, a2, b2, d1, e1, f1, g1, x1, h2, i1), (s1, a2, b2, d1, e1, f1, g1, x1, h2, i2), (s1, a2, b2, d1, e1, f1, g1, x1, h2, i3), (s1, a2, b2, d1, e1, f1, g2, x1, h1, i1), (s1, a2, b2, d1, e1, f1, g2, x1, h1, i2), (s1, a2, b2, d1, e1, f1, g2, x1, h1, i3), (s1, a2, b2, d1, e1, f1, g2, x1, h2, i1), (s1, a2, b2, d1, e1, f1, g2, x1, h2, i2), (s1, a2, b2, d1, e1, f1, g2, x1, h2, i3), (s1, a2, b2, d1, e1, f1, g3, x1, h1, i1), (s1, a2, b2, d1, e1, f1, g3, x1, h1, i2), (s1, a2, b2, d1, e1, f1, g3, x1, h1, i3), (s1, a2, b2, d1, e1, f1, g3, x1, h2, i1), (s1, a2, b2, d1, e1, f1, g3, x1, h2, i2), (s1, a2, b2, d1, e1, f1, g3, x1, h2, i3), (s1, a2, b2, d1, e1, f1, g4, x1, h1, i1), (s1, a2, b2, d1, e1, f1, g4, x1, h1, i2), (s1, a2, b2, d1, e1, f1, g4, x1, h1, i3), (s1, a2, b2, d1, e1, f1, g4, x1, h2, i1), (s1, a2, b2, d1, e1, f1, g4, x1, h2, i2), (s1, a2, b2, d1, e1, f1, g4, x1, h2, i3), (s1, a2, b2, d1, e1, f1, g5, x1, h1, i1), (s1, a2, b2, d1, e1, f1, g5, x1, h1, i2), (s1, a2, b2, d1, e1, f1, g5, x1, h1, i3), (s1, a2, b2, d1, e1, f1, g5, x1, h2, i1), (s1, a2, b2, d1, e1, f1, g5, x1, h2, i2), (s1, a2, b2, d1, e1, f1, g5, x1, h2, i3), (s1, a2, b2, d1, e2, f1, g1, x1, h1, i1), (s1, a2, b2, d1, e2, f1, g1, x1, h1, i2), (s1, a2, b2, d1, e2, f1, g1, x1, h1, i3), (s1, a2, b2, d1, e2, f1, g1, x1, h2, i1), (s1, a2, b2, d1, e2, f1, g1, x1, h2, i2), (s1, a2, b2, d1, e2, f1, g1, x1, h2, i3), (s1, a2, b2, d1, e2, f1, g2, x1, h1, i1), (s1, a2, b2, d1, e2, f1, g2, x1, h1, i2), (s1, a2, b2, d1, e2, f1, g2, x1, h1, i3), (s1, a2, b2, d1, e2, f1, g2, x1, h2, i1), (s1, a2, b2, d1, e2, f1, g2, x1, h2, i2), (s1, a2, b2, d1, e2, f1, g2, x1, h2, i3), (s1, a2, b2, d1, e2, f1, g3, x1, h1, i1), (s1, a2, b2, d1, e2, f1, g3, x1, h1, i2), (s1, a2, b2, d1, e2, f1, g3, x1, h1, i3), (s1, a2, b2, d1, e2, f1, g3, x1, h2, i1), (s1, a2, b2, d1, e2, f1, g3, x1, h2, i2), (s1, a2, b2, d1, e2, f1, g3, x1, h2, i3), (s1, a2, b2, d1, e2, f1, g4, x1, h1, i1), (s1, a2, b2, d1, e2, f1, g4, x1, h1, i2), (s1, a2, b2, d1, e2, f1, g4, x1, h1, i3), (s1, a2, b2, d1, e2, f1, g4, x1, h2, i1), (s1, a2, b2, d1, e2, f1, g4, x1, h2, i2), (s1, a2, b2, d1, e2, f1, g4, x1, h2, i3), (s1, a2, b2, d1, e2, f1, g5, x1, h1, i1), (s1, a2, b2, d1, e2, f1, g5, x1, h1, i2), (s1, a2, b2, d1, e2, f1, g5, x1, h1, i3), (s1, a2, b2, d1, e2, f1, g5, x1, h2, i1), (s1, a2, b2, d1, e2, f1, g5, x1, h2, i2), (s1, a2, b2, d1, e2, f1, g5, x1, h2, i3), (s1, a2, b2, d1, e3, f1, g1, x1, h1, i1), (s1, a2, b2, d1, e3, f1, g1, x1, h1, i2), (s1, a2, b2, d1, e3, f1, g1, x1, h1, i3), (s1, a2, b2, d1, e3, f1, g1, x1, h2, i1), (s1, a2, b2, d1, e3, f1, g1, x1, h2, i2), (s1, a2, b2, d1, e3, f1, g1, x1, h2, i3), (s1, a2, b2, d1, e3, f1, g2, x1, h1, i1), (s1, a2, b2, d1, e3, f1, g2, x1, h1, i2), (s1, a2, b2, d1, e3, f1, g2, x1, h1, i3), (s1, a2, b2, d1, e3, f1, g2, x1, h2, i1), (s1, a2, b2, d1, e3, f1, g2, x1, h2, i2), (s1, a2, b2, d1, e3, f1, g2, x1, h2, i3), (s1, a2, b2, d1, e3, f1, g3, x1, h1, i1), (s1, a2, b2, d1, e3, f1, g3, x1, h1, i2), (s1, a2, b2, d1, e3, f1, g3, x1, h1, i3), (s1, a2, b2, d1, e3, f1, g3, x1, h2, i1), (s1, a2, b2, d1, e3, f1, g3, x1, h2, i2), (s1, a2, b2, d1, e3, f1, g3, x1, h2, i3), (s1, a2, b2, d1, e3, f1, g4, x1, h1, i1), (s1, a2, b2, d1, e3, f1, g4, x1, h1, i2), (s1, a2, b2, d1, e3, f1, g4, x1, h1, i3), (s1, a2, b2, d1, e3, f1, g4, x1, h2, i1), (s1, a2, b2, d1, e3, f1, g4, x1, h2, i2), (s1, a2, b2, d1, e3, f1, g4, x1, h2, i3), (s1, a2, b2, d1, e3, f1, g5, x1, h1, i1), (s1, a2, b2, d1, e3, f1, g5, x1, h1, i2), (s1, a2, b2, d1, e3, f1, g5, x1, h1, i3), (s1, a2, b2, d1, e3, f1, g5, x1, h2, i1), (s1, a2, b2, d1, e3, f1, g5, x1, h2, i2), (s1, a2, b2, d1, e3, f1, g5, x1, h2, i3), (s1, a2, b2, d1, e4, f1, g1, x1, h1, i1), (s1, a2, b2, d1, e4, f1, g1, x1, h1, i2), (s1, a2, b2, d1, e4, f1, g1, x1, h1, i3), (s1, a2, b2, d1, e4, f1, g1, x1, h2, i1), (s1, a2, b2, d1, e4, f1, g1, x1, h2, i2), (s1, a2, b2, d1, e4, f1, g1, x1, h2, i3), (s1, a2, b2, d1, e4, f1, g2, x1, h1, i1), (s1, a2, b2, d1, e4, f1, g2, x1, h1, i2), (s1, a2, b2, d1, e4, f1, g2, x1, h1, i3), (s1, a2, b2, d1, e4, f1, g2, x1, h2, i1), (s1, a2, b2, d1, e4, f1, g2, x1, h2, i2), (s1, a2, b2, d1, e4, f1, g2, x1, h2, i3), (s1, a2, b2, d1, e4, f1, g3, x1, h1, i1), (s1, a2, b2, d1, e4, f1, g3, x1, h1, i2), (s1, a2, b2, d1, e4, f1, g3, x1, h1, i3), (s1, a2, b2, d1, e4, f1, g3, x1, h2, i1), (s1, a2, b2, d1, e4, f1, g3, x1, h2, i2), (s1, a2, b2, d1, e4, f1, g3, x1, h2, i3), (s1, a2, b2, d1, e4, f1, g4, x1, h1, i1), (s1, a2, b2, d1, e4, f1, g4, x1, h1, i2), (s1, a2, b2, d1, e4, f1, g4, x1, h1, i3), (s1, a2, b2, d1, e4, f1, g4, x1, h2, i1), (s1, a2, b2, d1, e4, f1, g4, x1, h2, i2), (s1, a2, b2, d1, e4, f1, g4, x1, h2, i3), (s1, a2, b2, d1, e4, f1, g5, x1, h1, i1), (s1, a2, b2, d1, e4, f1, g5, x1, h1, i2), (s1, a2, b2, d1, e4, f1, g5, x1, h1, i3), (s1, a2, b2, d1, e4, f1, g5, x1, h2, i1), (s1, a2, b2, d1, e4, f1, g5, x1, h2, i2), (s1, a2, b2, d1, e4, f1, g5, x1, h2, i3), (s1, a2, b2, d2, e1, f1, g1, x1, h1, i1), (s1, a2, b2, d2, e1, f1, g1, x1, h1, i2), (s1, a2, b2, d2, e1, f1, g1, x1, h1, i3), (s1, a2, b2, d2, e1, f1, g1, x1, h2, i1), (s1, a2, b2, d2, e1, f1, g1, x1, h2, i2), (s1, a2, b2, d2, e1, f1, g1, x1, h2, i3), (s1, a2, b2, d2, e1, f1, g2, x1, h1, i1), (s1, a2, b2, d2, e1, f1, g2, x1, h1, i2), (s1, a2, b2, d2, e1, f1, g2, x1, h1, i3), (s1, a2, b2, d2, e1, f1, g2, x1, h2, i1), (s1, a2, b2, d2, e1, f1, g2, x1, h2, i2), (s1, a2, b2, d2, e1, f1, g2, x1, h2, i3), (s1, a2, b2, d2, e1, f1, g3, x1, h1, i1), (s1, a2, b2, d2, e1, f1, g3, x1, h1, i2), (s1, a2, b2, d2, e1, f1, g3, x1, h1, i3), (s1, a2, b2, d2, e1, f1, g3, x1, h2, i1), (s1, a2, b2, d2, e1, f1, g3, x1, h2, i2), (s1, a2, b2, d2, e1, f1, g3, x1, h2, i3), (s1, a2, b2, d2, e1, f1, g4, x1, h1, i1), (s1, a2, b2, d2, e1, f1, g4, x1, h1, i2), (s1, a2, b2, d2, e1, f1, g4, x1, h1, i3), (s1, a2, b2, d2, e1, f1, g4, x1, h2, i1), (s1, a2, b2, d2, e1, f1, g4, x1, h2, i2), (s1, a2, b2, d2, e1, f1, g4, x1, h2, i3), (s1, a2, b2, d2, e1, f1, g5, x1, h1, i1), (s1, a2, b2, d2, e1, f1, g5, x1, h1, i2), (s1, a2, b2, d2, e1, f1, g5, x1, h1, i3), (s1, a2, b2, d2, e1, f1, g5, x1, h2, i1), (s1, a2, b2, d2, e1, f1, g5, x1, h2, i2), (s1, a2, b2, d2, e1, f1, g5, x1, h2, i3), (s1, a2, b2, d2, e2, f1, g1, x1, h1, i1), (s1, a2, b2, d2, e2, f1, g1, x1, h1, i2), (s1, a2, b2, d2, e2, f1, g1, x1, h1, i3), (s1, a2, b2, d2, e2, f1, g1, x1, h2, i1), (s1, a2, b2, d2, e2, f1, g1, x1, h2, i2), (s1, a2, b2, d2, e2, f1, g1, x1, h2, i3), (s1, a2, b2, d2, e2, f1, g2, x1, h1, i1), (s1, a2, b2, d2, e2, f1, g2, x1, h1, i2), (s1, a2, b2, d2, e2, f1, g2, x1, h1, i3), (s1, a2, b2, d2, e2, f1, g2, x1, h2, i1), (s1, a2, b2, d2, e2, f1, g2, x1, h2, i2), (s1, a2, b2, d2, e2, f1, g2, x1, h2, i3), (s1, a2, b2, d2, e2, f1, g3, x1, h1, i1), (s1, a2, b2, d2, e2, f1, g3, x1, h1, i2), (s1, a2, b2, d2, e2, f1, g3, x1, h1, i3), (31, a2, b2, d2, e2, f1, g3, x1, h2, i1), (s1, a2, b2, d2, e2, f1, g3, x1, h2, i2), (s1, a2, b2, d2, e2, f1, g3, x1, h2, i3), (s1, a2, b2, d2, e2, f1, g4, x1, h1, i1), (s1, a2, b2, d2, e2, f1, g4, x1, h1, i2), (s1, a2, b2, d2, e2, f1, g4, x1, h1, i3), (s1, a2, b2, d2, e2, f1, g4, x1, h2, i1), (s1, a2, b2, d2, e2, f1, g4, x1, h2, i2), (s1, a2, b2, d2, e2, f1, g4, x1, h2, i3), (s1, a2, b2, d2, e2, f1, g5, x1, h1, i1), (s1, a2, b2, d2, e2, f1, g5, x1, h1, i2), (s1, a2, b2, d2, e2, f1, g5, x1, h1, i3), (s1, a2, b2, d2, e2, f1, g5, x1, h2, i1), (s1, a2, b2, d2, e2, f1, g5, x1, h2, i2), (s1, a2, b2, d2, e2, f1, g5, x1, h2, i3), (s1, a2, b2, d2, e3, f1, g1, x1, h1, i1), (s1, a2, b2, d2, e3, f1, g1, x1, h1, i2), (s1, a2, b2, d2, e3, f1, g1, x1, h1, i3), (s1, a2, b2, d2, e3, f1, g1, x1, h2, i1), (s1, a2, b2, d2, e3, f1, g1, x1, h2, i2), (s1, a2, b2, d2, e3, f1, g1, x1, h2, i3), (s1, a2, b2, d2, e3, f1, g2, x1, h1, i1), (s1, a2, b2, d2, e3, f1, g2, x1, h1, i2), (s1, a2, b2, d2, e3, f1, g2, x1, h1, i3), (s1, a2, b2, d2, e3, f1, g2, x1, h2, i1), (s1, a2, b2, d2, e3, f1, g2, x1, h2, i2), (s1, a2, b2, d2, e3, f1, g2, x1, h2, i3), (s1, a2, b2, d2, e3, f1, g3, x1, h1, i1), (s1, a2, b2, d2, e3, f1, g3, x1, h1, i2), (s1, a2, b2, d2, e3, f1, g3, x1, h1, i3), (s1, a2, b2, d2, e3, f1, g3, x1, h2, i1), (s1, a2, b2, d2, e3, f1, g3, x1, h2, i2), (s1, a2, b2, d2, e3, f1, g3, x1, h2, i3), (s1, a2, b2, d2, e3, f1, g4, x1, h1, i1), (s1, a2, b2, d2, e3, f1, g4, x1, h1, i2), (s1, a2, b2, d2, e3, f1, g4, x1, h1, i3), (s1, a2, b2, d2, e3, f1, g4, x1, h2, i1), (s1, a2, b2, d2, e3, f1, g4, x1, h2, i2), (s1, a2, b2, d2, e3, f1, g4, x1, h2, i3), (s1, a2, b2, d2, e3, f1, g5, x1, h1, i1), (s1, a2, b2, d2, e3, f1, g5, x1, h1, i2), (s1, a2, b2, d2, e3, f1, g5, x1, h1, i3), (s1, a2, b2, d2, e3, f1, g5, x1, h2, i1), (s1, a2, b2, d2, e3, f1, g5, x1, h2, i2), (s1, a2, b2, d2, e3, f1, g5, x1, h2, i3), (s1, a2, b2, d2, e4, f1, g1, x1, h1, i1), (s1, a2, b2, d2, e4, f1, g1, x1, h1, i2), (s1, a2, b2, d2, e4, f1, g1, x1, h1, i3), (s1, a2, b2, d2, e4, f1, g1, x1, h2, i1), (s1, a2, b2, d2, e4, f1, g1, x1, h2, i2), (s1, a2, b2, d2, e4, f1, g2, x1, h1, i1), (s1, a2, b2, d2, e4, f1, g2, x1, h1, i2), (s1, a2, b2, d2, e4, f1, g2, x1, h1, i3), (s1, a2, b2, d2, e4, f1, g2, x1, h2, i1), (s1, a2, b2, d2, e4, f1, g2, x1, h2, i2), (s1, a2, b2, d2, e4, f1, g2, x1, h2, i3), (s1, a2, b2, d2, e4, f1, g3, x1, h1, i1), (s1, a2, b2, d2, e4, f1, g3, x1, h1, i2), (s1, a2, b2, d2, e4, f1, g3, x1, h1, i3), (s1, a2, b2, d2, e4, f1, g3, x1, h2, i1), (s1, a2, b2, d2, e4, f1, g3, x1, h2, i2), (s1, a2, b2, d2, e4, f1, g3, x1, h2, i3), (s1, a2, b2, d2, e4, f1, g4, x1, h1, i1), (s1, a2, b2, d2, e4, f1, g4, x1, h1, i2), (s1, a2, b2, d2, e4, f1, g4, x1, h1, i3), (s1, a2, b2, d2, e4, f1, g4, x1, h2, i1), (s1, a2, b2, d2, e4, f1, g4, x1, h2, i2), (s1, a2, b2, d2, e4, f1, g4, x1, h2, i3), (s1, a2, b2, d2, e4, f1, g5, x1, h1, i1), (s1, a2, b2, d2, e4, f1, g5, x1, h1, i2), (s1, a2, b2, d2, e4, f1, g5, x1, h1, i3), (s1, a2, b2, d2, e4, f1, g5, x1, h2, i1), (s1, a2, b2, d2, e4, f1, g5, x1, h2, i2), (s1, a2, b2, d2, e4, f1, g5, x1, h2, i3), (s1, a3, b1, d1, e1, f1, g1, x1, h1, i1), (s1, a3, b1, d1, e1, f1, g1, x1, h1, i2), (s1, a3, b1, d1, e1, f1, g1, x1, h1, i3), (s1, a3, b1, d1, e1, f1, g1, x1, h2, i1), (s1, a3, b1, d1, e1, f1, g1, x1, h2, i2), (s1, a3, b1, d1, e1, f1, g1, x1, h2, i3), (s1, a3, b1, d1, e1, f1, g2, x1, h1, i1), (s1, a3, b1, d1, e1, f1, g2, x1, h1, i2), (s1, a3, b1, d1, e1, f1, g2, x1, h1, i3), (s1, a3, b1, d1, e1, f1, g2, x1, h2, i1), (s1, a3, b1, d1, e1, f1, g2, x1, h2, i2), (s1, a3, b1, d1, e1, f1, g2, x1, h2, 1.3), (s1, a3, b1, d1, e1, f1, g3, x1, h1, i1), (s1, a3, b1, d1, e1, f1, g3, x1, h1, i2), (s1, a3, b1, d1, e1, f1, g3, x1, h1, i3), (s1, a3, b1, d1, e1, f1, g3, x1, h2, i1), (s1, a3, b1, d1, e1, f1, g3, x1, h2, i2), (s1, a3, b1, d1, e1, f1, g3, x1, h2, i3), (s1, a3, b1, d1, e1, f1, g4, x1, h1, i1), (s1, a3, b1, d1, e1, f1, g4, x1, h1, i2), (s1, a3, b1, d1, e1, f1, g4, x1, h1, i3), (s1, a3, b1, d1, e1, f1, g4, x1, h2, i1), (s1, a3, b1, d1, e1, f1, g4, x1, h2, i2), (s1, a3, b1, d1, e1, f1, g4, x1, h2, i3), (s1, a3, b1, d1, e1, f1, g5, x1, h1, i1), (s1, a3, b1, d1, e1, f1, g5, x1, h1, i2), (s1, a3, b1, d1, e1, f1, g5, x1, h1, i3), (s1, a3, b1, d1, e1, f1, g5, x1, h2, i1), (s1, a3, b1, d1, e1, f1, g5, x1, h2, i2), (s1, a3, b1, d1, e1, f1, g5, x1, h2, i3), (s1, a3, b1, d1, e2, f1, g1, x1, h1, i1), (s1, a3, b1, d1, e2, f1, g1, x1, h1, i2), (s1, a3, b1, d1, e2, f1, g1, x1, h1, i3), (s1, a3, b1, d1, e2, f1, g1, x1, h2, i1), (s1, a3, b1, d1, e2, f1, g1, x1, h2, i2), (s1, a3, b1, d1, e2, f1, g1, x1, h2, i3), (s1, a3, b1, d1, e2, f1, g2, x1, h1, i1), (s1, a3, b1, d1, e2, f1, g2, x1, h1, i2), (s1, a3, b1, d1, e2, f1, g2, x1, h1, i3), (s1, a3, b1, d1, e2, f1, g2, x1, h2, i1), (s1, a3, b1, d1, e2, f1, g2, x1, h2, i2), (s1, a3, b1, d1, e2, f1, g2, x1, h2, i3), (s1, a3, b1, d1, e2, f1, g3, x1, h1, i1), (s1, a3, b1, d1, e2, f1, g3, x1, h1, i2), (s1, a3, b1, d1, e2, f1, g3, x1, h1, i3), (s1, a3, b1, d1, e2, f1, g3, x1, h2, i1), (s1, a3, b1, d1, e2, f1, g3, x1, h2, i2), (s1, a3, b1, d1, e2, f1, g3, x1, h2, i3), (s1, a3, b1, d1, e2, f1, g4, x1, h1, i1), (s1, a3, b1, d1, e2, f1, g4, x1, h1, i2), (s1, a3, b1, d1, e2, f1, g4, x1, h1, i3), (s1, a3, b1, d1, e2, f1, g4, x1, h2, i1), (s1, a3, b1, d1, e2, f1, g4, x1, h2, i2), (s1, a3, b1, d1, e2, f1, g4, x1, h2, i3), (s1, a3, b1, d1, e2, f1, g5, x1, h1, i1), (s1, a3, b1, d1, e2, f1, g5, x1, h1, i2), (s1, a3, b1, d1, e2, f1, g5, x1, h1, i3), (s1, a3, b1, d1, e2, f1, g5, x1, h2, (s1, a3, b1, d1, e2, f1, g5, x1, h2, i2), (s1, a3, b1, d1, e2, f1, g5, x1, h2, i3), (s1, a3, b1, d1, e3, f1, g1, x1, h1, i1), (s1, a3, b1, d1, e3, f1, g1, x1, h1, i2), (s1, a3, b1, d1, e3, f1, g1, x1, h1, i3), (s1, a3, b1, d1, e3, f1, g1, x1, h2, i1), (s1, a3, b1, d1, e3, f1, g1, x1, h2, i2), (s1, a3, b1, d1, e3, f1, g1, x1, h2, i3), (s1, a3, b1, d1, e3, f1, g2, x1, h1, i1), (s1, a3, b1, d1, e3, f1, g2, x1, h1, i2), (s1, a3, b1, d1, e3, f1, g2, x1, h1, i3), (s1, a3, b1, d1, e3, f1, g2, x1, h2, i1), (s1, a3, b1, d1, e3, f1, g2, x1, h2, i2), (s1, a3, b1, d1, e3, f1, g2, x1, h2, i3), (s1, a3, b1, d1, e3, f1, g3, x1, h1, i1), (s1, a3, b1, d1, e3, f1, g3, x1, h1, i2), (s1, a3, b1, d1, e3, f1, g3, x1, h1, i3), (s1, a3, b1, d1, e3, f1, g3, x1, h2, i1), (s1, a3, b1, d1, e3, f1, g3, x1, h2, i2), (s1, a3, b1, d1, e3, f1, g3, x1, h2, i3), (s1, a3, b1, d1, e3, f1, g4, x1, h1, i1), (s1, a3, b1, d1, e3, f1, g4, x1, h1, i2), (s1, a3, b1, d1, e3, f1, g4, x1, h1, i3), (s1, a3, b1, d1, e3, f1, g4, x1, h2, i1), a3, b1, d1, e3, f1, g4, x1, h2, i2), (s1, a3, b1, d1, e3, f1, g4, x1, h2, i3), (s1, a3, b1, d1, e3, f1, g5, x1, h1, i1), (s1, a3, b1, d1, e3, f1, g5, x1, h1, i2), (s1, a3, b1, d1, e3, f1, g5, x1, h1, i3), (s1, a3, b1, d1, e3, f1, g5, x1, h2, i1), (s1, a3, b1, d1, e3, f1, g5, x1, h2, i2), (s1, a3, b1, d1, e3, f1, g5, x1, h2, i3), (s1, a3, b1, d1, e4, f1, g1, x1, h1, i1), (s1, a3, b1, d1, e4, f1, g1, x1, h1, i2), (s1, a3, b1, d1, e4, f1, g1, x1, h1, i3), (s1, a3, b1, d1, e4, f1, g1, x1, h2, i1), (s1, a3, b1, d1, e4, f1, g1, x1, h2, i2), (s1, a3, b1, d1, e4, f1, g1, x1, h2, i3), (s1, a3, b1, d1, e4, f1, g2, x1, h1, i1), (s1, a3, b1, d1, e4, f1, g2, x1, h1, i2), (s1, a3, b1, d1, e4, f1, g2, x1, h1, i3), (s1, a3, b1, d1, e4, f1, g2, x1, h2, i1), (s1, a3, b1, d1, e4, f1, g2, x1, h2, i2), (s1, a3, b1, d1, e4, f1, g2, x1, h2, i3), (s1, a3, b1, d1, e4, f1, g3, x1, h1, i1), (s1, a3, b1, d1, e4, f1, g3, x1, h1, i2), (s1, a3, b1, d1, e4, f1, g3, x1, h1, i3), (s1, a3, b1, d1, e4, f1, g3, x1, h2, i1), (s1, a3, b1, d1, e4, f1, g3, x1, h2, i2), (s1, a3, b1, d1, e4, f1, g3, x1, h2, i3), (s1, a3, b1, d1, e4, f1, g4, x1, h1, i1), (s1, a3, b1, d1, e4, f1, g4, x1, h1, i2), (s1, a3, b1, d1, e4, f1, g4, x1, h1, i3), (s1, a3, b1, d1, e4, f1, g4, x1, h2, i1), (s1, a3, b1, d1, e4, f1, g4, x1, h2, i2), (s1, a3, b1, d1, e4, f1, g4, x1, h2, i3), (s1, a3, b1, d1, e4, f1, g5, x1, h1, i1), (s1, a3, b1, d1, e4, f1, g5, x1, h1, i2), (s1, a3, b1, d1, e4, f1, g5, x1, h1, i3), (s1, a3, b1, d1, e4, f1, g5, x1, h2, i1), (s1, a3, b1, d1, e4, f1, g5, x1, h2, i2), (s1, a3, b1, d1, e4, f1, g5, x1, h2, i3),
(s1, a3, b1, d2, e1, f1, g1, x1, h1, i1), (s1, a3, b1, d2, e1, f1, g1, x1, h1, i2), (s1, a3, b1, d2, e1, f1, g1, x1, h1, i3), (s1, a3, b1, d2, e1, f1, g1, x1, h2, i1), (s1, a3, b1, d2, e1, f1, g1, x1, h2, i2), (s1, a3, b1, d2, e1, f1, g1, x1, h2, i3), (s1, a3, b1, d2, e1, f1, g2, x1, h1, i1), (s1, a3, b1, d2, e1, f1, g2, x1, h1, i2), (s1, a3, b1, d2, e1, f1, g2, x1, h1, i3), (s1, a3, b1, d2, e1, f1, g2, x1, h2, i1), (s1, a3, b1, d2, e1, f1, g2, x1, h2, i2), (s1, a3, b1, d2, e1, f1, g2, x1, h2, i3), (s1, a3, b1, d2, e1, f1, g3, x1, h1, i1), (s1, a3, b1, d2, e1, f1, g3, x1, h1, i2), (s1, a3, b1, d2, e1, f1, g3, x1, h1, i3), (s1, a3, b1, d2, e1, f1, g3, x1, h2, i1), (s1, a3, b1, d2, e1, f1, g3, x1, h2, i2), (s1, a3, b1, d2, e1, f1, g3, x1, h2, i3), (s1, a3, b1, d2, e1, f1, g4, x1, h1, i1), (s1, a3, b1, d2, e1, f1, g4, x1, h1, i2), (s1, a3, b1, d2, e1, f1, g4, x1, h1, i3), (s1, a3, b1, d2, e1, f1, g4, x1, h2, i1), (s1, a3, b1, d2, e1, f1, g4, x1, h2, i2), (s1, a3, b1, d2, e1, f1, g4, x1, h2, i3), (s1, a3, b1, d2, e1, f1, g5, x1, h1, i1), (s1, a3, b1, d2, e1, f1, g5, x1, h1, i2), (s1, a3, b1, d2, e1, f1, g5, x1, h1, i3), (s1, a3, b1, d2, e1, f1, g5, x1, h2, i1), (s1, a3, b1, d2, e1, f1, g5, x1, h2, i2), (s1, a3, b1, d2, e1, f1, g5, x1, h2, i3), (s1, a3, b1, d2, e2, f1, g1, x1, h1, i1), (s1, a3, b1, d2, e2, f1, g1, x1, h1, i2), (s1, a3, b1, d2, e2, f1, g1, x1, h1, i3), (s1, a3, b1, d2, e2, f1, g1, x1, h2, i1), (s1, a3, b1, d2, e2, f1, g1, x1, h2, i2), (s1, a3, b1, d2, e2, f1, g1, x1, h2, i3), (s1, a3, b1, d2, e2, f1, g2, x1, h1, i1), (s1, a3, b1, d2, e2, f1, g2, x1, h1, i2), (s1, a3, b1, d2, e2, f1, g2, x1, h1, i3), (s1, a3, b1, d2, e2, f1, g2, x1, h2, i1), (s1, a3, b1, d2, e2, f1, g2, x1, h2, i2), (s1, a3, b1, d2, e2, f1, g2, x1, h2, i3), (s1, a3, b1, d2, e2, f1, g3, x1, h1, i1), (s1, a3, b1, d2, e2, f1, g3, x1, h1, i2), (s1, a3, b1, d2, e2, f1, g3, x1, h1, i3), (s1, a3, b1, d2, e2, f1, g3, x1, h2, i1), (s1, a3, b1, d2, e2, f1, g3, x1, h2, i2), (s1, a3, b1, d2, e2, f1, g3, x1, h2, i3), (s1, a3, b1, d2, e2, f1, g4, x1, h1, i1), (s1, a3, b1, d2, e2, f1, g4, x1, h1, i2), (s1, a3, b1, d2, e2, f1, g4, x1, h1, i3), (s1, a3, b1, d2, e2, f1, g4, x1, h2, i1), (s1, a3, b1, d2, e2, f1, g4, x1, h2, i2), (s1, a3, b1, d2, e2, f1, g4, x1, h2, i3), (s1, a3, b1, d2, e2, f1, g5, x1, h1, i1), (s1, a3, b1, d2, e2, f1, g5, x1, h1, i2), (s1, a3, b1, d2, e2, f1, g5, x1, h1, i3), (s1, a3, b1, d2, e2, f1, g5, x1, h2, i1), (s1, a3, b1, d2, e2, f1, g5, x1, h2, i2), (s1, a3, b1, d2, e2, f1, g5, x1, h2, i3), (s1, a3, b1, d2, e3, f1, g1, x1, h1, i1), (s1, a3, b1, d2, e3, f1, g1, x1, h1, i2), (s1, a3, b1, d2, e3, f1, g1, x1, h1, i3), (s1, a3, b1, d2, e3, f1, g1, x1, h2, i1), (s1, a3, b1, d2, e3, f1, g1, x1, h2, i2), (s1, a3, b1, d2, e3, f1, g1, x1, h2, i3), (s1, a3, b1, d2, e3, f1, g2, x1, h1, i1), (s1, a3, b1, d2, e3, f1, g2, x1, h1, i2), (s1, a3, b1, d2, e3, f1, g2, x1, h1, i3), (s1, a3, b1, d2, e3, f1, g2, x1, h2, i1), (s1, a3, b1, d2, e3, f1, g2, x1, h2, i2), (s1, a3, b1, d2, e3, f1, g2, x1, h2, i3), (s1, a3, b1, d2, e3, f1, g3, x1, h1, i1), (s1, a3, b1, d2, e3, f1, g3, x1, h1, i2), (s1, a3, b1, d2, e3, f1, g3, x1, h1, i3), (s1, a3, b1, d2, e3, f1, g3, x1, h2, i1), (s1, a3, b1, d2, e3, f1, g3, x1, h2, i2), (s1, a3, b1, d2, e3, f1, g3, x1, h2, i3), (s1, a3, b1, d2, e3, f1, g4, x1, h1, i1), (s1, a3, b1, d2, e3, f1, g4, x1, h1, i2), (s1, a3, b1, d2, e3, f1, g4, x1, h1, i3), (s1, a3, b1, d2, e3, f1, g4, x1, h2, i1), (s1, a3, b1, d2, e3, f1, g4, x1, h2, i2), (s1, a3, b1, d2, e3, f1, g4, x1, h2, i3), (s1, a3, b1, d2, e3, f1, g5, x1, h1, i1), (s1, a3, b1, d2, e3, f1, g5, x1, h1, i2), (s1, a3, b1, d2, e3, f1, g5, x1, h1, i3), (s1, a3, b1, d2, e3, f1, g5, x1, h2, i1), (s1, a3, b1, d2, e3, f1, g5, x1, h2, i2), (s1, a3, b1, d2, e3, f1, g5, x1, h2, i3), (s1, a3, b1, d2, e4, f1, g1, x1, h1, i1), (s1, a3, b1, d2, e4, f1, g1, x1, h1, i2), (s1, a3, b1, d2, e4, f1, g1, x1, h1, i3), (s1, a3, b1, d2, e4, f1, g1, x1, h2, i1), (s1, a3, b1, d2, e4, f1, g1, x1, h2, i2), (s1, a3, b1, d2, e4, f1, g1, x1, h2, i3), (s1, a3, b1, d2, e4, f1, g2, x1, h1, i1), (s1, a3, b1, d2, e4, f1, g2, x1, h1, i2), (s1, a3, b1, d2, e4, f1, g2, x1, h1, i3), (s1, a3, b1, d2, e4, f1, g2, x1, h2, i1), (s1, a3, b1, d2, e4, f1, g2, x1, h2, i2), (s1, a3, b1, d2, e4, f1, g2, x1, h2, i3), (s1, a3, b1, d2, e4, f1, g3, x1, h1, i1), (s1, a3, b1, d2, e4, f1, g3, x1, h1, i2), (s1, a3, b1, d2, e4, f1, g3, x1, h1, i3), (s1, a3, b1, d2, e4, f1, g3, x1, h2, i1), (31, a3, b1, d2, e4, f1, g3, x1, h2, i2), (s1, a3, b1, d2, e4, f1, g3, x1, h2, i3), (s1, a3, b1, d2, e4, f1, g4, x1, h1, i1), (s1, a3, b1, d2, e4, f1, g4, x1, h1, i2), (s1, a3, b1, d2, e4, f1, g4, x1, h1, i3), (s1, a3, b1, d2, e4, f1, g4, x1, h2, i1), (s1, a3, b1, d2, e4, f1, g4, x1, h2, i2), (s1, a3, b1, d2, e4, f1, g4, x1, h2, i3), (s1, a3, b1, d2, e4, f1, g5, x1, h1, i1), (s1, a3, b1, d2, e4, f1, g5, x1, h1, i2), (s1, a3, b1, d2, e4, f1, g5, x1, h1, i3), (s1, a3, b1, d2, e4, f1, g5, x1, h2, i1), (s1, a3, b1, d2, e4, f1, g5, x1, h2, i2), (s1, a3, b1, d2, e4, f1, g5, x1, h2, i3), (s1, a3, b2, d1, e1, f1, g1, x1, h1, i1), (s1, a3, b2, d1, e1, f1, g1, x1, h1, i2), (s1, a3, b2, d1, e1, f1, g1, x1, h1, i3), (s1, a3, b2, d1, e1, f1, g1, x1, h2, i1), (s1, a3, b2, d1, e1, f1, g1, x1, h2, i2), (s1, a3, b2, d1, e1, f1, g1, x1, h2, i3), (s1, a3, b2, d1, e1, f1, g2, x1, h1, i1), (s1, a3, b2, d1, e1, f1, g2, x1, h1, i2), (s1, a3, b2, d1, e1, f1, g2, x1, h1, i3), (s1, a3, b2, d1, e1, f1, g2, x1, h2, i1), (s1, a3, b2, d1, e1, f1, g2, x1, h2, i2), (s1, a3, b2, d1, e1, f1, g2, x1, h2, i3), (s1, a3, b2, d1, e1, f1, g3, x1, h1, i1), (s1, a3, b2, d1, e1, f1, g3, x1, h1, i2), (s1, a3, b2, d1, e1, f1, g3, x1, h1, i3), (s1, a3, b2, d1, e1, f1, g3, x1, h2, i1), (s1, a3, b2, d1, e1, f1, g3, x1, h2, i2), (s1, a3, b2, d1, e1, f1, g3, x1, h2, i3), (s1, a3, b2, d1, e1, f1, g4, x1, h1, i1), (s1, a3, b2, d1, e1, f1, g4, x1, h1, i2), (s1, a3, b2, d1, e1, f1, g4, x1, h1, i3), (s1, a3, b2, d1, e1, f1, g4, x1, h2, i1), (s1, a3, b2, d1, e1, f1, g4, x1, h2, i2), (s1, a3, b2, d1, e1, f1, g4, x1, h2, i3), (s1, a3, b2, d1, e1, f1, g5, x1, h1, i1), (s1, a3, b2, d1, e1, f1, g5, x1, h1, i2), (s1, a3, b2, d1, e1, f1, g5, x1, h1, i3), (s1, a3, b2, d1, e1, f1, g5, x1, h2, i1), (s1, a3, b2, d1, e1, f1, g5, x1, h2, i2), (s1, a3, b2, d1, e1, f1, g5, x1, h2, i3), (s1, a3, b2, d1, e2, f1, g1, x1, h1, i1), (s1, a3, b2, d1, e2, f1, g1, x1, h1, i2), (s1, a3, b2, d1, e2, f1, g1, x1, h1, i3), (s1, a3, b2, d1, e2, f1, g1, x1, h2, i1), (s1, a3, b2, d1, e2, f1, g1, x1, h2, i2), (s1, a3, b2, d1, e2, f1, g1, x1, h2, i3), (s1, a3, b2, d1, e2, f1, g2, x1, h1, i1), (s1, a3, b2, d1, e2, f1, g2, x1, h1, i2), (s1, a3, b2, d1, e2, f1, g2, x1, h1, i3), (s1, a3, b2, d1, e2, f1, g2, x1, h2, i1), (s1, a3, b2, d1, e2, f1, g2, x1, h2, i2), (s1, a3, b2, d1, e2, f1, g2, x1, h2, i3), (s1, a3, b2, d1, e2, f1, g3, x1, h1, i1), (s1, a3, b2, d1, e2, f1, g3, x1, h1, i2), (s1, a3, b2, d1, e2, f1, g3, x1, h1, i3), (s1, a3, b2, d1, e2, f1, g3, x1, h2, i1), (s1, a3, b2, d1, e2, f1, g3, x1, h2, i2), (s1, a3, b2, d1, e2, f1, g3, x1, h2, i3), (s1, a3, b2, d1, e2, f1, g4, x1, h1, i1), (s1, a3, b2, d1, e2, f1, g4, x1, h1, i2), (s1, a3, b2, d1, e2, f1, g4, x1, h1, i3), (s1, a3, b2, d1, e2, f1, g4, x1, h2, i1), (s1, a3, b2, d1, e2, f1, g4, x1, h2, i2), (s1, a3, b2, d1, e2, f1, g4, x1, h2, i3), (s1, a3, b2, d1, e2, f1, g5, x1, h1, i1), (s1, a3, b2, d1, e2, f1, g5, x1, h1, i2), (s1, a3, b2, d1, e2, f1, g5, x1, h1, i3), (s1, a3, b2, d1, e2, f1, g5, x1, h2, i1), (s1, a3, b2, d1, e2, f1, g5, x1, h2, i2), (s1, a3, b2, d1, e2, f1, g5, x1, h2, i3), (s1, a3, b2, d1, e3, f1, g1, x1, h1, i1), (s1, a3, b2, d1, e3, f1, g1, x1, h1, i2), (s1, a3, b2, d1, e3, f1, g1, x1, h1, i3), (s1, a3, b2, d1, e3, f1, g1, x1, h2, i1), (s1, a3, b2, d1, e3, f1, g1, x1, h2, i2), (s1, a3, b2, d1, e3, f1, g1, x1, h2, i3), (s1, a3, b2, d1, e3, f1, g2, x1, h1, i1), (s1, a3, b2, d1, e3, f1, g2, x1, h1, i2), (s1, a3, b2, d1, e3, f1, g2, x1, h1, i3), (s1, a3, b2, d1, e3, f1, g2, x1, h2, i1), (s1, a3, b2, d1, e3, f1, g2, x1, h2, i2), (s1, a3, b2, d1, e3, f1, g2, x1, h2, i3), (s1, a3, b2, d1, e3, f1, g3, x1, h1, i1), (s1, a3, b2, d1, e3, f1, g3, x1, h1, i2), (s1, a3, b2, d1, e3, f1, g3, x1, h1, i3), (s1, a3, b2, d1, e3, f1, g3, x1, h2, i1), (s1, a3, b2, d1, e3, f1, g3, x1, h2, i2), (s1, a3, b2, d1, e3, f1, g3, x1, h2, i3), (s1, a3, b2, d1, e3, f1, g4, x1, h1, i1), (s1, a3, b2, d1, e3, f1, g4, x1, h1, i2), (s1, a3, b2, d1, e3, f1, g4, x1, h1, i3), (s1, a3, b2, d1, e3, f1, g4, x1, h2, i1), (s1, a3, b2, d1, e3, f1, g4, x1, h2, i2), (s1, a3, b2, d1, e3, f1, g4, x1, h2, i3), (s1, a3, b2, d1, e3, f1, g5, x1, h1, i1), (s1, a3, b2, d1, e3, f1, g5, x1, h1, i2), (s1, a3, b2, d1, e3, f1, g5, x1, h1, i3), (s1, a3, b2, d1, e3, f1, g5, x1, h2, i1), (s1, a3, b2, d1, e3, f1, g5, x1, h2, i2), (s1, a3, b2, d1, e3, f1, g5, x1, h2, i3), (s1, a3, b2, d1, e4, f1, g1, x1, h1, i1), (s1, a3, b2, d1, e4, f1, g1, x1, h1, i2), (s1, a3, b2, d1, e4, f1, g1, x1, h1, i3), (s1, a3, b2, d1, e4, f1, g1, x1, h2, i1), (s1, a3, b2, d1, e4, f1, g1, x1, h2, i2), (s1, a3, b2, d1, e4, f1, g1, x1, h2, i3), (s1, a3, b2, d1, e4, f1, g2, x1, h1, i1), (s1, a3, b2, d1, e4, f1, g2, x1, h1, i2), (s1, a3, b2, d1, e4, f1, g2, x1, h1, i3), (s1, a3, b2, d1, e4, f1, g2, x1, h2, i1), (s1, a3, b2, d1, e4, f1, g2, x1, h2, i2), (s1, a3, b2, d1, e4, f1, g2, x1, h2, i3), (s1, a3, b2, d1, e4, f1, g3, x1, h1, i1), (s1, a3, b2, d1, e4, f1, g3, x1, h1, i2), (s1, a3, b2, d1, e4, f1, g3, x1, h1, i3), (s1, a3, b2, d1, e4, f1, g3, x1, h2, i1), (s1, a3, b2, d1, e4, f1, g3, x1, h2, i2), (s1, a3, b2, d1, e4, f1, g3, x1, h2, i3), (s1, a3, b2, d1, e4, f1, g4, x1, h1, i1), (s1, a3, b2, d1, e4, f1, g4, x1, h1, i2), (s1, a3, b2, d1, e4, f1, g4, x1, h1, i3), (s1, a3, b2, d1, e4, f1, g4, x1, h2, i1), (s1, a3, b2, d1, e4, f1, g4, x1, h2, i2), (s1, a3, b2, d1, e4, f1, g4, x1, h2, i3), (s1, a3, b2, d1, e4, f1, g5, x1, h1, i1), (s1, a3, b2, d1, e4, f1, g5, x1, h1, i2), (s1, a3, b2, d1, e4, f1, g5, x1, h1, i3), (s1, a3, b2, d1, e4, f1, g5, x1, h2, i1), (s1, a3, b2, d1, e4, f1, g5, x1, h2, i2), (s1, a3, b2, d1, e4, f1, g5, x1, h2, i3), (s1, a3, b2, d2, e1, f1, g1, x1, h1, i1), (s1, a3, b2, d2, e1, f1, g1, x1, h1, i2), (s1, a3, b2, d2, e1, f1, g1, x1, h1, i3), (s1, a3, b2, d2, e1, f1, g1, x1, h2, i1), (s1, a3, b2, d2, e1, f1, g1, x1, h2, i2), (s1, a3, b2, d2, e1, f1, g1, x1, h2, i3), (s1, a3, b2, d2, e1, f1, g2, x1, h1, i1), (s1, a3, b2, d2, e1, f1, g2, x1, h1, i2), (s1, a3, b2, d2, e1, f1, g2, x1, h1, i3), (s1, a3, b2, d2, e1, f1, g2, x1, h2, i1), (s1, a3, b2, d2, e1, f1, g2, x1, h2, i2), (s1, a3, b2, d2, e1, f1, g2, x1, h2, i3), (s1, a3, b2, d2, e1, f1, g3, x1, h1, i1), (s1, a3, b2, d2, e1, f1, g3, x1, h1, i2), (s1, a3, b2, d2, e1, f1, g3, x1, h1, i3), (s1, a3, b2, d2, e1, f1, g3, x1, h2, i1), (s1, a3, b2, d2, e1, f1, g3, x1, h2, i2), (s1, a3, b2, d2, e1, f1, g3, x1, h2, i3), (s1, a3, b2, d2, e1, f1, g4, x1, h1, i1), (s1, a3, b2, d2, e1, f1, g4, x1, h1, i2), (s1, a3, b2, d2, e1, f1, g4, x1, h1, i3), (s1, a3, b2, d2, e1, f1, g4, x1, h2, i1), (s1, a3, b2, d2, e1, f1, g4, x1, h2, i2), (s1, a3, b2, d2, e1, f1, g4, x1, h2, i3), (s1, a3, b2, d2, e1, f1, g5, x1, h1, i1), (s1, a3, b2, d2, e1, f1, g5, x1, h1, i2), (s1, a3, b2, d2, e1, f1, g5, x1, h1, i3), (s1, a3, b2, d2, e1, f1, g5, x1, h2, i1), (s1, a3, b2, d2, e1, f1, g5, x1, h2, i2), (s1, a3, b2, d2, e1, f1, g5, x1, h2, i3), (s1, a3, b2, d2, e2, f1, g1, x1, h1, i1), (s1, a3, b2, d2, e2, f1, g1, x1, h1, i2), (s1, a3, b2, d2, e2, f1, g1, x1, h1, i3), (s1, a3, b2, d2, e2, f1, g1, x1, h2, i1), (s1, a3, b2, d2, e2, f1, g1, x1, h2, i2), (s1, a3, b2, d2, e2, f1, g1, x1, h2, i3), (s1, a3, b2, d2, e2, f1, g2, x1, h1, i1), (s1, a3, b2, d2, e2, f1, g2, x1, h1, i2), (s1, a3, b2, d2, e2, f1, g2, x1, h1, i3), (s1, a3, b2, d2, e2, f1, g2, x1, h2, i1), (s1, a3, b2, d2, e2, f1, g2, x1, h2, i2), (s1, a3, b2, d2, e2, f1, g2, x1, h2, i3), (s1, a3, b2, d2, e2, f1, g3, x1, h1, i1), (s1, a3, b2, d2, e2, f1, g3, x1, h1, i2), (s1, a3, b2, d2, e2, f1, g3, x1, h1, i3), (s1, a3, b2, d2, e2, f1, g3, x1, h2, i1), (s1, a3, b2, d2, e2, f1, g3, x1, h2, i2), (s1, a3, b2, d2, e2, f1, g3, x1, h2, i3), (s1, a3, b2, d2, e2, f1, g4, x1, h1, i1), (s1, a3, b2, d2, e2, f1, g4, x1, h1, i2), (s1, a3, b2, d2, e2, f1, g4, x1, h1, i3), (s1, a3, b2, d2, e2, f1, g4, x1, h2, i1), (s1, a3, b2, d2, e2, f1, g4, x1, h2, i2), (s1, a3, b2, d2, e2, f1, g4, x1, h2, i3), (s1, a3, b2, d2, e2, f1, g5, x1, h1, i1), (s1, a3, b2, d2, e2, f1, g5, x1, h1, i2), (s1, a3, b2, d2, e2, f1, g5, x1, h1, i3), (s1, a3, b2, d2, e2, f1, g5, x1, h2, i1), (s1, a3, b2, d2, e2, f1, g5, x1, h2, i2), (s1, a3, b2, d2, e2, f1, g5, x1, h2, i3), (s1, a3, b2, d2, e3, f1, g1, x1, h1, i1), (s1, a3, b2, d2, e3, f1, g1, x1, h1, i2), (s1, a3, b2, d2, e3, f1, g1, x1, h1, i3), (s1, a3, b2, d2, e3, f1, g1, x1, h2, i1), (s1, a3, b2, d2, e3, f1, g1, x1, h2, i2), (s1, a3, b2, d2, e3, f1, g1, x1, h2, i3), (s1, a3, b2, d2, e3, f1, g2, x1, h1, i1), (s1, a3, b2, d2, e3, f1, g2, x1, h1, i2), (s1, a3, b2, d2, e3, f1, g2, x1, h1, i3), (s1, a3, b2, d2, e3, f1, g2, x1, h2, i1), (s1, a3, b2, d2, e3, f1, g2, x1, h2, i2), (s1, a3, b2, d2, e3, f1, g2, x1, h2, i3), (s1, a3, b2, d2, e3, f1, g3, x1, h1, i1), (s1, a3, b2, d2, e3, f1, g3, x1, h1, i2), (s1, a3, b2, d2, e3, f1, g3, x1, h1, i3), (s1, a3, b2, d2, e3, f1, g3, x1, h2, i1), (s1, a3, b2, d2, e3, f1, g3, x1, h2, i2), (s1, a3, b2, d2, e3, f1, g3, x1, h2, i3), (s1, a3, b2, d2, e3, f1, g4, x1, h1, i1), (s1, a3, b2, d2, e3, f1, g4, x1, h1, i2), (s1, a3, b2, d2, e3, f1, g4, x1, h1, i3), (s1, a3, b2, d2, e3, f1, g4, x1, h2, i1), (s1, a3, b2, d2, e3, f1, g4, x1, h2, i2), (s1, a3, b2, d2, e3, f1, g4, x1, h2, i3), (s1, a3, b2, d2, e3, f1, g5, x1, h1, i1), (s1, a3, b2, d2, e3, f1, g5, x1, h1, i2), (s1, a3, b2, d2, e3, f1, g5, x1, h1, i3), (s1, a3, b2, d2, e3, f1, g5, x1, h2, i1), (s1, a3, b2, d2, e3, f1, g5, x1, h2, i2), (s1, a3, b2, d2, e3, f1, g5, x1, h2, i3), (s1, a3, b2, d2, e4, f1, g1, x1, h1, i1), (s1, a3, b2, d2, e4, f1, g1, x1, h1, i2), (s1, a3, b2, d2, e4, f1, g1, x1, h1, i3), (s1, a3, b2, d2, e4, f1, g1, x1, h2, i1), (s1, a3, b2, d2, e4, f1, g1, x1, h2, i2), (s1, a3, b2, d2, e4, f1, g1, x1, h2, i3), (s1, a3, b2, d2, e4, f1, g2, x1, h1, i1), (s1, a3, b2, d2, e4, f1, g2, x1, h1, i2), (s1, a3, b2, d2, e4, f1, g2, x1, h1, i3), (s1, a3, b2, d2, e4, f1, g2, x1, h2, i1), (s1, a3, b2, d2, e4, f1, g2, x1, h2, i2), (s1, a3, b2, d2, e4, f1, g2, x1, h2, i3), (s1, a3, b2, d2, e4, f1, g3, x1, h1, i1), (s1, a3, b2, d2, e4, f1, g3, x1, h1, i2), (s1, a3, b2, d2, e4, f1, g3, x1, h1, i3), (s1, a3, b2, d2, e4, f1, g3, x1, h2, i1), (s1, a3, b2, d2, e4, f1, g3, x1, h2, i2), (s1, a3, b2, d2, e4, f1, g3, x1, h2, i3), (s1, a3, b2, d2, e4, f1, g4, x1, h1, i1), (s1, a3, b2, d2, e4, f1, g4, x1, h1, i2), (s1, a3, b2, d2, e4, f1, g4, x1, h1, i3), (s1, a3, b2, d2, e4, f1, g4, x1, h2, i1), (s1, a3, b2, d2, e4, f1, g4, x1, h2, i2), (s1, a3, b2, d2, e4, f1, g4, x1, h2, i3), (s1, a3, b2, (12, e4, f1, g5, x1, h1, i1), (s1, a3, b2, d2, e4, f1, g5, x1, h1, i2), (s1, a3, b2, d2, e4, f1, g5, x1, h1, i3), (s1, a3, b2, d2, e4, f1, g5, x1, h2, i1), (s1, a3, b2, d2, e4, f1, g5, x1, h2, i2), (s1, a3, b2, d2, e4, f1, g5, x1, h2, i3).

Amongst the combinations above, particularly preferable combinations are as follows: (s1, a2, b1, d2, e2, f1, g1, x1, h1, i1), (s1, a2, b1, d2, e2, f1, g1, x1, h1, i2), (s1, a2, b1, d2, e2, f1, g1, x1, h1, i3), (s1, a2, b1, d2, e2, f1, g1, x1, h2, i1), (s1, a2, b1, d2, e2, f1, g1, x1, h2, i2), (s1, a2, b1, d2, e2, f1, g1, x1, h2, i3), (s1, a2, b1, d2, e2, f1, g2, x1, h1, i1), (s1, a2, b1, d2, e2, f1, g2, x1, h1, i2), (s1, a2, b1, d2, e2, f1, g2, x1, h1, i3), (s1, a2, b1, d2, e2, f1, g2, x1, h2, i1), (s1, a2, b1, d2, e2, f1, g2, x1, h2, i2), (s1, a2, b1, d2, e2, f1, g2, x1, h2, i3), (s1, a2, b1, d2, e2, f1, g4, x1, h1, i1), (s1, a2, b1, d2, e2, f1, g4, x1, h1, i2), (s1, a2, b1, d2, e2, f1, g4, x1, h1, i3), (s1, a2, b1, d2, e2, f1, g4, x1, h2, i1), (s1, a2, b1, d2, e2, f1, g4, x1, h2, i2), (s1, a2, b1, d2, e2, f1, g4, x1, h2, i3), (s1, a2, b1, d2, e3, f1, g1, x1, h1, i1), (s1, a2, b1, d2, e3, f1, g1, x1, h1, i2), (s1, a2, b1, d2, e3, f1, g1, x1, h1, i3), (s1, a2, b1, d2, e3, f1, g1, x1, h2, i1), (s1, a2, b1, d2, e3, f1, g1, x1, h2, i2), (s1, a2, b1, d2, e3, f1, g1, x1, h2, i3), (s1, a2, b1, d2, e3, f1, g2, x1, h1, i1), (s1, a2, b1, d2, e3, f1, g2, x1, h1, i2), (s1, a2, b1, d2, e3, f1, g2, x1, h1, i3), (s1, a2, b1, d2, e3, f1, g2, x1, h2, i1), (s1, a2, b1, d2, e3, f1, g2, x1, h2, i2), (s1, a2, b1, d2, e3, f1, g2, x1, h2, i3), (s1, a2, b1, d2, e3, f1, g4, x1, h1, i1), (s1, a2, b1, d2, e3, f1, g4, x1, h1, i2), (s1, a2, b1, d2, e3, f1, g4, x1, h1, i3), (s1, a2, b1, d2, e3, f1, g4, x1, h2, i1), (s1, a2, b1, d2, e3, f1, g4, x1, h2, i2), (s1, a2, b1, d2, e3, f1, g4, x1, h2, i3).

The compounds represented by formula (I) of the present invention can be manufactured, for example, by a general synthesis method described below.

[Formula 60]

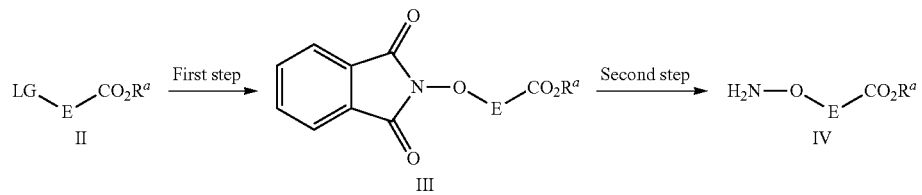

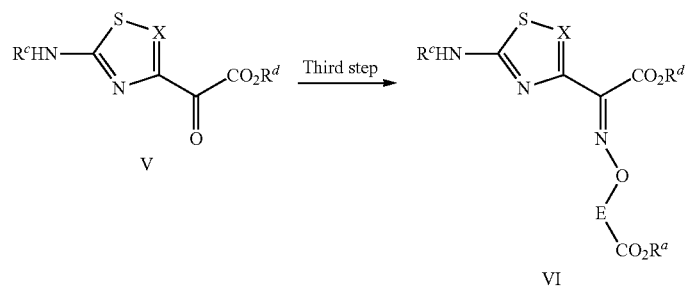

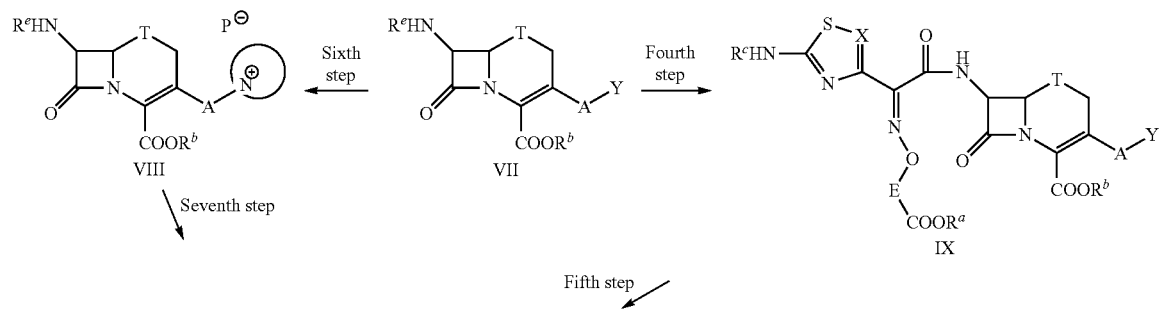

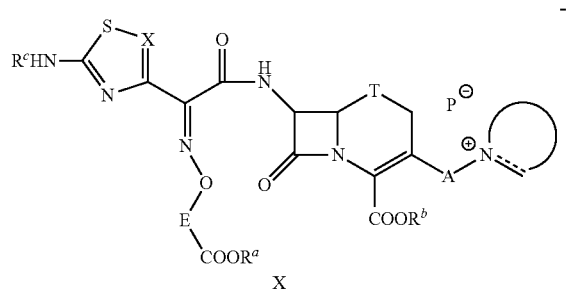 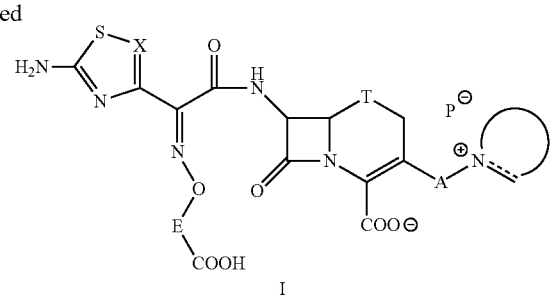

(wherein, E, F, X, A, T, $R^a$, $R^b$, $R^c$, $P^-$, and

[Formula 61]

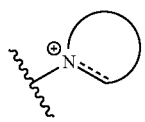

are defined as above; LG and Y are leaving groups (for example, hydroxy, halogen (Cl, Br, I), carbamoyloxy, acyloxy, methanesulfonyloxy, toluenesulfonyloxy that may be substituted, etc.); $R^d$ is hydrogen or a carboxy protecting group; $R^e$ is hydrogen or a amino protecting group.)

1) Raw Materials of the 7-Position Side Chain: Synthesis of Compound (IV)

The First Step:

Compound (III) is obtained by a reaction with N-hydroxyphthalimide in the presence of Compound (II) (LG is hydroxy) and Mitsunobu reagent, or in the presence of Compound (II) (LG is another leaving group) and a base (such as sodium hydroxide, sodium methoxide).

An amount of N-hydroxyphthalimide used is generally 1-5 molar equivalents, preferably, 1-2 molar equivalents, relative to Compound (II).

Examples of reaction solvents include ethers (e.g., dioxane, tetrahydrofuran, diethyl ether, tert-butyl methyl ether, diisopropyl ether), halogenated hydrocarbons (e.g., dichloromethane, chloroform, carbon tetrachloride), hydrocarbons (e.g., n-hexane, benzene, toluene), amides (e.g., formamide, N,N-dimethylformamide, N,N-dimethylacetamide, N-methylpyrrolidone), and the like, and mixed solvents and the like thereof.

A reaction temperature is in a range of, generally, about −50-100° C., preferably about −40-50° C., and more preferably about −30-0° C.

The Second Step:

N-Methylhydrazine or hydrazine was added and reacted to Compound (III) to provide Compound (IV).

An amount of N-methylhydrazine or hydrazine used is in a range of about 1-10 molar equivalents, preferably 1-5 molar equivalents, more preferably 1-2 molar equivalents, relative to Compound (III).

Examples of reaction solvents include ethers (e.g., dioxane, tetrahydrofuran, diethyl ether, tert-butyl methyl ether, diisopropyl ether), esters (e.g., ethyl formate, ethyl acetate, isopropyl acetate), halogenated hydrocarbons (e.g., dichloromethane, chloroform, carbon tetrachloride), hydrocarbons (e.g., n-hexane, benzene, toluene), alcohols (e.g., methanol, ethanol, isopropanol), amides (e.g., formamide, N,N-dimethylformamide, N,N-dimethylacetamide, N-methylpyrrolidone), ketones (e.g., acetone, methyl ethyl ketone), nitriles (e.g., MeCN, propionitrile), dimethylsulfoxide, water, and the like, and mixed solvents and the like thereof.

A reaction temperature is in a range of, generally, about 0-100° C., preferably about 0-50° C., more preferably about 10-30° C.

The Third Step:

Compound (IV) is added and reacted to Compound (V), which is commercially available or obtained by a known method, to provide Compound (VI). (For example, it is described in *Bioorganic & Medicinal Chemistry*, Vol. 15, p. 6716-6732 (2007)).

N-Methylhydrazine or hydrazine is added and reacted to Compound (III) to provide Compound (IV).

Examples of reaction solvents include ethers (e.g., dioxane, tetrahydrofuran, diethyl ether, tert-butyl methyl ether, diisopropyl ether), esters (e.g., ethyl formate, ethyl acetate, isopropyl acetate), halogenated hydrocarbons (e.g., dichloromethane, chloroform, carbon tetrachloride), hydrocarbons (e.g., n-hexane, benzene, toluene), alcohols (e.g., methanol, ethanol, isopropanol), amides (e.g., formamide, N,N-dimethylformamide, N,N-dimethylacetamide, N-methylpyrrolidone), ketones (e.g., acetone, methyl ethyl ketone), nitriles (e.g., MeCN, propionitrile), dimethylsulfoxide, water and the like, and mixed solvents and the like thereof.

A reaction temperature is in a range of, general, about 0-100° C., preferably about 0-50° C., more preferably about 10-30° C.

2) 7-Position Amidation and 3-Position Side Chain Formation; Synthesis of Compound (X)

The Fourth Step (7-Position Amidation Reaction):

Compound (IX) is provided by reacting Compound (VI) and Compound (VII), which are commercially available or synthesized according to methods described in literature (e.g., Japanese Laid-Open Publication No. 60-231684, Japanese Laid-Open Publication No. 62-149682, etc.). In this case, preferably, $R^a$ and $R^b$ are carboxy protecting groups, $R^c$ is an amino protecting group, and $R^d$ and $R^e$ are hydrogen.

An amount of Compound (VI) used is in a range of, generally, about 1-5 moles, preferably 1-2 moles, relative to 1 mole of Compound (VII).

Examples of reaction solvents include ethers (e.g., dioxane, tetrahydrofuran, diethyl ether, tert-butyl methyl ether, diisopropyl ether), esters (e.g., ethyl formate, ethyl acetate, isopropyl acetate), halogenated hydrocarbons (e.g., dichloromethane, chloroform, carbon tetrachloride), hydrocarbons (e.g., n-hexane, benzene, toluene), amides (e.g., formamide, N,N-dimethylformamide, N,N-dimethylacetamide, N-methylpyrrolidone), ketones (e.g., acetone, methyl ethyl ketone), nitriles (e.g., MeCN, propionitrile), dimethylsulfoxide, water, and the like, and mixed solvents and the like thereof.

A reaction temperature is in a range of, generally, about −40-80° C., preferably about −20-50° C., more preferably about −10-30° C.

Furthermore, a compound of which T is SO in Compound (IX) can be provided by oxidizing a compound of which T is S in Compound (IX). Examples of oxidizing agents include m-chloroperbenzoic acid (m-CPBA), hydrogen peroxide, peracetic acid, and the like.

The above-described amidation reaction may be carried out after a carboxy moiety is converted to a reactive derivative (e.g., inorganic base salt, organic base salt, acid halide, acid azide, acid anhydride, mixed acid anhydride, active amide, active ester, active thioester). Examples of such inorganic bases include alkali metals (e.g., Na, K, etc.), alkaline-earth metals (e.g., Ca, Mg), and the like. Examples of organic bases include trimethylamine, triethylamine, tert-butyldimethylamine, dibenzylmethylamine, benzyldimethylamine, N-methylmorpholine, diisopropylethylamine, and the like. Examples of acid halides include acid chlorides, acid bromides, and the like. Examples of mixed acid anhydrides include mixed acid anhydrides of mono-alkyl carbonate, mixed acid anhydrides of aliphatic carboxylic acid, mixed acid anhydrides of aromatic carboxylic acid, mixed acid anhydrides of organic sulfonic acid, and the like. Examples of active amides include amides with nitrogen-containing heterocyclic compound, and the like. Examples of active esters include organic phosphoric esters (e.g., diethoxyphosphoric esters, diphenoxyphosphoric esters, and the like), p-nitrophenyl esters, 2,4-dinitrophenyl esters, cyanomethyl esters, and the like. Examples of active thioesters include esters with aromatic heterocyclic thiol compound (e.g., 2-pyridylthiol esters), and the like. Furthermore, in the above-described reaction, a suitable condensing agent may be used as desired. For example, hydrochloric acid salt of 1-dimethylaminopropyl-3-ethylcarbodiimide (WSCD.HCl), N,N'-dicyclohexylcarbodiimide, N,N'-carbonyldiimidazole, N,N'-thiocarbonyldiimidazole, N-ethoxycarbonyl-2-ethoxy-1,2-dihydroquinoline, phosphorus oxychloride, alkoxyacetylene, 2-chloromethylpyridinium iodide, 2-fluoromethylpyridinium iodide, trifluoroacetic anhydride, and the like can be used as a condensing agent.

The Fifth Step (3-Position Side Chain Forming Reaction):

Compound (X) is provided by reacting Compound (IX) and a corresponding tertiary amine (i.e., saturated or unsaturated and monocyclic heterocycle or condensed-ring heterocycle having at least one or more N atoms which may be substituted). In this case, preferably, $R^a$ and $R^b$ are carboxy protecting groups, and $R^e$ is an amino protecting group.

An amount of a corresponding tertiary amine used is in a range of, generally, 1-5 moles, preferably 1-2 moles, relative to 1 mole of Compound (IX).

Examples of reaction solvents include ethers (e.g., dioxane, tetrahydrofuran, diethyl ether, tert-butyl methyl ether, diisopropyl ether), esters (e.g., ethyl formate, ethyl acetate, isopropyl acetate), halogenated hydrocarbons (e.g., dichloromethane, chloroform, carbon tetrachloride), hydrocarbons (e.g., n-hexane, benzene, toluene), amides (e.g., formamide, N,N-dimethylformamide, N,N-dimethylacetamide, N-methylpyrrolidone), ketones (e.g., acetone, methyl ethyl ketone), nitriles (e.g., MeCN, propionitrile), dimethylsulfoxide, water, and the like, and mixed solvents and the like thereof.

A reaction temperature is in a range of, generally, −20-60° C., preferably −10-40° C., more preferably 0-20° C.

Furthermore, a compound of which T is SO in Compound (X) can be provided by reducing the compound of which T is SO in Compound (X). Examples of reducing agents include potassium iodide-acetyl chloride, and the like.

3) 3-Position Side Chain Formation and 7-Position Amidation; Synthesis of Compound (X)

The Sixth Step (3-Position Side Chain Forming Reaction):

Compound (VIII) is provided by reacting Compound (VII) with a corresponding tertiary amine (i.e., saturated or unsaturated and monocyclic heterocycle or condensed-ring heterocycle having at least one or more N atoms which may be substituted). In this case, preferably, $R^b$ is a carboxy protecting group, and $R^e$ is an amino protecting group.

An amount of a corresponding tertiary amine used is in a range of, generally, 1-5 moles, preferably 1-2 moles, relative to 1 mole of Compound (VIII).

Examples of reaction solvents include ethers (e.g., dioxane, tetrahydrofuran, diethyl ether, tert-butyl methyl ether, diisopropyl ether), esters (e.g., ethyl formate, ethyl acetate, isopropyl acetate), halogenated hydrocarbons (e.g., dichloromethane, chloroform, carbon tetrachloride), hydrocarbons (e.g., n-hexane, benzene, toluene), amides (e.g., formamide, N,N-dimethylformamide, N,N-dimethylacetamide, N-methylpyrrolidone), ketones (e.g., acetone, methyl ethyl ketone), nitriles (e.g., MeCN, propionitrile), dimethylsulfoxide, water, and the like, and mixed solvents and the like thereof.

A reaction temperature is in a range of, generally, −20-60° C., preferably −10-40° C., more preferably 0-20° C.

The Seventh Step (7-Position Amidation Reaction):

Compound (X) is provided by reacting Compound (VIII) and Compound (VI). In this case, preferably, $R^a$ and $R^b$ are carboxy protecting groups, $R^c$ is an amino protecting group, $R^d$ and $R^e$ are hydrogen.

An amount of Compound (VI) used is in a range of, generally, about 1-5 moles, preferably 1-2 moles, relative to 1 mole of Compound (VIII).

Examples of reaction solvents include ethers (e.g., dioxane, tetrahydrofuran, diethyl ether, tert-butyl methyl ether, diisopropyl ether), esters (e.g., ethyl formate, ethyl acetate, isopropyl acetate), halogenated hydrocarbons (e.g., dichloromethane, chloroform, carbon tetrachloride), hydrocarbons (e.g., n-hexane, benzene, toluene), amides (e.g., formamide, N,N-dimethylformamide, N,N-dimethylacetamide, N-methylpyrrolidone), ketones (e.g., acetone, methyl ethyl ketone), nitriles (e.g., MeCN, propionitrile), dimethylsulfoxide, and the like, and mixed solvents and the like thereof.

A reaction temperature is in a range of, generally, about −40-80° C., preferably about −20-50° C., more preferably about −10-30° C.

The above-described amidation reaction may be carried out after a carboxy moiety is converted to a reactive derivative (e.g., inorganic base salt, organic base salt, acid halide, acid azide, acid anhydride, mixed acid anhydride, active amide, active ester, active thioester). Examples of such inorganic bases include alkali metal (e.g., Na, K, and the like), alkali earth metal (e.g., Ca, Mg). Examples of organic bases include trimethylamine, triethylamine, tert-butyldimethylamine, dibenzylmethylamine, benzyldimethylamine, N-methylmorpholine, diisopropylethylamine, and the like. Examples of acid halides include acid chlorides, acid bromides, and the like. Examples of mixed acid anhydrides include mixed acid anhydrides of mono-alkyl carbonate, mixed acid anhydrides of aliphatic carboxylic acid, mixed acid anhydrides of aromatic carboxylic acid, mixed acid anhydrides of organic sulfonic acid, and the like. Examples of active amides include amides with nitrogen-containing heterocyclic compound, and the like. Examples of active esters include organic phosphoric esters (e.g., diethoxyphosphoric ester, diphenoxyphosphoric ester, and the like), p-nitrophenyl ester, 2,4-dinitrophenyl ester, cyanomethyl ester, and the like. Examples of active thioesters include esters with aromatic heterocyclic thiol compound (e.g., 2-pyridylthiol esters), and the like. Furthermore, in the above-described reaction, a suitable condensing agent may be used as desired. For example, hydrochloric acid salt of 1-dimethylaminopropyl-3-ethylcarbodiimide (WSCD.HCl), N,N'-dicyclohexylcarbodiimide, N,N'-carbonyldiimidazole, N,N'-thiocarbonyldiimidazole, N-ethoxycarbonyl-2-ethoxy-1,2-dihydroquinoline, phosphorus oxychloride, alkoxyacetylene, 2-chloromethylpyridinium iodide, 2-fluoromethylpyridinium iodide, trifluoroacetic anhydride, and the like can be used as a condensing agent.

Furthermore, a compound of which T is SO in Compound (X) is obtained by reducing the compound of which T is SO in Compound (X). Examples of reducing agents include potassium iodide-acetyl chloride, and the like.

4) Deprotection Reaction

The Eighth Step:

Compound (I) is provided by subjecting Compound (X) to a deprotection reaction with a method well-known to those skilled in the art.

Examples of reaction solvents include ethers (e.g., anisole, dioxane, tetrahydrofuran, diethyl ether, tert-butyl methyl ether, diisopropyl ether), esters (e.g., ethyl formate, ethyl acetate, n-butyl acetate), halogenated hydrocarbons (e.g., dichloromethane, chloroform, carbon tetrachloride), hydrocarbons (e.g., n-hexane, benzene, toluene), amides (e.g., formamide, N,N-dimethylformamide, N,N-dimethylacetamide, N-methylpyrrolidone), ketones (e.g., acetone, methyl ethyl ketone), nitriles (e.g., MeCN, propionitrile), nitoros (e.g., nitromethane, nitroethane, nitrobenzene), dimethylsulfoxide, water, and the like. These solvents may be used alone or in a combination using two or more of such solvents.

A reaction temperature is in a range of, generally, about −30-100° C., preferably about 0-50° C., more preferably about 0-10° C.

As a catalyst, Lewis acid (e.g., $AlCl_3$, $SnCl_4$, $TiCl_4$), protonic acid (e.g., HCl, HBr, $H_2SO_4$, HCOOH), and the like can be used.

The obtained Compound (I) is further chemically modified, and thereby an ester, or a compound of which an amino on the thiazole ring at the 7-position thereof is protected, or a pharmaceutically acceptable salt, or a solvate thereof can be synthesized.

The compounds of the present invention have s wide antimicrobial activity spectrum, and may be used for prevention or therapy against a variety of diseases caused by causative bacteria in a variety of mammals including humans, for example, airway infectious diseases, urinary system infectious diseases, respiratory system infectious diseases, sepsis, nephritis, cholecystitis, oral cavity infectious diseases, endocarditis, pneumonia, bone marrow membrane myelitis, otitis media, enteritis, empyema, wound infectious diseases, opportunistic infection and the like.

The compounds of the present invention are effective in particular against Gram negative bacteria, preferably, Gram negative bacteria of enterobacteria (*E. coli, Klebsiella, Serratia, Enterobacter, Citrobacter, Morganella, Providentia, Proteus* and the like), Gram negative bacteria colonized in respiratory system (*Haemophilus, Moraxella* and the like), and Gram negative bacteria of glucose non fermentation (*Pseudomonas aeruginosa, Pseudomonas* other than *P. aeruginosa, Stenotrophomonas, Burkholdelia, Acinetobacter* and the like). Classes A, B, C and D beta-lactamase produced by these Gram negative bacteria are extremely stable against metallo-beta-lactamase belonging to Class B including in particular IMP type, VIM type, L-1 type and the like, as such, these are effective against a variety of beta-lactam drug resistant Gram negative bacteria including Cephem and Carbapenem. Moreover, the compounds of the present invention has antimicrobial activity against Gram positive bacteria including methicillin resistant *staphylococcus aureus* (MRSA), penicilline resistant *Staphylococcus pneumoniae*, and the like. Still more preferable compounds have features such as blood concentration in which such is highly bioavailable, long duration of effects, and/or significant tissue migration. More preferable compounds are safe in terms of side effects. More preferable compounds have high water solubility, and thus preferable as an injecting drug, in particular.

Compounds (I) may be administered parenterally or orally as an injection agent, capsules, tablets, and granules, and preferably, administered as an injecting agent. Amounts to be administered may be usually, per 1 kg of body weight of a patient or animal, about 0.1-100 mg/day, preferably, about 0.5-50 mg/day, if desired, divided into 2-4 times per day. Carriers when used as an injection agent is for example, distilled water, saline and the like, and further base and the like may be used for pH adjustment. When used as capsules, granules, tablets, carriers may be known excipients (for example, starch, lactose, sucrose, calcium carbonate, calcium phosphate and the like), binders (for example, starch, acacia gum, carboxymethyl cellulose, hydroxypropyl cellulose, crystalline cellulose, and the like), lubricants (for example, magnesium stearate, talc and the like), and the like.

Hereinafter, the present invention is described in more detail with working examples and experimental examples. However, the present invention is not limited to them.

In Examples, the meaning of each abbreviation is as described below.

AcOEt: ethyl acetate
THF: tetrahydrofuran
DMF: N,N-dimethylformamide
PMB-Cl: para-methoxybenzylchloride
i-$Pr_2$O: diisopropyl ether
MeOH: methyl alcohol
NaOH: sodium hydroxide
$Et_3$N: triethylamine
MsCl: methanesulfonylchloride
$MgSO_4$: magnesium sulfate
AcCl: acetylchloride
$AlCl_3$: aluminum chloride
ODS: octadodecylsilyl
MeCN: acetonitrile
DMA: dimethylacetamide
AcOi-Pr: isopropyl acetate
$NaHSO_3$: sodium hydrogen sulfite
$NaHSO_4$: sodium hydrogen sulfate
TFA: trifluoroacetic acid
WSCD.HCl: hydrochloric acid salt of N-ethyl-N'-(3-dimethylaminopropyl)carbodiimide
Me: methyl
Et: ethyl
Pr: propyl
Ph: phenyl
PMB: para-methoxybenzyl
t-Bu: tert-butyl
i-Pr: isopropyl
Boc: tert-butoxycarbonyl
BH: benzhydryl
Ms: methanesulfonyl
Trt: trityl
TBS: tert-butyldimethylsilyl
Bn: benzyl

EXAMPLE 1

Synthesis of Compound (I-1)

[Formula 62]

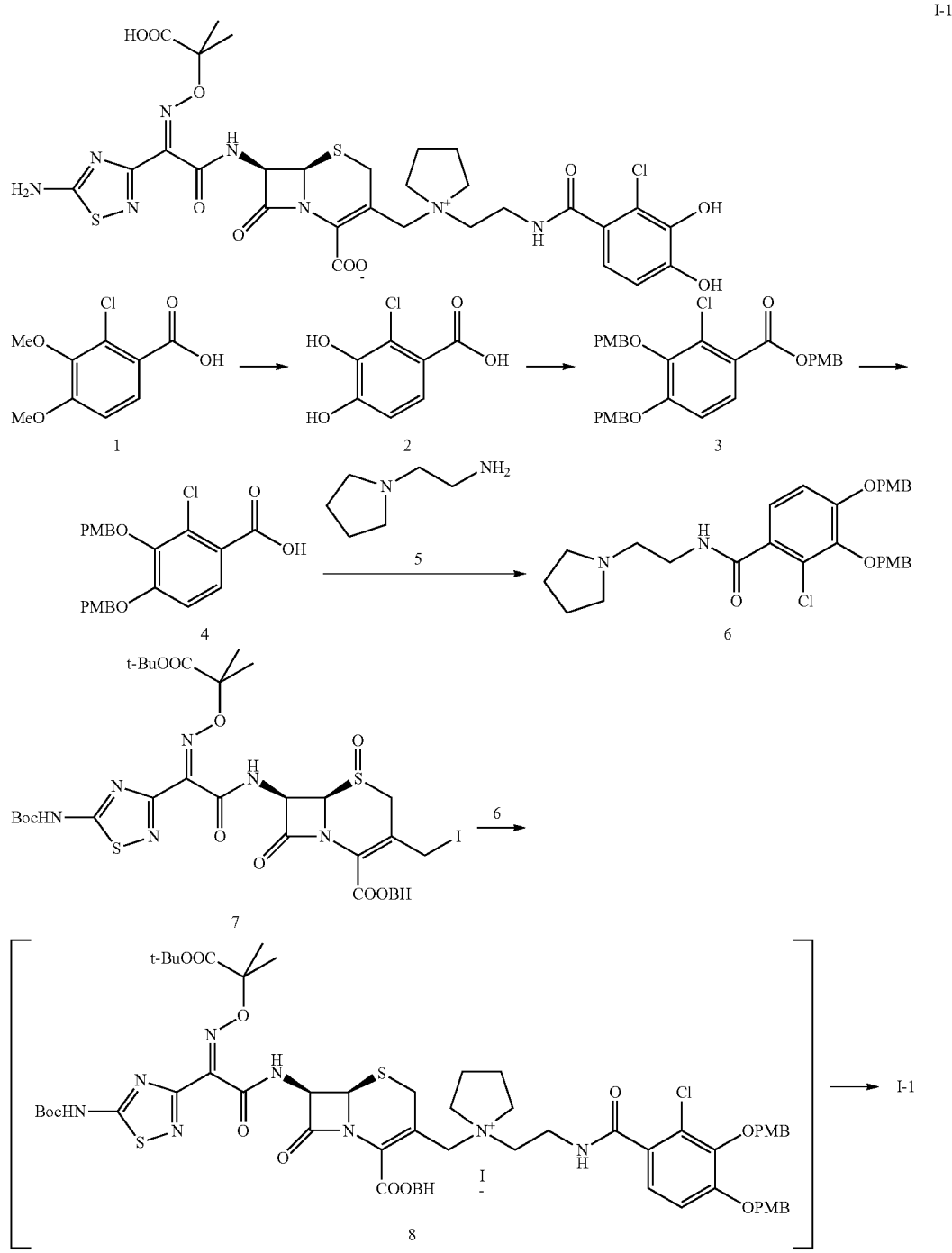

Step (1) Compound 1→Compound 2

A suspension of Compound 1 (10.83 g, 50 mmol) in dichloromethane (100 mL) was cooled to 0° C., and then BBr₃ (18.91 ml, 200 mmol) was added drop-wise thereto over 15 minutes. It was stirred at 0° C. for 15 minutes and then at room temperature for 3 hours. The reaction mixture was poured into 2M hydrochloric acid containing ice, followed by adding AcOEt and THF thereto, and then dichloromethane was evaporated under reduced pressure, subsequently separating the solution. The organic layer was washed with water two times, washed with saturated brine, and then dried over MgSO₄. MgSO₄ was removed by filtration, and then concentration and drying in vacuo yielded Compound 2 as a pale orange powder (5.46 g, 58% yield).

Compound 2:

¹H-NMR (DMSO-d₆) δ (delta): 6.78 (1H, d, J=8.4 Hz), 7.24 (1H, d, J=8.1 Hz), 9.28 (1H, br), 10.38 (1H, br), 12.56 (1H, br).

Step (2) Compound 2→Compound 3

To a solution of Compound 2 (5.43 g, 28.8 mmol) in DMF (58 mL) was added K₂CO₃ (13.93 g, 101 mmol), PMB-Cl (15.69 ml, 115 mmol), and sodium iodide (4.32 g, 28.8 mmol) in turn, followed by stirring at 70° C. for 3 hours. The reaction solution was cooled to room temperature, and then poured into water and AcOEt. At this time, because solid was precipitated, i-Pr₂O was added thereto, and thus the solid was fully precipitated. The solid was filtrated, washed with water, washed with i-Pr₂O, and then air-dried to yield Compound 3 as a pale orange solid (13.5 g, 86% yield).

Compound 3:

¹H-NMR (CDCl₃) δ (delta): 3.80 (3H, s), 3.81 (3H, s), 3.82 (3H, s), 4.93 (2H, s), 5.08 (2H, s), 5.27 (2H, s), 6.81-6.92 (7H, m), 7.32-7.40 (6H, m), 7.63 (1H, d, J=9.0 Hz).

Step (3): Compound 3→Compound 4

To a solution of Compound 3 (13.53 g, 24.64 mmol) in MeOH (100 mL) and THF (100 mL) was added aqueous 2M NaOH solution (37.0 ml, 73.9 mmol), followed by stirring at 70° C. for 80 minutes. After the reaction solution was cooled to room temperature, THF and MeOH were evaporated under reduced pressure, and then AcOEt, 2M hydrochloric acid, and water were added thereto. As a result, solid was precipitated. The solid was filtrated and then air-dried to yield Compound 4 as a white solid (8.58 g, 81% yield).

Compound 4:

¹H-NMR (DMSO-d₆) δ (delta): 3.75 (3H, s), 3.78 (3H, s), 4.88 (2H, s), 5.18 (2H, s), 6.86 (2H, d, J=8.7 Hz), 6.99 (2H, d, J=8.7 Hz), 7.23 (1H, d, J=9.0 Hz), 7.29 (2H, d, J=8.6 Hz), 7.45 (2H, d, J=8.6 Hz), 7.61 (1H, d, J=7.8 Hz).

Step (4): Compound 4→Compound 6

To a solution of Compound 4 (0.858 g, 2 mmol) in DMA (10 mL) was added Et₃N (0.36 ml, 2.6 mmol), followed by cooling to −15° C., and then MsCl (0.187 ml, 2.4 mmol) was added, subsequently further stirring at −15° C. for 1 hour. Compound 5 (0.507 ml, 4 mmol) was added thereto, followed by stirring for 1 hour at −15° C. To the reaction solution was added aqueous 5% sodium hydrogen carbonate solution and AcOEt, and then the solution was separated. After one-time extraction from the aqueous layer with AcOEt, the organic layer was washed with water, and then washed with saturated brine. The organic layer was dried over MgSO₄, subsequently MgSO₄ was removed by filtration, and then concentrated. To the residue AcOi-Pr was added, and then the precipitated solid was filtrated, dried in vacuo to yield Compound 6 as a white solid (0.708 g, 67% yield).

Compound 6:

¹H-NMR (DMSO-d₆) δ (delta): 1.65-1.68 (4H, m), 2.44-2.56 (4H, m), 3.26-3.34 (4H, m), 3.74 (3H, s), 3.76 (3H, s), 4.87 (2H, s), 5.14 (2H, s), 6.86 (2H, d, J=8.7 Hz), 6.97 (2H, d, J=8.7 Hz), 7.11 (1H, d, J=8.7 Hz), 7.18 (1H, d, J=8.7 Hz), 7.30 (2H, d, J=8.7 Hz), 7.42 (2H, d, J=8.7 Hz), 8.22 (1H, t, J=5.7 Hz).

Step (5): Compound 7→Compound (I-1)

To Compound 7 (0.935 g, 1 mmol) and Compound 6 (0.525 g, 1 mmol) DMF (3 mL) was added to dissolve them, followed by stirring at room temperature for 4 hours. DMF (3 mL) was further added thereto, followed by cooling to −40° C., and then potassium iodide (1.16 g, 7 mmol) and AcCl (0.285 ml, 4 mmol) were added thereto, subsequently stirring at 0° C. for 2 hours. The reaction solution was poured into ice water and AcOEt, and then the solution was separated. After one-time extraction from the aqueous layer with AcOEt, the organic layer was washed with water, and then washed with saturated brine. The organic layer was dried over MgSO₄, subsequently MgSO₄ was removed by filtration, and then concentration and subsequent drying in vacuo yielded Compound 8 as a brown oil. This was used for the next reaction without purification.

The whole amount of Compound 8 obtained was dissolved in dichloromethane (15 ml), followed by cooling to −40° C., and then anisole (1.09 ml, 10.00 mmol) and 2M AlCl₃-nitromethane solution (5.00 ml, 10 mmol) were added thereto in turn, subsequently stirring at 0° C. for 90 minutes. To the reaction solution was added 2M hydrochloric acid, MeCN, i-Pr₂O, and hexane that had been cooled to 0° C., subsequently stirring for a while. As a result, insolubles appeared. The supernatant and the insolubles were separated, after the solution of the supernatant was separated, the aqueous layer was combined with the insolubles. 2M hydrochloric acid and MeCN were added thereto, and thus the insolubles were dissolved. HP resin was added thereto, and then MeCN was evaporated under reduced pressure. The resulting mixed solution was purified by HP and ODS chromatography. The resulting solution of the title compound was concentrated in vacuo, and then lyophilized to yield Compound (I-1) as a white powder (246 mg, 33% yield).

Compound (I-1):

¹H-NMR (DMSO-d₆) δ (delta): 1.47 (6H, s), 1.99-2.09 (4H, m), 3.37-3.51 (8H, m), 3.76-3.80 (2H, m), 3.91 (1H, d, J=14.1 Hz), 5.08 (1H, d, J=13.2 Hz), 5.15 (1H, d, J=5.1 Hz), 5.72 (1H, dd, J=5.1, 8.3 Hz), 6.78 (2H, s), 8.21 (2H, m), 8.43 (1H, br), 9.51 (1H, d, J=8.1 Hz).

Elementary analysis for $C_{29}H_{33}ClN_8O_{10}S_2 \cdot 3.6H_2O$

Calcd.: C, 42.58; H, 4.95; Cl, 4.33; N, 13.70; S, 7.84(%).

Found: C, 42.55; H, 4.80; Cl, 4.16; N, 13.72; S, 7.62(%).

EXAMPLE 2

Synthesis of Compound (I-2)

[Formula 63]

I-2

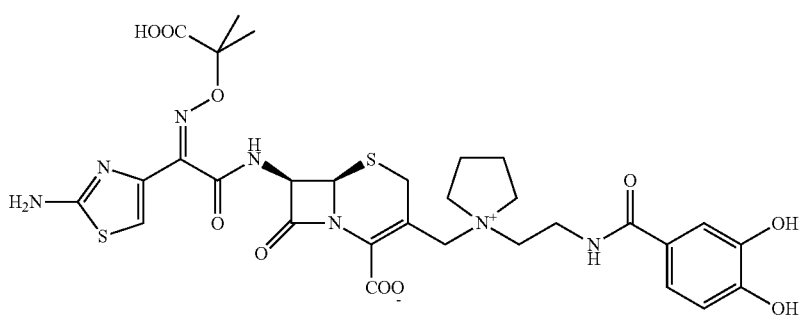

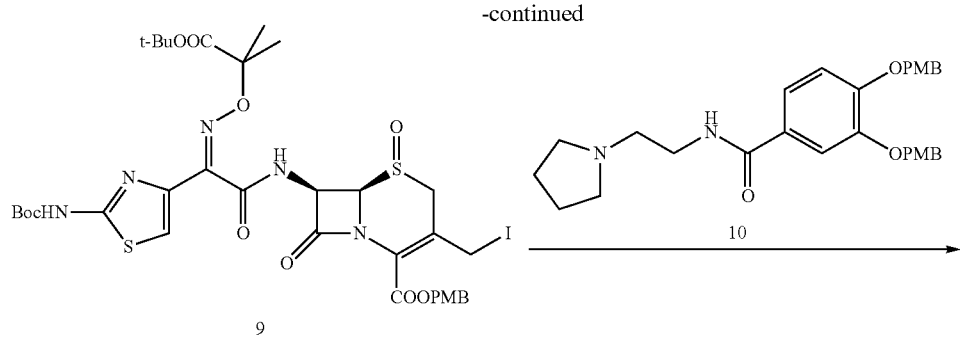

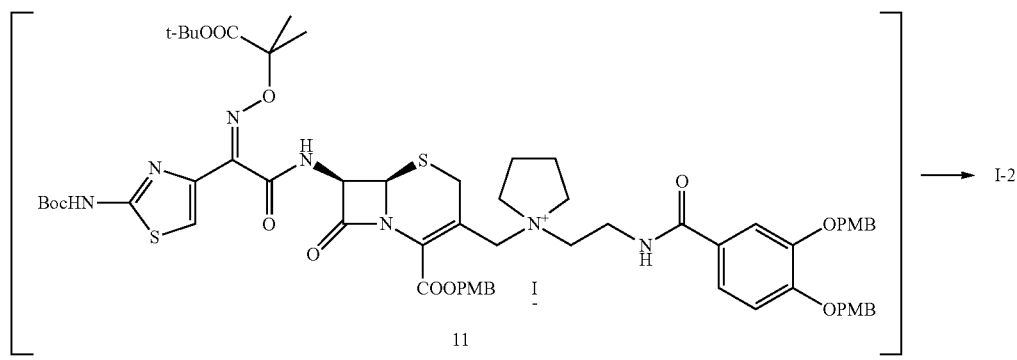

Step (1): Compound 9→Compound (I-2)

To Compound 9 (3.55 g, 4 mmol) and Compound 10 (1.96 g, 4 mmol) was added DMF (10 mL) to dissolve them, followed by stirring at room temperature for 3.5 hours. DMF (20 mL) was further added thereto, followed by cooling to −40° C., and then potassium iodide (4.65 g, 28 mmol) and AcCl (1.14 ml, 16 mmol) were added thereto, subsequently stirring at 0° C. for 1 hour. The reaction solution was poured into ice water and AcOEt, and then the solution was separated. After one-time extraction from the aqueous layer with AcOEt, the organic layer was washed with water, and then washed with saturated brine. The organic layer was dried over $MgSO_4$, followed by $MgSO_4$ was removed by filtration, and then concentration and subsequent drying in vacuo yielded Compound 13 as a reddish brown oil. This was used for the next reaction without purification.

The whole amount of Compound 11 obtained was dissolved in dichloromethane (60 ml), followed by cooling to −40° C., and then anisole (4.37 ml, 40 mmol) and 2M $AlCl_3$-nitromethane solution (20.00 ml, 40.0 mmol) were added thereto in turn, subsequently stirring at 0° C. for 40 minutes. While maintaining the reaction temperature at 0° C., i-$Pr_2O$ was added to the reaction solution, and then 2M hydrochloric acid was added small-portion-wise thereto, subsequently stirring. As a result, insolubles appeared, and then the resulting insolubles gathered and agglomerated. After the supernatant was removed, i-$Pr_2O$ was added to the mass of the insolubles, followed by washing the insolubles, and then the supernatant was discarded. This operation was repeated several times. Ice water and NeON were added to the insolubles to dissolve, and then HP resin was added thereto, subsequently evaporating NeON under reduced pressure. The resulting mixed solution was purified by HP and ODS chromatography. The resulting solution of the title compound was concentrated in vacuo, and subsequently lyophilized to yield Compound (I-2) as a pale yellow powder (0.65 g, 23% yield).

Compound (I-2):

$^1$H-NMR (DMSO-$d_6$) δ (delta): 1.45 (3H, s), 1.46 (3H, s), 1.98-2.08 (4H, m), 3.36-3.48 (8H, m), 3.77-3.84 (2H, m), 3.94 (1H, d, J=13.5 Hz), 5.03 (1H, d, J=13.2 Hz), 5.18 (1H, d, J=5.1 Hz), 5.76 (1H, dd, J=5.1, 8.1 Hz), 6.72 (1H, s), 6.77 (1H, d, J=8.4 Hz), 7.20 (1H, d, J=8.1 Hz), 8.53 (2H, m), 9.23 (1H, s), 9.43 (1H, d, J=8.1), 9.61 (1H, s).

Elementary analysis for $C_{30}H_{25}N_7O_{10}S_2 \cdot 4.9H_2O$

Calcd.: C, 44.70; H, 5.60; N, 12.16; S, 7.96(%).

Found: C, 44.69; H, 5.10; N, 12.28; S, 7.47(%).

EXAMPLE 3
Synthesis of Compound (I-3)
[Formula 64]
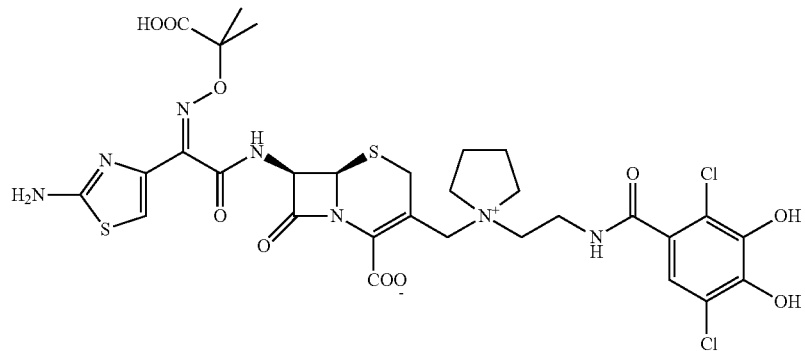
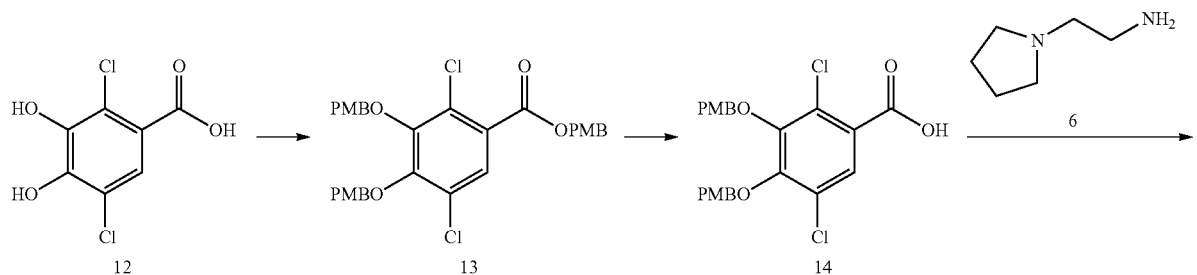
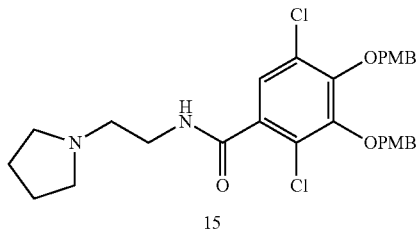
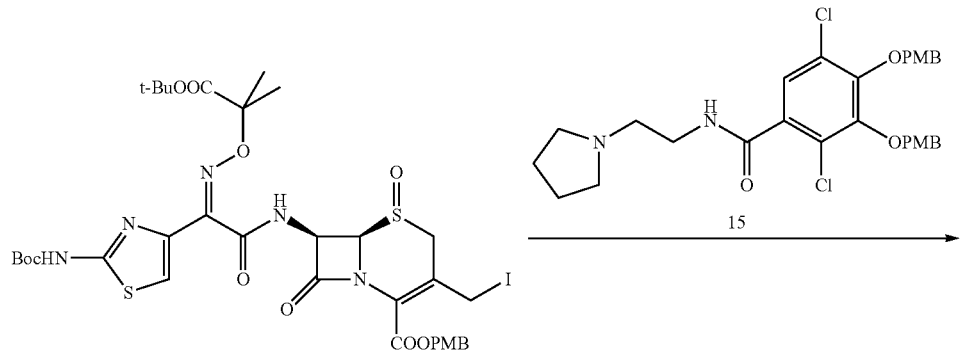

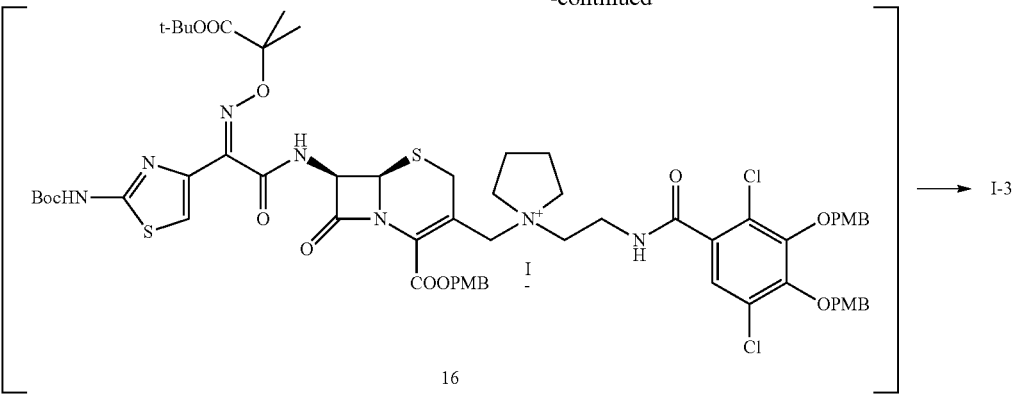

16

Step (1): Compound 12→Compound 13
To a solution of Compound 12 (2.23 g, 10 mmol) in DMF (22 mL) was added K₂CO₃ (4.84 g, 35 mmol), PMBCl (5.45 ml, 40 mmol), and potassium iodide (1.5 g, 10 mmol) in turn, followed by stirring at 70° C. for 1 hour. The reaction solution was cooled to room temperature, and then poured into ice water and AcOEt, followed by separating the solution. After one-time extraction from the aqueous layer with AcOEt, the organic layer was washed with water, and then washed with saturated brine. The organic layer was dried over MgSO₄, subsequently MgSO₄ was removed by filtration, and then concentrated. The crude product was purified by flash column chromatography to yield Compound 13 as a pale yellow liquid (5.37 g, 92% yield).
Compound 13:
¹H-NMR (CDCl₃) δ (delta): 3.816 (3H, s), 3.823 (3H, s), 3.83 (3H, s), 4.97 (2H, s), 5.05 (2H, s), 5.29 (2H, s), 6.86-6.93 (6H, m), 7.33-7.41 (6H, m), 7.65 (1H, s).
Step (2): Compound 13→Compound 14
To a solution of Compound 13 (5.37 g, 9.2 mmol) in MeOH (54 mL) and THF (54 mL) was added aqueous 2M NaOH solution (13.8 ml, 27.6 mmol), followed by stirring at 70° C. for 1 hour. The reaction solution was cooled to room temperature, followed by evaporating THF and MeOH under reduced pressure, and then AcOEt, 2M hydrochloric acid, and water were added thereto, subsequently separating the solution. After one-time extraction from the aqueous layer with AcOEt, the organic layer was washed with water, and then washed with saturated brine. The organic layer was dried over MgSO₄, subsequently MgSO₄ was removed by filtration, and then concentrated. i-Pr₂O was added to the residue, and then the precipitated solid was filtrated, dried in vacuo to yield Compound 14 as a white solid (2.19 g, 52% yield).
Compound 14:
¹H-NMR (DMSO-d₆) δ (delta): 3.76 (3H, s), 3.77 (3H, s), 4.98 (2H, s), 5.06 (2H, s), 6.91-6.97 (4H, m), 7.33-7.39 (4H, m), 7.65 (1H, s).
Step (3): Compound 14→Compound 15
To a solution of Compound 14 (1.390 g, 3 mmol) in DMA (14 mL) was added Et₃N (0.582 ml, 4.2 mmol), followed by cooling to −15° C., and then MsCl (0.304 ml, 3.9 mmol) was added, subsequently stirring at −15° C. for 70 minutes. Compound 5 (0.760 ml, 6 mmol) was added thereto, followed by further stirring at −15° C. for 1 hour. To the reaction solution was added water and AcOEt, followed by separating the solution. After one-time extraction from the aqueous layer with AcOEt, the organic layer was washed with water, and then washed with saturated brine. The organic layer was dried over MgSO₄, subsequently MgSO₄ was removed by filtration, and then the filtrate was concentrated. The crude product was purified by flash column chromatography to yield Compound 15 as a white powder (1.01 g, 60% yield).
¹H-NMR (CDCl₃) δ (delta): 1.81 (4H, br), 2.61 (4H, br), 2.75 (2H, m), 3.56-3.58 (2H, m), 3.823 (3H, s), 3.828 (3H, s), 4.98 (2H, s), 5.01 (2H, s), 6.87-6.92 (4H, m), 7.36-7.40 (4H, m), 7.47 (1H, s).
Step (4): Compound 9→Compound (I-3)
A solution of Compound 15 (0.89 g, 1.59 mmol) in DMF (5 mL) was degassed, and then Compound 9 (f=0.92) (1.54 g, 1.59 mmol) was added thereto, followed by stirring at room temperature for 5 hours. DMF (10 mL) was further added thereto, followed by cooling to −40° C., and then potassium iodide (1.85 g, 11.1 mmol) and AcCl (0.454 ml, 6.36 mmol) were added thereto, subsequently stirring at 0° C. for 2 hours. The reaction solution was poured into ice water and AcOEt, and then NaHSO₃ was added thereto, followed by separating the solution. After one-time extraction from the aqueous layer with AcOEt, the organic layer was washed with water, and then washed with saturated brine. The organic layer was dried over MgSO₄, subsequently MgSO₄ was removed by filtration, and then the filtrate was concentrated and subsequent drying in vacuo yielded Compound 16 as an orange powder. This was used for the next reaction without purification.
The whole amount of Compound 16 obtained was dissolved in dichloromethane (20 ml), followed by cooling to −40° C., and then anisole (1.74 ml, 15.9 mmol) and 2M AlCl₃-nitromethane solution (7.96 ml, 15.9 mmol) were added thereto in turn, subsequently stirring at 0° C. for 90 minutes. While maintaining the reaction temperature at 0° C., i-Pr₂O was added to the reaction solution, and then 2M hydrochloric acid was added small-portion-wise, subsequently stirring. As a result, insolubles appeared, and then the resulting insolubles gathered and agglomerated. After the supernatant was removed, i-Pr₂O was added to the mass of the insolubles, followed by washing the insolubles, and then the supernatant was discarded. This operation was repeated several times. Ice water and MeCN were added to the insolubles, followed by dissolving it, and then HP resin was added, subsequently evaporating MeCN under reduced pressure. The resulting mixed solution was purified by HP and ODS chromatography. The obtained solution of the title compound was concentrated in vacuo, and subsequently lyophilized to yield Compound (I-3) as a white powder (498 mg, 40% yield).
Compound (I-3):
¹H-NMR (DMSO-d₆) δ (delta): 1.44 (3H, s), 1.45 (3H, s), 2.04-2.09 (4H, m), 3.28-3.54 (8H, m), 3.75-3.86 (2H, m), 3.92 (1H, d, J=13.5 Hz), 5.05 (1H, d, J=13.5 Hz), 5.17 (1H, d, J=5.1 Hz), 5.73 (1H, dd, J=4.8, 8.1 Hz), 6.72 (1H, s), 6.98 (1H, s), 7.29 (2H, br), 8.58 (1H, m), 9.43 (1H, d, J=8.1 Hz).

Elementary analysis for $C_{30}H_{33}Cl_2N_7O_{10}S_2 \cdot 3.5H_2O$
Calcd.: C, 42.41; H, 4.74; Cl, 8.34; N, 11.54; S, 7.55(%).
Found: C, 42.54; H, 4.80; Cl, 7.78; N, 11.58; S, 7.45(%).

EXAMPLE 4

Synthesis of Compound (I-4)

Step (1): Compound 4→Compound 18

To a solution of Compound 4 (3.43 g, 8 mmol) in DMA (35 mL) was added $Et_3N$ (1.55 ml, 11.2 mmol), followed by cooling to −15° C., and then MsCl (0.810 ml, 10.4 mmol) was added, subsequently stirring at −15° C. for 1 hour. Compound 17 (2.02 ml, 16 mmol) was added thereto, followed by further stirring at −15° C. for 1 hour. Water and AcOEt was added to the reaction solution, and then separated. After one-time extraction from the aqueous layer with AcOEt, the organic layer was washed with water, and then washed with saturated brine. The organic layer was dried over $MgSO_4$, subsequently

[Formula 65]

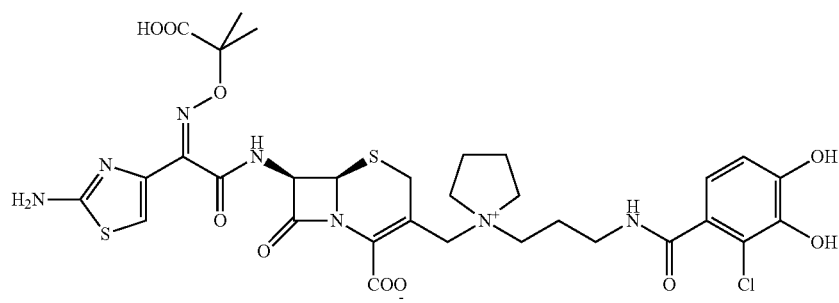

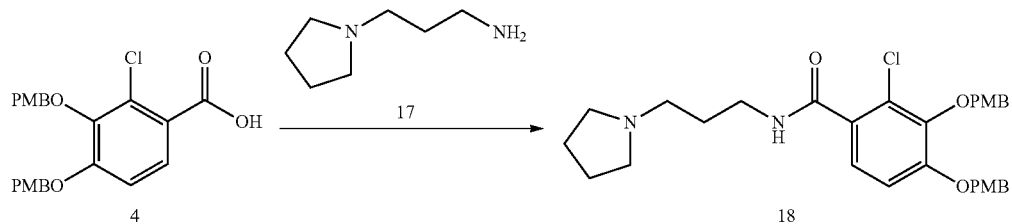

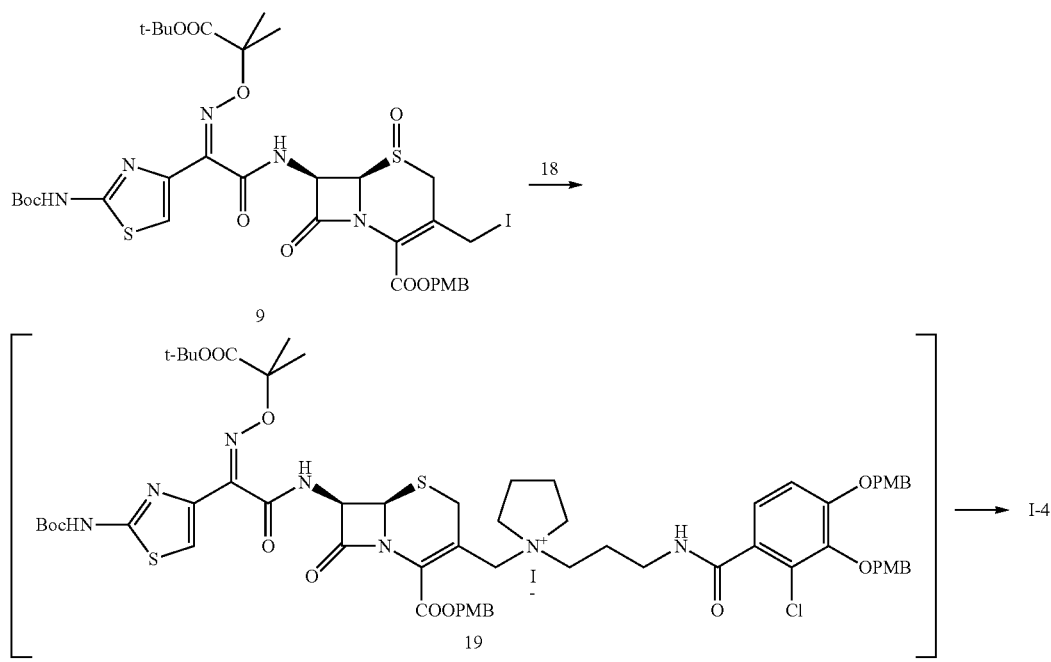

MgSO₄ was removed by filtration, and then the filtrate was concentrated. AcOi-Pr was added to the residue, and then the precipitated solid was filtrated, dried in vacuo to yield Compound 18 as a white solid (2.98 g, 69% yield).

Compound 18:

$^1$H-NMR (CDCl$_3$) δ (delta): 1.67 (4H, br), 1.77-1.81 (2H, m), 2.48 (4H, br), 2.62 (2H, t, J=6.3 Hz), 3.55 (2H, q, J=6.0 Hz), 3.80 (3H, s), 3.83 (3H, s), 4.94 (2H, s), 5.07 (2H, s), 6.84 (2H, d, J=8.4 Hz), 6.90-6.93 (3H, m), 7.34-7.37 (5H, m), 7.76 (1H, m).

Step (2): Compound 9→Compound (I-4)

A solution of Compound 18 (1.62 g, 3 mmol) in DMF (8 mL) was degassed, and then Compound 9 (f=0.92) (2.89 g, 3 mmol) was added thereto, followed by stirring at room temperature for 4.5 hours. DMF (16 mL) was further added thereto, followed by cooling to −40° C., and then potassium iodide (3.49 g, 21 mmol) and AcCl (0.856 ml, 12 mmol) were added thereto, subsequently stirring at 0° C. for 1 hour. To the reaction solution was poured ice water and AcOEt, and then NaHSO₃ was added, followed by separating the solution. After one-time extraction from the aqueous layer with AcOEt, the organic layer was washed with water, and then washed with saturated brine. The organic layer was dried over MgSO₄, subsequently MgSO₄ was removed by filtration, and then concentration and drying in vacuo yielded Compound 19 as a brown powder. This was used for the next reaction without purification.

The whole amount of Compound 19 obtained was dissolved in dichloromethane (40 ml), followed by cooling to −40° C., and then anisole (3.28 ml, 30 mmol) and 2M AlCl₃-nitromethane solution (15 ml, 30 mmol) were added thereto in turn, subsequently stirring at 0° C. for 2 hours. While maintaining the reaction temperature at 0° C., i-Pr₂O was added to the reaction solution, and then 2M hydrochloric acid was added small-portion-wise thereto, subsequently stirring. As a result, insolubles appeared, and then the resulting insolubles gathered and agglomerated. After the supernatant was removed, i-Pr₂O was added to the mass of the insolubles, followed by washing the insolubles, and then the supernatant was discarded. This operation was repeated several times. Ice water and MeCN were added to the insolubles, followed by dissolving it, and then HP resin was added thereto, subsequently evaporating MeCN under reduced pressure. The resulting mixed solution was purified by HP and ODS chromatography. The resulting solution of the title compound was concentrated in vacuo, and subsequently lyophilized to yield Compound (I-4) as a white powder (0.56 g, 24% yield).

Compound (I-4):

$^1$H-NMR (DMSO-d$_6$) δ (delta): 1.21 (3H, s), 1.22 (3H, s), 1.72-1.82 (6H, m), 3.19 (8H, m), 3.64 (2H, d, J=16.8 Hz), 3.71 (1H, d, J=13.8 Hz), 4.68 (1H, d, J=14.1 Hz), 4.94 (1H, d, J=5.1 Hz), 5.50-5.55 (1H, m), 6.49 (1H, s), 6.53 (2H, d, J=3.3 Hz), 7.07 (2H, br), 8.17 (1H, m), 9.04 (1H, br), 9.20 (1H, d, J=8.7), 9.90 (1H, br).

Elementary analysis for C$_{31}$H$_{36}$ClN$_7$O$_{10}$S$_2$·4.6H$_2$O
Calcd.: C, 43.85; H, 5.37; Cl, 4.18; N, 11.55; S, 7.55(%).
Found: C, 43.81; H, 5.19; Cl, 5.63; N, 11.58; S, 7.36(%).

EXAMPLE 5

Synthesis of Compound (I-5)

[Formula 66]

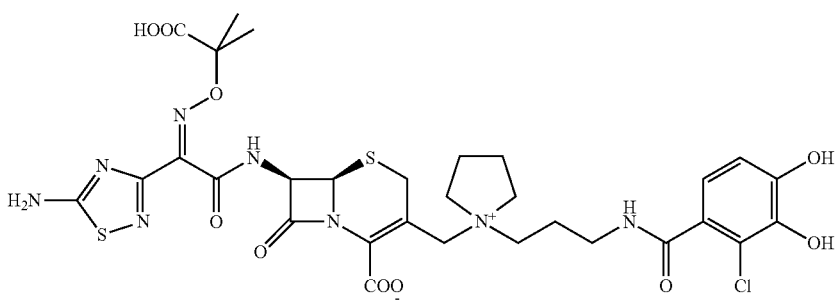

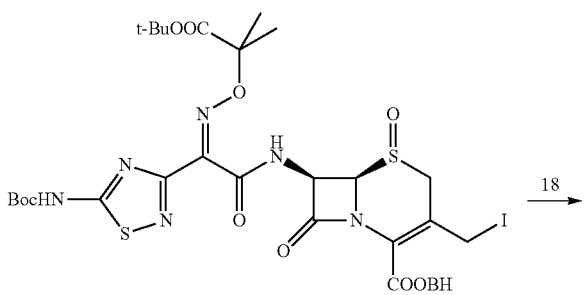

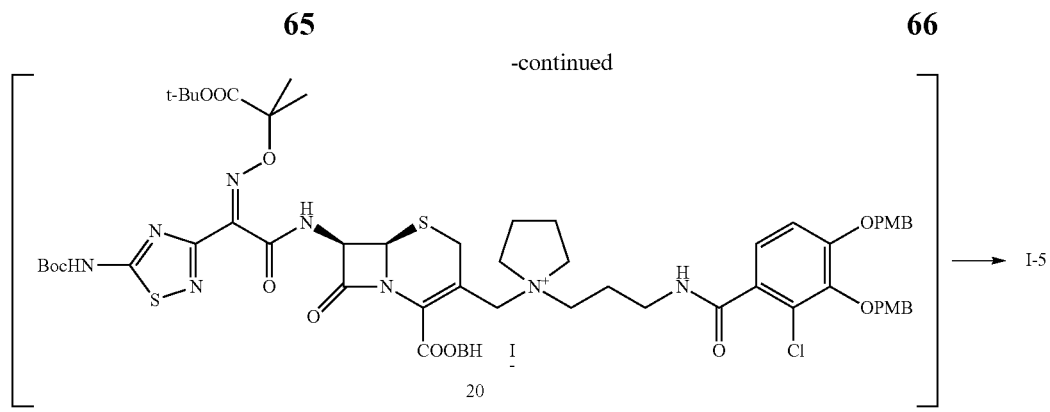

Step (1):

A solution of Compound 18 (1.62 g, 3 mmol) in DMF (9 mL) was degassed, and then Compound 7 (2.80 g, 3 mmol) was added thereto, followed by stirring at room temperature for 4.5 hours. DMF (18 mL) was further added thereto, followed by cooling to −40° C., potassium iodide (3.49 g, 21 mmol) and AcCl (0.856 ml, 12 mmol) were added, subsequently stirring at 0° C. for 2 hours. Ice water and AcOEt was poured to the reaction solution, and then NaHSO$_3$ was added, followed by separating the solution. After one-time extraction from the aqueous layer with AcOEt, the organic layer was washed with water, and then washed with saturated brine. The organic layer was dried over MgSO$_4$, subsequently MgSO$_4$ was removed by filtration, and then concentration and drying in vacuo yielded Compound 20 as a brown powder. This was used for the next reaction without purification.

The whole amount of Compound 20 obtained was dissolved in dichloromethane (40 ml), followed by cooling to −40° C., and then anisole (3.28 ml, 30 mmol) and 2M AlCl$_3$-nitromethane solution (15 ml, 30 mmol) were added in turn, subsequently stirring at 0° C. for 3 hours. While maintaining the reaction temperature at 0° C., i-Pr$_2$O was added to the reaction solution, and then 2M hydrochloric acid was added small-portion-wise thereto, subsequently stirring. As a result, insolubles appeared, and then the resulting insolubles gathered and agglomerated. After the supernatant was removed, to the mass of the insolubles was added i-Pr$_2$O, followed by washing the insolubles, and then the supernatant was discarded. This operation was repeated several times. Ice water and MeCN were added to the insolubles to dissolve, and then HP resin was added thereto, subsequently evaporating MeCN under reduced pressure. The resulting mixed solution was purified by HP and ODS chromatography. The obtained solution of the title compound was concentrated in vacuo, and subsequently lyophilized to yield Compound (I-5) as pale yellow powder (188 mg, 8% yield).

Compound (I-5):

$^1$H-NMR (DMSO-d$_6$) δ (delta): 1.46 (6H, s), 1.95-2.07 (6H, m), 3.27-3.37 (8H, m), 3.77-3.83 (3H, m), 5.02 (1H, d, J=14.1 Hz), 5.08 (1H, d, J=4.8 Hz), 5.64 (1H, dd, J=4.8, 8.4 Hz), 6.71-6.79 (2H, m), 8.20 (2H, br), 8.50 (1H, m), 9.23 (1H, br), 9.50 (1H, d, J=7.5).

Elementary analysis for C$_{30}$H$_{35}$ClN$_8$O$_{10}$S$_2$·4.5H$_2$O

Calcd.: C, 42.48; H, 5.23; Cl, 4.18; N, 13.21; S, 7.56(%).
Found: C, 42.64; H, 5.09; Cl, 3.91; N, 13.07; S, 7.17(%).

EXAMPLE 6

Synthesis of Compound (I-6)

[Formula 67]

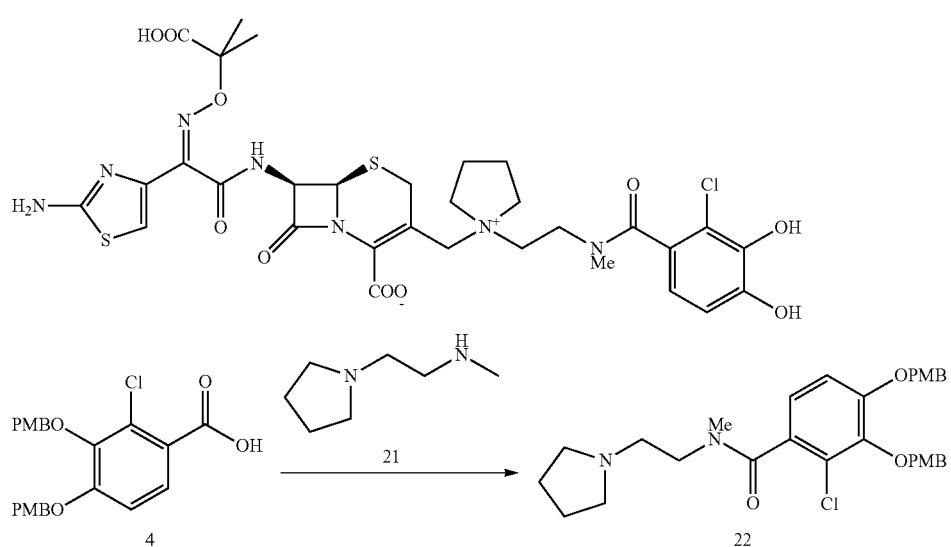

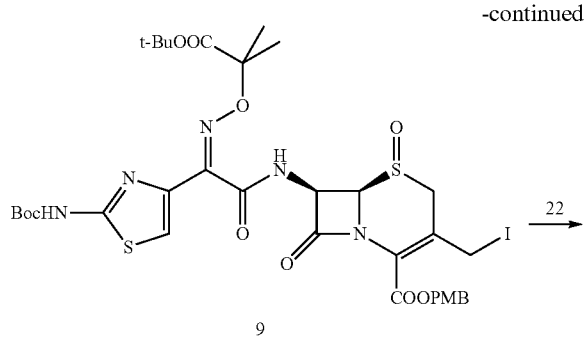

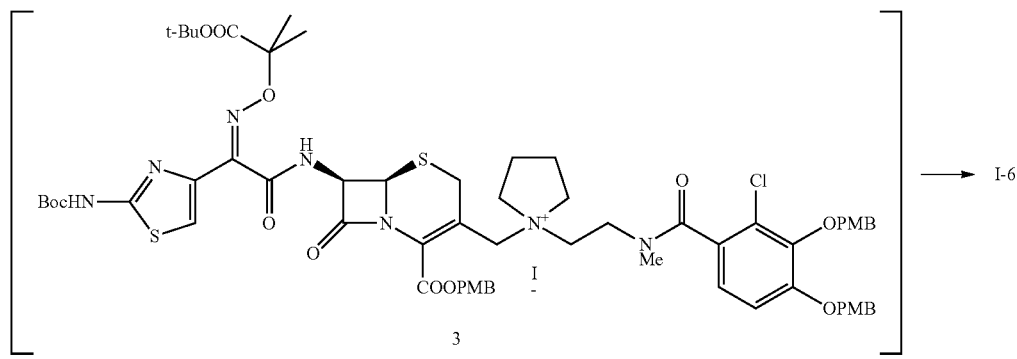

Step (1): Compound 4→Compound 22

To a solution of Compound 4 (2.57 g, 6 mmol) in DMA (25 mL) was added Et$_3$N (1.16 ml, 8.4 mmol), followed by cooling to −15° C., and then MsCl (0.608 ml, 7.8 mmol) was added, subsequently stirring at −15° C. for 50 minutes. Compound 21 (1.81 g, 12 mmol) was added thereto, followed by further stirring at −15° C. for 70 minutes. Water and AcOEt was added to the reaction solution, subsequently separating the solution. After one-time extraction from the aqueous layer with AcOEt, the organic layer was washed with water, and then washed with saturated brine. The organic layer was dried over MgSO$_4$, subsequently MgSO$_4$ was removed by filtration, and then concentrated. The crude product was combined with unpurified Compound 22 (4 mmol), which had been synthesized elsewhere, and then was purified by flash column chromatography to yield Compound 22 as a yellow oil (4.87 g, 84% yield).

Compound 22:

$^1$H-NMR (CDCl$_3$) δ (delta): 1.68 (2H, s), 1.77-1.80 (2H, m), 2.28-2.30 (2H, m), 2.53-2.60 (3H, m), 2.75 (1H, t, J=7.2), 2.81 (1.5H, s), 3.12 (1.5H, s), 3.17 (1H, m), 3.79 (3H, s), 3.83 (3H, s), 4.97 (2H, s), 5.05 (2H, s), 6.80-6.84 (2H, m), 6.89-6.97 (4H, m), 7.31-7.36 (4H, m).

Step (2): Compound 9→Compound (I-6)

A solution of Compound 22 (f=0.95) (1.70 g, 3 mmol) in DMF (8 mL) was degassed, and then Compound 9 (f=0.92) (2.89 g, 3 mmol) was added thereto, followed by stirring at room temperature for 4 hours. DMF (16 mL) was further added thereto, followed by cooling to −40° C., and then potassium iodide (3.49 g, 21 mmol) and AcCl (0.856 ml, 12 mmol) were added thereto, subsequently stirring at 0° C. for 1 hour. Ice water and AcOEt were poured to the reaction solution, and then NaHSO$_3$ was added, followed by separating the solution. After one-time extraction from the aqueous layer with AcOEt, the organic layer was washed with water, and then washed with saturated brine. The organic layer was dried over MgSO$_4$, subsequently MgSO$_4$ was removed by filtration, and then concentration and drying in vacuo yielded Compound 23 as an orange powder. This was used for the next reaction without purification.

The whole amount of Compound 23 obtained was dissolved in dichloromethane (40 ml), followed by cooling to −40° C., and then anisole (3.28 ml, 30 mmol) and 2M AlCl$_3$-nitromethane solution (15 ml, 30 mmol) were added thereto in turn, subsequently stirring at 0° C. for 1 hour. While maintaining the reaction temperature at 0° C., i-Pr$_2$O was added to the reaction solution, and then 2M hydrochloric acid was added small-portion-wise thereto, subsequently stirring. As a result, insolubles appeared, and then the resulting insolubles gathered and agglomerated. After the supernatant was removed, i-Pr$_2$O was added to the mass of the insolubles, followed by washing the insolubles, and then the supernatant was discarded. This operation was repeated several times. Ice water and MeCN were added to the insolubles, followed by dissolving it, and then HP resin was added thereto, subsequently evaporating MeCN under reduced pressure. The resulting mixed solution was purified by HP and ODS chromatography. The obtained solution of the title compound was concentrated in vacuo, and subsequently lyophilized to yield Compound (I-6) as a white powder (0.94 g, 41% yield).

Compound (I-6):

$^1$H-NMR (DMSO-d$_6$) δ (delta): 1.43 (3H, s), 1.44 (3H, s), 2.06 (4H, m), 2.80 (3H, s), 3.43 (8H, br), 3.71-3.87 (2H, m), 3.99 (1H, d, J=13.5 Hz), 5.03 (1H, d, J=13.5 Hz), 5.15 (1H, d, J=5.1 Hz), 5.72 (1H, dd, J=5.1, 8.4 Hz), 6.56 (1H, d, J=8.1 Hz), 6.71 (1H, s), 6.80 (1H, d, J=8.1 Hz), 7.27 (2H, br), 9.43 (1H, d, J=8.1 Hz).

Elementary analysis for C$_{31}$H$_{36}$ClN$_7$O$_{10}$S$_2$.4.2H$_2$O
Calcd.: C, 44.22; H, 5.32; Cl, 4.21; N, 11.65; S, 7.62(%).
Found: C, 44.20; H, 5.32; Cl, 4.25; N, 11.73; S, 7.84(%).

EXAMPLE 7

Synthesis of Compound (I-7)

[Formula 68]

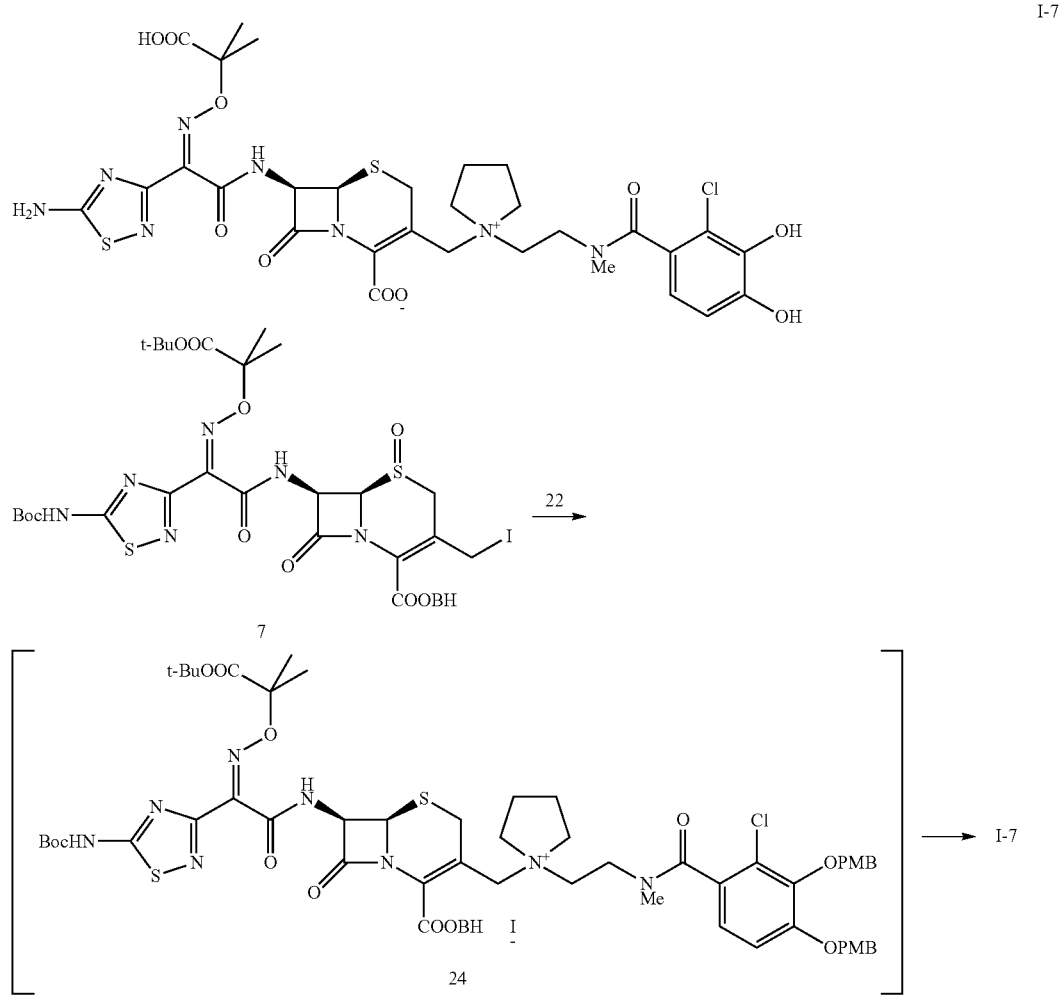

Step (1): Compound 7→Compound (I-7)

A solution of Compound 22 (f=0.95) (1.70 g, 3 mmol) in DMF (8 mL) was degassed, and then Compound 7 (2.80 g, 3 mmol) was added thereto, followed by stirring at room temperature for 4 hours. DMF (16 mL) was further added thereto, followed by cooling to −40° C., and then potassium iodide (3.49 g, 21 mmol) and AcCl (0.856 ml, 12 mmol) were added, subsequently stirring at 0° C. for 1.5 hours. To the reaction solution was poured ice water and AcOEt, and then NaHSO$_3$ was added, followed by separating the solution. After one-time extraction from the aqueous layer with AcOEt, the organic layer was washed with water, and then washed with saturated brine. The organic layer was dried over MgSO$_4$, subsequently MgSO$_4$ was removed by filtration, and then concentration and drying in vacuo yielded Compound 24 as a brown powder. This was used for the next reaction without purification.

The whole amount of Compound 24 obtained was dissolved in dichloromethane (40 ml), followed by cooling to −40° C., and then anisole (3.28 ml, 30 mmol) and 2M AlCl$_3$-nitromethane solution (15 ml, 30 mmol) were added in turn, subsequently stirring at 0° C. for 1 hour. While maintaining the reaction temperature at 0° C., i-Pr$_2$O was added to the reaction solution, and then 2M hydrochloric acid was added small-portion-wise thereto, subsequently stirring. As a result, insolubles appeared, and then the resulting insolubles gathered and agglomerated. After the supernatant was removed, i-Pr$_2$O was added to the mass of the insolubles, followed by washing the insolubles, and then the supernatant was discarded. This operation was repeated several times. Ice water and MeCN were added to the insolubles to dissolve it, and then HP resin was added thereto, subsequently evaporating MeCN under reduced pressure. The resulting mixed solution was purified by HP and ODS chromatography. The obtained solution of the title compound was concentrated in vacuo, and subsequently lyophilized to yield Compound (I-7) as a white powder (0.78 g, 34% yield).

Compound (I-7):

$^1$H-NMR (DMSO-d$_6$) δ (delta): 1.47 (6H, s), 2.07 (4H, br), 2.82 (3H, s), 3.35-3.57 (8H, m), 3.76-3.88 (2H, m), 4.01 (1H, d, J=12.9 Hz), 5.06 (1H, d, J=13.5 Hz), 5.16 (1H, d, J=5.1 Hz), 5.73 (1H, dd, J=5.4, 8.4 Hz), 6.58 (1H, d, J=7.8 Hz), 6.82 (1H, d, J=8.1 Hz), 8.21 (2H, br), 9.49 (1H, d, J=8.4).

Elementary analysis for $C_{30}H_{35}ClN_8O_{10}S_2 \cdot 4.1H_2O$
Calcd.: C, 42.84; H, 5.18; Cl, 4.22; N, 13.32; S, 7.62(%).
Found: C, 42.81; H, 5.10; Cl, 4.30; N, 13.36; S, 7.77(%).

EXAMPLE 8

Synthesis of Compound (I-8)

[Formula 69]

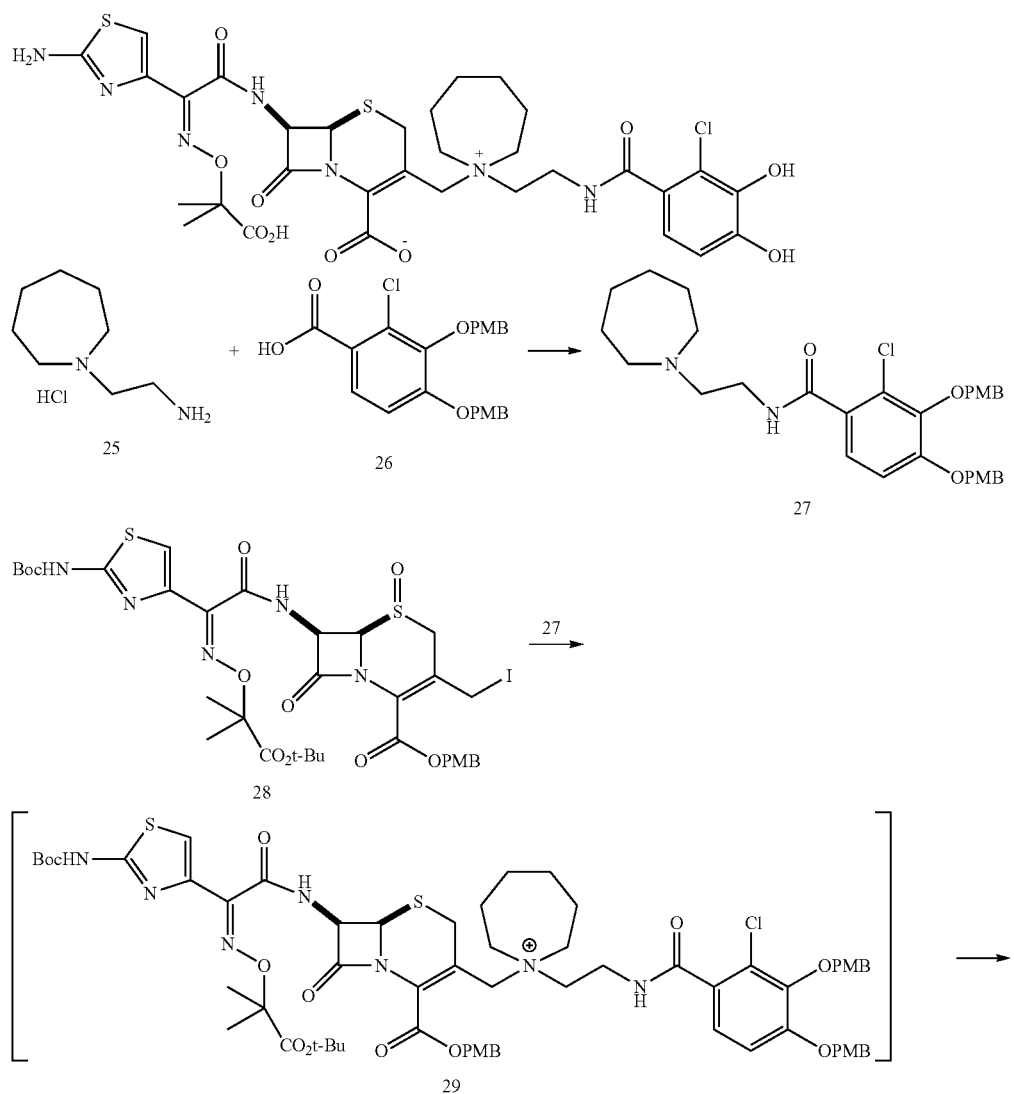

pressure. Isopropyl ether was added to the residue to precipitate solid, and then collected to yield Compound 27 (1.90 g, 98% yield).

Compound 27:
$^1$H-NMR (CDCl$_3$) δ (delta): 1.48-1.85 (8H, m), 2.63-2.75 (6H, m), 3.40-3.50 (2H, m), 3.80 (3H, s), 3.83 (3H, s), 6.80-6.84 (2H, m), 6.85-7.00 (3H, m), 7.15-7.20 (1H, m), 7.32-7.37 (m, 3H), 7.48-7.52 (1H, m).

Step (1): Compound 25→Compound 27

To a solution of Compound 26 (1.25 g, 7.0 mmol) in dimethylacetamide (12 mL) was added triethylamine (2.43 mL, 17.5 mmol), followed by cooling to −15° C., and then methanesulfonyl chloride (0.35 mL, 4.55 mmol) was added, subsequently stirring for 1 hour at −15° C. Then a solution of Compound 25 in dimethylacetamide (5 mL) was added thereto, followed by stirring for 1 hour. Into the reaction solution was added ethyl acetate (50 mL) and 5% sodium hydrogen carbonate solution. The organic layer was washed with water, washed with saturated brine, dried over magnesium sulfate, filtrated, and then evaporated under reduced Step (2): Compound 28→Compound 29→Compound (I-8)

Compound 28 (888 mg, 1 mmol) and Compound 27 (553 mg, 1 mmol) were dissolved in dimethylformamide (2 mL), followed by stirring at room temperature for 3 hours. Dimethylformamide (2 mL) and potassium iodide (1.16 g, 7 mmol) were added thereto, followed by cooling to −40° C., and then acetyl chloride (0.285 mL, 4 mmol) was added thereto, subsequently stirring at 0° C. for 1 hour. To the reaction solution was added water and ethyl acetate. The organic layer was washed with water, washed with saturated brine, dried over magnesium sulfate, filtrated, and then evaporated under reduced pressure to yield Compound 29 as a powder.

Compound 29 was dissolved in methylene chloride (10 ml) and anisole (1 ml), followed by cooling to −40° C. 2M AlCl$_3$-nitromethane solution (5 ml) was added, subsequently stirring at 0° C. for 50 minutes. To the reaction solution was added aqueous 2M HCl (60 ml), acetonitrile (50 ml), and ether (100 ml). The aqueous layer was washed with ether, concentrated in vacuo, and then subjected into HP-20SS column chromatography eluting the desired compound with acetonitrile-water. Collected fractions were concentrated in vacuo. The concentrated solution was lyophilized to yield Compound (1-8) as a white powder (252 mg, 32% yield).

Compound (I-8):
$^1$H-NMR (D$_2$O) δ (delta): 1.49 (3H, s), 1.50 (3H, s), 1.60-1.80 (4H, m), 1.82-2.10 (4H, m), 3.39-3.70 (6H, m), 3.72-3.85 (4H, m), 3.93 (1H, d, J=13.8 Hz), 4.14 (1H, d, J=13.8 Hz), 5.36 (1H, d, J=5.1 Hz), 5.87 (1H, d, J=5.1 Hz), 6.70-6.72 (2H, m), 6.98 (1H, s).

Elementary analysis for C$_{32}$H$_{38}$ClN$_7$O$_{10}$S$_2$·4.8H$_2$O
Calcd.: C, 44.34; H, 5.54; Cl, 4.09; N, 11.31; O, 27.32; S, 7.40(%).
Found: C, 44.51; H, 5.39; Cl, 3.79; N, 11.30; S, 7.44(%).

EXAMPLE 9

Synthesis of Compound (I-9)

[Formula 70]

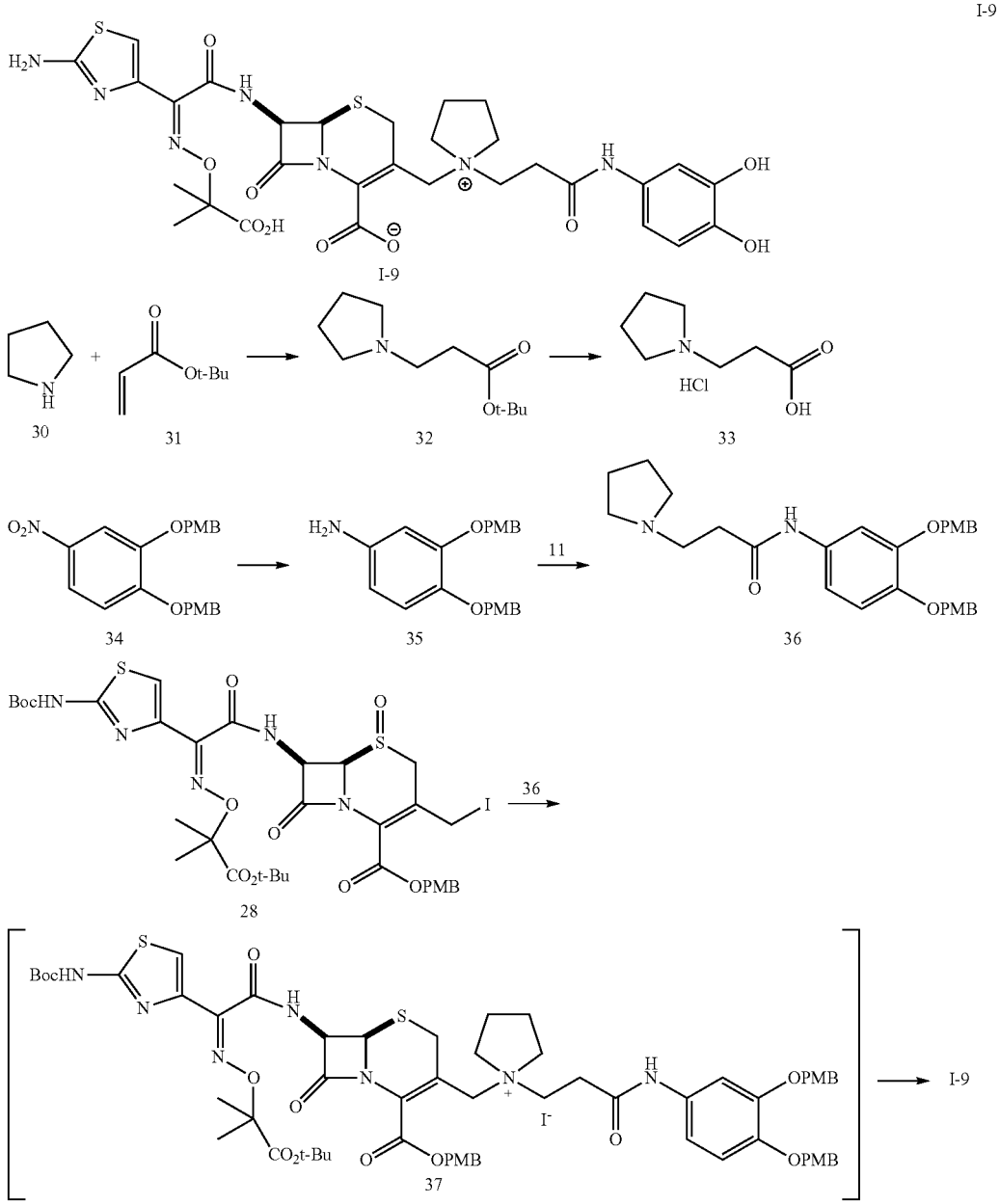

Step (1): Compound 30→Compound 32

To a solution of Compound 31 (2 g, 28.1 mmol) in THF (10 mL) was added Compound 30 (5.41 g, 42.2 mmol), followed by stirring at room temperature for 2 hours. Ethyl acetate and water were added thereto, followed by extraction from the aqueous layer with ethyl acetate, and then the organic layer was washed with saturated brine. The organic layer was dried over magnesium sulfate, filtrated, and then concentrated in vacuo to yield the title compound 32 (4.98 g, 89% yield).

Compound 32:

$^1$H-NMR (CDCl$_3$) δ (delta): 1.46 (9H, s), 1.74-1.80 (4H, m), 2.40-2.60 (m, 6H), 2.70-2.75 (m, 2H).

Step (2): Compound 32→Compound 33

To a solution of Compound 32 (4.98 g, 25 mmol) in methylene chloride (20 mL) was added trifluoroacetic acid (20 mL), followed by stirring overnight. After concentration in vacuo, 4M HCl in ethyl acetate solution (9.37 mL, 37.5 mmol) was added thereto. The precipitated solid of Compound 33 was washed with ethyl acetate (3.74 g, 83% yield).

Compound 33:

$^1$H-NMR (D$_2$O) δ (delta): 1.95-2.20 (4H, m), 2.84-2.89 (2H, m), 3.10-3.20 (2H, m), 3.44-3.52 (2H, m), 3.62-3.80 (2H, m).

Step (3): Compound 34→Compound 35

A solution of Compound 34 (7.08 g, 17.9 mmol) in ethyl acetate (350 mL) and methylene chloride (100 mL) was degassed under reduced pressure, and then replaced with nitrogen. Platinum dioxide (350 mg, 1.54 mmol) was added thereto, followed by hydrogenation. After 2 hours, the reaction solution was filtrated, and then the filtrate was evaporated under reduced pressure. Isopropyl ether was added to the residue to precipitate solid, and then collection of the precipitated solid yielded Compound 35 (5.64 g, 86% yield).

Compound 35:

$^1$H-NMR (CDCl$_3$) δ (delta): 3.80 (3H, s), 3.81 (3H, s), 4.94 (2H, s), 5.01 (2H, s), 6.18-6.23 (1H, m), 6.30-6.32 (1H, m), 6.72-6.78 (1H, m), 6.80-6.90 (4H, m), 7.26-7.42 (4H, m).

Step (4): Compound 33+Compound 35→Compound 36

To a solution of Compound 33 (359 mg, 2 mmol) in dimethylacetamide (6 mL) was added triethylamine (1.38 mL, 10 mmol), followed by cooling to −15° C., and then methanesulfonyl chloride (0.21 mL, 2.80 mmol) was added, subsequently stirring for 1 hour at −15° C. A solution of Compound 35 in dimethylacetamide (5 mL) was added, and then the solution was allowed to warm up to room temperature. Ethyl acetate (50 mL) was added into the reaction solution and 5% sodium hydrogen carbonate solution was added. The organic layer was washed with water, washed with saturated brine, dried over magnesium sulfate, filtrated, and then evaporated under reduced pressure. The residue was purified by silica gel column chromatography to yield Compound 36 (266 mg, 27% yield).

Compound 36:

$^1$H-NMR (CDCl$_3$) δ (delta): 1.82-1.87 (4H, m), 2.50-2.60 (2H, m), 2.62-2.66 (4H, m), 2.80-2.86 (m, 2H), 3.79 (3H, s), 3.80 (3H, s), 5.02 (2H, s), 5.07 (2H, s), 6.70-6.90 (m, 6H), 7.29-7.50 (5H, m).

Step (5): Compound 28+Compound 36→Compound (I-9)

Compound 28 (517 mg, 0.54 mmol) and Compound 36 (266 mg, 0.54 mmol) was dissolved in dimethylformamide (4 mL), followed by stirring at room temperature for 3 hours. Dimethylformamide (3 mL) and potassium iodide (630 mg, 3.79 mmol) were added thereto, followed by cooling to −40° C., and then acetyl chloride (0.155 mL, 2.17 mmol) was added thereto, subsequently stirring at 0° C. for 1 hour. Then 1M phosphorus tribromide in methylene chloride solution (1.08 mL) was further added at 0° C. thereto, subsequently stirring for 30 minutes. To the reaction solution was added water and ethyl acetate. The organic layer was washed with water, washed with saturated brine, dried over magnesium sulfate, filtrated, and then evaporated under reduced pressure to yield Compound 37 as a powder.

Compound 37 was dissolved in methylene chloride (10 ml) and anisole (0.6 ml), followed by cooling to −40° C. 2M AlCl$_3$-nitromethane solution (2.7 ml) was added thereto, subsequently stirring at 0° C. for 50 minutes. To the reaction solution was added aqueous 2M HCl (60 mL), acetonitrile (50 mL), and ether (100 mL). The aqueous layer was washed with ether, followed by concentration in vacuo, and then subjected into HP-20SS column chromatography, subsequently eluting the desired compound with acetonitrile-water. Collected fractions were concentrated in vacuo. The concentrated solution was lyophilized to yield Compound (I-9) as a white powder (129 mg, 33% yield).

Compound (I-9):

$^1$H-NMR (D$_2$O) δ (delta): 1.49 (3H, s), 1.50 (3H, s), 2.10-2.30 (4H, m), 2.80-3.12 (2H, m), 3.41-3.80 (8H, m), 4.02 and 3.92 (2H, ABq, J=15.5 Hz), 5.34 (1H, d, J=4.8 Hz), 5.84 (1H, d, J=4.8 Hz), 6.77-6.80 (1H, m), 6.83-6.96 (1H, m), 6.90-6.98 (2H, m).

Elementary analysis for C$_{30}$H$_{35}$N$_7$O$_{10}$S$_2$.4.6H$_2$O

Calcd.: C, 45.00; H, 5.56; N, 12.25; O, 29.18; S, 8.01(%).

Found: C, 45.02; H, 5.39; N, 12.35; S, 7.92(%).

EXAMPLE 10

Synthesis of Compound (I-10)

[Formula 71]

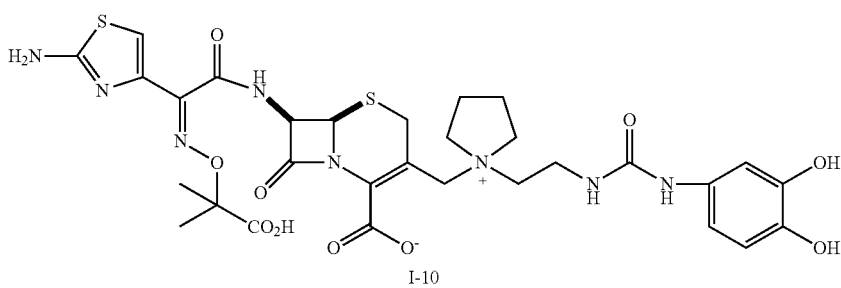

I-10

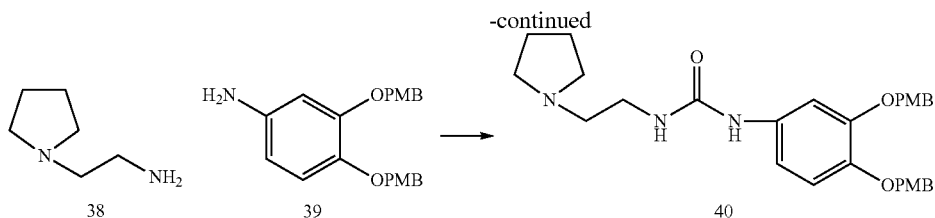

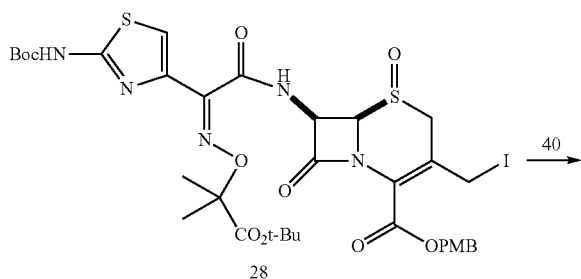

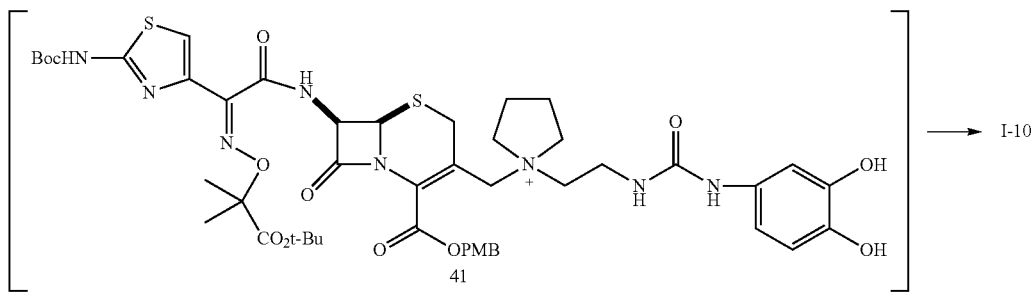

Step (1): Compound 39+Compound 38→Compound 40

To Compound 39 (914 mg, 2.5 mmol) was added tetrahydrofuran (100 mL), followed by cooling to 0° C. Triphosgene (297 mg, 1 mmol) and triethylamine (0.52 mL, 3.75 mmol) were added, subsequently stirring at room temperature for 30 minutes. After cooling to 0° C. again, triethylamine (0.52 mL, 3.75 mmol) and Compound 38 (314 mg, 2.75 mmol) were added, followed by stirring at room temperature for 30 minutes. Ethyl acetate (50 mL) and 5% sodium hydrogen carbonate solution were added into the reaction solution. After extraction from the aqueous layer with ethyl acetate, the organic layer was washed with saturated brine, dried over magnesium sulfate, filtrated, and then evaporated under reduced pressure. Isopropyl ether was then added to the residue to precipitate solid. Collection of the precipitated solid yielded Compound 40 (1.06 g, 84% yield).

Compound 40:

$^1$H-NMR (CDCl$_3$) δ (delta): 1.62-1.68 (4H, m), 2.43-2.55 (4H, m), 2.62 (2H, t, J=5.7 Hz), 3.31 (2H, dd, J=5.1, 11.1 Hz), 3.79 (3H, s), 3.80 (3H, s), 5.00 (2H, s), 5.03 (2H, s), 6.60-6.69 (1H, m), 6.82-6.88 (5H, m), 7.11-7.13 (1H, m), 7.27-7.37 (4H, m).

Step (2): Compound 28→Compound 41→Compound (I-10)

Compound 28 (955 mg, 1 mmol) and Compound 40 (506 mg, 1 mmol) were dissolved in dimethylformamide (4 mL), followed by stirring at room temperature for 3 hours. Dimethylformamide (3 mL) and potassium iodide (630 mg, 3.79 mmol) were added thereto, followed by cooling to −40° C., and then acetyl chloride (0.155 mL, 2.17 mmol) was added thereto, subsequently stirring at 0° C. for 1 hour. Water and ethyl acetate were added to the reaction solution. The organic layer was washed with water, washed with saturated brine, dried over magnesium sulfate, filtrated, and then evaporated under reduced pressure to yield Compound 41 (738 mg) as a powder.

Compound 41 (1.38 g) was dissolved in methylene chloride (10 ml) and anisole (1 ml), followed by cooling to −40° C. 2M AlCl$_3$-nitromethane solution (5 ml) was then added, subsequently stirring at 0° C. for 50 minutes. Aqueous 2M HCl (60 mL), acetonitrile (50 mL), and ether (100 mL) were then added to the reaction solution. The aqueous layer was washed with ether, subsequently concentrating in vacuo, and then subjected into HP-20SS column chromatography, followed by eluting the desired compound with acetonitrile-water. Collected fractions were concentrated in vacuo. The concentrated solution was lyophilized to yield Compound (I-10) as a white powder (98.3 mg, 13% yield).

Compound (I-10):

$^1$H-NMR (D$_2$O) δ (delta): 1.48 (3H, s), 1.49 (3H, s), 2.12-2.20 (4H, m), 3.20-3.80 (10H, m), 3.90 (1H, d, J=16.8 Hz), 4.04 (1H, d, J=16.8 Hz), 5.32 (1H, d, J=4.8 Hz), 5.84 (1H, d, J=4.8 Hz), 6.60-6.70 (1H, m), 6.80-6.85 (2H, m), 6.96 (1H, s).

Elementary analysis for C$_{30}$H$_{36}$N$_8$O$_{10}$S$_2$·4.6H$_2$O

Calcd.: C, 44.18; H, 5.59; N, 13.74; O, 28.64; S, 7.86(%).

Found: C, 44.26; H, 5.38; N, 13.74; S, 7.56(%).

EXAMPLE 11
Synthesis of Compound (I-11)
[Formula 72]
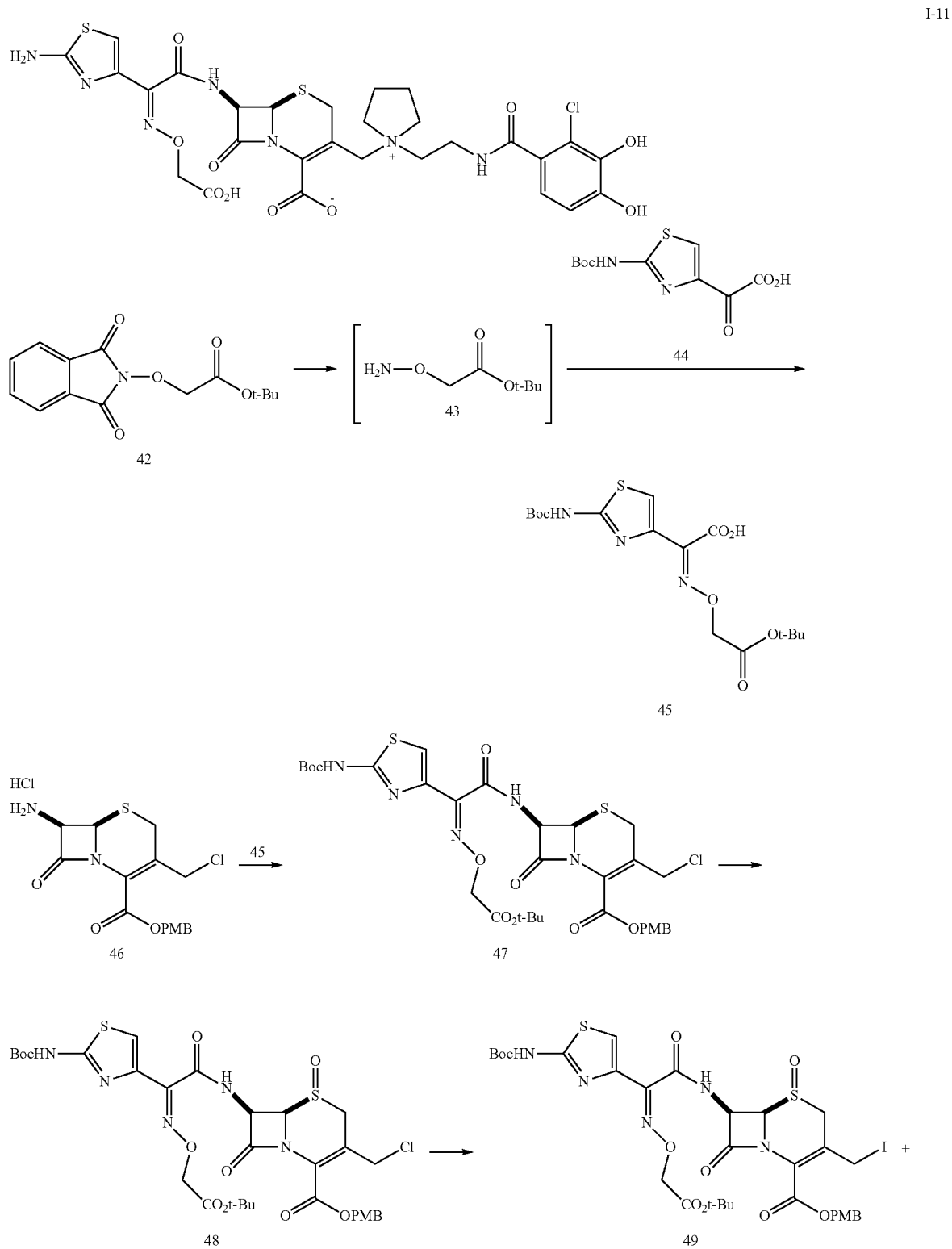

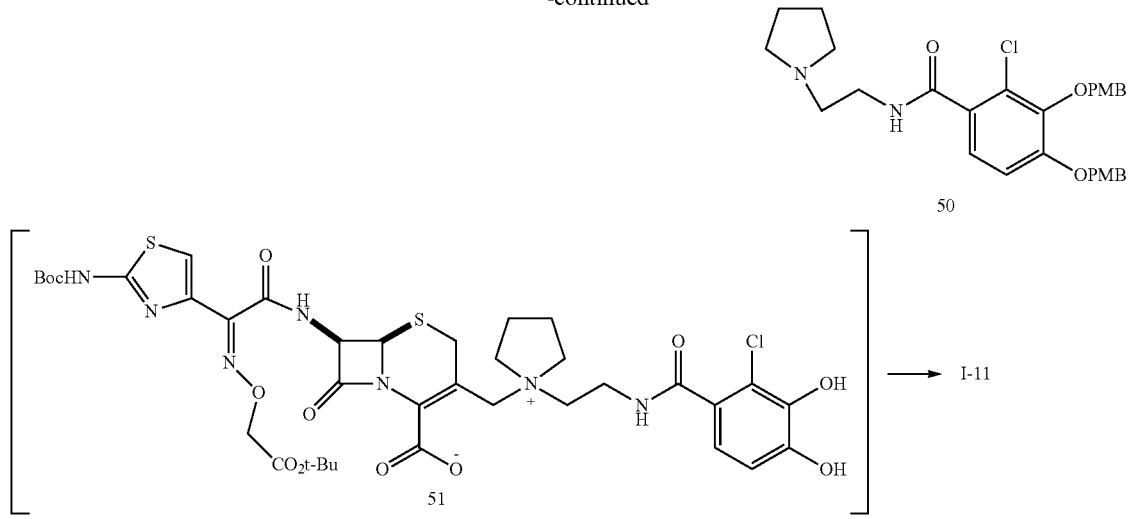

Step (1): Compound 42→Compound 43→Compound 45

A solution of Compound 42 (2.77 g, 10 mmol) in methylene chloride (12 mL) was cooled to 0° C., and then methylhydrazine (0.53 mL, 10 mmol) was added thereto, followed by stirring for minutes. The reaction solution was filtrated, and then concentrated until the filtrate reached about half-volume. After Methanol (25 mL) was added thereto followed by cooling to 0° C., Compound 44 (2.72 g, 10 mmol) was added thereto, subsequently stirring for 30 minutes and then stirring at room temperature for 90 minutes. Then ethyl acetate (200 mL) and 0.2M HCl solution were added thereto. The organic layer was washed with water, washed with saturated brine, dried over magnesium sulfate, filtrated, and then evaporated under reduced pressure. To the residue was added ether, and then collection of the precipitated solid yielded Compound 45 (3.22 g, 80% yield).

Compound 45:

$^1$H-NMR (DMSO-d$_6$) δ (delta): 1.42 (9H, s), 1.47 (9H, s), 4.62 (2H, s), 7.41 (1H, s).

Step (2): Compound 45→Compound 47

To a solution of Compound 45 (3.22 g, 8.02 mmol) in dimethylacetamide (30 mL) was added triethylamine (1.45 mL, 10.4 mmol), followed by cooling to −15° C. Methanesulfonyl chloride (0.75 mL, 9.63 mmol) was added, followed by stirring for 15 minutes, and then N-methylmorpholine (1.76 mL, 16.0 mmol) and Compound 46 (3.09 g, 7.62 mmol) were added thereto, subsequently stirring for 1 hour. Then ethyl acetate (200 mL) and dilute hydrochloric acid were added thereto. The organic layer was separated, washed with aqueous 5% sodium hydrogen carbonate solution, washed with water, washed with saturated brine, dried over magnesium sulfate, filtrated, and then evaporated under reduced pressure. The residue was purified by silica gel column chromatography to yield the desired compound (5.28 g, 88% yield).

Compound 47:

$^1$H-NMR (CDCl$_3$) δ (delta): 1.42 (9H, s), 1.49 (9H, s), 3.61 and 3.48 (2H, ABq, J=18.0 Hz), 3.81 (3H, s), 4.47 (2H, s), 4.77 and 4.72 (2H, ABq, J=17.1 Hz), 5.05 (1H, d, J=4.8 Hz), 5.20 (1H, d, J=12.0 Hz), 5.25 (1H, d, J=12.0 Hz), 5.93 (1H, dd, J=4.8, 8.7 Hz), 6.87-6.91 (2H, m), 7.33-7.37 (m, 3H), 8.10-8.15 (1H, br), 8.74 (1H, d, J=8.7 Hz).

Step (3): Compound 47→Compound 48

A solution of Compound 47 (5.28 g, 7.02 mmol) in methylene chloride (50 mL) was cooled to −40° C., and then m-chloroperbenzoic acid (1.62 g, 7.02 mmol) was added, subsequently warming up from −40° C. to −10° C. gradually. Aqueous 5% sodium thiosulfate solution was added to terminate the reaction. Methylene chloride was evaporated under reduced pressure, and then ethyl acetate and water were added thereto. The organic layer was washed with aqueous 5% sodium hydrogen carbonate solution, washed with saturated brine, dried over magnesium sulfate, filtrated, and then evaporated under reduced pressure. This was used for the next reaction without purification. The yielded amount was 5.39 g (100% yield).

Compound 48:

$^1$H-NMR (CDCl$_3$) δ (delta): 1.42 (9H, s), 1.54 (9H, s), 3.40 (1H, dd, J=1.5, 18.3 Hz), 3.80 (1H, d, J=18.3 Hz), 4.22 (1H, d, J=12.6 Hz), 4.57 (1H, dd, J=1.5, 4.8 Hz), 4.74 (2H, s), 5.10 (1H, d, J=12.6 Hz), 5.24 (1H, d, J=12.0 Hz), 5.29 (1H, d, J=12.0 Hz), 6.07 (1H, dd, J=4.5, 9.2 Hz), 6.88-6.92 (2H, m), 7.34-7.37 (2H, m), 8.38 (1H, d, J=9.2 Hz).

Step (4): Compound 48→Compound 49

Compound 48 (5.39 g, 3.15 mmol) in THF (60 mL) was cooled to 15° C., and then potassium iodide (3.15 g, 21.05 mmol) was added, followed by stirring for 1 hour. Then ethyl acetate and aqueous 5% sodium thiosulfate solution were added thereto. The organic layer was washed with water, washed with saturated brine, dried over magnesium sulfate, filtrated, and then evaporated under reduced pressure. This was used for the next reaction without purification. The yielded amount was 5.42 g (90% yield).

Compound 49:

$^1$H-NMR (CDCl$_3$) δ (delta): 1.41 (9H, s), 1.50 (9H, s), 3.55 (1H, d, J=18.0 Hz), 3.72 (1H, d, J=18.0 Hz), 3.80 (3H, s), 4.17 (d, 1H, J=9.6 Hz), 4.57 (1H, d, J=4.5 Hz), 4.71 (2H, s), 4.79 (1H, d, J=9.6 Hz), 5.24 (1H, d, J=11.7 Hz), 5.30 (1H, d, J=11.7 Hz), 6.02 (1H, dd, J=4.5, 9.6 Hz), 6.80-6.92 (2H, m), 7.24-7.39 (3H, m), 8.36 (d, 1H, J=9.6 Hz).

Step (5): Compound 49+Compound 50→Compound 51

Compound 49 (1.85 g, 2 mmol) and Compound 50 (1.05 g, 2 mmol) were dissolved in dimethylformamide (2 mL), followed by stirring at room temperature for 2 hours. Dimethylformamide (4 mL) and potassium iodide (2.32 g, 14 mmol) were added thereto, followed by cooling to −40° C., and then acetyl chloride (0.571, 8.00 mmol) was added, subsequently stirring at 0° C. for 1 hour. To the reaction solution was added water and ethyl acetate. The organic layer was washed with water, washed with saturated brine, dried over magnesium sulfate, filtrated, and then evaporated under reduced pressure to yield Compound 51 as a powder.

Compound 51 was dissolved in methylene chloride (20 ml) and anisole (2 ml), followed by cooling to −40° C. 2M AlCl$_3$-nitromethane solution (10 ml) was then added thereto, subsequently stirring at 0° C. for 50 minutes. To the reaction solution was added then aqueous 2M HCl (50 mL), acetonitrile (50 mL), and ether (100 mL). The aqueous layer was washed with ether, subsequently concentrating in vacuo, and then subjected into HP-20SS column chromatography, followed by eluting the desired compound with acetonitrile-water. Collected fractions were concentrated in vacuo. The concentrated solution was lyophilized to yield Compound (I-11) as a white powder (430 mg, 30% yield).

Compound (I-11):

$^1$H-NMR (D$_2$O) δ (delta): 2.10-2.35 (4H, m), 3.40-3.80 (10H, m), 3.94 (1H, d, J=14.1 Hz), 4.12 (1H, d, J=14.1 Hz), 4.57 (2H, s), 5.34 (1H, d, J=4.8 Hz), 5.87 (1H, d, J=4.8 Hz), 6.67 (2H, s), 7.02 (1H, s).

Elementary analysis for C$_{28}$H$_{30}$ClN$_7$O$_{10}$S$_2$·4.0H$_2$O

Calcd.: C, 42.24; H, 4.81; Cl, 4.45; N, 12.31; O, 28.13; S, 8.05(%).

Found: C, 42.52; H, 4.73; Cl, 4.21; N, 12.46; S, 7.70(%).

Reference Example 1

General Synthesis Methods of Side Chain Amines (a)-(n)

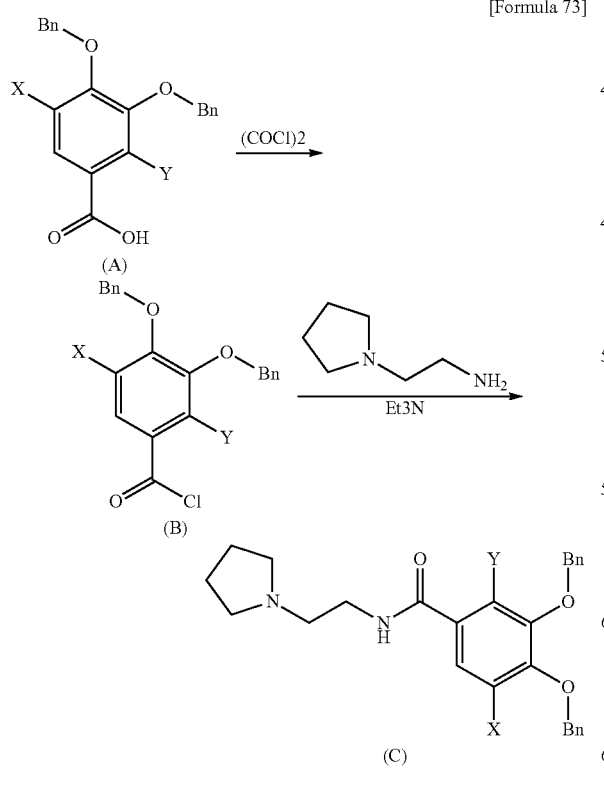

[Formula 73]

As illustrated in the synthesis route above, an equivalent mole of oxalyl chloride was added to a methylene chloride (10 V) solution (suspension) of benzoic acid derivative (A), which corresponds to side chains (a)-(n), followed by stirring at room temperature for 2 hours. After concentration in vacuo until reaching about-half volume, the resultant was added to an amine (1.0 equivalent/Et$_3$N (1.2 equivalent)/THF solution), which corresponds to side chains (a)-(n), that had been cooled to −20° C., subsequently stirring for 30 minutes. Diluting with methylene chloride, washing with water, drying, and then concentrating the filtrate yielded desired amine (C) (side chains (a)-(n)) (90% or higher yield). Physical constants of side chains (a)-(n) are shown below.

Side Chain (a)

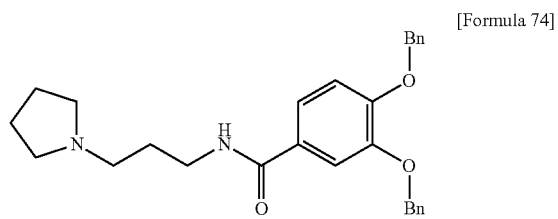 [SMILES: O=C(NCCCN1CCCC1)c1ccc(OCc2ccccc2)c(OCc2ccccc2)c1]

[Formula 74]

$^1$H-NMR (CDCl$_3$) δ (delta): 1.72-1.88 (6H, m), 2.50-2.62 (4H, m), 2.68 (2H, t, J=5.7 Hz), 3.52-3.57 (2H, m), 5.19 (4H, s), 6.90 (1H, d, J=8.7 Hz), 7.21-7.60 (11H, m), 7.56 (1H, d, J=1.8 Hz), 8.49 (1H, bs).

LC/MS (ES+): 445 (M+H$^+$)

Side Chain (b)

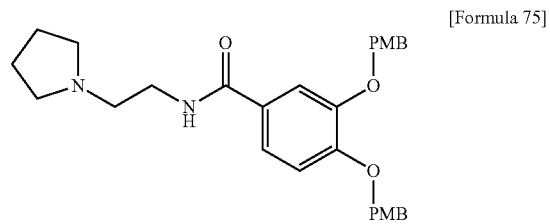

[Formula 75]

$^1$H-NMR (CDCl$_3$) δ (delta): 1.72 (4H, bs), 2.59 (4H, bs), 2.70 (2H, t, J=4.5 Hz), 3.51-3.55 (2H, m), 3.79 (6H, s), 5.10 (4H, s), 6.81-6.95 (6H, m), 7.26-7.37 (5H, m), 7.53 (1H, bs).

LC/MS (ES+): 491 (M+H$^+$)

Side Chain (c)

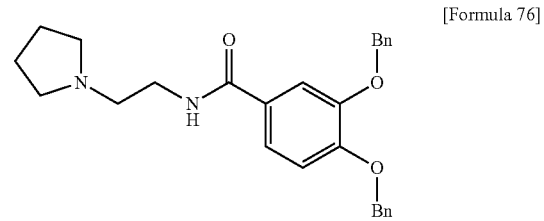 [SMILES: O=C(NCCN1CCCC1)c1ccc(OCc2ccccc2)c(OCc2ccccc2)c1]

[Formula 76]

$^1$H-NMR (CDCl$_3$) δ (delta): 1.75-3.05 (12H, m), 5.17 (2H, s), 5.18 (2H, s), 6.85-6.97 (3H, m), 6.25-6.45 (11H, m).

LC/MS (ES+): 431 (M+H$^+$)

Side Chain (d)

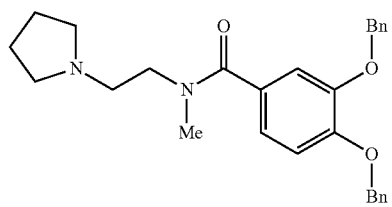

[Formula 77]

$^1$H-NMR (DMSO-$d_6$) δ (delta): 1.45-3.60 (12H, m), 2.89 (3H, s), 5.15 (2H, s), 5.17 (2H, s), 6.90-7.16 (3H, m), 7.22-7.48 (10H, m).
LC/MS (ES+): 445 (M+H$^+$)

Side Chain (e)

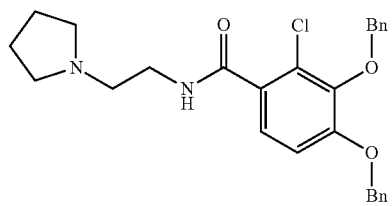

[Formula 78]

$^1$H-NMR (CDCl$_3$) δ (delta): 1.70-1.83 (4H, m), 2.50-2.59 (4H, m), 2.70 (2H, t, J=6.3 Hz), 3.52-3.60 (2H, m), 5.04 (2H, s), 5.16 (2H, s), 6.89-6.96 (2H, m), 7.26-7.51 (11H, m).
LC/MS (ES+): 465 (M+H$^+$)

Side Chain (f)

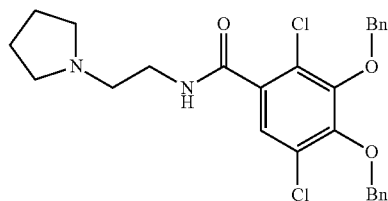

[Formula 79]

$^1$H-NMR (CDCl$_3$) δ (delta): 1.63-1.86 (4H, m), 2.57 (4H, bs), 2.72 (2H, d, J=6.0 Hz), 3.52-3.59 (2H, m), 5.07 (2H, s), 5.13 (2H, s), 6.96 (1H, bs), 7.23-7.50 (12H, m).
LC/MS (ES+): 499 (M+H$^+$)

Side Chain (g)

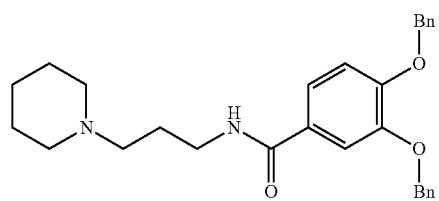

[Formula 80]

$^1$H-NMR (CDCl$_3$) δ (delta): 1.38-1.80 (8H, m), 3.35-3.56 (6H, m), 5.18 (2H, s), 5.19 (2H, s), 6.91 (1H, d, J=8.4 Hz), 7.24-7.52 (11H, m), 7.57 (1H, d, J=2 Hz), 8.32 (1H, b.s).
LC/MS (ES+): 459 (M+H$^+$)

Side Chain (h)

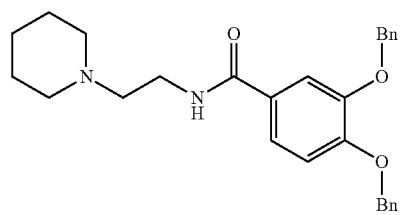

[Formula 81]

$^1$H-NMR (CDCl$_3$) δ (delta): 1.47-1.48 (2H, m), 1.52-1.63 (4H, bs), 2.35-2.50 (4H, m), 2.57 (2H, t, J=4.5 Hz), 3.49-3.53 (2H, m), 5.20 (2H, s), 5.21 (2H, s), 6.93 (1H, d, J=6.3 Hz), 7.03 (1H, bs), 7.25-7.55 (12H, m).
LC/MS (ESI positive): 445 (M+H$^+$)

Side Chain (i)

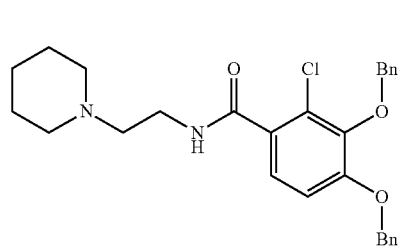

[Formula 82]

$^1$H-NMR (CDCl$_3$) δ (delta): 1.40-1.63 (8H, m), 2.42 (2H, bs), 2.54 (2H, t, J=6 Hz), 3.50-3.58 (2H, m), 5.05 (2H, d, J=4.8 Hz), 5.17 (2H, d, J=4.8 Hz), 6.96 (1H, d, J=8.7 Hz), 7.10 (1H, bs), 7.22-7.58 (11H, m).
LC/MS (ES+): 479 (M+H$^+$)

Side Chain (j)

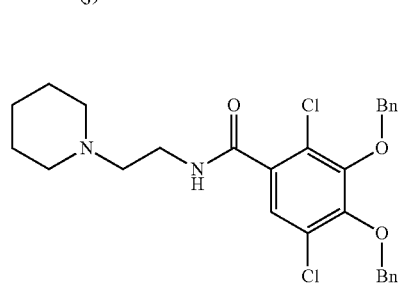

[Formula 83]

$^1$H-NMR (CDCl$_3$) δ (delta): 1.40-1.75 (6H, m), 2.42 (4H, bs), 2.53 (2H, t, J=6 Hz), 3.48-3.56 (2H, m), 7.01 (1H, bs), 7.25-7.62 (10H, m), 7.56 (1H, s).
LC/MS (ES+): 513 (M+H$^+$)

Side Chain (k)

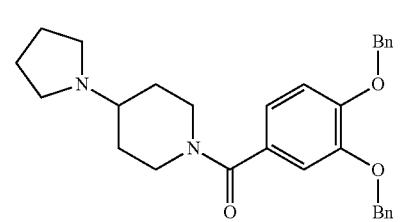

[Formula 84]

87

¹H-NMR (CDCl₃) δ (delta): 1.30-1.95 (14H, m), 2.45-2.58 (4H, m), 2.45-2.90 (1H, m), 5.18 (2H, s), 5.19 (2H, s), 6.89-6.96, 3H, m), 7.23-7.45 (12H, m).
LC/MS (ES+): 471 (M+H⁺)
Side Chain (l)

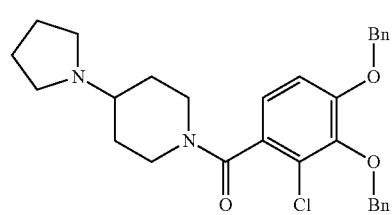
[Formula 85]

¹H-NMR (CDCl₃) δ (delta): 1.45-1.70 (4H, m), 1.80 (4H, bs), 2.12-2.30 (1H, m), 2.83-3.10 (1H, m), 2.57 (4H, bs), 2.83-3.10 (2H, m), 4.55-4.72 (1H, m), 6.85-6.92 (2H, m), 7.23-7.70 (10H, m).
LC/MS (ES+): 505 (M+H⁺)
Side Chain (m)

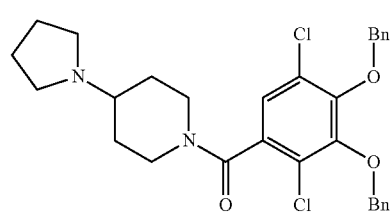
[Formula 86]

88

¹H-NMR (CDCl₃) δ (delta): 1.30-1.70 (4H, m), 1.81 (5H, bs), 1.93-2.12 (1H, m), 2.25-2.34 (1H, m), 2.57 (4H, bs), 4.50-4.61 (1H, m), 5.02-5.09 (4H, m), 7.24-7.50 (11H, m).
LC/MS (ES+): 539 (M+H⁺)
Side Chain (n)

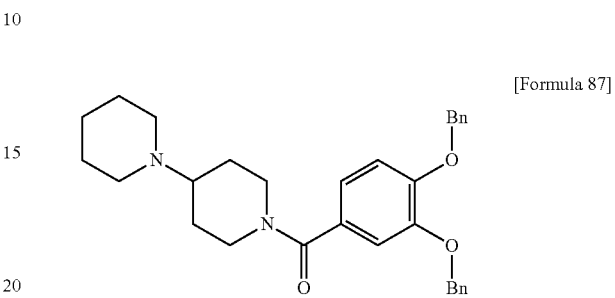
[Formula 87]

¹H-NMR (CDCl₃) δ (delta): 1.38-1.80 (8H, m), 3.35-3.56 (6H, m), 5.18 (2H, s), 5.19 (2H, s), 6.91 (1H, d, J=8.4 Hz), 7.24-7.52 (11H, m), 7.57 (1H, d, J=2 Hz), 8.32 (1H, b.s).
LC/MS (ES+): 485 (M+H⁺)

Reference Example 2

By methods below, Compound (F) or (G) was synthesized.

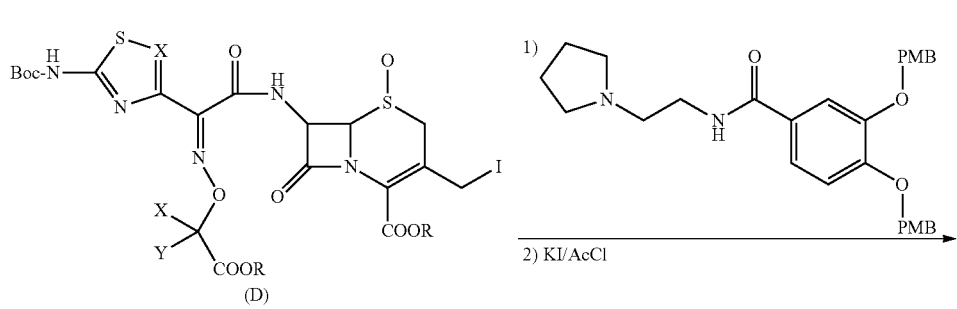
[Formula 88]

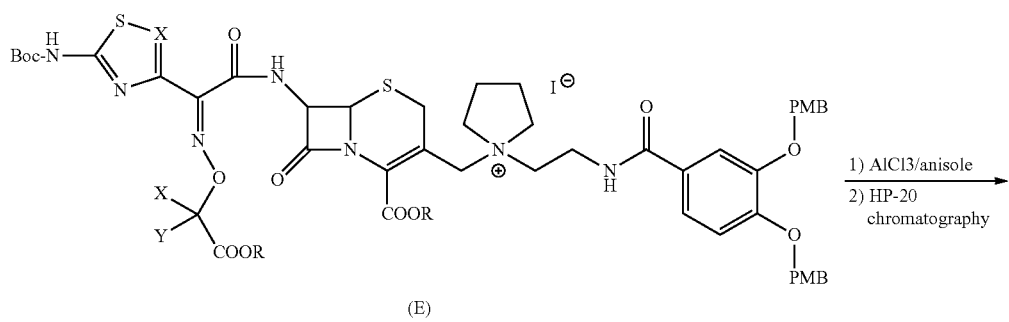

-continued

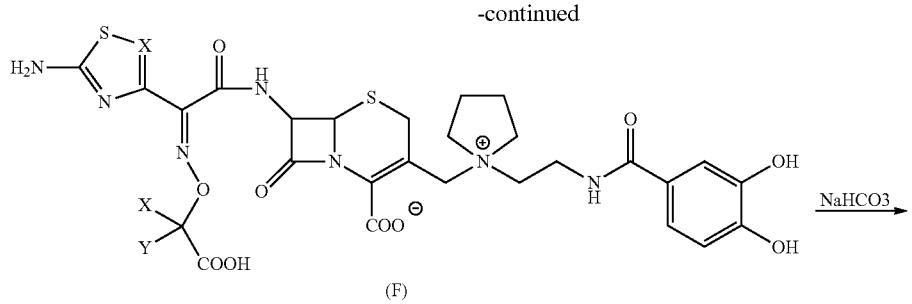

(F)

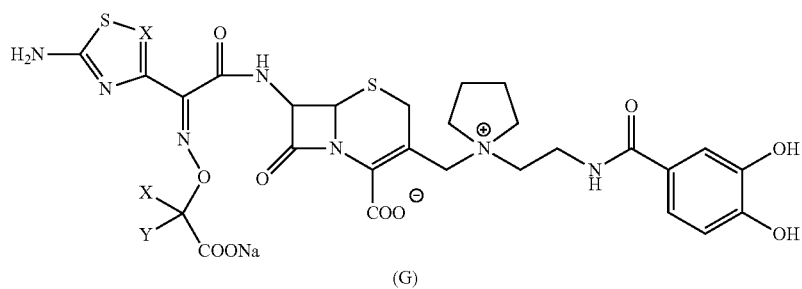

(G)

Cephem (D), which is a raw material obtained by a known method, was dissolved in DMF (5 V), and then an amine (equivalent mole) of side chain (a)-(n), shown above, was added, followed by stirring at room temperature for several hours. After ice-cooling, potassium iodide (7 equivalents) and acetyl chloride (5 equivalents) were added, subsequently stirring for 1 hour. To 5% brine (50 V) containing sodium thiosulfate was slowly added with stirring. The precipitated deposit was filtrated, and then washed with water, followed by lyophilization. The dried matter (E) was dissolved in methylene chloride (20 V) and nitromethane (10 V), followed by adding, at room temperature, anisole (10 equivalents) and then 2M aluminum chloride/nitromethane solution (10 equivalents), subsequently stirring for 1 hour. After reacting, the reaction mixture was poured into cold 1M hydrochloric acid/acetonitrile/isopropyl ether (3/1/5). The aqueous layer was separated, subjected into HP-20 column chromatography, and then purified. After eluting with acetonitrile/water, the eluate was concentrated in vacuo, and then lyophilized to yield objective (F). As required, desired compound (F) was dissolved in sodium hydrogen carbonate solution, and then subjected into HP-20 column chromatography. Eluted fractions were concentrated, and then lyophilized to yield sodium salt (G).

Examples of Compound (F) or (G) (Compound (I-12)-Compound (I-34)) are shown below.

EXAMPLE 12

Compound (I-12)

[Formula 89]

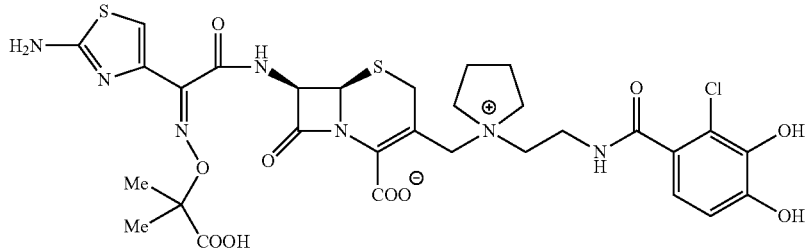

$^1$H-NMR (DMSO-$d_6$) δ (delta): 1.45 (3H, s), 1.46 (3H, s), 1.92-2.19 (4H, m,), 3.00-3.95 (11H, m), 3.95, 5.07 (2H, ABq, J=13.8 Hz), 5.16 (1H, d, J=5.1 Hz), 5.73 (1H, dd, J=5.1, 9.6 Hz), 6.73 (1H, s), 6.78 (2H, s), 7.29 (2H, bs), 8.43 (1H, bs), 9.44 (1H, d, J=8.4).

LC/MS (ES+): 752 (M+H$^+$)

IR (KBr) cm$^{-1}$: 3308, 1773, 1607, 1532, 1471

Elementary analysis for $C_{30}H_{34}ClN_7O_{10}S_2 \cdot 3.8H_2O$

Calcd.: C, 43.99; H, 5.24; Cl, 4.49; N, 12.11; S, 7.77(%).

Found: C, 43.91; H, 5.11; Cl, 4.32; N, 11.95; S, 7.81(%).

EXAMPLE 13
Compound (I-13)
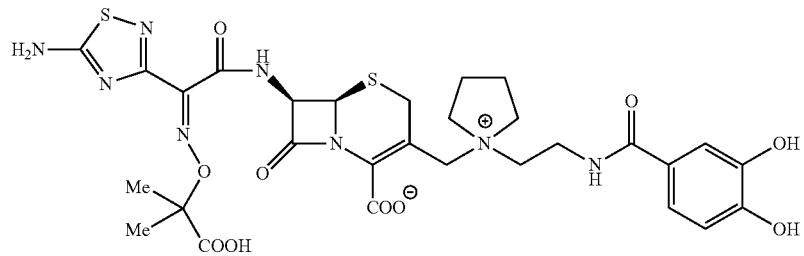
[Formula 90]
$^1$H-NMR (DMSO-$d_6$) δ (delta): 1.40 (3H, s), 1.41 (3H, s), 1.72-2.10 (4H, m), 3.05-3.80 (10H, m), 3.85, 5.02 (2H, ABq, J=9.9 Hz), 5.09 (1H, d, J=3.9 Hz), 5.67 (1H, dd, J=3.9, 6.5 Hz), 6.72 (1H, d, J=6.0 Hz), 7.14 (1H, d, J=6 Hz), 7.23 (1H, s).
LC/MS (ES+): 719 (M+H$^+$)
IR (KBr) cm$^{-1}$: 3301, 1777, 1599, 1514, 1464
Elementary analysis for $C_{29}H_{34}ClN_8O_{10}S_2 \cdot 3.9H_2O$
Calcd.: C, 44.15; H, 5.51; N, 14.05; S, 8.18(%).
Found: C, 44.14; H, 5.34; N, 14.20; S, 8.13(%).
EXAMPLE 14
Compound (I-14)
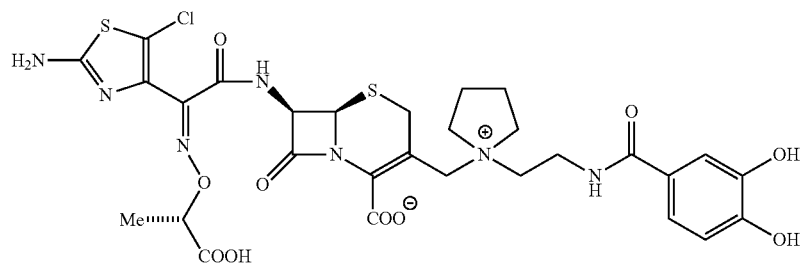
[Formula 91]
$^1$H-NMR (DMSO-$d_6$) δ (delta): 1.43 (3H, d, J=5.1 Hz), 1.84-2.16 (4H, m), 3.20-5.10 (13H, m), 5.14 (1H, d, J=3.9 Hz), 5.74 (1H, dd, J=3.9, 6.3 Hz), 6.78 (1H, d, J=6.0 Hz), 7.21 (1H, d, J=6.3 Hz), 7.31 (1H, s).
LC/MS (ES+): 738 (M+H$^+$)
IR (KBr) cm$^{-1}$: 3301, 1778, 1599, 1542, 1512

EXAMPLE 15
Compound (I-15)
[Formula 92]
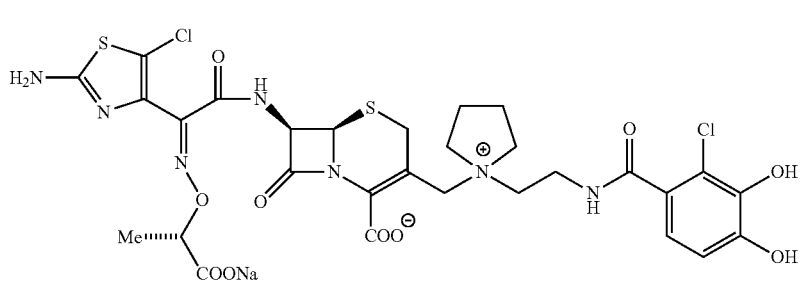
LC/MS (ES+): 772 (M+H$^+$)
IR (KBr) cm$^{-1}$: 3292, 1771, 1589, 1537, 1473
EXAMPLE 16
Compound (I-16)
[Formula 93]
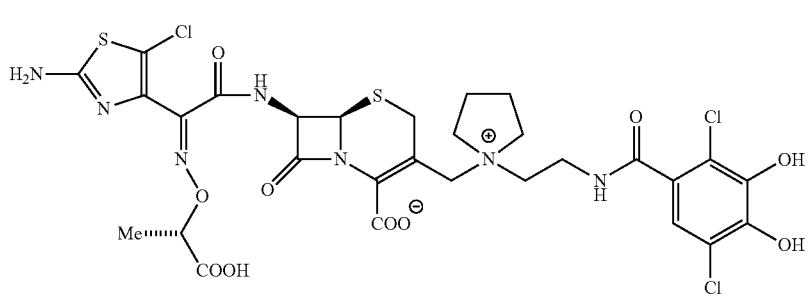
$^1$H-NMR (DMSO-d$_6$+CD$_3$OD) δ (delta): 1.41 (3H, d, J=7.2 Hz), 1.79-2.23 (4H, m), 2.98-3.90 (10H, m), 3.94, 5.03 (2H, ABq, J=13.5 Hz), 4.57 (1H, q, J=6.6 Hz), 5.14 (1H, d, J=5.4 Hz), 6.9 (1H, bs).
LC/MS (ES+): 808 (M+H$^+$)
IR (KBr) cm$^{-1}$: 3305, 1779, 1613, 1538, 1474, 1403
Elementary analysis for C$_{29}$H$_{30}$Cl$_3$N$_7$O$_{10}$S$_2$·2.4H$_2$O
Calcd.: C, 40.81; H, 3.83; N, 12.11(%).
Found: C, 40.96; H, 4.13; N, 11.53; (%).
EXAMPLE 17
Compound (I-17)
[Formula 94]
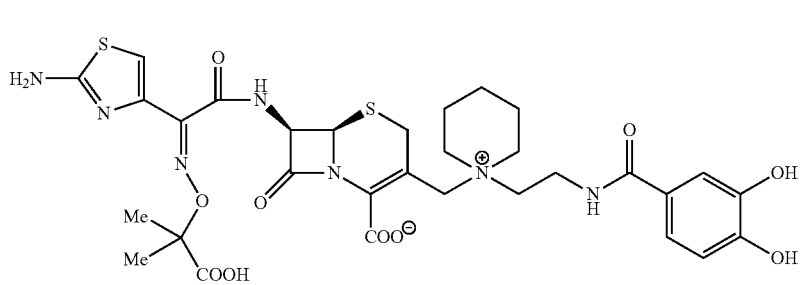

$^1$H-NMR (DMSO-d$_6$) δ (delta): 1.46 (3H, s), 1.47 (3H, s), 1.50-1.99 (6H, m), 2.80-3.93 (10H, m), 3.97, 5.01 (2H, ABq, J=14.4 Hz), 5.18 (1H, d, J=4.8 Hz), 5.75 (1H, dd, J=4.8, 7.8 Hz), 6.74 (1H, s), 6.79 (1H, d, J=8.1 Hz), 7.21 (1H, d, J=8.1 Hz), 7.30 (3H, s), 8.52 (1H, bs).

LC/MS (ES+): 732 (M+H$^+$)

IR (KBr) cm$^{-1}$: 3301, 1774, 1600, 1515, 1470

Elementary analysis for C$_{31}$H$_{37}$N$_7$O$_{10}$S$_2$.4.5H$_2$O

Calcd.: C, 45.88; H, 5.91; N, 11.81; S, 7.87(%).

Found: C, 45.80; H, 5.70; N, 12.06; S, 7.89(%).

EXAMPLE 18

Compound (1-18)

[Formula 95]

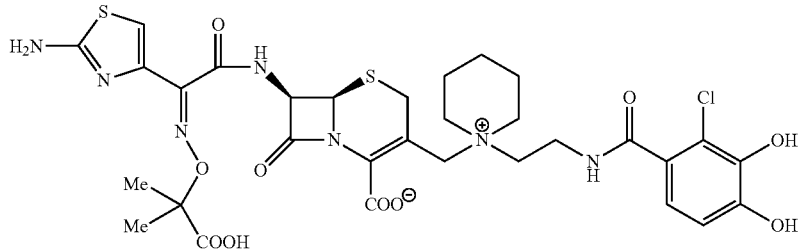

$^1$H-NMR (DMSO-d$_6$) δ (delta): 1.43 (3H, s), 1.49 (3H, s), 1.22-1.95 (6H, m), 3.07-4.08 (11H, m), 4.95-5.13 (1H, m), 5.15 (1H, d, J=4.8 Hz), 5.72-5.83 (1H, m), 6.63-6.84 (3H, m).

LC/MS (ES+): 766 (M+H$^+$)

IR (KBr) cm$^{-1}$: 3324, 1770, 1600, 1537, 1470

Elementary analysis for C$_{31}$H$_{36}$ClN$_7$O$_{10}$S$_2$.8H$_2$O

Calcd.: C, 41.07; H, 6.54; N, 10.37; S, 6.75(%).

Found: C, 40.90; H, 5.76; N, 10.77; S, 7.04(%).

EXAMPLE 19

Compound (I-19)

[Formula 96]

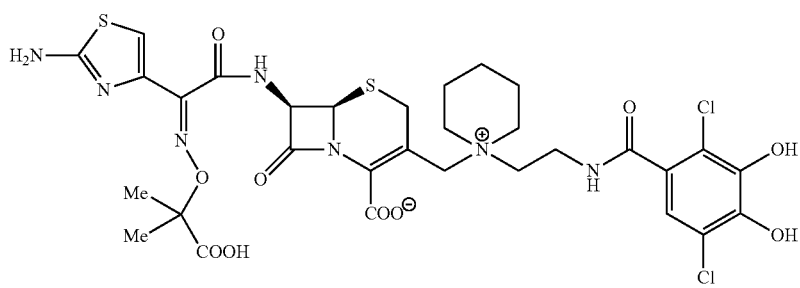

$^1$H-NMR (DMSO-d$_6$) δ (delta): 1.44 (3H, s), 1.46 (3H, s), 1.58-1.97 (6H, m), 3.08-3.95 (10H, m), 4.44, 5.07 (2H, Abq, J=14.1 Hz), 5.18 (1H, d, J=5.1 Hz), 5.78 (1H, dd, J=5.1, 8.1 Hz), 6.72 (1H, s), 7.00 (1H, s), 7.30 (2H, bs), 8.50 (1H, bs), 9.43 (1H, d, J=8.1 Hz).

LC/MS (ES+): 800 (M+H$^+$)

IR (KBr) cm$^{-1}$: 3322, 1778, 1614, 1531, 1470

Elementary analysis for C$_{31}$H$_{35}$Cl$_2$N$_7$O$_{10}$S$_2$.5.0H$_2$O

Calcd.: C, 41.91; H, 5.36; N, 10.66(%).

Found: C, 41.80; H, 5.09; N, 11.01(%).

EXAMPLE 20
Compound (I-20)
[Formula 97]
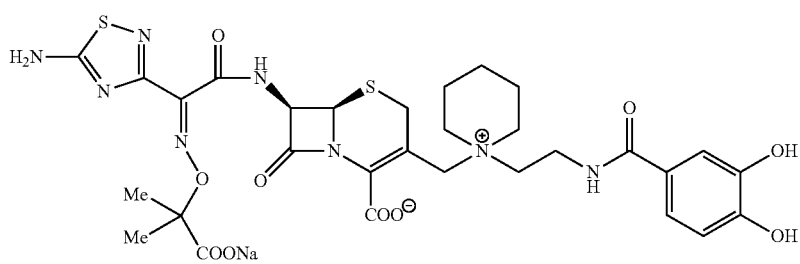
¹H-NMR (D$_2$O) δ (delta): 1.36 (6H, S), 1.50-1.91 (6H, m), 2.92-4.06 (13H, m), 4.58-4.80 (1H, m), 5.21 (1H, d, J=3.9 Hz), 5.72 (1H, d, J=3.9 Hz), 6.58 (1H, d, J=6.6 Hz), 7.04 (2H, bs).
LC/MS (ES+): 733 (M+H$^+$)
IR (KBr) cm$^{-1}$: 3296, 1772, 1592, 1519, 1468
EXAMPLE 21
Compound (I-21)
[Formula 98]
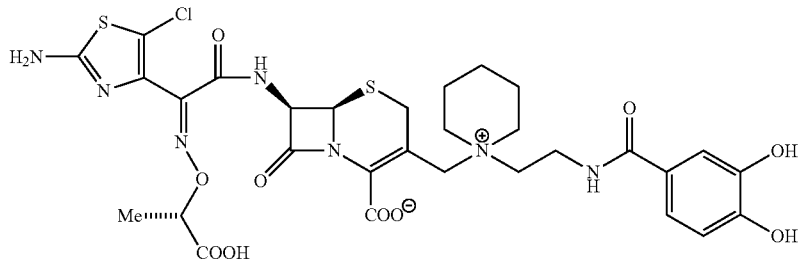
¹H-NMR (DMSO-d$_6$+CD$_2$OD) δ (delta): 1.45 (3H, d, J=7.2 Hz), 1.50-1.95 (6H, m), 2.83-3.90 (10H, m), 3.96, 5.09 (2H, ABq, J=13.8 Hz), 4.63 (1H, q, J=6.3 Hz), 5.16 (1H, d, J=5.1 Hz), 5.73 (1H, d, J=5.1 Hz), 6.79 (1H, d, J=8.4 Hz), 7.21 (1H, dd, J=2.4, 8.4 Hz), 7.30 (1H, d, J=2.4 Hz).
LC/MS (ES+): 752 (M+H$^+$)
IR (KBr) cm$^{-1}$: 3308, 1779, 1601, 1538, 1513, 1453
Elementary analysis for C$_{30}$H$_{34}$ClN$_7$O$_{10}$S$_2$.3.8H$_2$O
Calcd.: C, 44.12; H, 5.27; Cl, 4.40; N, 11.74; S, 7.58(%).
Found: C, 43.91; H, 5.11; Cl, 4.32; N, 11.95; S, 7.81(%).

EXAMPLE 22
Compound (I-22)
[Formula 99]
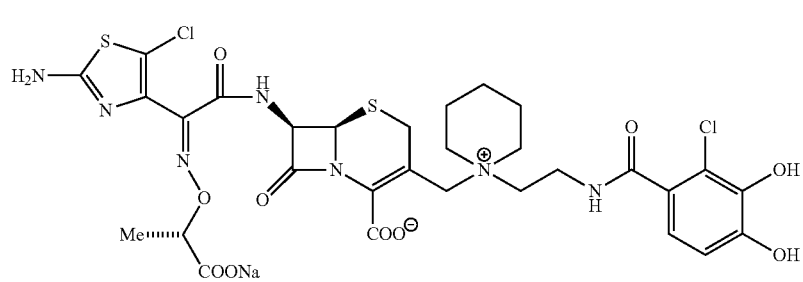
LC/MS (ES+): 786 (M+H$^+$)
IR (KBr) cm$^{-1}$: 3290, 1772, 1599, 1539, 1473
EXAMPLE 23
Compound (I-23)
[Formula 100]
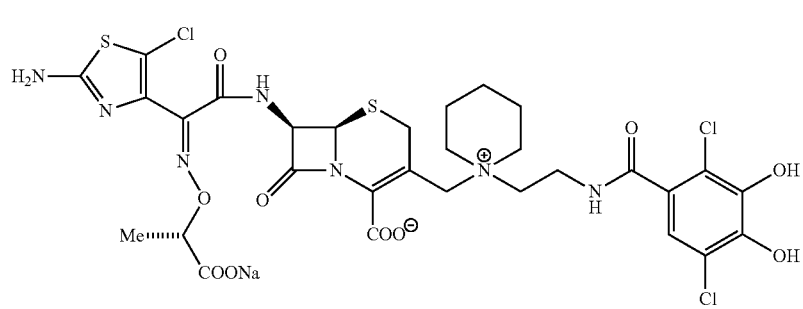
$^1$H-NMR (D$_2$O) δ (delta): 1.11 (3H, d, J=7.2 Hz), 1.03-1.74 (6H, m), 2.82-3.38 (11H, m), 4.20-4.60 (2H, m), 5.00 (1H, d, J=5.1 Hz), 5.54 (1H, d, J=5.1 Hz), 6.63 (1H, s).
LC/MS (ES+): 822 (M+H$^+$)
IR (KBr) cm$^{-1}$: 3298, 1770, 1600, 1538, 1470
EXAMPLE 24
Compound (I-24)
[Formula 101]
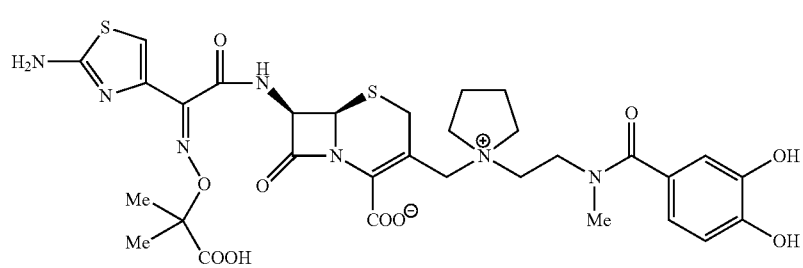

$^1$H-NMR (DMSO-d$_6$+CD$_3$OD) δ (delta): 1.45 (3H, s), 1.47 (3H, s), 1.83-2.21 (4H, m), 3.00 (3H, s), 3.25-3.97 (10H, m), 4.01, 4.96 (2H, Abq, J=13.5 Hz), 5.14 (1H, d, J=5.1 Hz), 6.74 (1H, d, J=5.1 Hz), 6.72-6.80 (3H, m), 6.87 (1H, s).
LC/MS (ES+): 732 (M+H$^+$)
IR (KBr) cm$^{-1}$: 3194, 1778, 1595, 1530, 1490
Elementary analysis for C$_{31}$H$_{37}$N$_7$O$_{10}$S$_2$.3.4H$_2$O
Calcd.: C, 47.01; H, 5.65; N, 12.23; S, 8.05(%).
Found: C, 46.95; H, 5.57; N, 12.36; S, 8.09(%).

EXAMPLE 25

Compound (I-25)

[Formula 102]

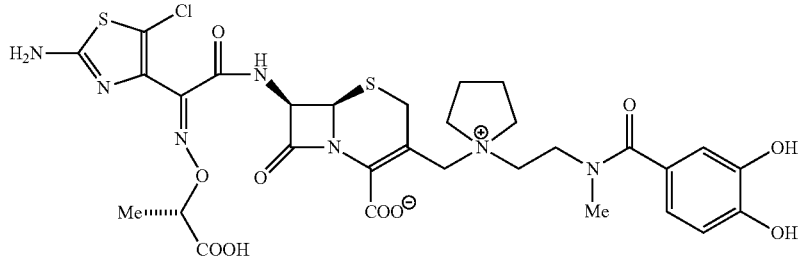

$^1$H-NMR (DMSO-d$_6$+CD$_3$OD) δ (delta): 1.42 (3H, d, J=6.9 Hz), 1.52-2.21 (4H, m), 2.99 (3H, s), 3.09-4.00 (10H, m), 4.05, 4.90 (2H, ABq, J=12 Hz), 4.60 (1H, q, J=6.9 Hz), 5.12 (1H, d, J=5.1 Hz), 5.75 (1H, d, J=5.1 Hz), 6.70-6.98 (3H, m).
LC/MS (ES+): 752 (M+H$^+$)
IR (KBr) cm$^{-1}$: 3308, 1779, 1669, 1593, 1537, 1489, 1447
Elementary analysis for C$_{30}$H$_{34}$ClN$_7$O$_{10}$S$_2$.1.9H$_2$O
Calcd.: C, 45.44; H, 4.54; Cl, 5.01; N, 12.88(%).
Found: C, 45.82; H, 4.84; Cl, 4.51; N, 12.45(%).

EXAMPLE 26

Compound (I-26)

[Formula 103]

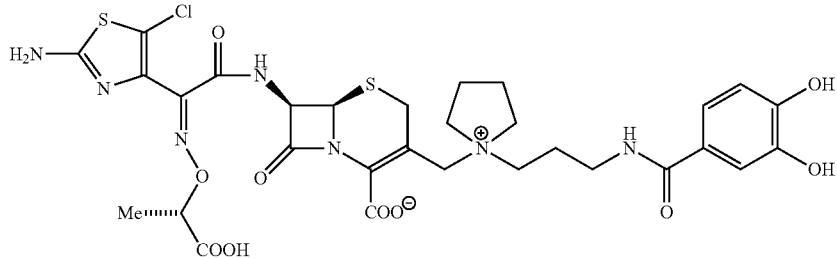

$^1$H-NMR (DMSO-d$_6$) δ (delta): 1.43 (3H, d, J=7.2 Hz), 1.78-2.16 (6H, m), 2.93-3.82 (10H, m), 3.82, 5.03 (2H, ABq, J=14.1 Hz), 4.60 (1H, q, J=7.2 Hz), 4.74 (1H, d, J=4.8 Hz), 5.54 (1H, dd, J=4.8, 8.4 Hz), 6.71 (1H, d J=8.1 Hz), 6.30-6.40 (2H, m).
LC/MS (ES+): 752 (M+H$^+$)
IR (KBr) cm$^{-1}$: 3311, 1777, 1595, 1540, 1512, 1457
Elementary analysis for C$_{30}$H$_{39}$ClN$_7$O$_{10}$S$_2$.2.5H$_2$O
Calcd.: C, 45.10; H, 4.90; Cl, 4.59; N, 12.59(%).
Found: C, 45.20; H, 4.93; Cl, 4.45; N, 12.30(%).

EXAMPLE 27
Compound (I-27)
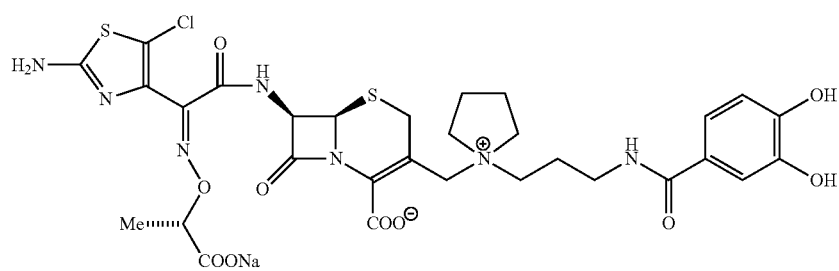
[Formula 104]
$^1$H-NMR (D$_2$O) δ (delta): 1.29 (3H, d, J=6.9 Hz), 1.33-1.97 (8H, m), 2.88-3.90 (11H, m), 4.38-4.67 (2H, m), 4.76 (1H, d, J=5.1 Hz), 5.50 (1H, d, J=5.1 Hz), 6.65 (1H, d, J=8.1 Hz), 6.98-7.17 (2H, m).
LC/MS (ES+): 766 (M+H$^+$)
IR (KBr) cm$^{-1}$: 3929, 1776, 1594, 1543, 1447, 1397
EXAMPLE 28
Compound (I-28)
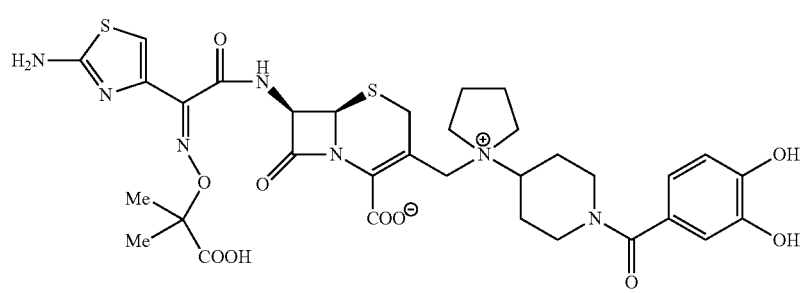
[Formula 105]
$^1$H-NMR (DMSO-d$_5$) δ (delta): 1.43 (3H, s), 1.46 (3H, s), 1.50-2.22 (8H, m), 2.60-4.30 (11H, m), 3.95, 5.01 (2H, ABq, J=12.9 Hz), 5.17 (1H, b, J=4.8 Hz), 5.73 (1H, dd, J=4.8, 7.8), 6.60-6.97 (4H, m), 7.27 (2H, bs), 9.49 (1H, bs).
LC/MS (ES+): 758 (M+H$^+$)
IR (KBr) cm$^{-1}$: 3196, 1778, 1590, 1530, 1444
Elementary analysis for C$_{33}$H$_{39}$N$_7$O$_{10}$S$_2$.3.5H$_2$O
Calcd.: C, 47.97; H, 5.51; N, 12.24(%).
Found: C, 48.28; H, 5.65; N, 11.94(%).

EXAMPLE 29
Compound (I-29)
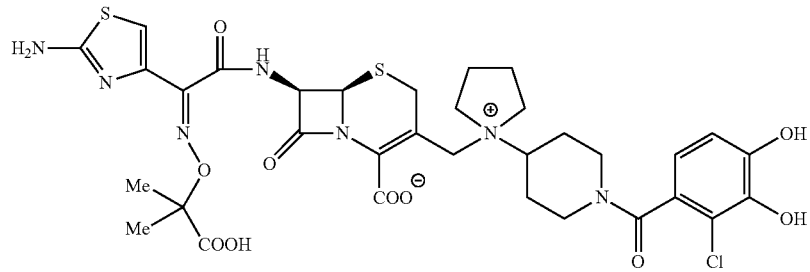
[Formula 106]
$^1$H-NMR (DMSO-$d_6$) δ (delta): 1.44 (3H, s), 1.46 (3H, s), 1.30-2.33 (6H, m), 2.60-4.06 (11H, m), 4.44-4.72 (1H, m), 4.83-5.03 (1H, m), 6.47-6.88 (3H, m), 7.28 (2H, bs).
LC/MS (ES+): 792 (M+H$^+$)
IR (KBr) cm$^{-1}$: 3302, 2970, 1773, 1606, 1532, 1445
Elementary analysis for $C_{33}H_{38}ClN_7O_{10}S_2 \cdot 4.8H_2O$
Calcd.: C, 45.23; H, 5.63; Cl, 4.10; N, 10.89; S, 7.08(%).
Found: C, 45.10; H, 5.46; Cl, 4.03; N, 11.16; S, 7.30(%).
EXAMPLE 30
Compound (I-30)
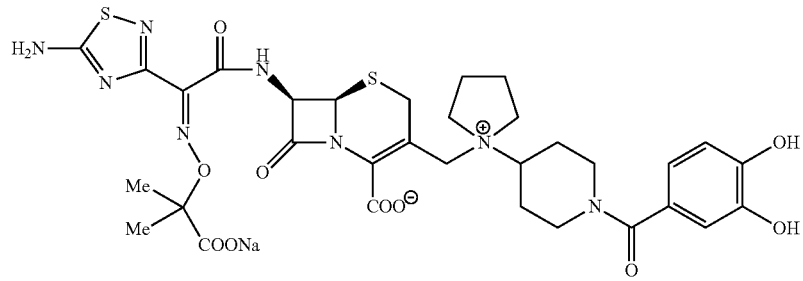
[Formula 107]
$^1$H-NMR (D$_2$O) δ (delta): 1.34 (3H, s), 1.36 (3H, s), 1.52-2.29 (8H, m), 2.68-3.80 (11H, m), 3.88, 4.53 (2H, ABq, J=13.8 Hz), 5.17 (1H, d, J=5.1 Hz), 5.71 (1H, d, J=5.1 Hz), 6.60-6.82 (3H, m).
LC/MS (ES+): 759 (M+H$^+$)
IR (KBr) cm$^{-1}$: 3309, 1772, 1588, 1526, 1448

EXAMPLE 31
Compound (I-31)
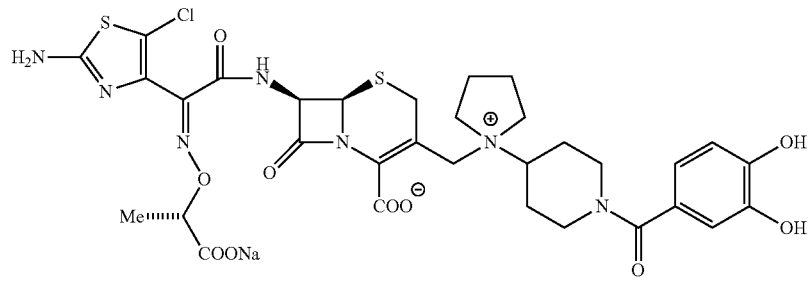
[Formula 108]
$^1$H-NMR (D$_2$O) δ (delta): 1.30 (3H, d, J=6.9 Hz), 1.55-2.28 (8H, m), 2.63-4.10 (11H, m), 4.38-4.62 (2H, m), 5.17, d, J=4.8 Hz, 5.72 (1H, d, J=4.8 Hz), 6.63-6.82 (3H, m).
LC/MS (ES+): 778 (M+H$^+$)
IR (KBr) cm$^{-1}$: 3292, 1773, 1589, 1446, 1374
Elementary analysis for C$_{32}$H$_{35}$ClN$_7$O$_{10}$S$_2$Na.7.5H$_2$O
Calcd.: C, 41.33; H, 5.86; Cl, 3.53; N, 10.31(%).
Found: C, 41.09; H, 5.39; Cl, 3.79; N, 10.48(%).
EXAMPLE 32
Compound (I-32)
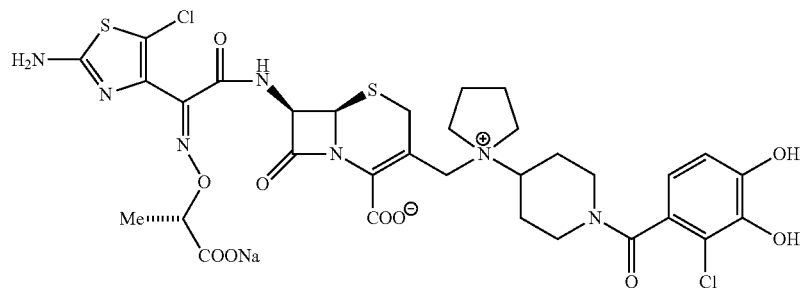
[Formula 109]
LC/MS (ES+): 812 (M+H$^+$)
IR (KBr) cm$^{-1}$: 3313, 1772, 1599, 1541, 1449

EXAMPLE 33
Compound (I-33)
[Formula 110]
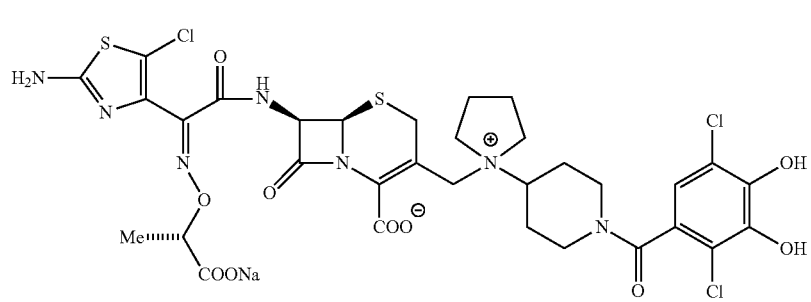
LC/MS (ES+): 845 (M+H$^+$)
IR (KBr) cm$^{-1}$: 3315, 1769, 1597, 1540
EXAMPLE 34
Compound (I-34)
[Formula 111]
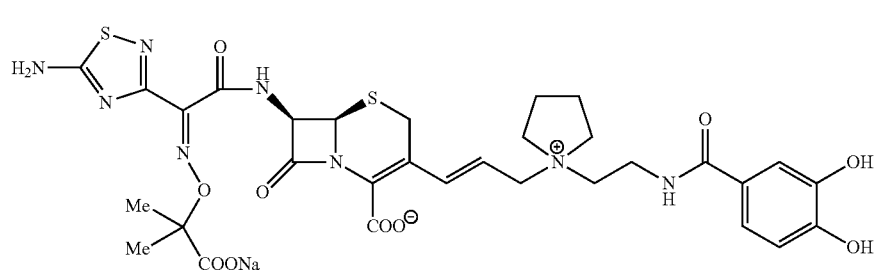
LC/MS (ES+): 745 (M+H$^+$)
IR (KBr) cm$^{-1}$: 3305, 1770, 1673, 1589, 1521
EXAMPLE 35
Synthesis of Compound (I-35)
[Formula 112]
I-35
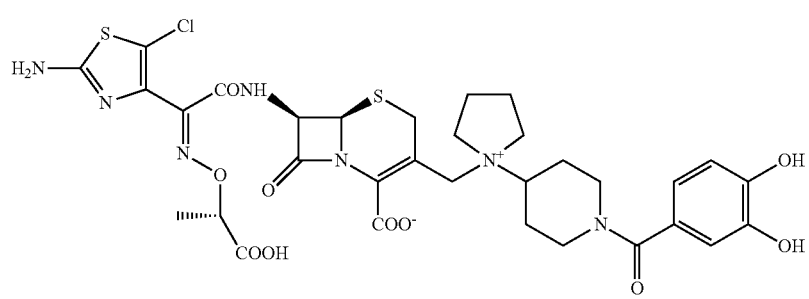

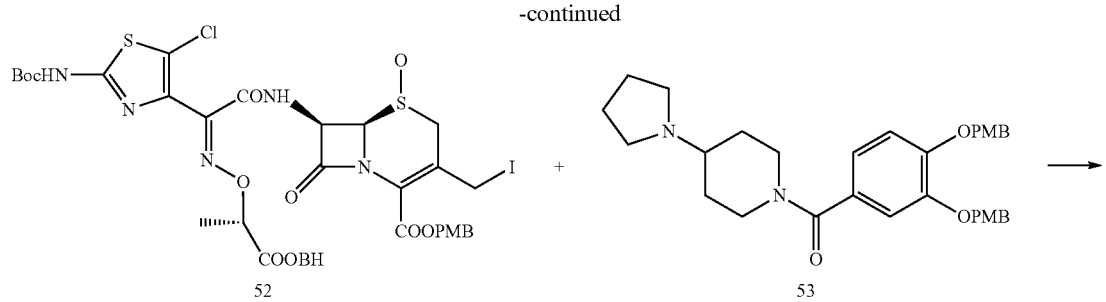

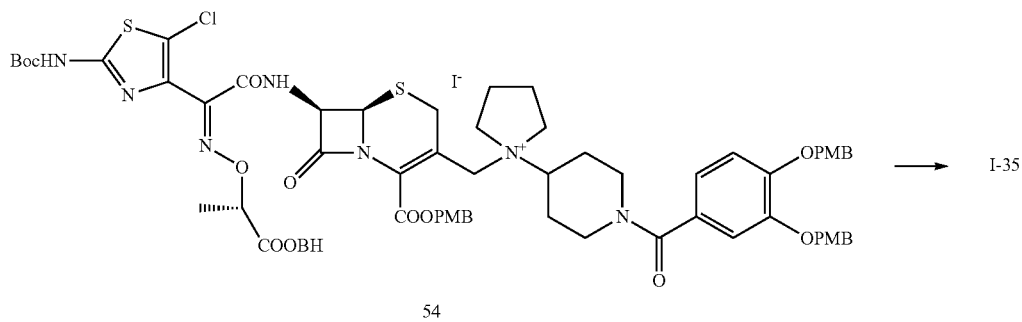

Step (1): Compound 52+Compound 43→Compound 54

Compound 52 (3.65 g, 3.58 mmol) and Compound 53 (1.90 g, 3.58 mmol) were dissolved in dimethylformamide (10 ml), followed by stirring at room temperature for 6 hours. To the reaction solution was added DMF (30 ml), subsequently cooling to −40° C., and then potassium iodide (4.16 g, 25.06 mmol) followed by AcCl (1.022 ml, 14.32 mmol) were added. After stirring for 1 hour under ice-cooling, the reaction solution was poured to the mixed solution of ethyl acetate and aqueous $NaHSO_3$ solution. The organic layer was separated, washed with water, dried, and then evaporated to yield Compound 54 as a powder. The resulting Compound 54 was used for the next reaction without purification.

Step (2): Compound 54→Compound (I-35)

Compound 54 (3.58 mmol) was dissolved in methylene chloride (20 ml) and anisole (3.9 ml), followed by cooling to −30° C. 2M $AlCl_3$-nitromethane solution (17.9 ml, 35.8 mmol) was then added, subsequently stirring for 30 minutes. To the reaction solution was then added i-$Pr_2O$ (40 ml) followed by 2M-hydrochloric acid, subsequently stirring for 5 minutes. As a result, oily deposit precipitated. The supernatant solution was removed by decantation, and then dilute hydrochloric acid and MeCN were added to the deposit to dissolve. HP-20SS resin was added to the solution, followed by concentration, and then subjected into HP-20SS column chromatography, subsequently eluting with water-acetonitrile. Fractions containing the desired compound were concentrated in vacuo, and then lyophilized to yield Compound (I-35) as a powder (180 mg, 6% yield).

Compound (I-35):

$^1$H-NMR ($D_2O$) δ (delta): 1.43 (3H, d, J=6.9 Hz), 1.60-2.19 (8H, m), 2.80-3.62 (9H, m), 3.42, 3.75 (2H, ABq, J=15.6 Hz), 3.95, 4.98 (2H, ABq, J=12.9 Hz), 4.61 (1H, q, J=7.2 Hz), 5.14 (1H, d, J=5.1 Hz), 5.71 (1H, dd, J=4.8, 8.4 Hz), 6.45 (1H, m), 6.71 (1H, d, J=8.1 Hz), 6.75 (1H, d, J=8.1 Hz), 6.86 (1H, s), 7.43 (2H, bs), 9.32-9.68 (3H, m).

MS (ESI): 778$^+$ (M+H)$^+$

Elementary analysis for $C_{32}H_{36}N_7O_{10}S_2Cl_1 \cdot 5.5H_2O$
Calcd.: C, 43.81; H, 5.40; N, 11.18; S, 7.31; Cl, 4.04(%).
Found: C, 43.78; H, 5.26; N, 11.29; S, 7.39; Cl, 3.93(%).

EXAMPLE 37

Synthesis of Compound (I-37)

[Formula 113]

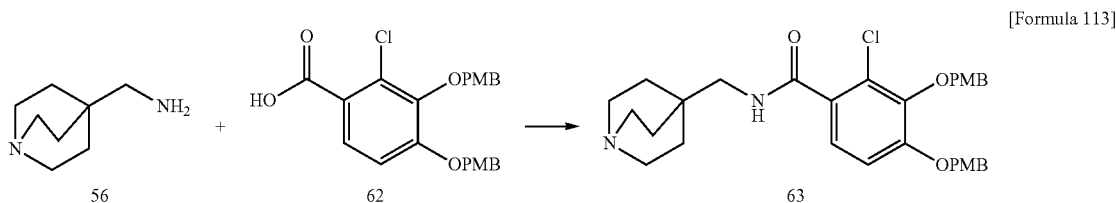

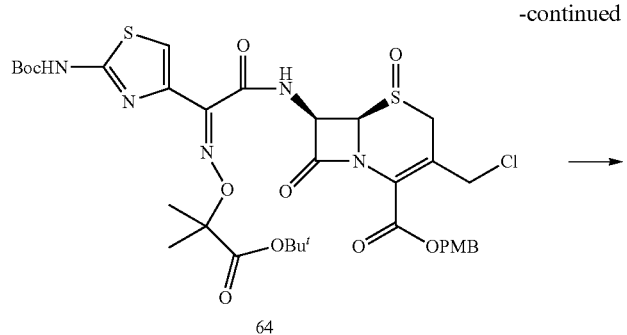

64

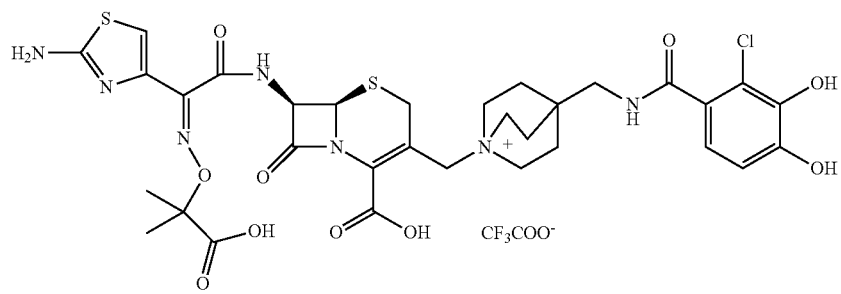

I-37

Step (1): Compound 62→Compound 63

To a solution of Compound 62 (1.72 g, 4.0 mmol) in dimethylformamide (7 mL), under ice-cooling with stirring, was added 1-hydroxybenzotriazole (595 mg, 4.40 mmol) and hydrochloric acid salt of ethyldimethylaminopropylcarbodiimide (843 mg, 4.40 mmol). After stirring at room temperature for 1 hour, the reaction solution was ice-cooled again, a solution of Compound 56 (1.03 g, 7.37 mmol) in dimethylformamide (3 mL) was added over 5 minutes. After stirring at the same temperature for 4 hours, the solvent was evaporated under reduced pressure. The residue was poured into cold water (30 mL), and then adjusted to pH 10 with 20% aqueous sodium carbonate solution. The precipitation was filtrated, and then dried in vacuo to yield Compound 63 (1.99 g, 90% yield).

Compound 63:

$^1$H-NMR (DMSO-$d_6$) δ (delta): 1.49 (6H, t, J=7.8 Hz), 2.95 (6H, t, J=7.8 Hz), 3.26 (2H, d, J=6.3 Hz), 3.80 (3H, s), 3.83 (3H, s), 4.95 (2H, s), 5.09 (2H, s), 6.36 (1H, t, 6.3 Hz), 6.82-6.96 (5H, m), 7.25 (1H, s), 7.31-7.36 (4H, m), 7.47 (1H, d, J=8.7 Hz).

Step (2): Compound 64→Compound (I-37)

To a solution of Compound 64 (637 mg, 0.8 mmol) in dimethylformamide (2.0 mL) was added Compound 63 (507 mg, 0.92 mmol) and sodium bromide (165 mg, 1.6 mmol) under ice-cooling. The reaction solution was stirred for 3 hours in a water bath at 15° C., and then dimethylformamide (4 mL) was added, and subsequently cooled to −40° C. At −40° C., phosphorus tribromide (151 μL, 1.6 mmol) was then added, followed by stirring at the same temperature for 1 hour. The reaction solution was poured into 5% brine (100 mL), subsequently stirring for 15 minutes, and then the precipitation was filtrated. The filter residue was then dried in vacuo to yield a light brown solid. A solution of this solid in methylene chloride (4 mL) was added to a solution of TFA (7.0 mL) with anisole (746 μL) under ice-cooling with stirring. This reaction solution was stirred at room temperature for 1.5 hours, and then TFA was evaporated under reduced pressure, while maintaining the temperature of the water bath at 25° C. or below. The residue was added into diisopropyl ether (80 mL) under ice-cooling with stirring, followed by filtrating the precipitation. The residue was concentrated in vacuo to yield Compound (I-37) (808 mg, 69% yield) as a powder.

Compound (I-37):

$^1$H-NMR (D$_2$O) δ (delta): 1.48 (3H, s), 1.50 (3H, s), 1.95 (6H, brs), 3.32-3.51 (9H, m), 3.88 (2H, m), 4.60 (1H, d, J=13.5 Hz), 5.35 (1H, d, J=5.1 Hz), 5.86 (1H, d, J=5.1 Hz), 6.68 (1H, d, J=8.4 Hz), 6.73 (1H, d, J=8.4 Hz).

Elementary analysis for $C_{30}H_{37}ClF_3N_7O_{12}S_2 \cdot 4.0H_2O \cdot 0.4CF_3COOH \cdot 0.3(C_3H_7OC_3H_7)$ Calcd.: C, 42.19; H, 4.39; N, 9.01; S, 5.54; Cl, 3.53; F, 7.91(%).

Found: C, 42.24; H, 4.80; N, 9.42; S, 6.16; Cl, 3.41; F, 7.67(%).

EXAMPLE 38

Synthesis of Compound (I-38)

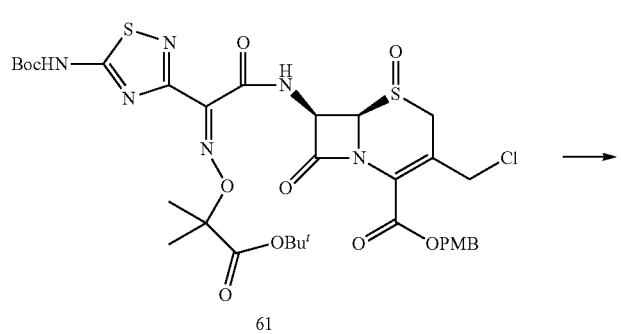

[Formula 114]

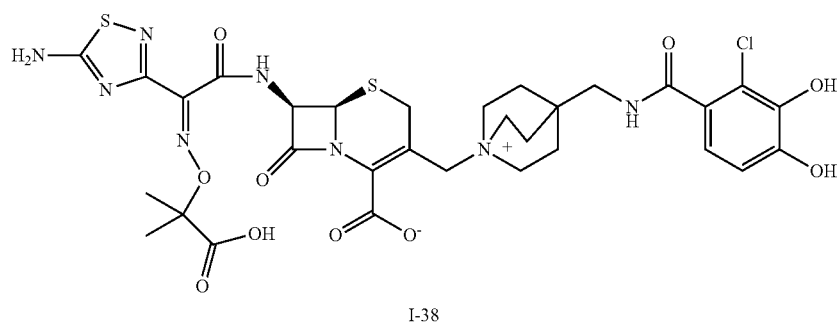

Step (1): Compound 61→Compound (I-38)

To a solution of Compound 61 (675 mg, 0.8 mmol) in dimethylformamide (2.0 mL) was added Compound 63 (485 mg, 0.88 mmol) and sodium bromide (165 mg, 1.6 mmol) under ice-cooling. The reaction solution was stirred for 3 hours in a water bath at 15° C., and then dimethylformamide (4 mL) was added thereto, and subsequently cooled to −40° C. At −40° C., phosphorus tribromide (151 μL, 1.6 mmol) was then added thereto, followed by stirring at the same temperature for 1 hour. The reaction solution was poured into 5% brine (100 mL), subsequently stirring for 15 minutes, and then the precipitation was filtrated. The filter residue was dried in vacuo to yield a light brown solid. A solution of this solid in methylene chloride (4 mL) was added to a solution of TFA (7.0 mL) with anisole (738 μL, 6.76 mmol) under ice-cooling with stirring. This reaction solution was stirred at room temperature for 1.5 hours, and then TFA was evaporated under reduced pressure, while maintaining the temperature of the water bath at 25° C. or below. The residue was added into diisopropyl ether (80 mL) under ice-cooling with stirring, followed by filtrating the precipitation. This solid was dried, dissolved in aqueous sodium hydrogen carbonate, and then subjected into ODS column chromatography, followed by eluting the desired compound with water-acetonitrile. The fractions containing the desired compound were concentrated in vacuo, and then the concentrated solution was lyophilized to yield a powder (264 mg). This powder was dissolved in water/acetonitrile/0.1M HCl. HP20SS was added thereto, concentrated, and then subjected into HP column chromatography eluting the desired compound with water-acetonitrile. The fractions containing the desired compound were concentrated in vacuo, and then the concentrated solution was lyophilized to yield Compound (I-38) (100 mg, 13% yield) as a powder.

Compound (I-38):

$^1$H-NMR (D$_2$O) δ (delta): 1.52 (3H, s), 1.53 (3H, s), 1.94 (6H, t, J=7.5 Hz), 3.34-3.51 (9H, m), 3.85-3.91 (2H, m), 4.58 (1H, d, J=13.5 Hz), 5.35 (1H, d, J=4.8 Hz), 5.88 (1H, d, J=4.8 Hz), 6.85 (1H, d, J=8.4 Hz), 6.89 (1H, d, J=8.4 Hz).

Elementary analysis for C$_{31}$H$_{35}$ClN$_8$O$_{10}$S$_2$·4.9H$_2$O

Calcd.: C, 43.07; H, 5.30; N, 12.89; S, 7.06(%).

Found: C, 42.92; H, 5.30; N, 12.92; S, 7.39(%).

EXAMPLE 41

Synthesis of Compound (I-41)

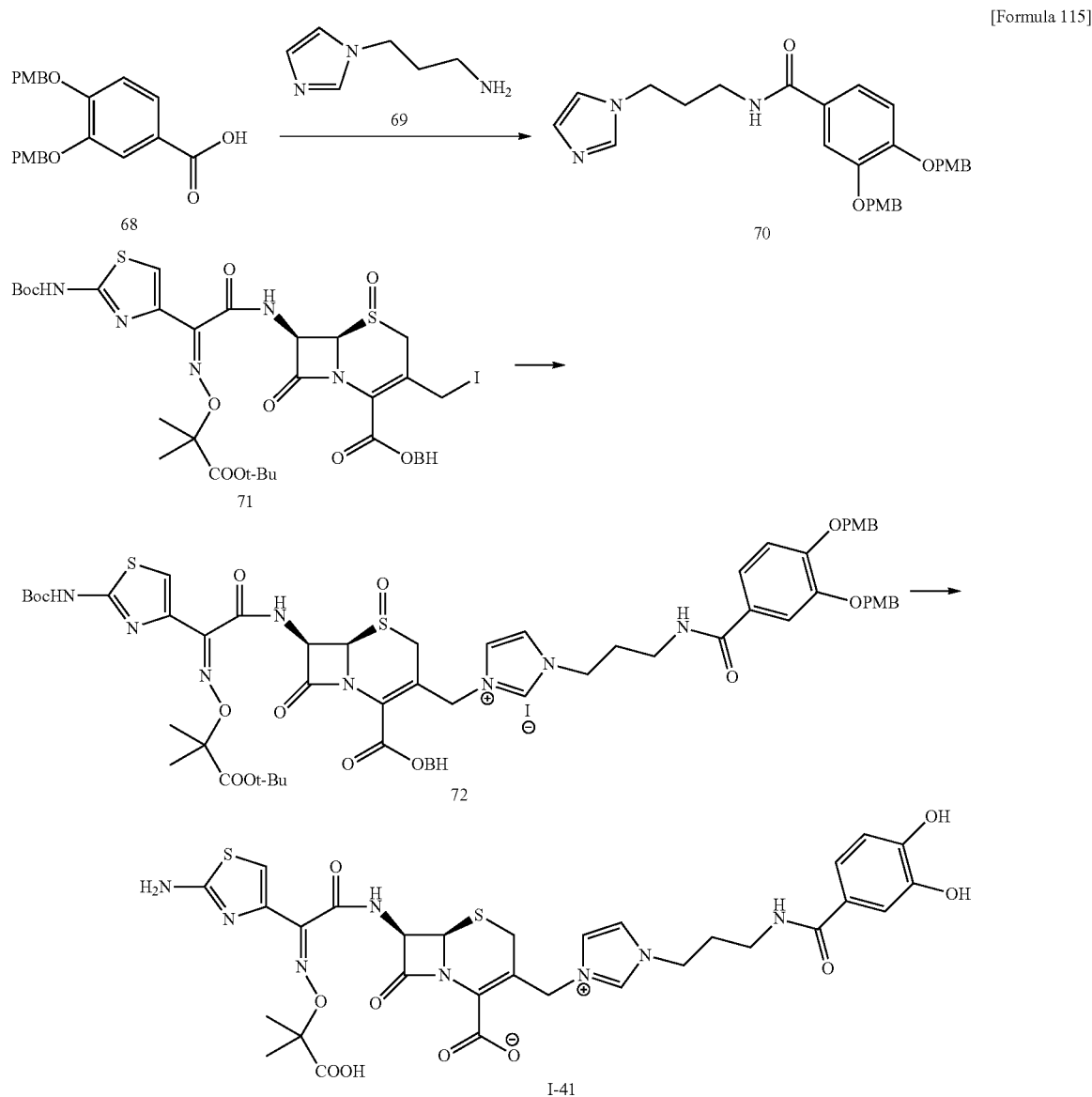

Step (1): Compound 68→Compound 70

Compound 68 (1.58 g, 4.00 mmol) was dissolved in dichloromethane (30 ml), and then Compound 69 (0.48 ml, 4.00 mmol) and WSCD.HCl (920 mg, 4.80 mmol) were added, followed by stirring at room temperature for 3 hours. After adding water, the organic layer was washed with water, washed with saturated brine, and then dried over magnesium sulfate, subsequently evaporating the solvent under reduced pressure. Diethyl ether was added to the resulting residue, and then filtrated to yield Compound 70 as a colorless powder (1.71 g, 85% yield).

Compound 70:

$^1$H-NMR (CDCl$_3$) δ (delta): 2.09 (2H, m), 3.43 (2H, m), 3.80 (3H, s), 3.81 (3H, s), 4.03 (2H, t, J=6.9 Hz), 5.09 (2H, s), 5.10 (2H, s), 6.28 (1H, t, J=6.5 Hz), 6.86-6.91 (5H, m), 6.96 (1H, s), 7.06 (1H, s), 7.20 (1H, dd, J=8.4, 2.0 Hz), 7.31-7.36 (4H, m), 7.45-7.50 (2H, m).

Step (2): Compound 71→Compound 72→Compound (I-41)

Compound 71 (934 mg, 1.00 mmol) was dissolved in dimethylformamide (2 ml), and then Compound 70 (0.48 ml, 4.00 mmol) was added, followed by stirring at room temperature for 2.5 hours. Dimethylformamide (6 ml) was added, and then the reaction solution was cooled to −40° C. Subsequently, potassium iodide (1.16 g, 7.00 mmol) and acetyl chloride (0.357 ml, 5.00 mmol) were added, and the mixture was allowed to warm up to 0° C. over 1 hour and further stirring at 0° C. for 1 hour. Ethyl acetate and aqueous NaHSO$_4$ solution were added. The organic layer was washed with water, washed with saturated brine, dried over magnesium sulfate, filtrated, and then concentrated in vacuo to yield Compound 72 as a powder.

The above-described crude Compound 72 (1.42 g) was dissolved in methylene chloride (15 ml) and anisole (1.1 ml), and subsequently cooled to −25° C. 2M AlCl₃-nitromethane solution (5.0 ml) was added, followed by stirring at temperature between −25° C. and −5° C. for 1 hour. The reaction solution was then transferred into a solution of 1N-HCl:MeCN (1:1) at 0° C. Diisopropyl ether was added, followed by separation and extraction. To the aqueous layer was added HP-20SS resin, and then acetonitrile was evaporated under reduced pressure. The mixed solution was subjected into HP-20SS column chromatography eluting the desired compound with acetonitrile-water. Fractions containing the desired compound were collected, and then concentrated in vacuo. The concentrated solution was lyophilized to yield Compound (I-41) as a powder (470 mg, 60% yield).

Compound (I-41):

¹H-NMR (DMSO-d₆) δ (delta): 1.42 (6H, br), 2.05 (2H, br), 3.17-4.20 (6H, m), 4.87 (1H, d, J=12.0 Hz), 5.03 (1H, m), 5.15 (1H, d, J=12.0 Hz), 5.71 (1H, m), 6.71 (1H, s), 6.77 (1H, d, J=4.0 Hz), 7.16 (1H, d, J=4.0 Hz), 7.28 (3H, br), 7.76 (1H, s), 7.93 (1H, s), 8.27 (1H, br), 9.28 (1H, s), 9.52 (1H, br).

MS (ESI): 729⁺ (M+H)⁺

Elementary analysis for $C_{30}H_{32}N_6O_{10}S_2 \cdot 3.0H_2O$
Calcd.: C, 45.88; H, 4.78; N, 14.55; S, 8.44(%).
Found: C, 46.03; H, 4.89; N, 14.31; S, 8.19(%).

EXAMPLE 42

Synthesis of Compound (I-42)

[Formula 116]

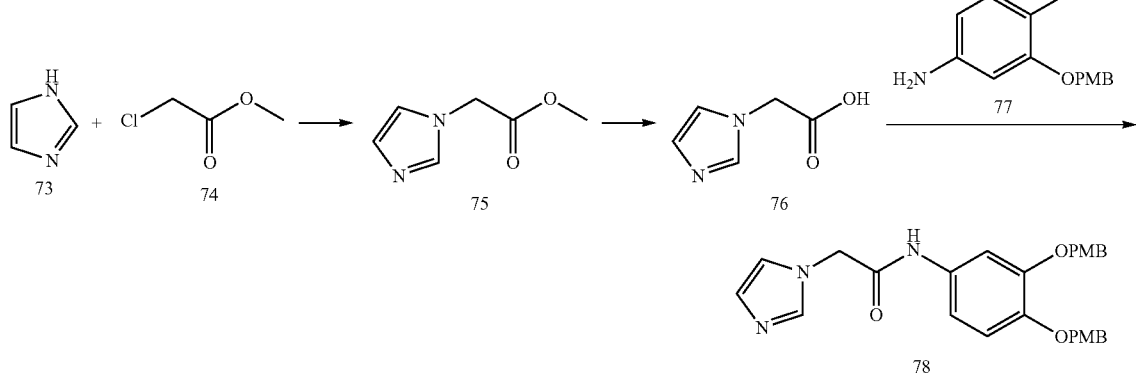

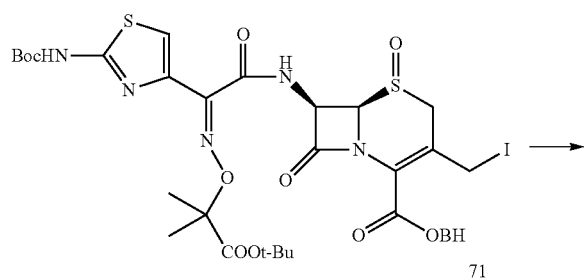

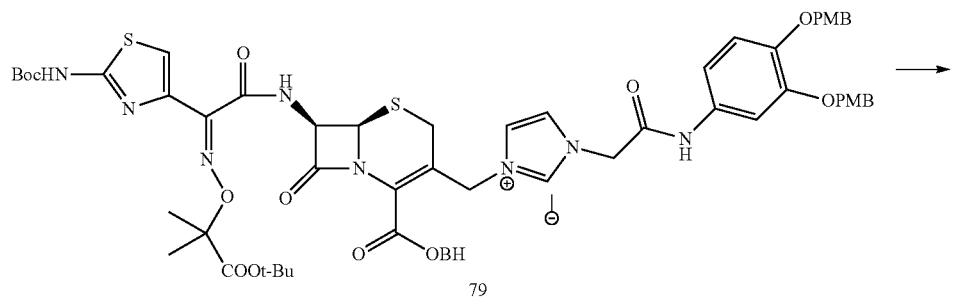

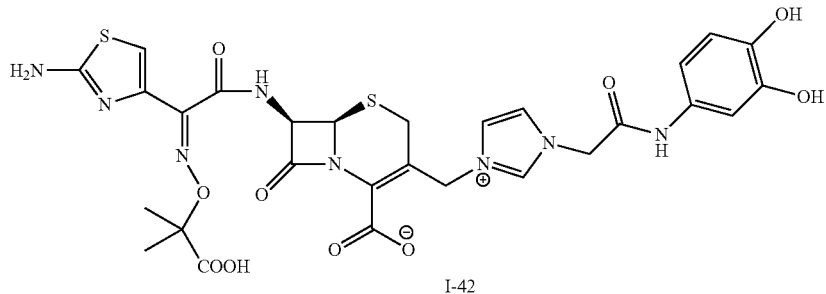

I-42

Step (1): Compound 73+Compound 74→Compound 75→Compound 76

To Compound 73 (2.04 g, 30.0 mmol) was added toluene (8 ml), dimethylformamide (0.8 mL), potassium iodide (199 mg, 1.2 mmol), and potassium carbonate (3.73 g, 27 mmol), subsequently stirring at room temperature for 15 minutes. To the reaction solution was added Compound 74 (3.94 ml, 45 mmol), followed by stirring at 65° C. for 2 hours. Ethyl acetate and water were added to the reaction solution. The organic layer was washed with water, washed with saturated brine, dried over magnesium sulfate, filtrated, and then concentrated in vacuo to yield Compound 75 (3.28 g).

To Compound 75 (3.28 g, 23.4 mmol) was added water (10 ml), followed by heating at reflux for 5 hours. The reaction solution was concentrated, followed by adding methanol thereto, and then filtration yielded Compound 76 (3.28 g).
Compound 76:

$^1$H-NMR (DMSO-$d_6$) δ (delta): 4.82 (2H, s), 6.89 (1H, s), 7.14 (1H, s), 7.63 (1H, s).

Step (2): Compound 76+Compound 77→Compound 78

To Compound 76 (126 mg, 1.0 mmol) was added dichloromethane (4 ml), Compound 77 (365 mg, 1.00 mmol), and WSCD.HCl (249 mg, 1.30 mmol), followed by stirring at 0° C. for 1 hour and then at room temperature for 1 hour. Dimethylformamide (2 ml) was added, subsequently stirring for 1 hour, and then concentrated in vacuo to evaporate dichloromethane. Dimethylformamide (2 ml) was added, and then allowed to stand for 3 days. Dichloromethane and water were then added. The organic layer was washed with water, washed with saturated brine, dried over magnesium sulfate, and then filtrated to yield Compound 78 (390 mg, 58% yield, 70% potency).

Step (3): Compound 71+Compound 78→Compound 79→Compound (I-42)

Compound 71 (538 mg, 0.58 mmol) was dissolved in dimethylformamide (2 ml), and then Compound 78 (390 mg, 0.58 mmol, 70% potency) was added thereto, followed by stirring at 0° C. for 2 hours and then at room temperature for 3 hours. Dimethylformamide (6 ml) was added, and then the reaction solution was cooled to −40° C. Subsequently, potassium iodide (670 mg, 4.04 mmol) and acetyl chloride (0.206 ml, 2.88 mmol) were added, followed by stirring at −40° C. for 30 minutes and further at 0° C. for 1 hour. Ethyl acetate and aqueous NaHSO$_4$ solution were added. The organic layer was washed with water, washed with saturated brine, dried over magnesium sulfate, filtrated, and then concentrated in vacuo to yield Compound 79 as a powder.

The above-described crude Compound 79 was dissolved in methylene chloride (10 ml) and anisole (0.63 ml), followed by cooling to −30° C. 2M AlCl$_3$-nitromethane solution (2.89 ml) was added thereto, subsequently stirring at temperature between −30° C. and −10° C. for 1 hour. The reaction solution was transferred into a solution of 1N-HCl:MeCN (1:1) at 0° C. Diisopropyl ether was added, and then the solution was separated. HP-20SS resin was added to the aqueous layer, and then acetonitrile was evaporated under reduced pressure. The mixed solution was subjected into HP-20SS column chromatography, subsequently eluting the desired compound with acetonitrile-water. Fractions containing the desired compound were collected, and then concentrated in vacuo. The concentrated solution was lyophilized to yield Compound (I-42) as a powder (70 mg, 17% yield).

Compound (I-42):

$^1$H-NMR (DMSO-$d_6$) δ (delta): 1.42 (6H, d, J=5.6 Hz), 2.91-3.91 (2H, m), 4.77 (1H, d, J=13.6 Hz), 4.99 (1H, m), 5.11 (2H, br), 5.20 (1H, d, J=13.6 Hz), 5.66 (1H, m), 6.58 (1H, d, J=8.4 Hz), 6.64 (1H, s), 6.74 (1H, d, J=8.4 Hz), 7.04 (1H, s), 7.20 (1H, br), 7.63 (1H, s), 7.91 (1H, s), 9.29 (1H, s), 9.50 (1H, br), 10.4 (1H, s).

MS (ESI): 701$^+$ (M+H)$^+$

Elementary analysis for $C_{28}H_{28}N_8O_{10}S_2 \cdot 4.4H_2O$
Calcd.: C, 43.02; H, 4.53; N, 14.33; S, 8.50(%).
Found: C, 43.12; H, 4.76; N, 14.37; S, 8.22(%).

EXAMPLE 43
Synthesis of Compound (II-1)
[Formula 117]
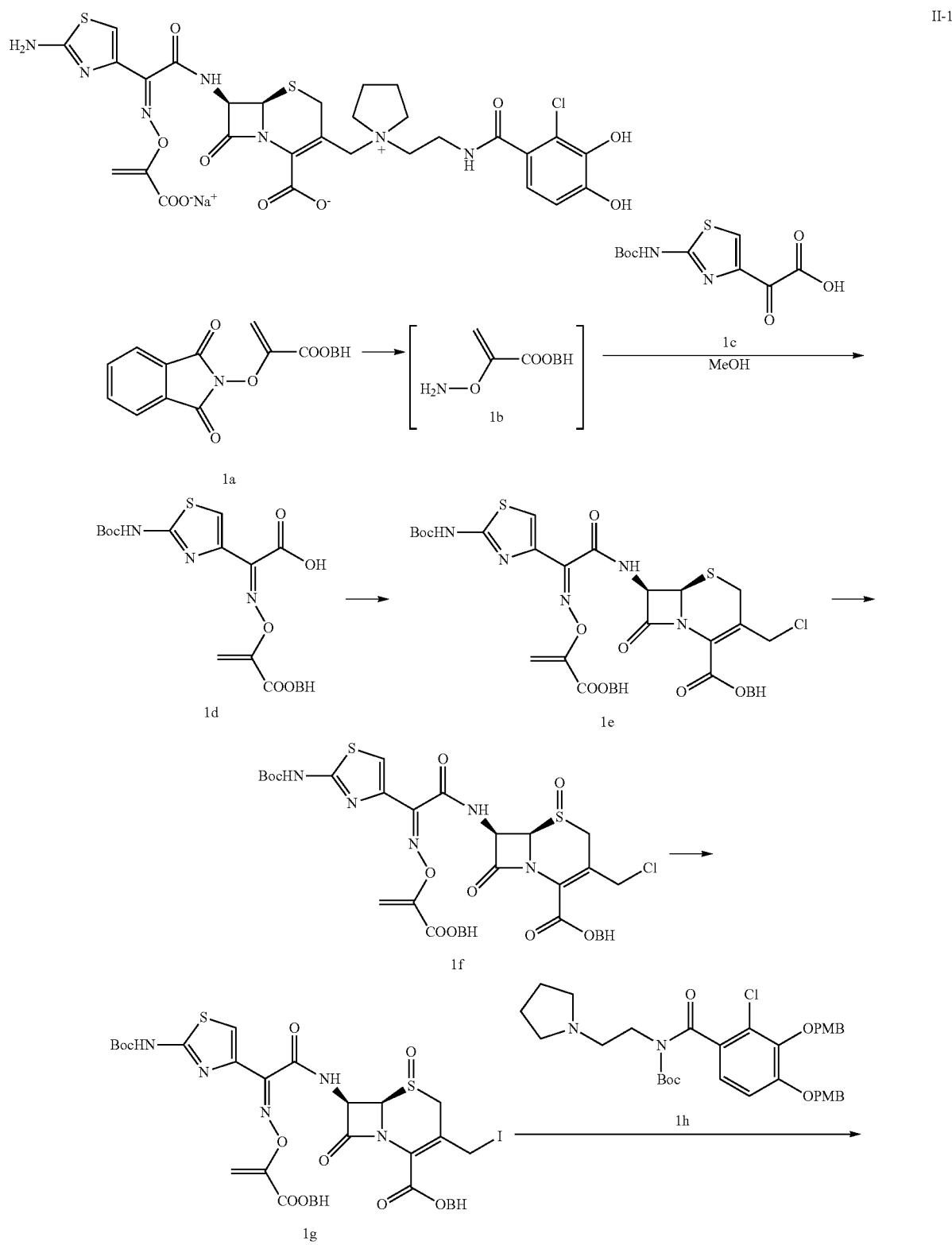

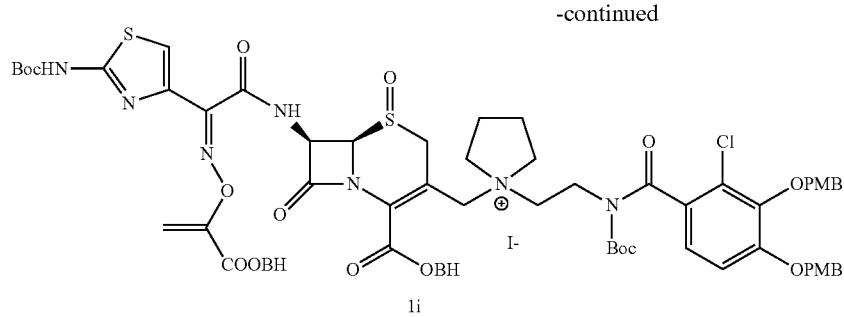

1i

Step (1): Compound 1a→Compound 1d

Compound 1a (3 g, 7.51 mmol) was dissolved in methylene chloride (30 mL), followed by cooling to −30° C., and then methylhydrazine (0.402 mL, 7.51 mmol) was added thereto, subsequently stirring for 40 minutes. The reaction solution was filtrated, and then to the filtrate was added methanol (15 mL) followed by Compound 1c (2.045 g, 7.51 mmol), subsequently stirring. The reaction solution was concentrated in vacuo, and then to the residue was purified water, followed by extraction with ethyl acetate. The separated organic layer was washed with purified water, washed with saturated brine, and then dried over anhydrous magnesium sulfate. Magnesium sulfate was removed by filtration, and then the solvent was evaporated under reduced pressure to yield Compound 1d as a yellow oily substance (3.96 g, 100% yield.).

$^1$H-NMR (CDCl$_3$) δ (delta): 7.40-7.13 (10H, m), 6.86 (1H, s), 5.71-5.56 (2H, m), 1.11 (9H, s).

Step (2): Compound 1d→Compound 1e

Hydrochloric acid salt (3.41 g, 7.56 mmol) of diphenylmethyl 7-amino-3-chloromethyl-3-cephem-4-carboxylate was suspended in ethyl acetate (40 mL), and then Compound 1d was added thereto, and subsequently cooled to −40° C. To the reaction solution was added phenyl dichlorophosphate (1.356 ml, 9.08 mmol), and then added drop-wise N-methylmorpholine (2.459 mL, 22.69 mmol), followed by stirring at −40° C. To the reaction solution was then added aqueous 10% succinic acid solution. The organic layer was separated, washed with aqueous 5% sodium hydrogen carbonate, washed with purified water, and then washed with saturated brine. The organic layer was dried over anhydrous magnesium sulfate, and then magnesium sulfate was removed by filtration. The solvent was evaporated under reduced pressure, and then the resulting residue was purified by silica gel chromatography to yield 1e as a yellow oily substance (3.65 g, 49% yield).

$^1$H-NMR (CDCl$_3$) δ (delta): 7.46-7.20 (21H, m), 6.93 (1H, s), 6.92 (1H, s), 5.89 (1H, dd, J=9.2, 5.0 Hz), 5.87 (1H, d, J=1.8 Hz), 5.63 (1H, d, J=1.8 Hz), 4.87 (1H, d, J=5.0 Hz), 4.47 (1H, d, J=12.0 Hz), 4.29 (1H, d, J=11.1 Hz), 3.42 (1H, d, J=18.5 Hz), 3.23 (1H, d, J=18.8 Hz), 1.52 (9H, s).

Step (3): Compound 1e→Compound 1f

Compound 1e (3.67 g, 3.71 mmol) was dissolved in methylene chloride (40 mL), and subsequently cooled to −30° C. 65% m-chloroperbenzoic acid (0.984 g, 3.71 mmol) was added, followed by stirring for 80 minutes. Aqueous 1% sodium hydrogen sulfite solution (40 mL) was added, and then the organic layer was separated. The organic layer washed with aqueous 5% sodium hydrogen carbonate, washed with purified water, washed with saturated brine, and then dried over anhydrous magnesium sulfate. Magnesium sulfate was removed by filtration, and then the solvent was evaporated under reduced pressure. The resulting residue was subjected into silica gel chromatography to yield Compound 1f as a yellow oily substance (2.67 g, 77% yield).

$^1$H-NMR (CDCl$_3$) δ (delta): 7.49-7.26 (24H, m), 6.94 (1H, s), 6.89 (1H, s), 6.16 (1H, dd, J=9.8, 4.7 Hz), 5.75 (1H, d, J=2.0 Hz), 5.57 (1H, d, J=2.0 Hz), 5.29 (1H, br s), 4.88 (1H, d, J=12.4 Hz), 4.13-4.10 (1H, m), 3.37 (1H, d, J=18.6 Hz), 2.81 (1H, d, J=19.7 Hz), 1.52 (9H, s).

Step (4): Compound 1f→Compound 1g

Compound 1f (2.67 g, 2.85 mmol) was dissolved in tetrahydrofuran (25 mL), and then degassed under light-shielded condition. Under nitrogen atmosphere, to the reaction solution was then added potassium iodide (1.28 g, 8.55 mmol), subsequently stirring. To the reaction solution was then added aqueous 4% sodium hydrogensulfite solution (25 mL), followed by extraction from the aqueous layer with ethyl acetate. The separated organic layer was washed with purified water, washed with saturated brine, and then dried over anhydrous magnesium sulfate. Magnesium sulfate was removed by filtration, and then the solvent was evaporated under reduced pressure to yield Compound 1g as a yellow oily substance.

$^1$H-NMR (CDCl$_3$) δ (delta): 7.50-7.26 (36H, m), 6.98 (1H, s), 6.90 (1H, s), 6.12 (1H, dd, J=9.5, 4.6 Hz), 5.73 (1H, d, J=1.9 Hz), 5.54 (1H, d, J=1.9 Hz), 5.28 (1H, br s), 4.74 (1H, d, J=9.3 Hz), 4.10-4.04 (1H, m), 3.30 (1H, d, J=17.2 Hz), 2.96 (1H, d, J=18.1 Hz), 1.59-1.47 (9H, m).

Step (5): Compound 1g→Compound 1i→Compound (II-1)

Compound 1g (1.12 g, 1 mmol) was dissolved in dimethylacetamide (3 mL), and then Compound 1h (659 mg, 1 mmol) was added thereto, subsequently stirring at room temperature for five and half hours. To the reaction solution was added purified water, followed by extraction with ethyl acetate. The organic layer was washed with purified water, washed with saturated brine, and then dried over anhydrous magnesium sulfate. Magnesium sulfate was removed by filtration, and then the solvent was evaporated under reduced pressure to yield Compound 1i.

Then, Compound 1i was dissolved in methylene chloride (15 mL), and subsequently cooled to −50° C. To the reaction solution was then added phosphorus tribromide (0.189 mL, 2 mmol), followed by stirring at −50° C. for 1 hour. Anisole (1.09 mL, 10 mmol) and 2 mol/L aluminum chloride/nitromethane solution (5 mL, 10 mmol) were then added thereto, followed by stirring at 0° C. To the reaction solution was then added purified water (30 mL) and diisopropyl ether (50 mL). To the reaction solution was added acetonitrile and 2 N hydrochloric acid, and then the precipitation was dissolved, subsequently the aqueous layer was separated. The organic layer was extracted with a mixed solution of water/acetonitrile/dilute hydrochloric acid, and then to the combined aqueous layer was HP20SS resin, followed by concentration. The concentrated suspension was subjected into HP20SS/ODS column chromatography, subsequently eluting with water-acetonitrile. An aqueous 0.2 N sodium hydroxide solution was used for fractions containing the desired compound to obtain a sodium salt, and then concentrated in vacuo. The concentrated solution was lyophilized to yield Compound (II-1) as a powder (245 mg, 32% yield).

MS (m+1)=736.00

Elementary analysis for $C_{29}H_{29}Cl_1N_7O_{10}S_2Na_1(H_2O)_{4.5}(NaHCO_3)_{1.1}$ Calcd.: C, 38.81; H, 4.23; Cl, 3.81; N, 10.52; S, 6.88; Na, 5.18.

Found: C, 38.56; H, 4.50; Cl, 4.55; N, 11.08; S, 7.19; Na, 5.38.

$^1$H-NMR (D$_2$O) δ (delta): 7.18 (1H, s), 6.78-6.75 (2H, m), 5.91 (1H, d, J=4.9 Hz), 5.32-5.28 (2H, m), 5.15 (1H, br s), 4.74-4.82 (1H, m), 4.10 (1H, d, J=13.9 Hz), 3.82-3.54 (13H, m), 2.21-2.07 (5H, m).

EXAMPLE 44

Synthesis of Compound (II-2)

[Formula 118]

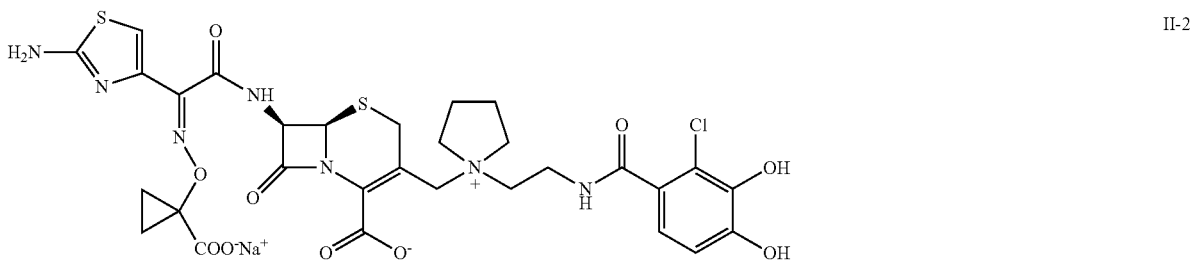

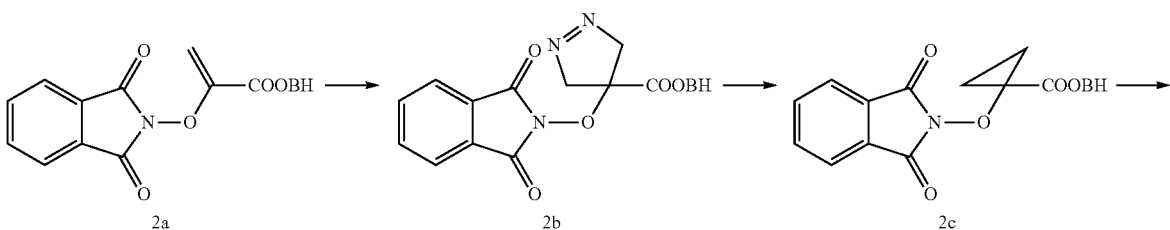

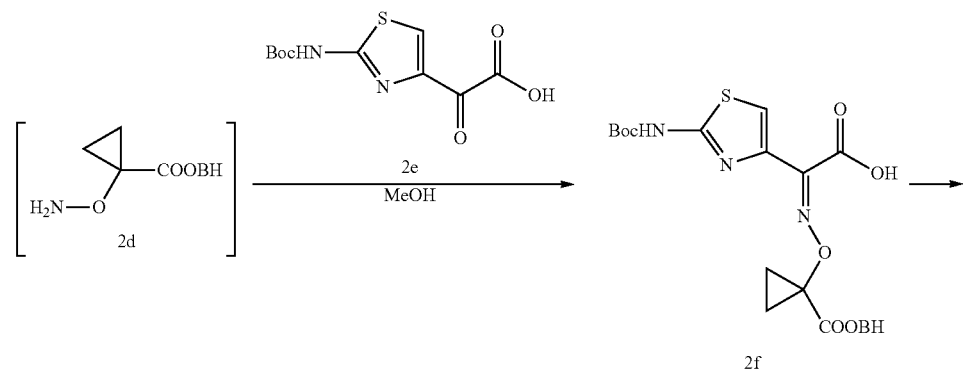

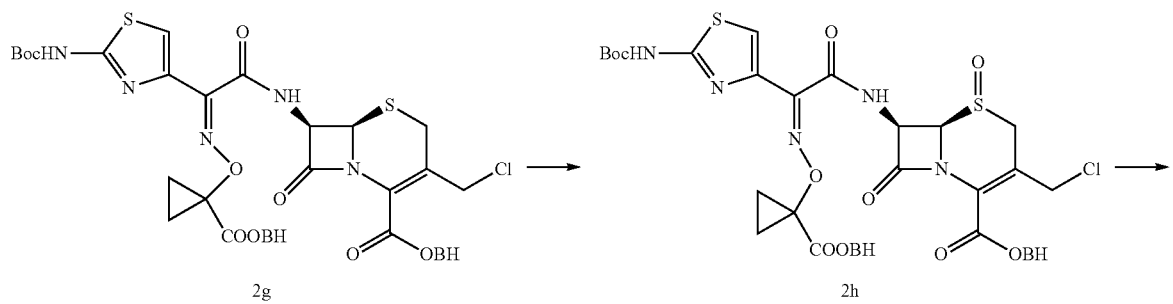

-continued

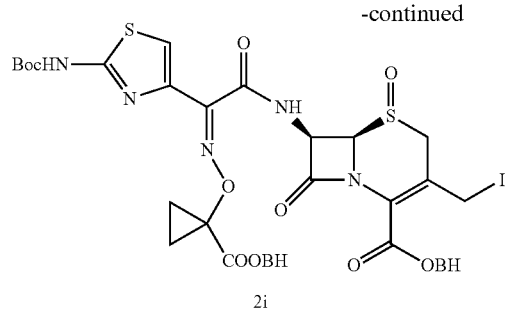

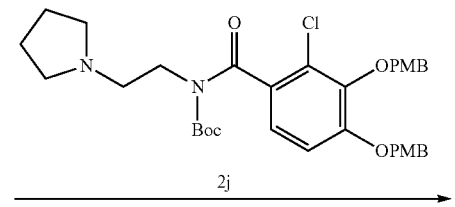

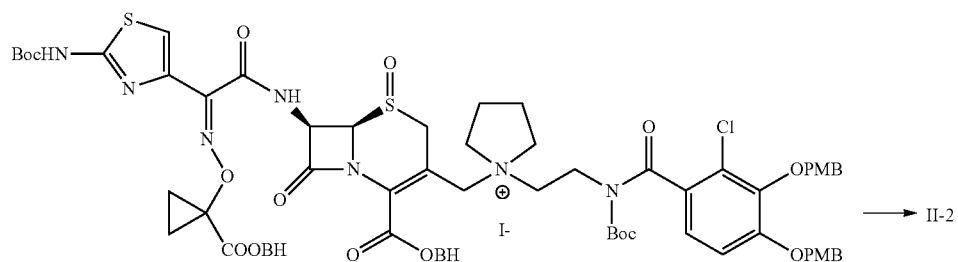

Step (1): Compound 2a→Compound 2b

Compound 2a (3.77 g, 9.44 mmol) was suspended in diethyl ether (280 mL), and then an ether solution (100 mL) of diazomethane (29.1 mmol), prepared from N-methyl-N-nitrosourea (3 g, 29.1 mmol), was added. After stirring at 0° C. overnight, diethyl ether was concentrated in vacuo until the volume reached about 200 mL, and then filtrated. Collection of the filtrated residue yielded Compound 2b (2.911 g, 70% yield). This was used for the next step (2) without purification, etc.

Step (2): Compound 2b→Compound 2c

Compound 2b (2.911 g, 6.59 mmol) was suspended in toluene (30 mL), and then subjected to heating at reflux for 8 hours and 30 minutes. After the reaction solution was cooled, the precipitated solid was filtrated, and then dried in vacuo to yield Compound 2c (1.35 g, 3.28 mmol).

$^1$H-NMR (DMSO-d$_6$) δ (delta): 7.85 (4H, s), 7.50-7.21 (10H, m), 6.86 (1H, s), 1.78 (2H, dd, J=8.6, 5.4 Hz), 1.52 (2H, dd, J=8.6, 5.4 Hz).

Step (3): Compound 2c→Compound 2g

Compound 2c (1.35 g, 3.27 mmol) was used, and treated similarly as described above to yield Compound 2g (2.52 g, 92% yield).

$^1$H-NMR (CDCl$_3$) δ (delta): 8.19 (1H, br s), 8.02 (1H, d, J=9.1 Hz), 7.49-7.18 (27H, m), 6.97 (1H, s), 6.89 (1H, s), 5.98 (1H, dd, J=9.1, 5.0 Hz), 5.02 (1H, d, J=5.0 Hz), 4.52 (1H, d, J=11.8 Hz), 4.32 (1H, d, J=11.8 Hz), 3.48 (1H, d, J=18.3 Hz), 3.23 (1H, d, J=18.3 Hz), 1.75-1.54 (15H, m).

Step (4): Compound 2g→Compound 2h

Compound 2g (2.52 g, 2.5 mmol) was used, and treated similarly as described above to yield Compound 2h (2.07 g, 87% yield).

$^1$H-NMR (CDCl$_3$) δ (delta): 8.32 (1H, br s), 7.86 (1H, d, J=9.7 Hz), 7.49-7.20 (27H, m), 6.97 (1H, s), 6.91 (1H, s), 6.16 (1H, dd, J=9.7, 4.5 Hz), 4.90 (1H, d, J=13.4 Hz), 4.54 (1H, dd, J=4.6, 1.3 Hz), 4.18 (1H, d, J=12.3 Hz), 3.73 (1H, d, J=18.5 Hz), 3.32 (1H, d, J=18.6 Hz), 1.64-1.53 (15H, m).

Step (5): Compound 2h→Compound 2i

Compound 2h (2.07 g, 2.18 mmol) was used, and treated similarly as described above to yield Compound 2i (2.23 g, 91% yield).

$^1$H-NMR (CDCl$_3$) δ (delta): 8.36 (1H, br s), 7.86 (1H, d, J=9.7 Hz), 7.50-7.10 (23H, m), 6.98 (1H, s), 6.90 (1H, s), 6.11 (1H, dd, J=9.7, 4.9 Hz), 4.75 (1H, d, J=9.0 Hz), 4.52 (1H, dd, J=4.9, 1.1 Hz), 4.07 (1H, d, J=9.5 Hz), 3.66 (1H, d, J=18.8 Hz), 3.49 (1H, d, J=18.8 Hz), 1.69-1.43 (15H, m).

Step (6): Compound 2i→Compound 2k→Compound (II-2)

Compound 2i (1.12 g, 1 mmol) was used, and treated similarly as described above to yield Compound (II-2) (312 mg, 40% yield).

MS (m+1)=750.00

Elementary analysis for $C_{30}H_{31}ClN_7O_{10}S_2Na(H_2O)_3$ $(NaHCO_3)_1(NaCl)_{1.5}(H_2O)_{1.3}$ Calcd.: C, 36.46; H, 4.01; Cl, 8.68; N, 9.60; S, 6.28; Na, 7.88.

Found: C, 36.48; H, 4.15; Cl, 4.26; N, 9.82; S, 6.33; Na, 7.93.

$^1$H-NMR (D$_2$O) δ (delta): 7.03 (1H, br s), 6.84-6.73 (2H, m), 5.84 (1H, d, J=4.5 Hz), 5.34 (1H, d, J=4.5 Hz), 4.76-4.71 (1H, m), 4.11 (1H, d, J=13.3 Hz), 3.98-3.42 (11H, m), 2.31-2.05 (4H, m), 1.43-1.17 (4H, m).

EXAMPLE 45

Synthesis of Compound (II-3)

$^1$H-NMR (CDCl$_3$) δ (delta): 7.77-7.69 (4H, m), 7.56 (2H, dd, J=7.7, 1.7 Hz), 7.39-7.36 (3H, m), 7.31-7.23 (7H, m), 7.18-7.15 (3H, m), 7.09-7.01 (2H, m), 6.93 (1H, s), 6.04 (1H, s).

[Formula 119]

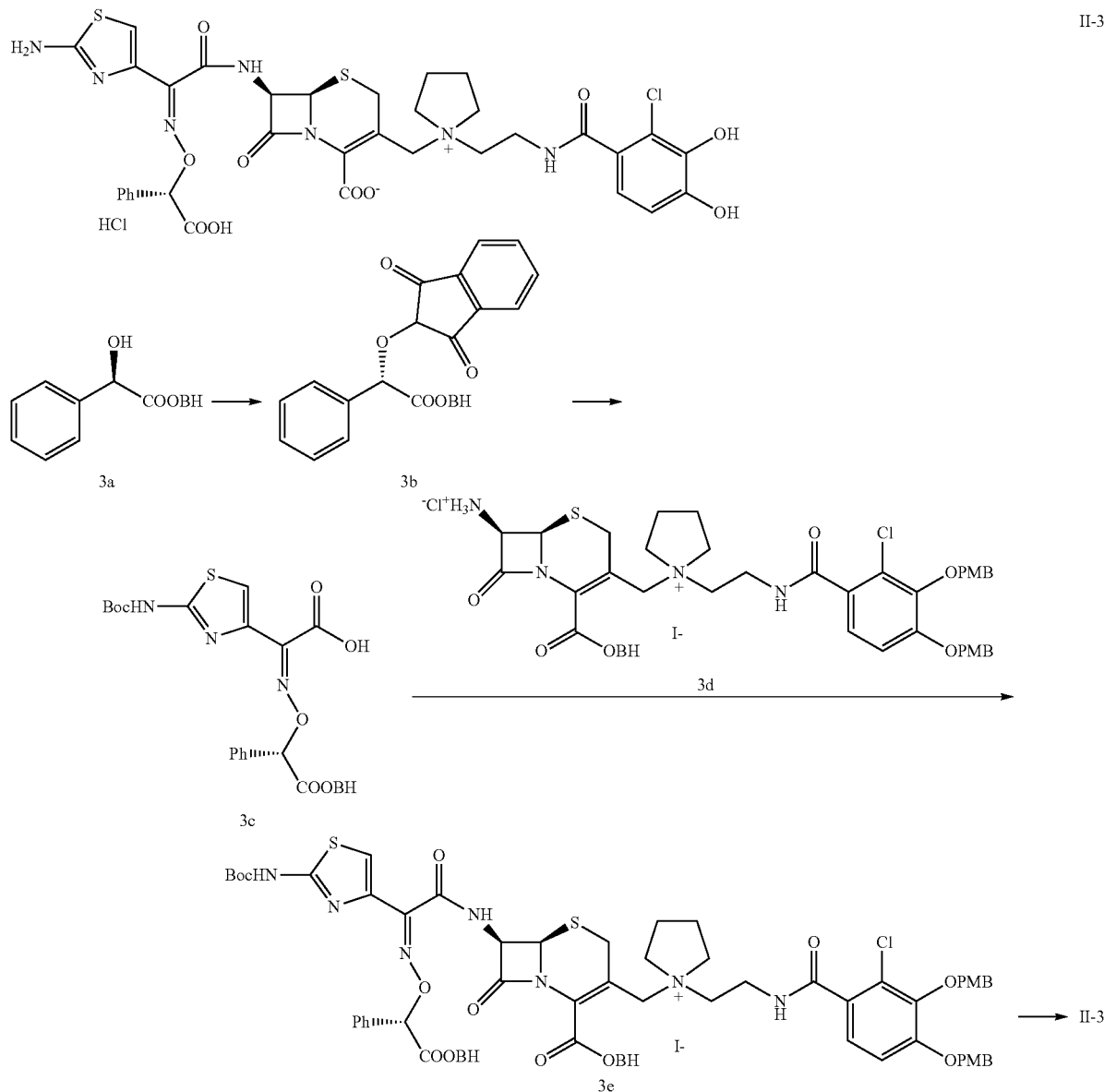

Step (1): Compound 3a→Compound 3b

Compound 3a (18.6 g, 58.4 mmol) was dissolved in tetrahydrofuran (190 mL), and then N-hydroxyphthalimide (11.44 g, 70.1 mmol) and triphenylphosphine (18.39 g, 70.1 mmol) were added thereto. To the reaction solution was then added drop-wise diisopropyl azodicarboxylate (13.63 mL, 70.1 mmol), subsequently stirring at room temperature. The reaction solution was concentrated in vacuo, and then to the resulting residue was added methanol (300 mL), followed by stirring at 0° C. The precipitated solid was filtrated and then dried under reduced pressure to yield Compound 3b (8.70 g, 32% yield).

Step (2): Compound 3b→Compound (II-3)

Compound 3b (4.63 g, 10 mmol) was used, and treated similarly to described above to yield Compound 3c. Compound 3c (1.068 g, 1 mmol) was dissolved in methylene chloride (10 mL), and then Compound 3d (0.588 g, 1 mmol), hydrochloric acid salt (0.23 g, 1.2 mmol) of 1-(dimethylaminopropyl)-3-ethylcarbodiimide, and pyridine (0.105 mL, 1.3 mmol) were added thereto, followed by stirring at −10° C. for 1 hour. To the reaction solution was added purified water, followed by extraction from aqueous layer with methylene chloride. The organic layer was washed with purified water, washed with saturated brine, and dried over anhydrous magnesium sulfate. Magnesium sulfate was removed by filtration, and then the solvent was evaporated under reduced pressure to yield Compound 3e.

Then Compound 3e was dissolved in methylene chloride (15 mL), and subsequently cooled to −30° C. Anisole (1.1 mL, 10 mmol) and 2 mol/L aluminum chloride/nitromethane solution (5 mL, 10 mmol) were added, followed by stirring at 0° C. To the reaction solution was then added purified water (30 mL) and diisopropyl ether (50 mL). Acetonitrile and 2 N hydrochloric acid were added to the treated reaction solution to dissolve the precipitation, then the aqueous layer was separated. The organic layer was extracted with a mixed solution of purified water/acetonitrile/dilute hydrochloric acid, and then HP20SS resin was added to the combined aqueous layers, followed by concentration. The concentrated suspension was subjected into HP20SS/ODS column chromatography, subsequently eluting the desired compound with aqueous dilute hydrochloric acid-acetonitrile, and then fractions containing the desired compound were concentrated in vacuo. The concentrated solution was lyophilized to yield Compound (II-3) as a powder (91 mg, 11% yield).

Elementary analysis for $C_{34}H_{34}ClN_7O_{10}S_2(H_2O)_4(HCl)_{1.5}$

Calcd.: C, 44.05; H, 4.73; Cl, 9.56; N, 10.58; S, 6.92.

Found: C, 43.80; H, 4.55; Cl, 9.53; N, 10.41; S, 6.65.

$^1$H-NMR (DMSO-$d_6$) δ (delta): 10.20 (1H, br s), 9.64 (1H, d, J=7.0 Hz), 8.53 (1H, br s), 7.51-7.36 (6H, m), 6.85-6.75 (3H, m), 5.94 (1H, dd, J=8.0, 5.0 Hz), 5.58 (1H, s), 5.26 (1H, d, J=5.0 Hz), 4.65 (1H, d, J=13.7 Hz), 4.30 (1H, d, J=14.3 Hz), 3.93 (1H, d, J=16.6 Hz), 3.69-3.50 (9H, m), 2.17-1.96 (4H, br m).

EXAMPLE 46

Synthesis of Compound (II-4)

[Formula 120]

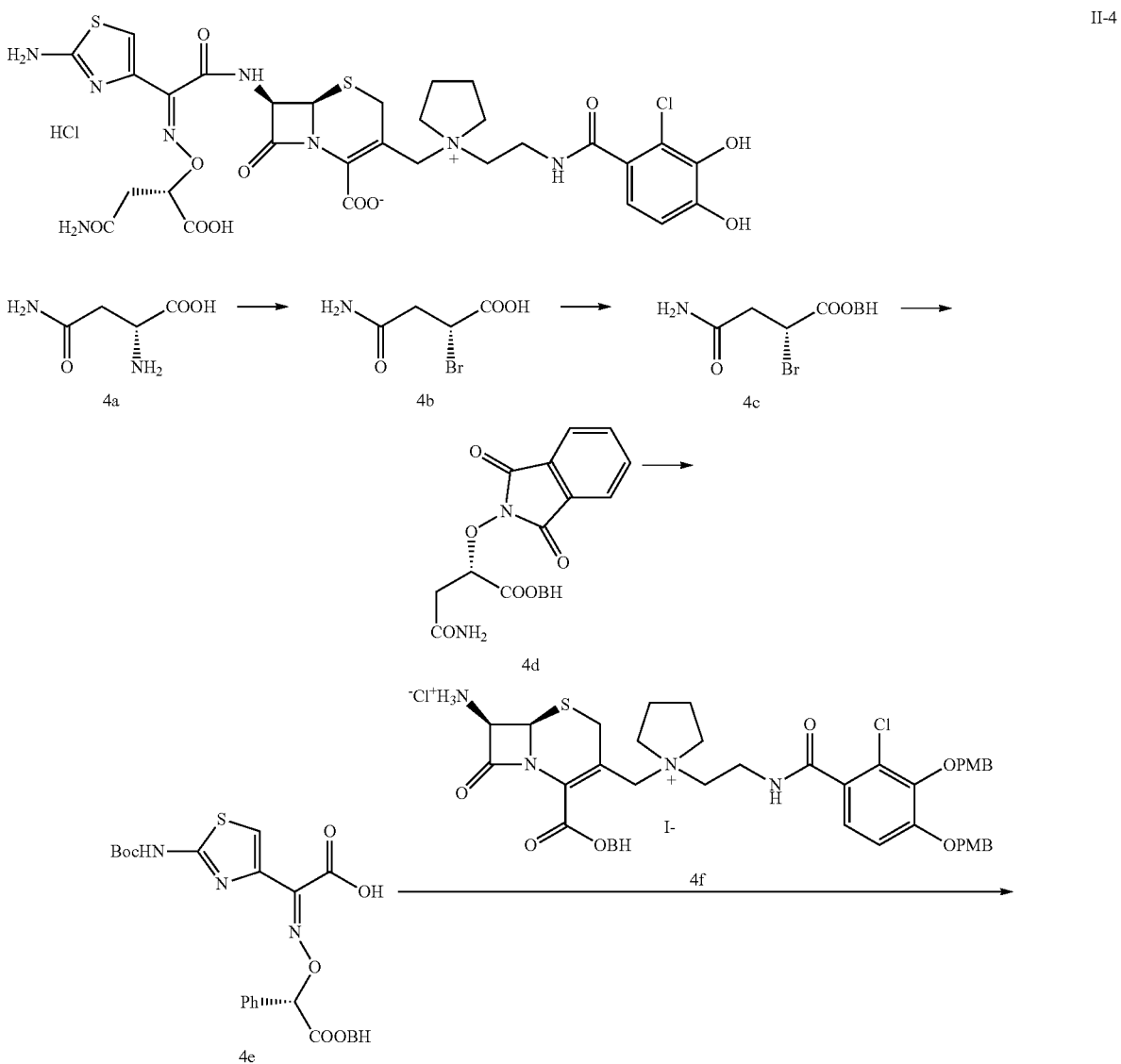

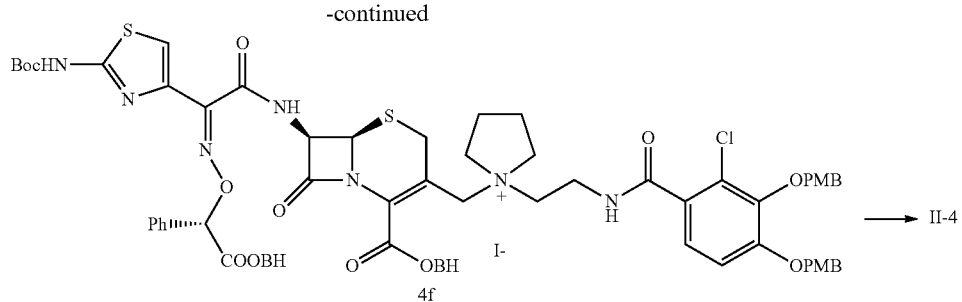

4f

Step (1): Compound 4a→Compound 4c

D-arginine 4a (10.42 g, 70 mmol) was dissolved in aqueous 2 N sulfuric acid solution, and then potassium bromide was added thereto, and subsequently cooled to −10° C. Sodium nitrite (9.58 g, 139 mmol) was then added to the reaction solution, followed by stirring. The reaction solution was extracted with tetrahydrofuran, and then the organic layer was dried over anhydrous magnesium sulfate. Magnesium sulfate was removed by filtration, and then the solvent was evaporated under reduced pressure to yield 11.14 g of Compound 4b.

Compound 4b (5.88 g) was suspended in chloroform (60 mL) and tetrahydrofuran (30 mL), diphenyldiazomethane (6.12 g, 31.5 mmol), followed by stirring at room temperature for two and half hours. The reaction solution was concentrated in vacuo, and then ethyl acetate and aqueous 5% sodium hydrogen carbonate were added, subsequently separating the organic layer. The organic layer was washed with purified water, washed with saturated brine, and then dried over anhydrous magnesium sulfate. Magnesium sulfate was removed by filtration, and then the solvent was evaporated under reduced pressure. The resulting residue was subjected into silica gel chromatography to yield Compound 4c as an oily substance (8.62 g, 79% yield).

$^1$H-NMR (CDCl$_3$) δ (delta): 7.42-7.30 (14H, m), 6.87 (1H, s), 4.81 (1H, dd, J=8.1, 6.6 Hz), 3.16 (1H, dd, J=15.7, 8.1 Hz), 2.88 (1H, dd, J=15.7, 6.5 Hz).

Step (2): Compound 4c→Compound 4d

N-hydroxyphthalimide (7.77 g, 47.7 mmol) was dissolved in dimethylformamide (85 mL), and then potassium carbonate (4.94 g, 35.7 mmol) was added thereto, subsequently stirring at room temperature. To the reaction solution was then added a solution of Compound 4c (8.63 g, 23.83 mmol) in dimethylformamide (45 mL), followed by stirring at room temperature for 6 hours and 40 minutes. The reaction solution was poured into 400 mL of purified water, and then the precipitated amorphous solid was filtrated. The obtained solid was then suspended in methanol. The resulting solid was filtrated, and then the residue was dried in vacuo to yield Compound 4d (1.83 g, 17%).

$^1$H-NMR (CDCl$_3$) δ (delta): 7.78-7.71 (4H, m), 7.35-7.22 (10H, m), 6.91 (1H, s), 6.51 (1H, br s), 5.45 (1H, br s), 5.25 (1H, dd, J=7.5, 5.0 Hz), 3.04 (1H, dd, J=16.5, 7.5 Hz), 2.95 (1H, dd, J=16.5, 5.0 Hz).

Step (3): Compound 4d→Compound (II-4)

Compound 4d was used, and treated similarly as described above to yield Compound (II-4) (88 mg, 11% yield).

MS (m+1)=781.03

Elementary analysis for $C_{30}H_{33}ClN_8O_{11}S_2(H_2O)_{3.8}(HCl)_{0.5}$

Calcd.: C, 41.52; H, 4.77; Cl, 6.13; N, 12.91; S, 7.39.
Found: C, 41.52; H, 4.73; Cl, 6.29; N, 12.94; S, 7.48.

$^1$H-NMR (DMSO-d$_6$) δ (delta): 10.23 (1H, br s), 9.47 (1H, d, J=8.2 Hz), 9.34 (1H, br s), 8.45 (1H, br s), 7.42 (1H, br s), 7.29 (2H, s), 6.97 (1H, br s), 6.81-6.75 (3H, m), 5.78 (1H, dd, J=8.2, 5.0 Hz), 5.19 (1H, d, J=5.2 Hz), 5.00-4.87 (2H, m), 4.02 (1H, d, J=13.1 Hz), 3.88 (1H, d, J=17.1 Hz), 3.81-3.17 (6H, m), 2.64 (2H, d, J=6.4 Hz), 2.16-1.98 (4H, m).

EXAMPLE 47

Synthesis of Compound (II-5)

[Formula 121]

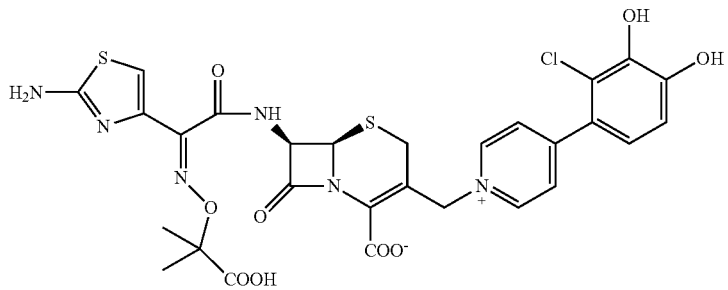

II-5

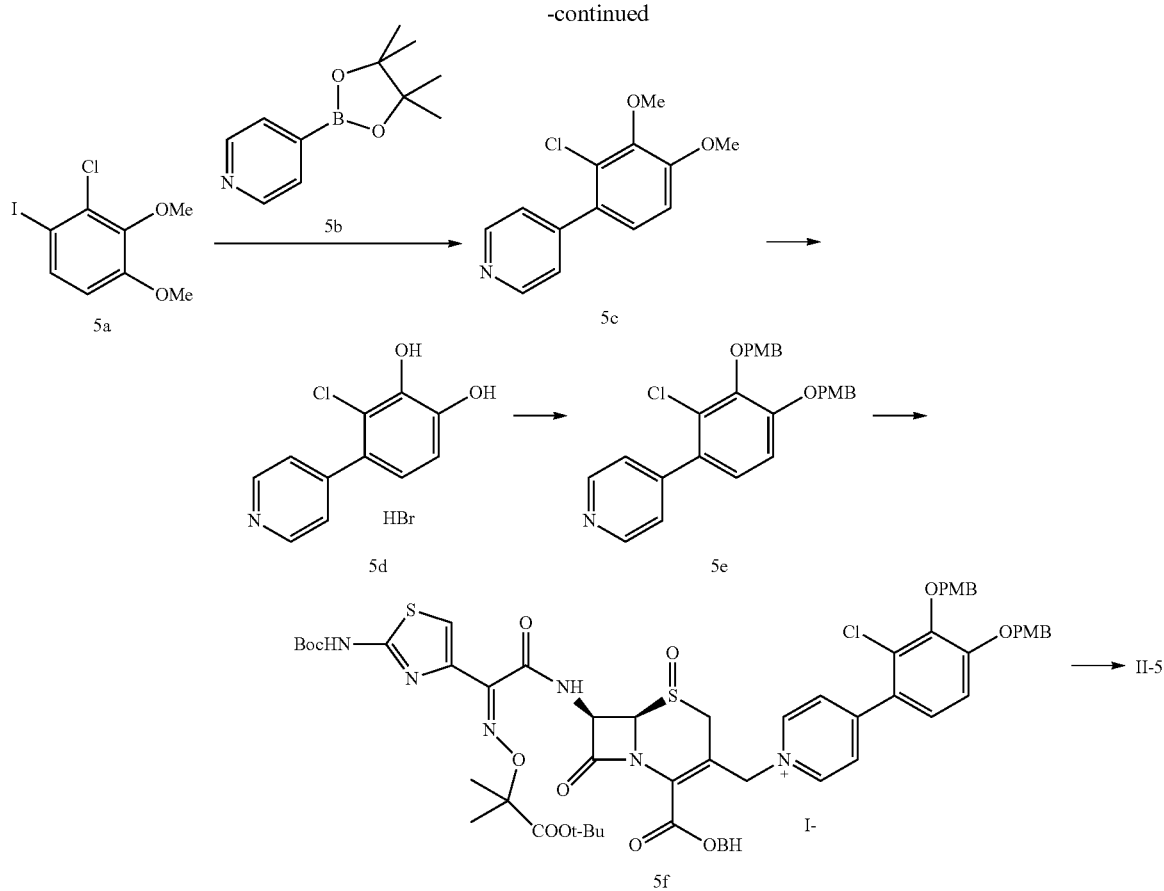

Step (1): Compound 5a→Compound 5c

Compound 5a (Ref. *Journal of Labelled Compound and Radiopharmaceuticals* 45; 5; 2002; 371-378) (1194 mg, 4 mmol) was dissolved in 1,4-dioxane (10 mL). Then purified water (1 mL), Compound 5b (820 mg, 4 mmol), potassium carbonate (1658 mg, 12 mmol), and tetrakistriphenylphosphine palladium (231 mg, 0.2 mmol) were added thereto in turn, followed by heating at reflux. Purified water was added to the reaction solution, followed by extraction from the aqueous layer with ethyl acetate. The organic layer was washed with purified water, and then washed with saturated brine. After the organic layer was dried over anhydrous magnesium sulfate, magnesium sulfate was removed by filtration, and then the solvent was evaporated under reduced pressure. To the resulting residue was then added diisopropyl ether. Insolubles were filtrated, washed with diisopropyl ether, and then dried in vacuo to yield Compound 5c (415 mg, 42% yield).

$^1$H-NMR (CDCl$_3$) δ (delta): 8.64 (2H, dd, J=4.5, 1.6 Hz), 7.35 (2H, dd, J=4.5, 1.6 Hz), 7.05 (1H, d, J=8.5 Hz), 6.91 (1H, d, J=8.5 Hz), 3.93 (3H, s), 3.91 (3H, s).

Step (2): Compound 5c→Compound 5d

Compound 5c (415 mg, 1.66 mmol) was dissolved in methylene chloride (4 mL), and then a 1 mol/L solution of boron tribromide in methylene chloride (4.16 mL, 4.16 mmol) was added thereto, followed by stirring at room temperature for 30 minutes. To the reaction solution was added methanol, and then the solvent was evaporated under reduced pressure. The resulting residue was filtrated, washed with methylene chloride, and then dried in vacuo to yield Compound 5d.

$^1$H-NMR (D$_2$O) δ (delta): 8.74 (2H, d, J=6.4 Hz), 8.14 (2H, d, J=6.4 Hz), 7.06 (1H, d, J=8.5 Hz), 7.01 (1H, d, J=8.5 Hz).

Step (3): Compound 5d→Compound 5e

Compound 5d (332 mg, 1.097 mmol) was suspended in dimethylformamide (3 mL), and then potassium carbonate (531 mg, 3.84 mmol) and 4-methoxybenzyl chloride (0.329 mL, 2.414 mmol) were added thereto in turn, subsequently stirring at room temperature. Purified water was then added to the reaction solution, followed by extraction from the aqueous layer with ethyl acetate. The organic layer was washed with purified water, and then washed with saturated brine. The organic layer was dried over anhydrous magnesium sulfate, subsequently removing magnesium sulfate by filtration, and then the solvent was evaporated under reduced pressure. The resulting residue was subjected into silica gel chromatography to yield Compound 5e (276 mg, 55% yield).

$^1$H-NMR (CDCl$_3$) δ (delta): 8.65 (2H, dt, J=7.6, 2.7 Hz), 7.37 (6H, dt, J=9.5, 3.6 Hz), 7.03-6.97 (2H, m), 6.93 (2H, ddd, J=9.3, 5.0, 2.5 Hz), 6.84 (2H, dt, J=9.2, 2.5 Hz), 5.10 (2H, s), 5.01 (2H, s), 3.84 (3H, s), 3.80 (3H, s).

Step (4): Compound 5e→Compound 5f→Compound (II-5)

Compound 5e (276 mg, 0.598 mmol) was used, and treated similarly as described above to yield Compound (II-5) (240 mg, 58% yield).

MS (m+1)=689.08

Elementary analysis for C$_{28}$H$_{25}$ClN$_6$O$_9$S$_2$(H$_2$O)$_{2.6}$

Calcd.: C, 45.70; H, 4.14; Cl, 4.82; N, 11.42; S, 8.71.

Found: C, 45.96; H, 4.05; Cl, 4.85; N, 11.39; S, 8.36.

$^1$H-NMR (DMSO-d$_6$) δ (delta): 9.44-9.36 (3H, m), 8.21 (2H, d, J=6.7 Hz), 7.27 (2H, s), 6.94 (2H, s), 6.69 (1H, s), 5.73

(1H, dd, J=8.3, 5.0 Hz), 5.64 (1H, d, J=13.4 Hz), 5.14-5.04 (2H, m), 3.56 (1H, d, J=17.8 Hz), 3.15 (1H, d, J=17.8 Hz), 1.40 (6H, s).

EXAMPLE 48

Synthesis of Compound (II-6)

[Formula 122]

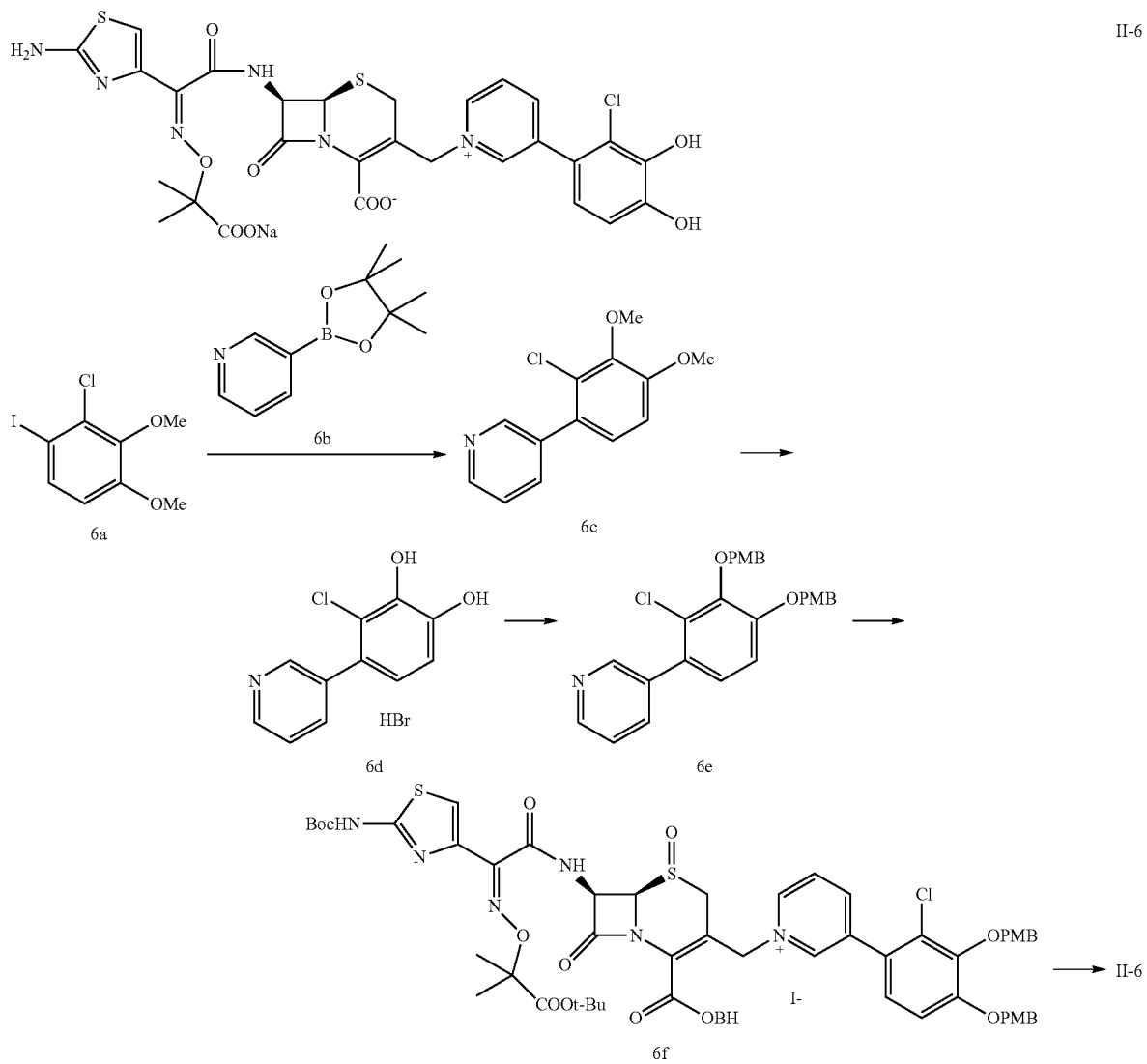

Step (1): Compound 6a→Compound 6c

Compound 6a (2.99 g, 10 mmol) and Compound 6b (2.26 g, 11 mmol) were used, and treated similarly as described above to yield Compound 6c (1.92 g, 77% yield).

$^1$H-NMR (CDCl$_3$) δ (delta): 8.68-8.62 (1H, m), 8.59 (1H, td, J=3.1, 1.6 Hz), 7.76 (1H, dtd, J=7.8, 1.6, 1.6 Hz), 7.34 (1H, ddt, J=7.8, 4.8, 1.1 Hz), 7.05 (1H, dd, J=8.6, 1.2 Hz), 6.92 (1H, dd, J=8.6, 1.2 Hz), 3.96-3.90 (6H, m).

Step (2): Compound 6c→Compound 6d→Compound 6e→Compound 6f→Compound (II-6)

Compound 6c (1.9 g, 7.61 mmol) was used, and treated similarly as described above to yield Compound 6d (1.54 g, 67% yield). Then Compound 6d (1.54 g, 5.90 mmol) was used, and treated similarly to described above to yield Compound 6e (1.16 g, 49% yield). Compound 6f (1.16 g, 1.09 mmol) was used, and treated similarly as described above to yield Compound (II-6) (410 mg, 53% yield).

MS (m+1)=689.10

Elementary analysis for $C_{28}H_{24}Cl_1N_6O_9S_2(H_2O)_3(NaHCO_3)_{1.1}$

Calcd.: C, 41.88; H, 3.76; Cl, 4.25; N, 10.07; S, 7.68; Na, 3.03.

Found: C, 41.84; H, 4.15; Cl, 4.65; N, 10.35; S, 7.65; Na, 3.30.

$^1$H-NMR (D$_2$O) δ (delta): 9.10 (1H, s), 8.89 (1H, d, J=5.8 Hz), 8.58 (1H, d, J=8.1 Hz), 8.08 (1H, t, J=7.1 Hz), 6.95-6.90 (3H, m), 5.83 (1H, d, J=4.7 Hz), 5.64 (1H, d, J=14.6 Hz), 5.33 (1H, d, J=15.1 Hz), 5.28 (1H, d, J=4.7 Hz), 3.68 (1H, d, J=17.8 Hz), 3.22 (1H, d, J=17.8 Hz), 1.44 (6H, s).

EXAMPLE 49

Synthesis of Compound (II-7)

[Formula 123]

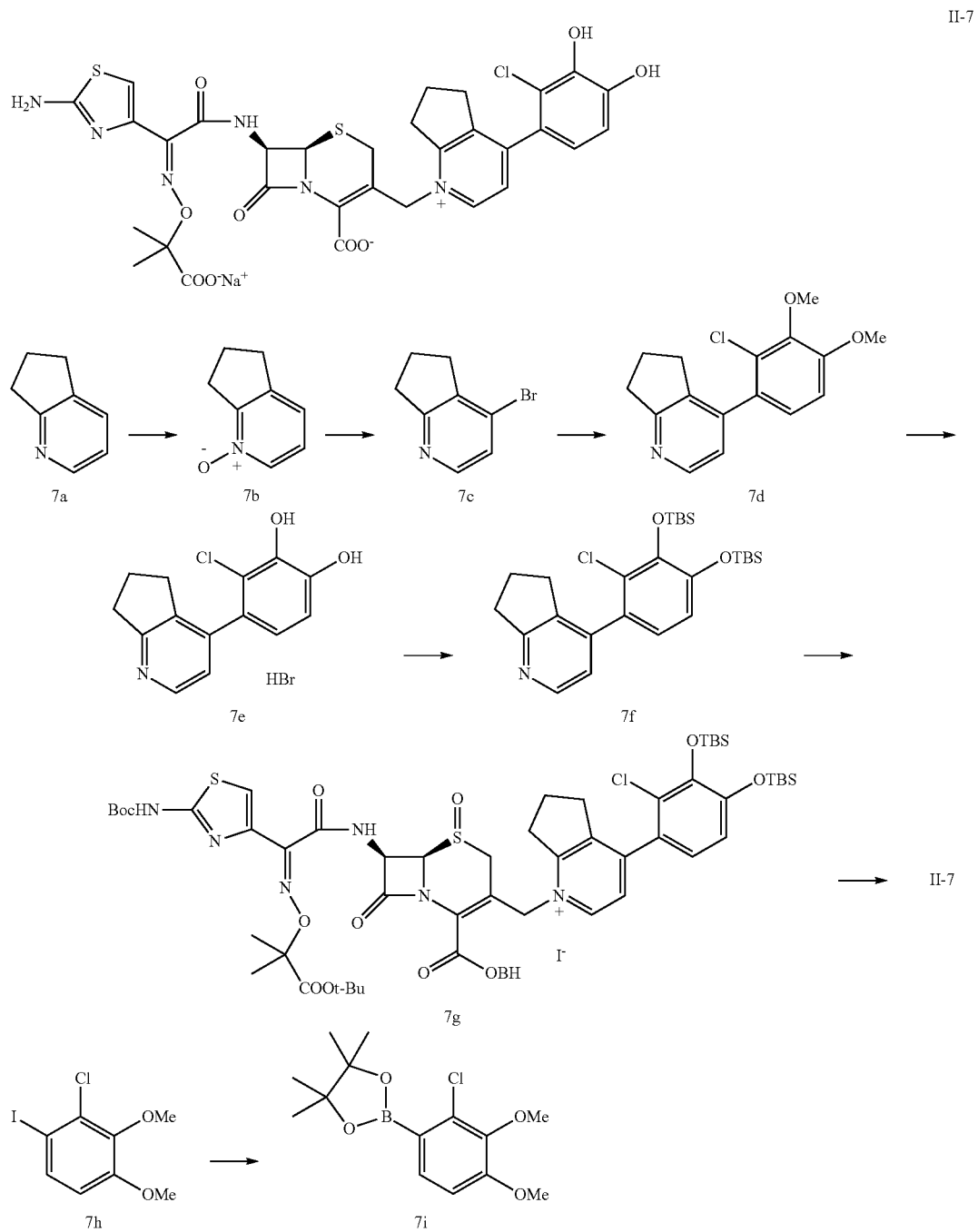

Step (1): Compound 7a→Compound 7b

Compound 7a (8.34 g, 70 mmol) was dissolved in methylene chloride (80 mL), and then m-chloroperbenzoic acid (18.58 g, 70 mmol) was added thereto, subsequently stirring at 0° C. for 45 minutes. To the reaction solution was added an aqueous solution of sodium hydrogen sulfite (8.01 g, 77 mmol), and then adjusted to pH 10 with aqueous 2 N sodium hydroxide solution. After extraction from the aqueous layer with chloroform and tetrahydrofuran, the organic layer was dried over anhydrous magnesium sulfate. Magnesium sulfate was removed by filtration, and then the solvent was evaporated under reduced pressure to yield Compound 7b as a gray solid (8.46 g, 89% yield).

$^{1}$H-NMR (CDCl$_3$) δ (delta): 8.05 (1H, d, J=6.3 Hz), 7.14-7.05 (2H, m), 3.18 (2H, t, J=7.6 Hz), 3.03 (2H, t, J=7.6 Hz), 2.28-2.10 (2H, m).

Step (2): Compound 7b→Compound 7c

Compound 7b (4 g, 29.6 mmol) was dissolved in chloroform (20 mL), and subsequently cooled to 0° C. To the reaction solution was added phosphorus oxybromide (16.97 g, 59.2 mmol), followed by heating at reflux. Ice (5 g) was added into the reaction solution, and then adjusted to pH 10 with aqueous 2 N sodium hydroxide solution. The aqueous layer was then extracted with chloroform. The separated organic layer was washed with purified water, washed with saturated brine, and then dried over anhydrous magnesium sulfate. Magnesium sulfate was removed by filtration, and then the solvent was evaporated under reduced pressure. The resulting residue was subjected into silica gel chromatography to yield Compound 7c (922 mg, 16% yield).

$^1$H-NMR (CDCl$_3$) δ (delta): 8.12 (1H, d, J=5.5 Hz), 7.22 (1H, d, J=5.5 Hz), 3.12 (2H, t, J=7.7 Hz), 2.98 (2H, t, J=7.7 Hz), 2.22-2.09 (2H, m).

Step (3): Compound 7h→Compound 7i

Compound 7h (2.19 g, 7.34 mmol) was dissolved in dimethylsulfoxide (20 mL), and then 4,4,4',4',5,5,5',5'-octamethyl-2,2'-bi(1,3,2-dioxaborane) (2.05 g, 8.07 mmol), [1,1'-bis(diphenylphosphino)ferrocene]dichloropalladium(II).methylene chloride complex (599 mg, 0.734 mmol), and potassium acetate (2.16 g, 22.01 mmol) were added thereto in turn, subsequently heating to 80° C. and stirring. To the reaction solution was then added purified water, followed by extraction with ethyl acetate. The organic layer was washed with purified water, and then washed with saturated brine. After the organic layer was dried over anhydrous magnesium sulfate, magnesium sulfate was removed by filtration, and then the solvent was evaporated under reduced pressure. The resulting residue was subjected into silica gel chromatography to yield Compound 7i (413 mg, 19% yield).

$^1$H-NMR (CDCl$_3$) δ (delta): 7.43 (1H, d, J=8.4 Hz), 6.79 (1H, d, J=8.4 Hz), 3.88 (3H, s), 3.83 (3H, s), 1.36 (14H, s).

Step (4): Compound 7c→Compound 7d→Compound 7e

Compound 7c (923 mg, 4.66 mmol) and Compound 7i (1.08 g, 3.60 mmol) were used, and treated similarly to described above to yield Compound 7d (845 mg, 81% yield). Then Compound 7d (845 mg, 2.92 mmol) was used, and treated similarly to described above to yield Compound 7e (741.6 mg, 74.1% yield.)

$^1$H-NMR (DMSO-d$_6$) δ (delta): 10.28 (1H, br s), 9.54 (1H, br s), 8.64 (1H, d, J=6.0 Hz), 7.65 (1H, d, J=6.0 Hz), 6.89 (1H, d, J=8.2 Hz), 6.75 (1H, d, J=8.2 Hz), 3.27 (2H, t, J=7.5 Hz), 2.90 (2H, t, J=7.5 Hz), 2.22-2.12 (2H, m).

Step (5): Compound 7e→Compound 7f

Compound 7e (741 mg, 2.16 mmol) was dissolved in dimethylformamide (7 mL), and then triethylamine (0.899 mL, 6.49 mmol), imidazole (442 mg, 6.49 mmol), and chloro-t-butyldimethylsilane (978 mg, 6.49 mmol) were added, subsequently stirring at room temperature. To the reaction solution was then added purified water, followed by extraction with ethyl acetate. The organic layer was washed with purified water, and then washed with saturated brine. After the organic layer was dried over anhydrous magnesium sulfate, magnesium sulfate was removed by filtration, and then the solvent was evaporated under reduced pressure. To the resulting residue was added diisopropyl ether, and then filtrated. The residue was washed with diisopropyl ether to yield Compound 7f (971 mg, 92% yield).

$^1$H-NMR (CDCl$_3$) δ (delta): 8.35 (1H, d, J=5.2 Hz), 6.93 (1H, d, J=5.2 Hz), 6.80 (1H, d, J=8.3 Hz), 6.67 (1H, d, J=8.3 Hz), 3.08 (2H, t, J=7.7 Hz), 2.77 (2H, t, J=7.2 Hz), 2.13-2.03 (2H, m), 1.04 (9H, s), 1.00 (9H, s), 0.26 (6H, s), 0.22 (6H, s).

Step (6): Compound 7f→Compound 7g→Compound (II-7)

Compound 7f (490 mg, 1 mmol) was used, and treated similarly to described above to yield Compound (II-7) (287 mg, 38% yield).

MS (m+1)=729.21

Elementary analysis for $C_{31}H_{28}ClN_6O_9S_2Na(H_2O)_{5.5}$

Calcd.: C, 43.79; H, 4.62; Cl, 4.17; N, 9.88; S, 7.54; Na, 2.70.

Found: C, 44.09; H, 4.57; Cl, 5.02; N, 8.82; S, 6.71; Na, 2.76.

$^1$H-NMR (DMSO-d$_5$) δ (delta): 9.15 (1H, d, J=6.8 Hz), 7.70 (1H, d, J=6.8 Hz), 6.79 (1H, d, J=8.1 Hz), 6.71 (1H, s), 6.59 (1H, dd, J=10.5, 8.2 Hz), 5.76 (1H, t, J=6.2 Hz), 5.50 (1H, d, J=13.9 Hz), 5.13 (1H, s), 5.06 (1H, d, J=5.0 Hz), 3.46 (1H, d, J=11.7 Hz), 3.15 (1H, d, J=17.5 Hz), 2.94 (3H, q, J=7.0 Hz), 2.25-2.07 (2H, m), 1.41 (6H, d, J=16.8 Hz).

EXAMPLE 50

Synthesis of Compound (II-8)

[Formula 124]

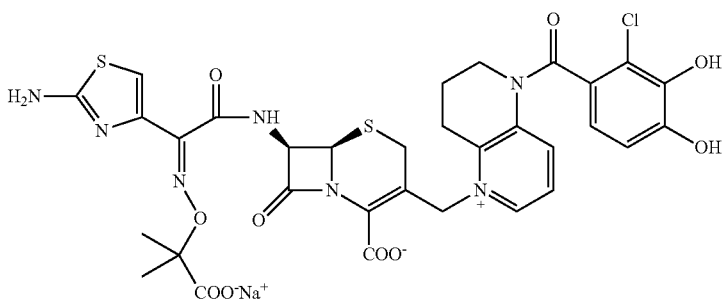

II-8

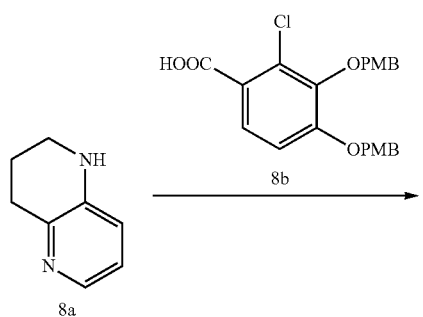

-continued

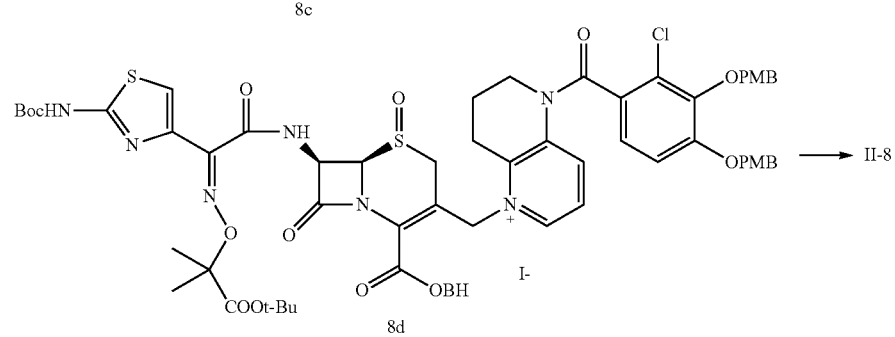

Step (1): Compound 8a→Compound 8c

Compound 8b (3.26 g, 7.6 mmol) was dissolved in dimethylacetamide, and subsequently cooled to −15° C. To the reaction solution was then added triethylamine (1.475 ml, 10.64 mmol) and methanesulfonyl chloride (0.829 mL, 10.64 mmol), followed by stirring. To the reaction solution was then added a solution of Compound 8a (1.02 g, 7.6 mmol) dissolved in dimethylacetamide (1 mL), subsequently stirring at 0° C. Purified water was added to the reaction solution, followed by extraction with ethyl acetate. The organic layer was washed with purified water, and then washed with saturated brine. After the organic layer was dried over anhydrous magnesium sulfate, magnesium sulfate was removed by filtration, and then the solvent was evaporated under reduced pressure. The resulting residue was subjected into silica gel chromatography to yield Compound 8c (1.25 g, 30% yield).

MS (m+1)=545.2

Step (2): Compound 8c→Compound 8d→Compound (II-8)

Compound 8c (623 mg, 1 mmol) was used, and treated similarly to described above to yield Compound (II-8) (305 mg, 34% yield).

MS (m+1)=772.16

Elementary analysis for $C_{32}H_{29}ClN_7O_{10}S_2Na(NaHCO_3)_{0.2}(H_2O)_{4.7}$ Calcd.: C, 43.18; H, 4.34; Cl, 3.96; N, 10.95; S, 7.16; Na, 3.08.

Found: C, 44.09; H, 4.57; Cl, 5.02; N, 8.82; S, 6.71; Na, 2.76.

EXAMPLE 51

Synthesis of Compound (II-9)

[Formula 125]

II-9

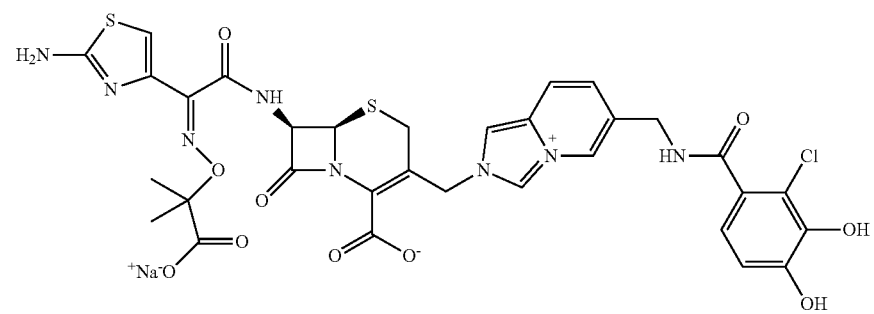

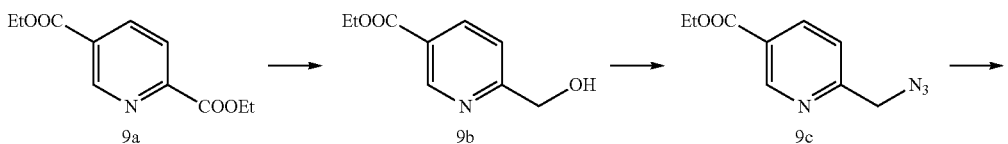

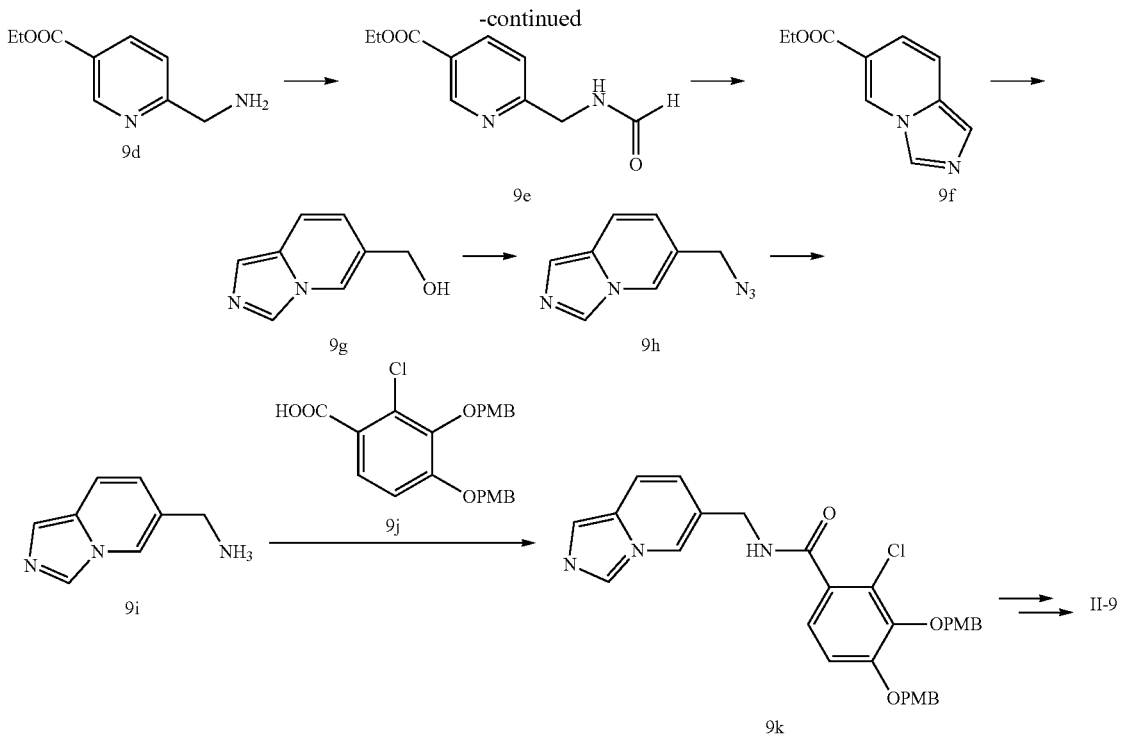

Step (1): Compound 9a→Compound 9b

Compound 9a (12.8 g, 57.3 mmol) was dissolved in ethanol, and subsequently cooled to −5° C. To the reaction solution was added sodium borohydride (1.41 g, 37.3 mmol), and then calcium chloride (4.14 g, 37.3 mmol) was added small-portion-wise, followed by stirring for 45 minutes. The reaction solution was poured into purified water (120 mL), and then ethanol was concentrated in vacuo. The precipitated solid was filtrated to yield Compound 9b (4.71 g, 45% yield).

$^1$H-NMR (CDCl$_3$) δ (delta): 9.16 (1H, d, J=1.8 Hz), 8.29 (1H, dd, J=1.8, 8.4 Hz), 7.35 (1H, d, J=8.4 Hz), 4.83 (2H, br s), 4.42 (2H, q, J=6.9 Hz), 3.69 (1H, s), 1.42 (3H, t, J=6.9 Hz).

Step (2): Compound 9b→Compound 9c

Compound 9b (7.56 g, 41.7 mmol) was suspended in methylene chloride, and subsequently cooled to 0° C. To the reaction solution was then added triethylamine (6.36 mL, 45.9 mmol) and methanesulfonyl chloride (3.57 mL, 45.9 mmol) in turn, followed by stirring at 0° C. Purified water was then added to the reaction solution, followed by extraction with ethyl acetate. The organic layer was washed with purified water, and then washed with saturated brine. After the organic layer was dried over anhydrous magnesium sulfate, magnesium sulfate was removed by filtration, and then the solvent was concentrated in vacuo. The resulting residue was dissolved in dimethylformamide (110 mL), and then sodium azide (4.07 g, 62.6 mmol) was added, subsequently stirring at 60° C. To the reaction solution was added purified water, followed by extraction with ethyl acetate. The organic layer was washed with purified water, and then washed with saturated brine. After the organic layer was dried over anhydrous magnesium sulfate, magnesium sulfate was removed by filtration, and then the solvent was concentrated in vacuo. The resulting residue was then subjected into silica gel chromatography to yield Compound 9c (8.18 g, 95% yield).

$^1$H-NMR (CDCl$_3$) δ (delta): 9.18 (1H, d, J=2.1 Hz), 8.32 (1H, dd, J=8.1, 2.1 Hz), 7.44 (1H, d, J=8.5 Hz), 4.57 (2H, br s), 4.42 (2H, q, J=7.0 Hz), 1.42 (3H, t, J=7.0 Hz).

Step (3): Compound 9c→Compound 9d

Compound 9c (8.18 g, 39.7 mmol) was dissolved in tetrahydrofuran (80 mL), and then triphenylphosphine (11.45 g, 43.6 mmol) was added, subsequently stirring until gas evolution ceased. To the reaction solution was then added purified water (7.15 g, 397 mmol), followed by stirring at 60° C. The solvent was evaporated under reduced pressure, and then the resulting residue was subjected into silica gel chromatography to yield Compound 9d as green oily substance (6.81 g, 95% yield).

$^1$H-NMR (CDCl$_3$) δ (delta): 9.15 (1H, d, J=2.0 Hz), 8.25 (1H, dd, J=8.0, 2.0 Hz), 7.38 (1H, d, J=8.0 Hz), 4.41 (2H, q, J=7.4 Hz), 4.05 (2H, s), 1.71 (2H, s), 1.41 (3H, t, J=7.4 Hz).

Step (4): Compound 9d→Compound 9e

To formic acid (7.25 mL) was added acetic anhydride (7.14 mL, 76 mmol), subsequently heating to 50° C. for 30 minutes, and thus a mixed acid anhydride was prepared. Compound 9d (6.81 g, 37.8 mmol) was dissolved in methylene chloride (70 mL), and then the prepared mixed acid anhydride wad added drop-wise thereto, followed by stirring at room temperature. To the reaction solution was then added aqueous saturated sodium hydrogen carbonate, followed by extraction with ethyl acetate. The organic layer was washed with purified water, and then washed with saturated brine. After the organic layer was dried over anhydrous magnesium sulfate, magnesium sulfate was removed by filtration, and then the solvent was evaporated under reduced pressure. The resulting residue was then subjected into silica gel chromatography to yield Compound 9e (7.16 g, 91% yield).

$^1$H-NMR (CDCl$_3$) δ (delta): 9.14 (1H, d, J=2.1 Hz), 8.35 (1H, s), 8.28 (1H, dd, J=2.1, 8.1 Hz), 7.35 (1H, d, J=8.1 Hz), 6.88 (1H, br s), 4.68 (2H, d, J=5.2 Hz), 4.42 (2H, q, J=7.1 Hz), 1.42 (3H, t, J=7.1 Hz).

Step (5): Compound 9e→Compound 9f

Compound 9e (7.15 g, 34.3 mmol) was dissolved in toluene (70 mL), and then phosphorus oxychloride (6.38 mL, 68.7 mmol) was added, followed by reflux under heating. To the reaction solution was then added aqueous saturated sodium hydrogen carbonate, followed by extraction with ethyl acetate. The organic layer was washed with purified water, and then washed with saturated brine. The organic layer was dried over anhydrous magnesium sulfate, subsequently removing magnesium sulfate by filtration, and then the solvent was evaporated under reduced pressure. To the resulting residue was added diisopropyl ether, and then filtrated. The filtrated residue was washed with diisopropyl ether to yield Compound 9f as a yellow solid (5.38 g, 82% yield).

$^1$H-NMR (CDCl$_3$) δ (delta): 8.75-8.70 (1H, m), 8.21 (1H, s), 7.47-7.41 (2H, m), 7.23 (1H, dd, J=9.7, 1.2 Hz), 4.40 (2H, q, J=7.1 Hz), 1.41 (3H, t, J=7.1 Hz).

Step (6): Compound 9f→Compound 9g

Compound 9f (2.85 g, 15 mmol) was dissolved in tetrahydrofuran (30 mL), and subsequently cooled to −78° C. To the reaction solution was then added drop-wise a 1 mol/L diisobutyl aluminum hydride/toluene solution (37.5 mL, 37.5 mmol), followed by stirring at −78° C. To the reaction solution was added sodium sulfate decahydrate, and then anhydrous sodium sulfate was added, subsequently stirring while warming up to room temperature. The treated reaction solution was then filtrated. The filtrate was evaporated under reduced pressure, and then the resulting residue was subjected into silica gel chromatography to yield Compound 9g (1.18 g, 53% yield).

$^1$H-NMR (CDCl$_3$) δ (delta): 8.06 (1H, s), 7.95-7.91 (1H, m), 7.46-7.36 (2H, m), 6.70 (1H, dd, J=9.3, 1.3 Hz), 4.66-4.62 (2H, m).

Step (7): Compound 9g→Compound 9h

Compound 9g (1.18 g, 7.96 mmol) was dissolved in dimethylformamide (10 mL), and subsequently cooled to 0° C. To the reaction solution was added diphenylphosphoryl azide (2.05 mL, 9.56 mmol), and then 1,8-diazabicyclo[5.4.0]undec-7-ene (1.44 mL, 9.56 mmol) was added drop-wise thereto, followed by stirring at room temperature. Purified water was then added to the reaction solution, followed by extraction with ethyl acetate. The organic layer was washed with purified water, and then washed with saturated brine. The organic layer was dried over anhydrous magnesium sulfate, and then magnesium sulfate was removed by filtration. The solvent was evaporated under reduced pressure, and then the resulting residue was subjected into silica gel chromatography to yield Compound 9h.

$^1$H-NMR (CDCl$_3$) δ (delta): 8.02 (1H, s), 7.93-7.90 (1H, m), 7.47 (1H, d, J=9.4 Hz), 7.44 (1H, s), 6.66 (1H, dd, J=9.4, 1.3 Hz), 4.29 (2H, s).

Step (8): Compound 9h→Compound 9i→Compound 9k

Compound 9h (1.13 g, 6.53 mmol) was used, and treated similarly as described above to yield Compound 9l. Compound 9i was dissolved in dimethylformamide, and then Compound 9j (3.08 g, 7.18 mmol), 1-hydroxybenzotriazole (971 mg, 7.18 mmol), and hydrochloric acid salt (345 mg, 1.8 mmol) of 1-(dimethylaminopropyl)-3-ethylcarbodiimide were added in turn, subsequently stirring at room temperature. To the reaction solution was added purified water, and then the precipitated solid was filtrated. The filtrated residue was washed with ethyl acetate to yield Compound 9k (2.2 g, 60% yield).

$^1$H-NMR (DMSO-d$_6$) δ (delta): 8.93-8.80 (2H, m), 8.33 (1H, s), 7.69-7.59 (2H, m), 7.43 (2H, d, J=8.6 Hz), 7.31 (2H, d, J=8.6 Hz), 7.21 (2H, s), 7.03-6.93 (3H, m), 6.90-6.83 (2H, m), 5.16 (2H, s), 4.88 (2H, s), 4.37 (2H, d, J=5.7 Hz), 3.78-3.73 (6H, m).

Step (9): Compound 9k→Compound (II-9)

Compound 9k (558 mg, 1 mmol) was treated similarly as described above to yield Compound (II-9) (377 mg, 47% yield).

MS (m+1)=785.31

Elementary analysis for C$_{32}$H$_{28}$ClN$_8$O$_{10}$S$_2$Na(NaHCO$_3$)$_{0.3}$(H$_2$O)$_{5.8}$ Calcd.: C, 41.41; H, 4.29; Cl, 3.78; N, 11.96; S, 6.85; Na, 3.19.

Found: C, 41.19; H, 4.23; Cl, 4.03; N, 12.24; S, 6.87; Na, 2.79.

$^1$H-NMR (D$_2$O) δ (delta): 9.41 (1H, s), 8.25 (1H, s), 8.00 (1H, s), 7.68 (1H, d, J=9.8 Hz), 7.18 (1H, d, J=9.6 Hz), 6.95-6.86 (2H, m), 6.79 (1H, d, J=8.4 Hz), 5.81 (1H, d, J=4.6 Hz), 5.40 (1H, d, J=14.5 Hz), 5.26 (1H, d, J=4.9 Hz), 5.18 (1H, d, J=14.5. Hz), 4.51 (2H, s), 3.65 (1H, d, J=18.0 Hz), 3.24 (1H, d, J=18.0 Hz), 1.52-1.38 (6H, m).

EXAMPLE 52

Synthesis of Compound (II-10)

[Formula 126]

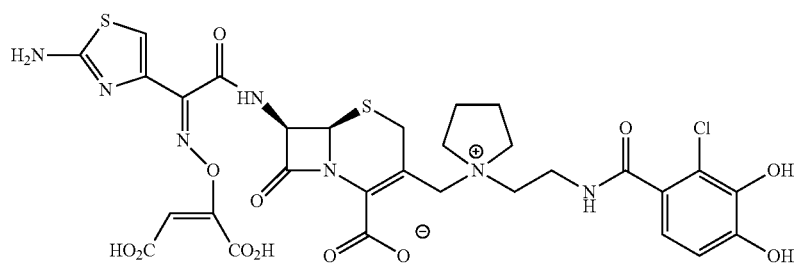

II-10

151
152
-continued
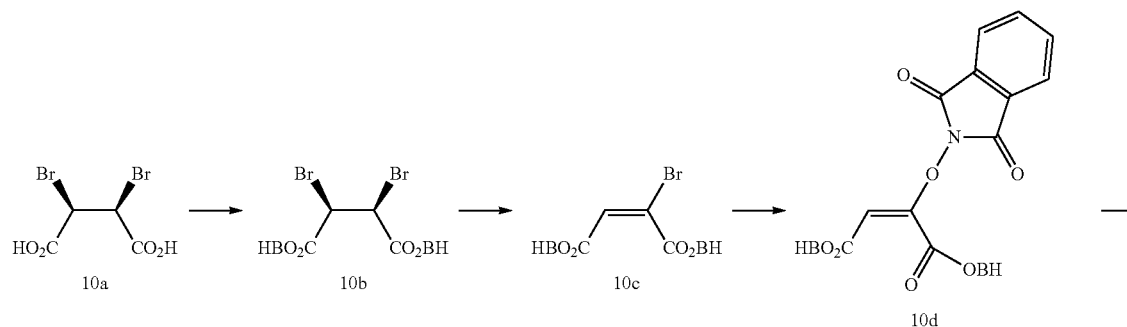
10a → 10b → 10c → 10d →
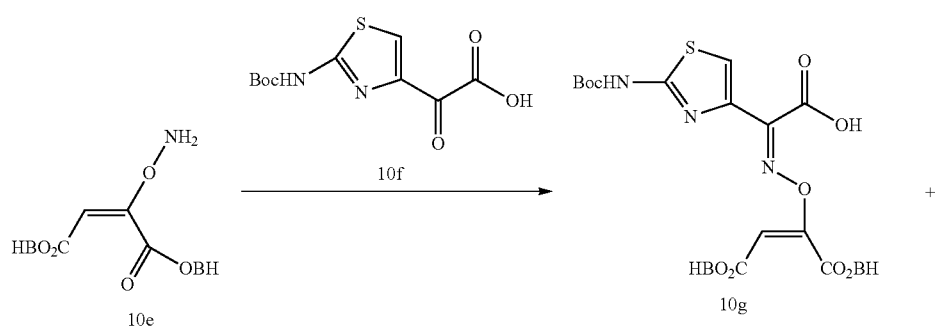
10e + 10f → 10g +
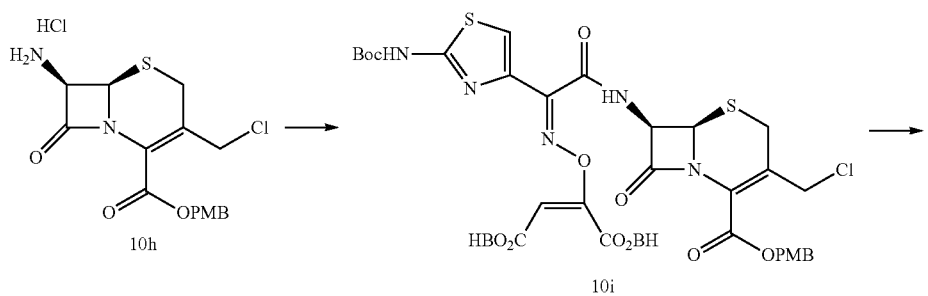
10h → 10i →
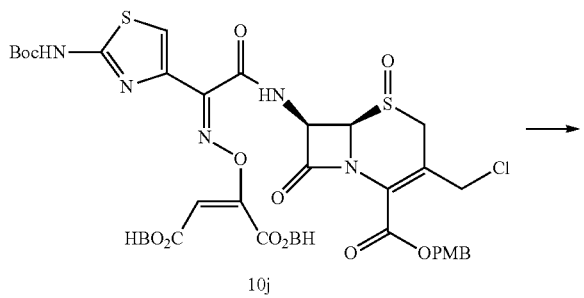
10j →
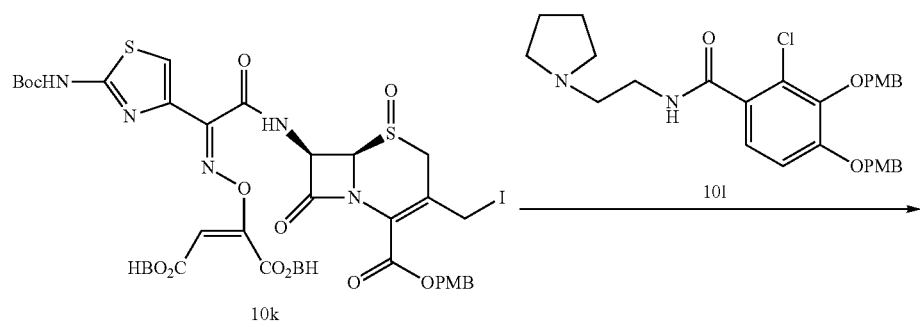
10k + 10l →

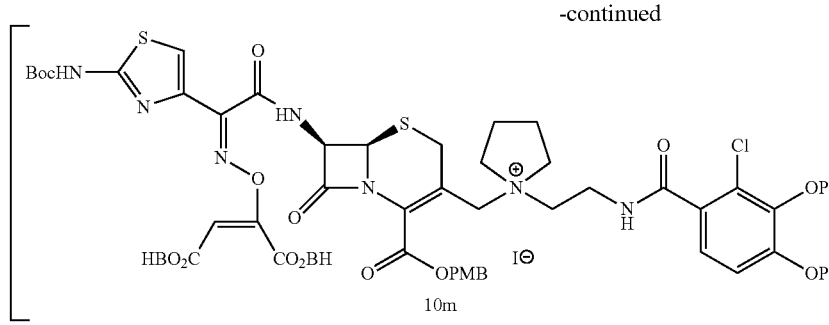
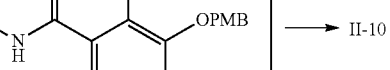

Step (1): Compound 10a→Compound 10b

Compound 10a (11.04 g, 40 mmol) was dissolved in diethyl ether (100 mL) and methylene chloride (400 mL), and then diphenyldiazomethane (17.09 g, 88 mmol) was added thereto, subsequently stirring at room temperature for 1 hour. The reaction solution was concentrated in vacuo, and then hexane was added thereto. The resulting solid was filtrated to yield Compound 10b (22.6 g, 93%).

$^1$H-NMR (DMSO-$d_6$) δ (delta): 5.15 (2H, s), 6.93 (2H, s), 7.30-7.50 (20H, m).

Step (2): Compound 10b→Compound 10c

Compound 10b (12.17 g, 20 mmol) was dissolved in dimethylformamide (60 mL), and then triethylamine (3.05 mL, 22.0 mmol) was added thereto, subsequently stirring at room temperature for 1 hour. The reaction solution was then poured into aqueous dilute hydrochloric acid solution, followed by extraction with ethyl acetate. The organic layer was washed with water, and then washed with saturated brine. After drying over anhydrous magnesium sulfate, the solvent was evaporated under reduced pressure to yield Compound 10c (10.3 g, 98%).

$^1$H-NMR (CDCl$_3$) δ (delta): 5.29 (1H,$), 6.59 (1H, s), 6.60 (1H, s), 7.10-7.50 (20H, m).

Step (3): Compound 10c→Compound 10d

N-hydroxyphthalimide (2.28 g, 14 mmol) was suspended in dimethylformamide (10 mL), and then sodium hydride (60%, 480 mg, 12 mmol) followed by Compound 10c were added thereto, subsequently stirring at room temperature for 30 minutes. The reaction solution was then poured into ice-cold water, followed by extraction with ethyl acetate. The organic layer was washed with aqueous 10% sodium hydrogen carbonate, and then washed with saturated brine. After drying over anhydrous magnesium sulfate followed by filtration, the solvent was evaporated under reduced pressure. To the residue was added diethyl ether, and then the resulting solid was filtrated to yield Compound 10d (2.50 g, 41%).

$^1$H-NMR (CDCl$_3$) δ (delta): 5.87 (1H, s), 6.84 (1H, s), 6.86 (1H, s), 7.10-7.40 (20H, m), 7.27-7.90 (4H, m).

Step (4): Compound 10d→Compound 10e→Compound 10g

Compound 10d was dissolved in methylene chloride (70 mL), subsequently cooled to −78° C., and then methylhydrazine (0.60 mL, 11.34 mmol) was added thereto, followed by stirring for 1 hour under ice-cooling. The precipitated solid was filtrated, and then the filtrate was concentrated in vacuo. To the residue was then added ethyl acetate. The separated organic layer was washed with aqueous 5% sodium hydrogen carbonate, and then washed with saturated brine. After drying over anhydrous magnesium sulfate followed by filtration, the solvent was concentrated in vacuo. To the residue was added methanol (100 mL), and then, at 0° C., Compound 10f was added, subsequently stirring overnight. The reaction solution was concentrated in vacuo, and then ethyl acetate was added thereto. The separated organic layer was washed with aqueous 0.2 N hydrochloric acid, and then washed with saturated brine. After drying over anhydrous magnesium sulfate followed by filtration, the solvent was concentrated in vacuo. The resulting residue was purified by silica gel column chromatography to yield Compound 10g (2.91 g, 35%).

$^1$H-NMR (DMSO-$d_6$) δ (delta): 1.49 (9H, s), 6.12 (1H, s), 6.80-7.00 (3H, m), 7.20-7.60 (20H, m).

Step (5): Compound 10g+Compound 10h→Compound 10i

Compound 10g (2.91 g, 3.97 mmol) was dissolved in methylene chloride (30 mL), subsequently cooled to −30° C., and then Compound 10h (1.60 g, 3.97 mmol), N-methylmorpholine (2.18 mL, 19.8 mmol), and phenyl dichlorophosphate (0.589 mL, 3.97 mmol) were added thereto in turn. The reaction solution was stirred at −30° C. for 1 hour. Aqueous dilute hydrochloric acid solution was added to the reaction solution, followed by concentration in vacuo. After the concentrated solution was extracted with ethyl acetate, the organic layer was washed with aqueous 5% sodium hydrogen carbonate, and then washed with saturated brine. After drying over anhydrous magnesium sulfate followed by filtration, the solvent was concentrated in vacuo. The resulting residue was purified by silica gel column chromatography to yield Compound 10i (2.79 g, 88%).

$^1$H-NMR (DMSO-$d_6$) δ (delta): 1.53 (9H, s), 3.25 (1H, d, J=18.0 Hz), 3.46 (1H, d, J=18.0 Hz), 3.78 (3H, s), 4.33 (1H, d, J=11.7 Hz), 4.57 (1H, d, J=11.7 Hz), 4.81 (1H, d=4.8 Hz), 5.16 (1H, d, J=5.7 Hz), 5.21 (1H, d, J=5.7 Hz), 5.85-5.90 (1H, m), 6.03 (1H, s), 6.80-7.00 (7H, m), 7.10-7.40 (20H, m).

Step (6): Compound 10i→Compound 10j

Compound 10i (2.79 g, 2.26 mmol) was dissolved in methylene chloride (30 mL), subsequently cooled to −40° C., and then 65% m-chloroperbenzoic acid (573 mg, 2.49 mmol) was added thereto, followed by warming up to −10° C. over 2 hours. To the reaction solution was added aqueous 5% sodium thiosulfate solution, and then concentrated in vacuo. The concentrated solution was then extracted with ethyl acetate. The organic layer was washed with aqueous 5% sodium hydrogen carbonate, and then washed with saturated brine. The organic layer was dried over anhydrous magnesium sulfate, and then the solvent was evaporated under reduced pressure to yield Compound 10j (2.61 g, 100%).

$^1$H-NMR (CDCl$_3$) δ (delta): 1.45 (9H, s), 3.39 (1H, d, J=17.7 Hz), 3.79 (3H, s), 4.00-4.30 (2H, m), 4.93 (1H, d, J=17.7 Hz), 5.16 (1H, d, J=11.7 Hz), 5.33 (1H, d, J=11.7 Hz), 5.80-6.20 (2H, m), 6.80-7.10 (4H, m), 7.11-7.60 (24H, m).

Step (7): Compound 10j→Compound 10k

Compound 10j (2.48 g, 2.26 mmol) was dissolved in tetrahydrofuran (30 mL), subsequently cooled to 15° C., and then potassium iodide (1.06 g, 6.78 mmol) was added thereto, followed by stirring for 1 hour. To the reaction solution was added aqueous 5% sodium thiosulfate solution, and then the solvent was concentrated in vacuo. The concentrated solution was extracted with ethyl acetate, and then the organic layer was washed with saturated brine. The organic layer was dried over anhydrous magnesium sulfate, and then the solvent was evaporated under reduced pressure to yield Compound 10k (2.72 g, 98%).

$^1$H-NMR (CDCl$_2$) δ (delta): 1.43 (9H, m), 3.35 (1H, d, J=18.3 Hz), 3.79 (3H, s), 4.00-4.30 (2H, m), 4.63 (1H, d, J=18.3 Hz), 5.15 (1H, d, J=11.7 Hz), 5.35 (1H, d, J=11.7 Hz), 5.90-6.20 (2H, m), 6.80-7.14 (4H, m), 7.15-7.60 (24H, m).

Step (8): Compound 10k→Compound 10m→Compound (II-10)

Compound 10k (1.23 g, 1 mmol) and Compound 10l (525 mg, 1 mmol) were dissolved in dimethylformamide (3 mL), subsequently stirring at room temperature for 2 hours. The reaction solution was diluted with dimethylformamide (6 mL), and then potassium iodide (1.16 g, 7 mmol) was added, followed by cooling to −40° C. Acetyl chloride (0.285 mL, 4 mmol) was then added, subsequently stirring at 0° C. for 1 hour. Ice and ethyl acetate were then added thereto. The organic layer was separated, washed with water, and then washed with saturated brine. After drying over anhydrous magnesium sulfate followed by filtration, the solvent was evaporated under reduced pressure to yield Compound 10m.

Then Compound 10m was dissolved in methylene chloride (10 mL) and anisole (0.6 mL), and subsequently cooled to −40° C. To the reaction solution was then added 2M-aluminum chloride/nitromethane solution (2.7 mL), followed by stirring at 0° C. for 50 minutes. To the reaction solution was then added aqueous 2 N hydrochloric acid (60 mL), acetonitrile (50 mL), and diethyl ether (100 mL). The aqueous layer was separated, and then washed with diethyl ether. The solvent was then concentrated in vacuo. The concentrated solution was subjected into HP-20SS column chromatography eluting with acetonitrile-water, and then desired fractions were concentrated in vacuo. The concentrated solution was lypholized to yield Compound (II-10) as a white powder (205 mg, 26%).

$^1$H-NMR (D$_2$O) δ (delta): 2.22-2.40 (4H, m), 3.40-4.20 (12H, m), 5.34 (1H, d, J=4.8 Hz), 5.65 (1H, s), 5.85 (1H, d, J=4.8 Hz), 6.72 (2H, s), 7.19 (1H, s).

Elementary analysis for $C_{30}H_{30}ClN_7O_{12}S_2 \cdot 3.0H_2O$

Calcd.: C, 43.19; H, 4.35; Cl, 4.25; N, 11.75; O, 28.77; S, 7.69(%).

Found: C, 43.12; H, 4.47; Cl, 4.22; N, 11.79; S, 7.55(%).

EXAMPLE 53

Synthesis of Compound (II-11)

[Formula 127]

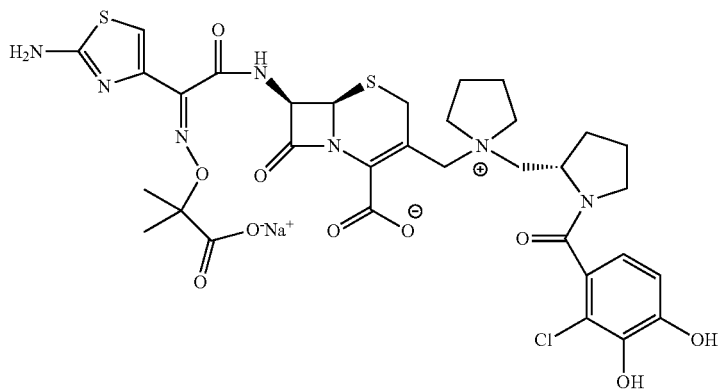

II-11

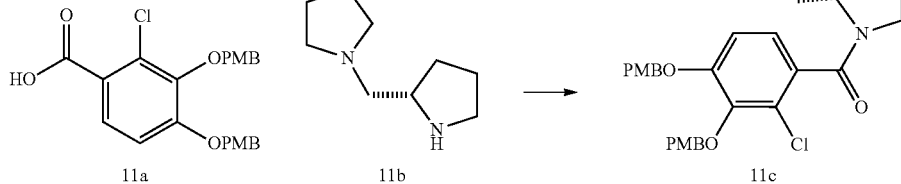

11a     11b     11c

-continued

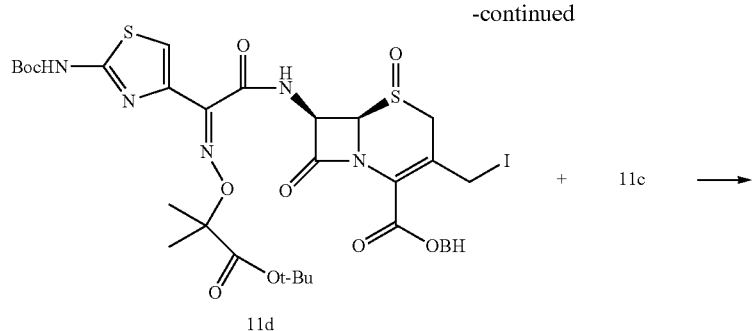

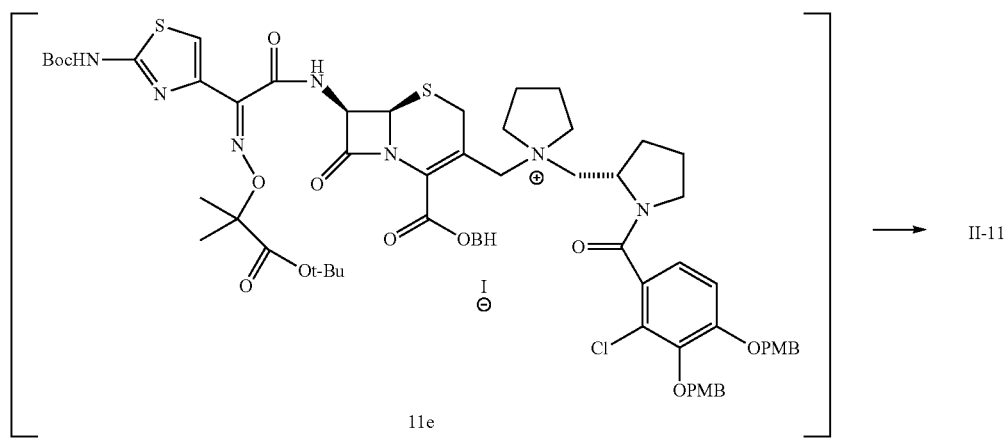

Step (1): Compound 11a+Compound 11b→Compound 11c

Compound 11a (3.00 g, 7.0 mmol) was dissolved in dimethylacetamide (30 mL), and then triethylamine (1.26 mL, 9.10 mmol) was added, and subsequently cooled to −15° C. To the reaction solution was added methanesulfonyl chloride (0.66 mL, 8.40 mmol), followed by stirring for 1 hour at −15° C. To the reaction solution was then added a solution of Compound 11b in dimethylacetamide (5 mL), subsequently stirring for 1 hour. Ethyl acetate (50 mL) and 5% sodium hydrogen carbonate solution were added into the reaction solution, and then the organic layer was separated. The organic layer was washed with water, and then washed with saturated brine. After drying over anhydrous magnesium sulfate, the solvent was evaporated under reduced pressure. The resulting residue was purified by silica gel column chromatography to yield title compound 11c (3.63 g, 92%).

$^1$H-NMR (CDCl$_3$) δ (delta): 1.50-2.10 (8H, m), 2.20-2.80 (4H, m), 2.81-3.10 (2H, m), 3.40-4.00 (9H, m), 4.80-5.05 (m, 2H), 5.06-5.20 (m, 2H), 6.80-7.00 (4H, m), 7.20-7.40 (6H, m).

Step (2): Compound 11d+Compound 11c→Compound 11e→Compound (II-11)

Compound 11d (1.06 g, 1 mmol) and Compound 11c (565 mg, 1 mmol) were dissolved in dimethylformamide (3 mL), subsequently stirring at room temperature for 2 hours. The reaction solution was diluted with dimethylformamide (6 mL), followed by cooling to −40° C., and then phosphorus tribromide (0.189 mL, 2 mmol) was added thereto, subsequently stirring for 1 hour. Ice and ethyl acetate were then added to the reaction solution. The separated organic layer was washed with water, and then washed with saturated brine.

After drying over anhydrous magnesium sulfate followed by filtration, the solvent was concentrated in vacuo to yield Compound 11e.

Then, Compound 11e was dissolved in methylene chloride (10 mL) and anisole (0.6 mL), and subsequently cooled to −40° C. 2M-aluminum chloride/nitromethane solution (2.7 mL) was then added to the reaction solution, followed by stirring at 0° C. for 50 minutes. To the reaction solution was then added aqueous 2 N hydrochloric acid (60 mL), acetonitrile (50 mL), and diethyl ether (100 mL). The aqueous layer was separated, and then washed with diethyl ether. The solvent was then concentrated in vacuo. The concentrated solution was subjected into HP-20SS column chromatography eluting with acetonitrile-water, and then fractions containing the desired Compound were collected.

Collected aqueous solution was adjusted to pH=6 with aqueous 0.02 N sodium hydroxide solution, and then concentrated in vacuo. The concentrated solution was lyophilized to yield Compound (II-11) as a white powder (222 mg, 27%).

$^1$H-NMR (D$_2$O) δ (delta): 1.48 (3H, s), 1.50 (3H, s), 1.80-2.60 (8H, m), 3.90 (1H, d, J=14.1 Hz), 4.24 (1H, d, J=14.1 Hz), 5.36 (1H, d, J=4.8 Hz), 5.86 (1H, d, J=4.8 Hz), 6.50-6.90 (2H, m), 6.98 (1H, s).

Elementary analysis for $C_{33}H_{38}ClN_7O_{10}S_2Na \cdot 4.8H_2O \cdot 0.8(NaHCO_3)$ Calcd.: C, 41.90; H, 5.03; Cl, 3.66; N, 10.12; O, 28.40; S, 6.22; Na, 4.27(%).

Found: C, 41.74; H, 5.03; Cl, 3.24; N, 10.61; S, 6.97; Na, 4.79(%).

EXAMPLE 54

Synthesis of Compound (II-12)

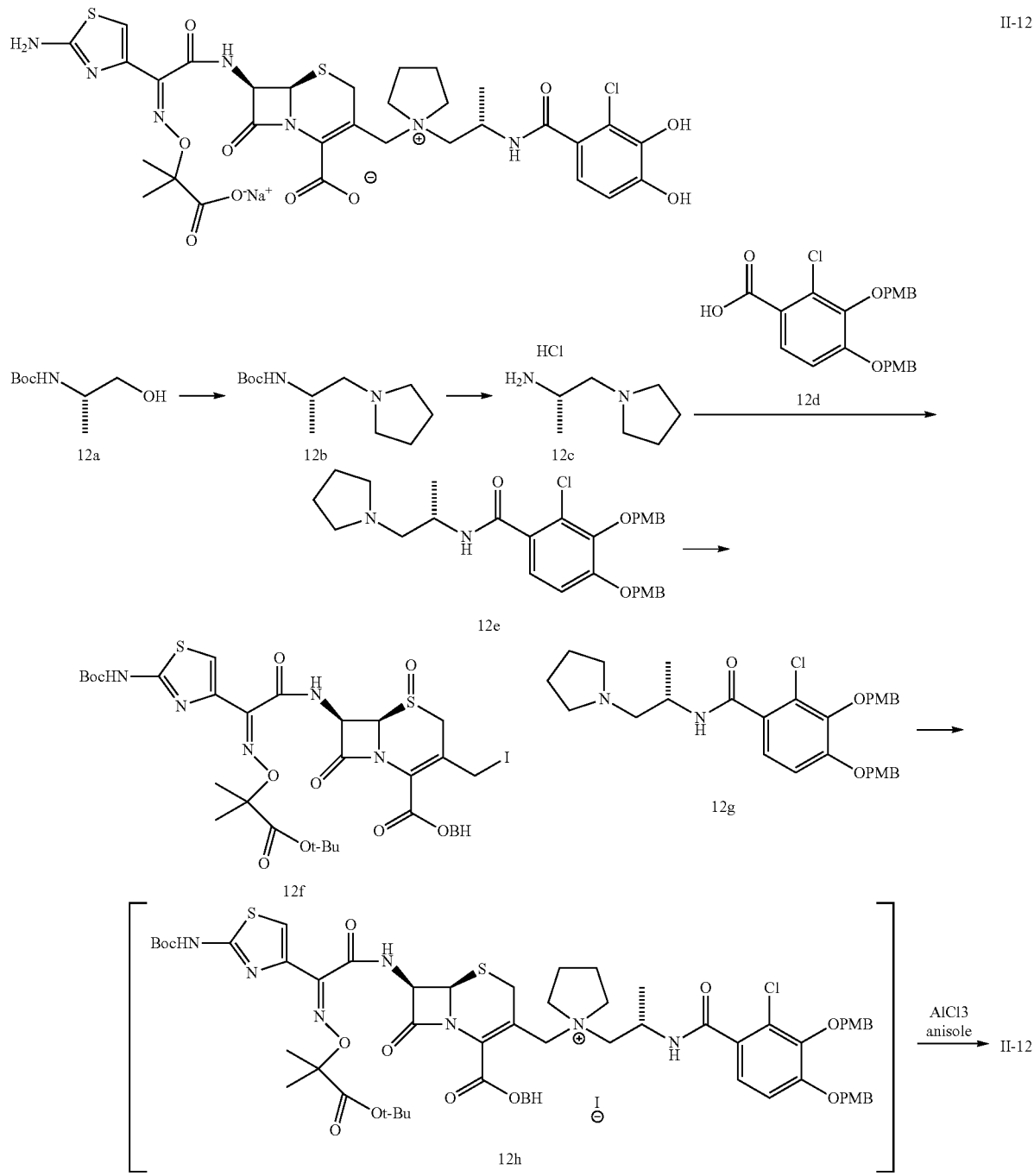

Step (1): Compound 12a→Compound 12b

Compound 12a (2.63 g, 15 mmol) and triethylamine (4.16 mL, 30 mmol) were dissolved in methylene chloride (20 mL), and then cooled to 0° C. To the reaction solution was then added methanesulfonyl chloride (1.29 mL, 16.5 mmol), subsequently warming up to room temperature gradually. The reaction solution was stirred at room temperature for 0.5 hour, and then triethylamine (4.16 mL, 30 mmol) and methanesulfonyl chloride (1.29 mL, 16.5 mmol) were added. To the reaction solution was then added 5% sodium hydrogen carbonate solution, followed by extraction with methylene chloride. The organic layer was dried over anhydrous magnesium sulfate, filtrated, and then concentrated in vacuo. To the concentrated solution was then pyrrolidine (16.1 mL, 195 mmol), subsequently heating to 50° C. with stirring. To the reaction solution was added aqueous 1 N hydrochloric acid solution, and then the aqueous layer was separated. To the aqueous layer was added aqueous 1 N sodium hydroxide solution, and then extracted with ethyl acetate followed by methylene chloride. The organic layer was dried over magnesium sulfate, followed by filtration, and then the solvent was concentrated in vacuo to Compound 12b as a crude product. Compound 12b was used for the next reaction without purification.

$^1$H-NMR (CDCl$_3$) δ (delta): 1.76 (3H, d, J=6.6 Hz), 1.44 (9H, s), 1.70-1.90 (4H, m), 2.20-2.65 (6H, m), 3.35-3.50 (1H, s).

Step (2): Compound 12b→Compound 12c

The crude product (an amount equivalent to 2 mmol), which contains Compound 12b obtained in the previous step, was dissolved in methylene chloride (1 mL), and then trifluoroacetic acid (4.62 mL) was added thereto, subsequently standing overnight. The reaction solution was concentrated in vacuo, and then methylene chloride (2 mL) was added thereto. 4 N hydrochloric acid/ethyl acetate (1.25 mL, 5 mmol) was then added at 0° C. thereto, followed by stirring. The solvent was then concentrated in vacuo to yield Compound 12c as a crude product. Compound 12c was used for the next reaction without purification.

$^1$H-NMR (D$_2$O) δ (delta): 1.45 (3H, d, J=6.0 Hz), 1.80-2.40 (4H, m), 3.00-3.50 (4H, m), 3.51-3.64 (2H, m), 3.68-4.00 (1H, m).

Step (3): Compound 12c+Compound 12d→Compound 12e

Compound 12d (686 mg, 1.6 mmol) was dissolved in dimethylformamide (7 mL), and then cooled to 0° C. Hydrochloric acid salt (337 mg, 1.76 mmol) of N-(3-dimethylaminopropyl)-N'-ethylcarbodiimide, and 1-hydroxybenzotriazole (270 mg, 1.76 mmol) were added in turn, subsequently stirring at room temperature for 30 minutes. After the reaction solution was cooled to 0° C., a dimethylformamide (2 mL) solution of a composition (an amount equivalent to 2 mmol), which comprises Compound 12c obtained in Step (2), was added thereto, followed by adding triethylamine (0.99 mL, 7.2 mmol). Into the reaction solution was then added ethyl acetate (50 mL) and 5% sodium hydrogen carbonate solution. The separated organic layer was washed with water, and then washed with saturated brine. The organic layer was dried over anhydrous magnesium sulfate, and then the solvent was evaporated under reduced pressure to yield Compound 12e (714 mg, 83% yield from Compound 12a).

$^1$H-NMR (CDCl$_3$) δ (delta): 1.32 (3H, d, J=6.3 Hz), 1.60-1.80 (4H, m), 2.40-2.80 (6H, m), 3.80 (3H, s), 3.83 (3H, s), 4.10-4.25 (1H, m), 4.94 (2H, s), 5.07 (2H, s), 6.80-7.00 (6H, m), 7.25-7.50 (4H, m).

Step (4): Compound 12f+Compound 12e→Compound 12g→Compound (II-12)

Treatment similar to that described above yielded Compound (II-12) (140 mg, 18%).

$^1$H-NMR (D$_2$O) δ (delta): 1.20-1.80 (9H, m), 2.00-2.40 (4H, m), 3.20-3.80 (8H, m), 3.95 (1H, d, J=14.1 Hz), 4.20 (1H, d, J=14.1 Hz), 5.36 (1H, d, J=4.8 Hz), 5.89 (1H, d, J=4.8 Hz), 6.60-6.80 (2H, m), 6.97 (1H, s).

Elementary analysis for $C_{33}H_{38}ClN_7O_{10}S_2Na \cdot 4.8H_2O \cdot 0.8$ (NaHCO$_3$)

Calcd.: C, 41.90; H, 5.03; Cl, 3.66; N, 10.12; O, 28.40; S, 6.22; Na, 4.27(%).

Found: C, 41.74; H, 5.03; Cl, 3.24; N, 10.61; S, 6.97; Na, 4.79(%).

EXAMPLE 55

Synthesis of Compound (II-13)

[Formula 129]

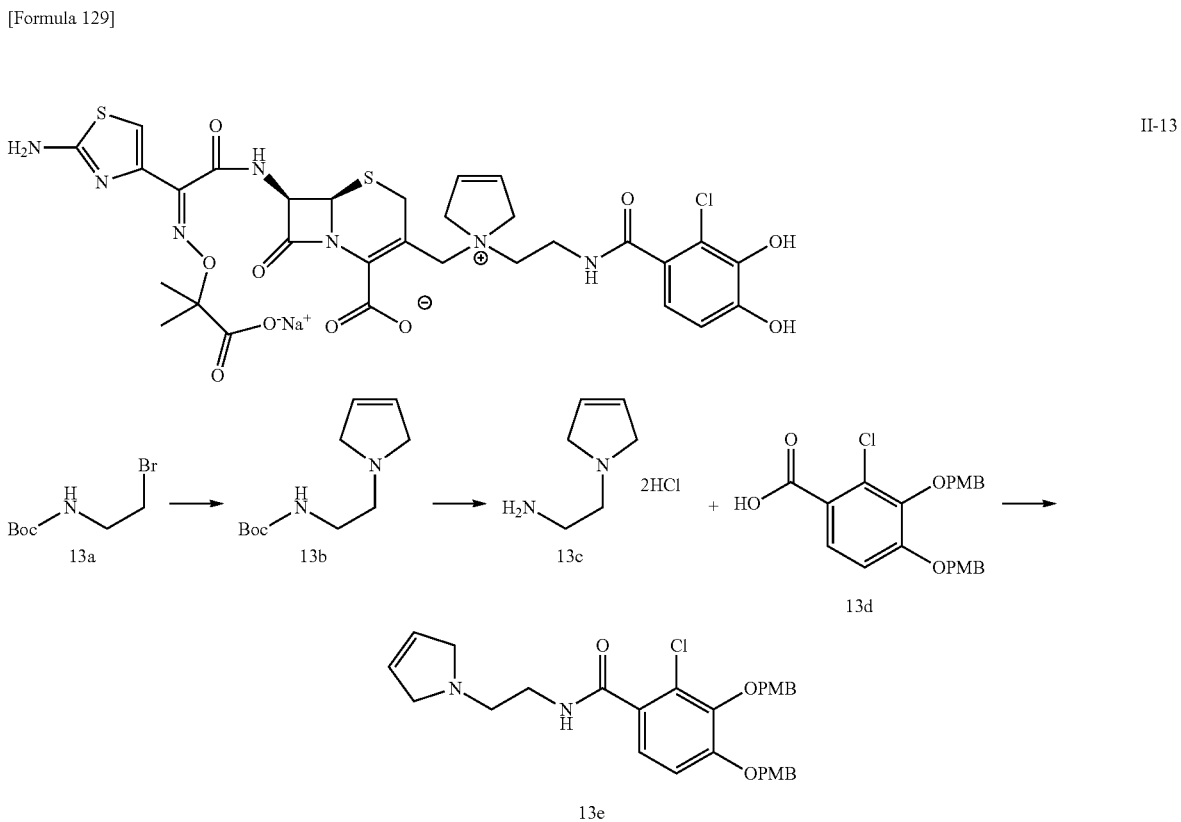

-continued

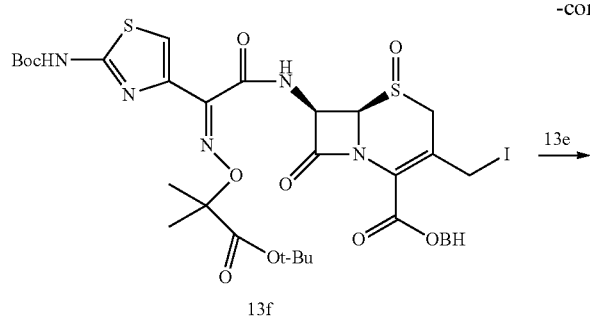

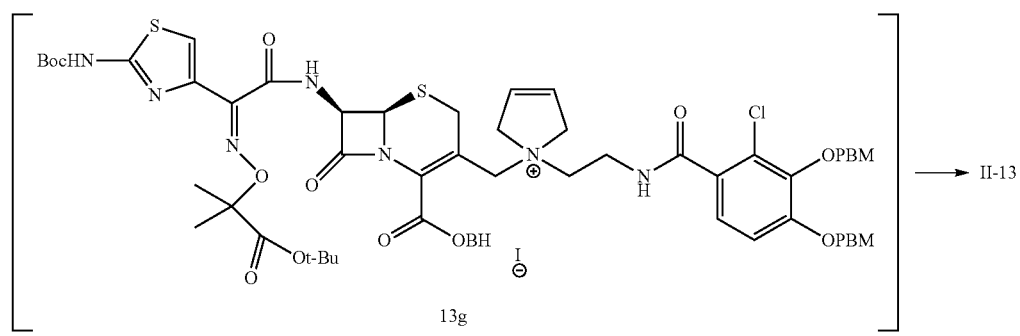

Step (1): Compound 13a→Compound 13b

Compound 13a (336 mg, 1.5 mmol) and 3-pyrroline (0.251 mL, 3.3 mmol) were dissolved in acetonitrile, and then potassium iodide (249 mg, 1.5 mmol) and potassium carbonate (622 mg, 4.5 mmol) were added, subsequently heating to 50° C. for 1 hour. 1 N hydrochloric acid and ethyl acetate were added, and then the aqueous layer was separated. To the separated aqueous layer was added aqueous 1 N sodium hydroxide solution, and then the aqueous layer was extracted with ethyl acetate, followed by methylene chloride (two times). The organic layer was dried over anhydrous magnesium sulfate, followed by filtration, and then the solvent was evaporated under reduced pressure to yield Compound 13b (288 mg, 90% yield).

$^1$H-NMR (CDCl$_3$) δ (delta): 1.44 (9H, s), 2.70-2.90 (2H, m), 3.10-3.40 (2H, m), 3.60-3.70 (4H, m), 5.77 (2H, s).

Step (2): Compound 13b→Compound 13c

Compound 13b (289 mg, 1.36 mmol) was dissolved in methylene chloride (1 mL), and then trifluoroacetic acid (3 mL) was added thereto, subsequently standing overnight. The reaction solution was then evaporated under reduced pressure. The residue was dissolved in methylene chloride (2 mL), and then a 4 N hydrochloric acid/ethyl acetate solution (0.85 mL) was added thereto, followed by stirring. The solvent was evaporated under reduced pressure to yield Compound 13c as a crude product. Compound 13c was used for the next reaction without purification.

$^1$H-NMR (D$_2$O) δ (delta): 3.40-3.50 (2H, m), 3.60-3.80 (2H, m), 4.00-4.60 (4H, m), 5.95 (2H, s).

Step (3): Compound 13c+Compound 13d→Compound 13e

Treatment similar as described above yielded Compound 13e (468 mg, 85%).

$^1$H-NMR (CDCl$_3$) δ (delta): 2.80-3.00 (2H, m), 3.51-3.55 (6H, m), 3.79 (3H, s), 3.80 (3H, s), 4.96 (2H, s), 5.07 (2H, s), 5.77 (2H, s), 6.80-7.00 (4H, m), 7.25-7.60 (6H, m).

Step (4): Compound 13f+Compound 13e→Compound 13g→Compound (II-13)

Treatment similar as described above yielded Compound (II-13) (300 mg, 43%).

$^1$H-NMR (D$_2$O) δ (delta): 1.48 (3H, s), 1.50 (3H, s), 3.40-4.00 (6H, m), 4.20-4.60 (6H, m), 5.33 (1H, d, J=5.1 Hz), 5.85 (1H, d, J=5.1 Hz), 5.99 (2H, s), 6.72 (2H, s), 6.97 (1H, s).

Elementary analysis for C$_{30}$H$_{31}$ClN$_7$O$_{10}$S$_2$Na.4.1H$_2$O.1.0 (NaHCO$_3$)

Calcd.: C, 40.03; H, 4.36; Cl, 3.81; N, 10.54; O, 29.42; S, 6.90; Na, 4.94(%).

Found: C, 39.90; H, 4.46; Cl, 3.71; N, 10.88; S, 7.12; Na, 5.32(%).

EXAMPLE 56

Synthesis of Compound (II-14)

$^1$H-NMR (CDCl$_3$) δ (delta): 1.70-1.90 (6H, m), 2.90-3.10 (6H, m), 3.80 (3H, s), 3.81 (3H, s), 5.01 (2H, s), 5.05 (2H, s), 6.80-7.00 (5H, m), 7.20-7.40 (6H, m).

[Formula 130]

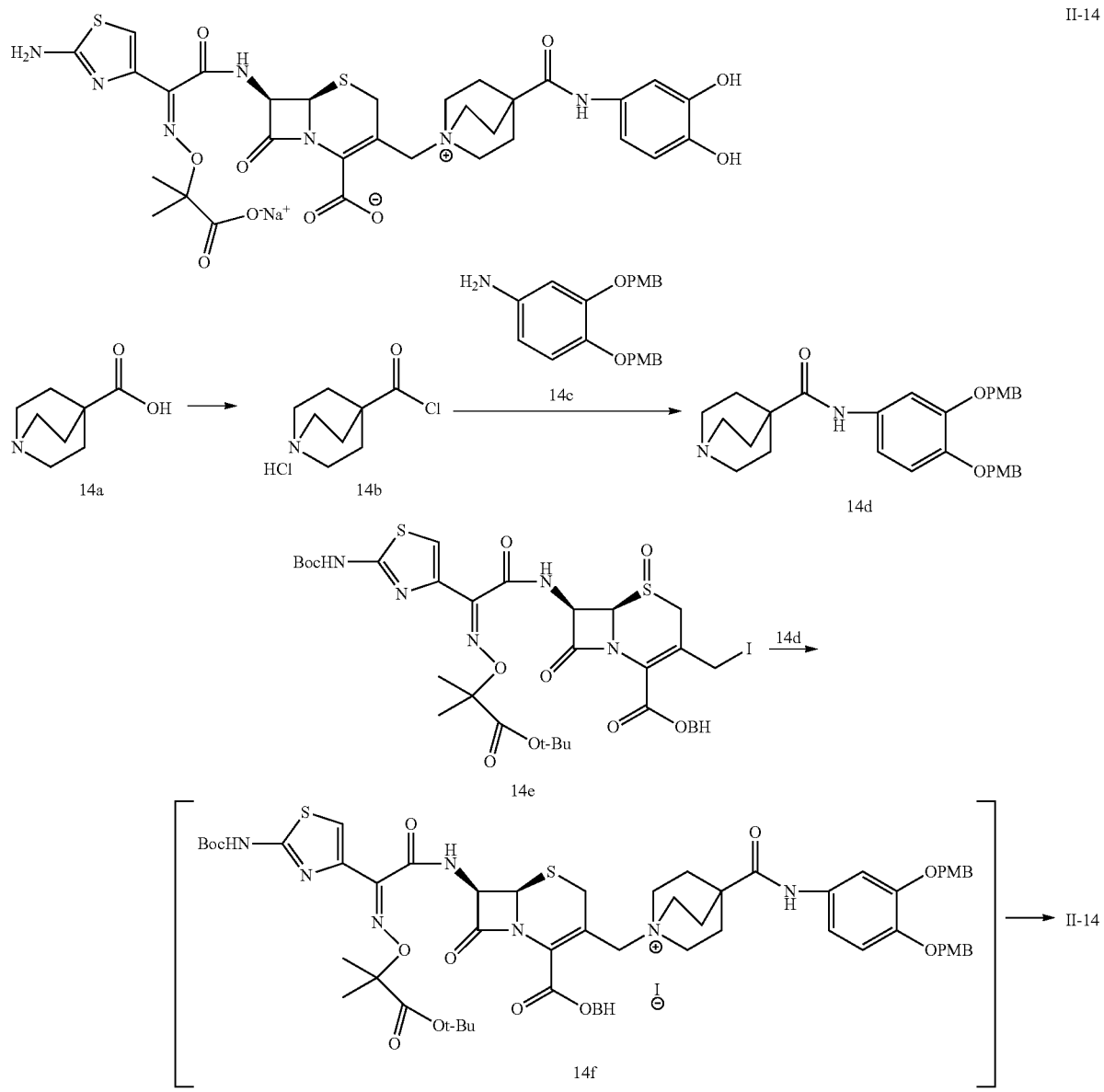

Step (1): Compound 14a→Compound 14c→Compound 14d

Compound 14a (859 mg, 5.54 mmol) was suspended in thionyl chloride (3.94 mL, 54.0 mmol), subsequently stirring at 80° C. for 2 hours. After thionyl chloride was evaporated under reduced pressure, dimethylacetamide was added to the residue. The reaction solution was cooled to 0° C., and then Compound 14c (1.64 g, 4.5 mmol) was added thereto, followed by adding triethylamine (1.25 mL, 9 mmol). The reaction solution was then poured into aqueous sodium carbonate, followed by extraction with ethyl acetate. The organic layer was dried over anhydrous magnesium sulfate, and then the solvent was evaporated under reduced pressure to yield Compound 14d (1.70 g, 75%).

Step (2): Compound 14e+Compound 14d→Compound 14f→Compound (II-14)

Treatment similar as described above yielded Compound (II-14) (318 mg, 44%).

$^1$H-NMR (D$_2$O) δ (delta): 1.49 (3H, s), 1.51 (3H, s), 2.10-2.40 (6H, m), 3.20-4.00 (10H, m), 5.35 (1H, d, J=4.8 Hz), 5.88 (1H, d, J=4.8 Hz), 6.70-6.80 (1H, m), 6.80-6.90 (2H, m), 6.97 (1H, s).

Elementary analysis for C$_{31}$H$_{35}$N$_7$O$_{10}$S$_2$Na.4.3H$_2$O

Calcd.: C, 46.12; H, 5.44; N, 12.15; O, 28.34; S, 7.94(%).

Found: C, 46.01; H, 5.20; N, 12.13; S, 8.05(%).

EXAMPLE 57
Synthesis of Compound (II-15)
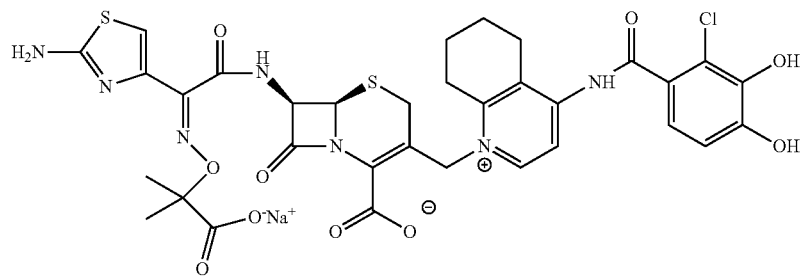
II-15
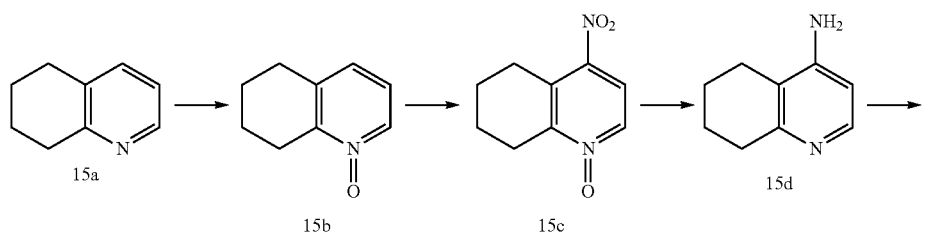
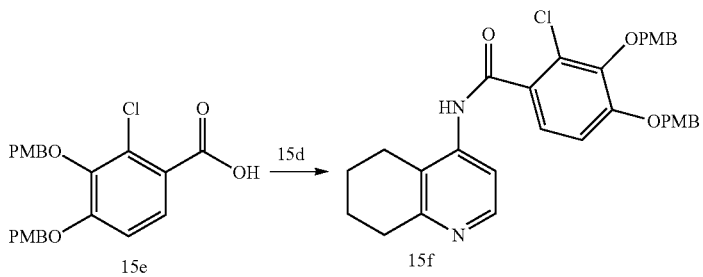
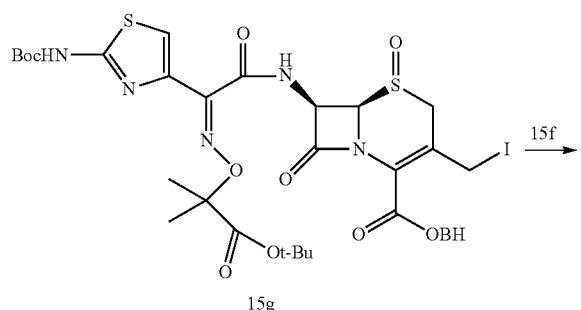
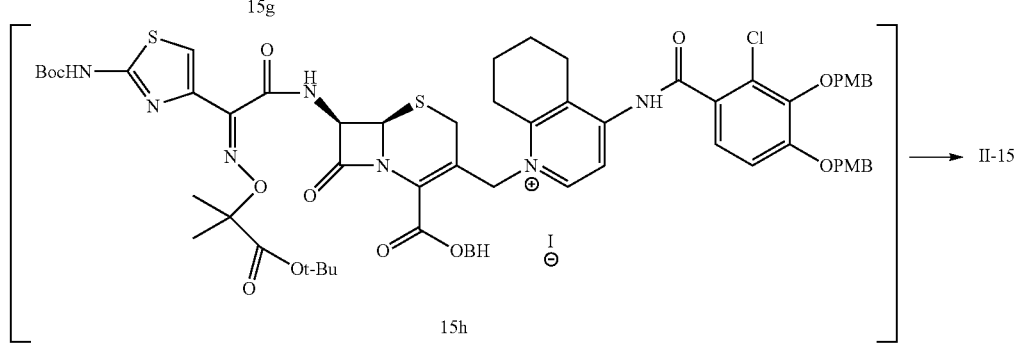
15h Step (1): Compound 15a→Compound 15d
Synthesis of Compound 15d from Compound 15a was carried out according to WO 2002/076979.

Step (2): Compound 15e+Compound 15d→Compound 15f
Compound 15e (1.51 g, 3.52 mmol) was dissolved in methylene chloride (20 mL), and then diisopropylethylamine (1.48 mL, 8.45 mmol), 1-methylimidazole, Compound 15d (621 mg, 4.19 mmol), and diphenyl chlorophosphate (0.872 mL, 4.19 mmol) were added in turn, followed by stirring. The solvent was concentrated in vacuo, and then the residue was purified by silica gel column chromatography to yield Compound 15f (981 mg, 50%).

$^1$H-NMR (CDCl$_3$) δ (delta): 1.80-2.00 (2H, m), 2.60-2.72 (2H, m), 2.82-3.00 (2H, m), 3.80 (3H, s), 3.84 (3H, s), 4.99 (2H, s), 5.13 (2H, s), 6.80-8.40 (12H, m).

Step (3): Compound 15g+Compound 15f→Compound 15h→Compound (II-15)
Treatment similar as described above yielded Compound (II-15) (249 mg, 31%).

$^1$H-NMR (D$_2$O) δ (delta): 1.48 (6H, s), 1.60-2.00 (4H, m), 2.60-2.80 (2H, m), 2.90-3.10 (2H, m), 3.23 (1H, d, J=18.3 Hz), 3.43 (1H, d, J=18.3 Hz), 5.13 (1H, d, J=14.7 Hz), 5.23 (1H, d, J=4.5 Hz), 5.82 (1H, d, J=4.5 Hz), 6.73-6.77 (1H, m), 6.92 (1H, s), 7.00-7.07 (1H, m), 8.33-8.35 (1H, m), 8.44-8.47 (1H, m).

EXAMPLE 58

Synthesis of Compound (II-16)

[Formula 132]

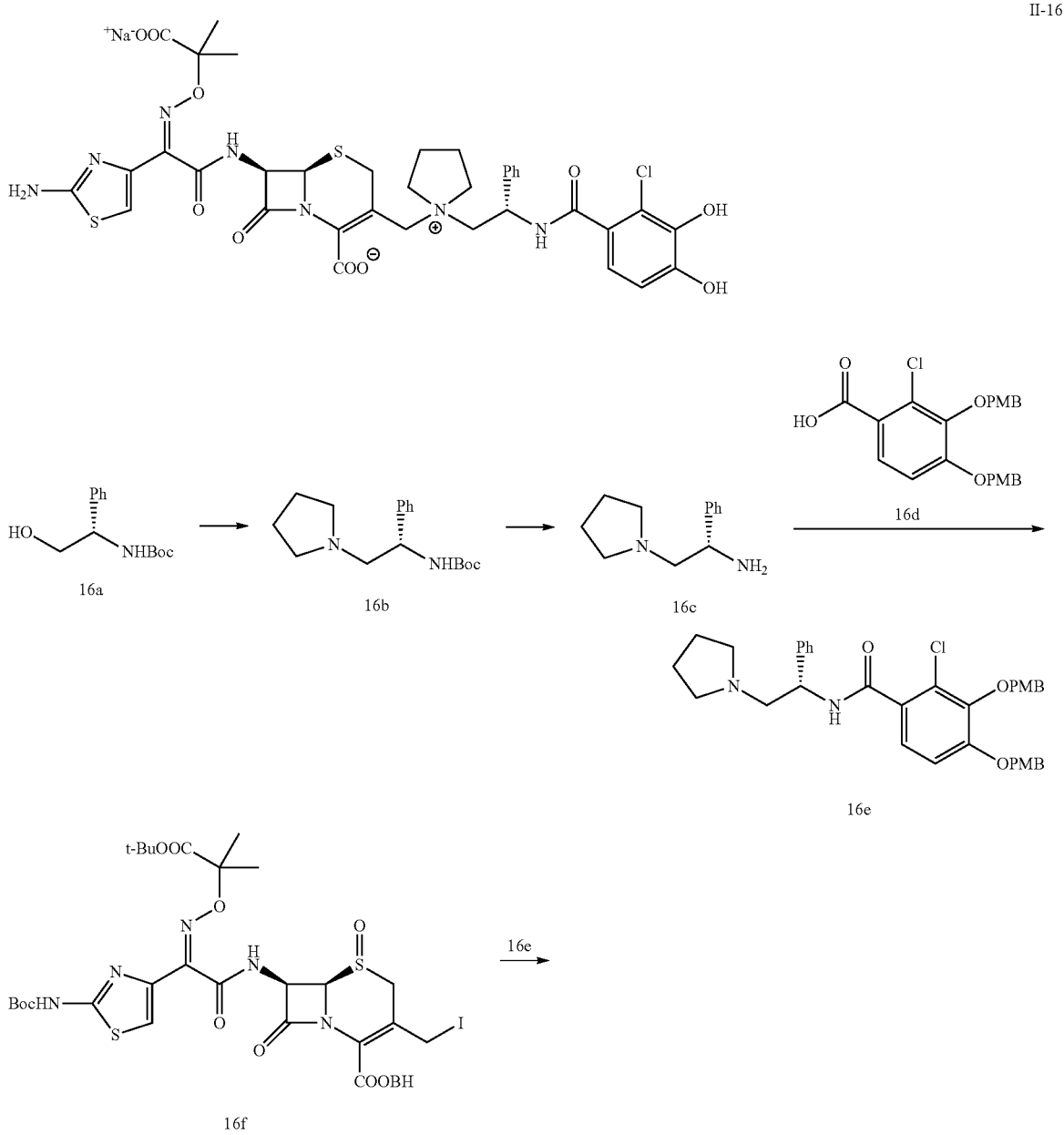

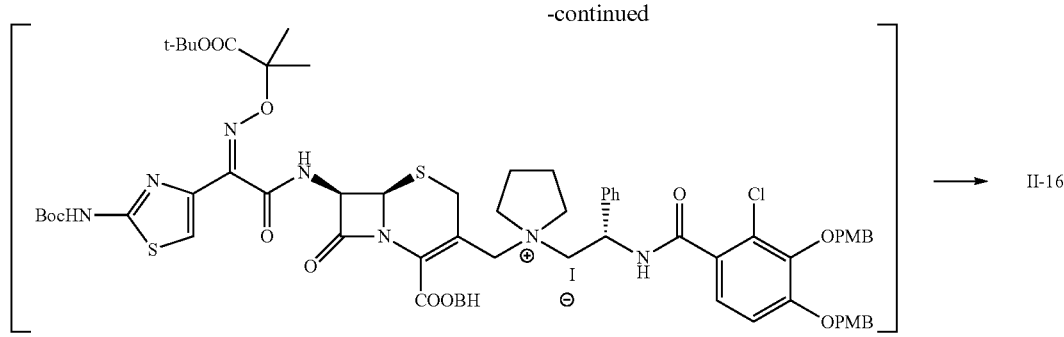

16g

Step (1): Compound 16a→Compound 16b

Compound 16a (7.12 g, 30 mmol) was dissolved in methylene chloride (50 mL), and then triethylamine (8.32 mL, 60 mmol) was added. The reaction solution was cooled to 0° C., and then methanesulfonyl chloride (2.57 mL, 33 mmol) was added drop-wise over 10 minutes. After the reaction solution was stirred at room temperature for 20 minutes, aqueous saturated sodium hydrogen carbonate was added thereto, subsequently the organic layer was separated. After the organic layer was dried over anhydrous sodium sulfate, sodium sulfate was removed by filtration, and then the solvent was concentrated in vacuo. Pyrrolidine (32.3 mL, 390 mmol) was then added to the resulting concentrated residue, followed by heating to 50° C. for 2.5 hours with stirring. Excess pyrrolidine was evaporated under reduced pressure, and then water was added to the resulting concentrated residue, followed by extraction with ethyl acetate. The organic layer was washed with water, washed with saturated brine, and then dried over anhydrous magnesium sulfate. Magnesium sulfate was removed by filtration, and then the solvent was concentrated in vacuo. The resulting crude product was purified by silica gel column chromatography to yield 16b as a white solid (7.23 g, 83%).

$^1$H-NMR (CDCl$_3$) δ (delta): 1.39 (9H, s), 1.73-1.77 (4H, m), 2.42-2.57 (5H, m), 2.76 (1H, dd, J=9.9, 12.3 Hz), 4.59 (1H, br), 5.54 (1H, d, J=4.2 Hz), 7.20-7.34 (5H, m).

Step (2): Compound 16b→Compound 16c→Compound 16e

Compound 16b (7.23 g, 24.9 mmol) was dissolved in methylene chloride (35 mL), and then trifluoroacetic acid (34.5 ml, 448 mmol) was added, subsequently stirring at room temperature overnight. The solvent was evaporated under reduced pressure, and then ethyl acetate was added to the resulting concentrated residue, followed by extraction with aqueous 2 N hydrochloric acid solution. An aqueous 2 N sodium hydroxide solution was then added to the aqueous layer until the aqueous layer had a pH 7-8, followed by extraction with methylene chloride. The organic layer was dried over anhydrous sodium sulfate, and then sodium sulfate was removed by filtration. The solvent was concentrated under reduced pressure, and then further dried in vacuo to yield Compound 16c as a brown oil. The obtained 16c was used for the next reaction without purification.

Compound 16d (6.43 g, 15 mmol) was dissolved in dimethylformamide (70 mL), subsequently cooled to 0° C., and then hydrochloric acid salt (3.16 g, 16.5 mmol) of N-(3-dimethylaminopropyl)-N'-ethylcarbodiimide and 1-hydroxybenzotriazole (2.53 g, 16.5 mmol) were added thereto in turn, followed by stirring at room temperature for 1.5 hours. The reaction solution was cooled to 0° C., and then Compound 16c (3.43 g, 18 mmol) and triethylamine (6.24 mL, 45 mmol) were added thereto, subsequently stirring at 0° C. for 2 hours and then standing at room temperature overnight. Water and tetrahydrofuran were added to the reaction mixture, followed by extraction with ethyl acetate. The organic layer was washed with aqueous saturated sodium hydrogen carbonate, washed with saturated brine, and then dried over anhydrous magnesium sulfate. Magnesium sulfate was removed by filtration, and then the solvent was concentrated in vacuo. Isopropyl acetate was then added to the residue obtained. The resulting solid was filtered, and then dried in vacuo to yield Compound 16e as a white solid (6.31 g, 70%).

$^1$H-NMR (DMSO-d$_6$) δ (delta): 1.66 (4H, br), 2.50 (4H, br), 2.56 (1H, q, J=6.3 Hz), 2.81 (1H, dd, J=9.3, 12.0 Hz), 3.74 (3H, s), 3.76 (3H, s), 4.87 (2H, s), 5.06 (1H, dd, J=9.0, 15.0 Hz), 5.16 (2H, s), 6.87 (2H, d, J=8.7 Hz), 6.97 (2H, d, J=8.7 Hz), 7.09 (1H, d, J=8.4 Hz), 7.18-7.26 (2H, m), 7.29-7.34 (4H, m), 7.37-7.40 (2H, m), 7.42 (2H, d, J=8.7 Hz).

Step (3): Compound 16e+Compound 16f→Compound 16g→Compound (II-16)

Compound 16e (1.20 g, 2.0 mmol) was suspended in a mixed solvent of dimethylformamide (6 mL) and tetrahydrofuran (4 mL). Then Compound 16f (2.12 g, 2.0 mmol) and sodium hydrogen carbonate (0.34 g, 4.0 mmol) were added thereto in turn, subsequently stirring at room temperature for 4 hours. The reaction solution was cooled to −40° C., and then phosphorus tribromide (0.377 mL, 4 mmol) was added, subsequently stirring at 0° C. for 1 hour. Ice-cold water was added to the reaction mixture, followed by extraction with ethyl acetate. The organic layer was washed with water, washed with saturated brine, and then dried over anhydrous magnesium sulfate. Magnesium sulfate was then removed by filtration. The solvent was concentrated under reduced pressure, and then further dried in vacuo to yield Compound 16g as a brown formed solid. The obtained Compound 16g was used for the next reaction without purification.

The whole amount of Compound 16g obtained was dissolved in methylene chloride (30 mL), subsequently cooled to −40° C., and then anisole (2.19 mL, 20 mmol) and 2M-aluminum chloride/nitromethane solution (10 mL, 20 mmol) were added thereto in turn, followed by stirring at 0° C. for 1 hour. To the reaction solution was then added aqueous 2 N hydrochloric acid solution, acetonitrile, and diisopropyl ether that had been cooled to 0° C., subsequently stirring to completely dissolve insolubles. To the separated aqueous layer was added HP20-SS resin, and then acetonitrile was concentrated in vacuo. The resulting mixed solution was purified by ODS column chromatography. To the obtained solution of the desired Compound was then added aqueous 0.2 N sodium hydroxide solution until the solution had pH=6.0. Excess sodium hydroxide was then neutralized by adding one piece of dry ice. The resulting solution was concentrated in vacuo, and then lyophilized to yield Compound (II-16) as a white powder (0.48 g, 28%).

$^1$H-NMR (D$_2$O) δ (delta): 1.48 (3H, s), 1.49 (3H, s), 3.42-3.94 (9H, m), 4.25 (1H, d, J=14.4 Hz), 5.25 (1H, d, J=4.8 Hz), 5.71 (1H, br), 5.83 (1H, d, J=4.8 Hz), 6.57 (1H, d, J=8.4 Hz), 6.67 (1H, d, J=8.1 Hz), 7.48 (5H, br).

Elementary analysis for: $C_{36}H_{37}ClN_7O_{10}S_2Na.0.1NaHCO_3.4.8H_2O$

Calcd.: C, 45.87; H, 4.98; Cl, 3.75; N, 10.37; S, 6.79(%).
Found: C, 45.85; H, 5.05; Cl, 3.93; N, 10.29; S, 6.72(%).

EXAMPLE 59

Synthesis of Compound (II-17)

[Formula 133]

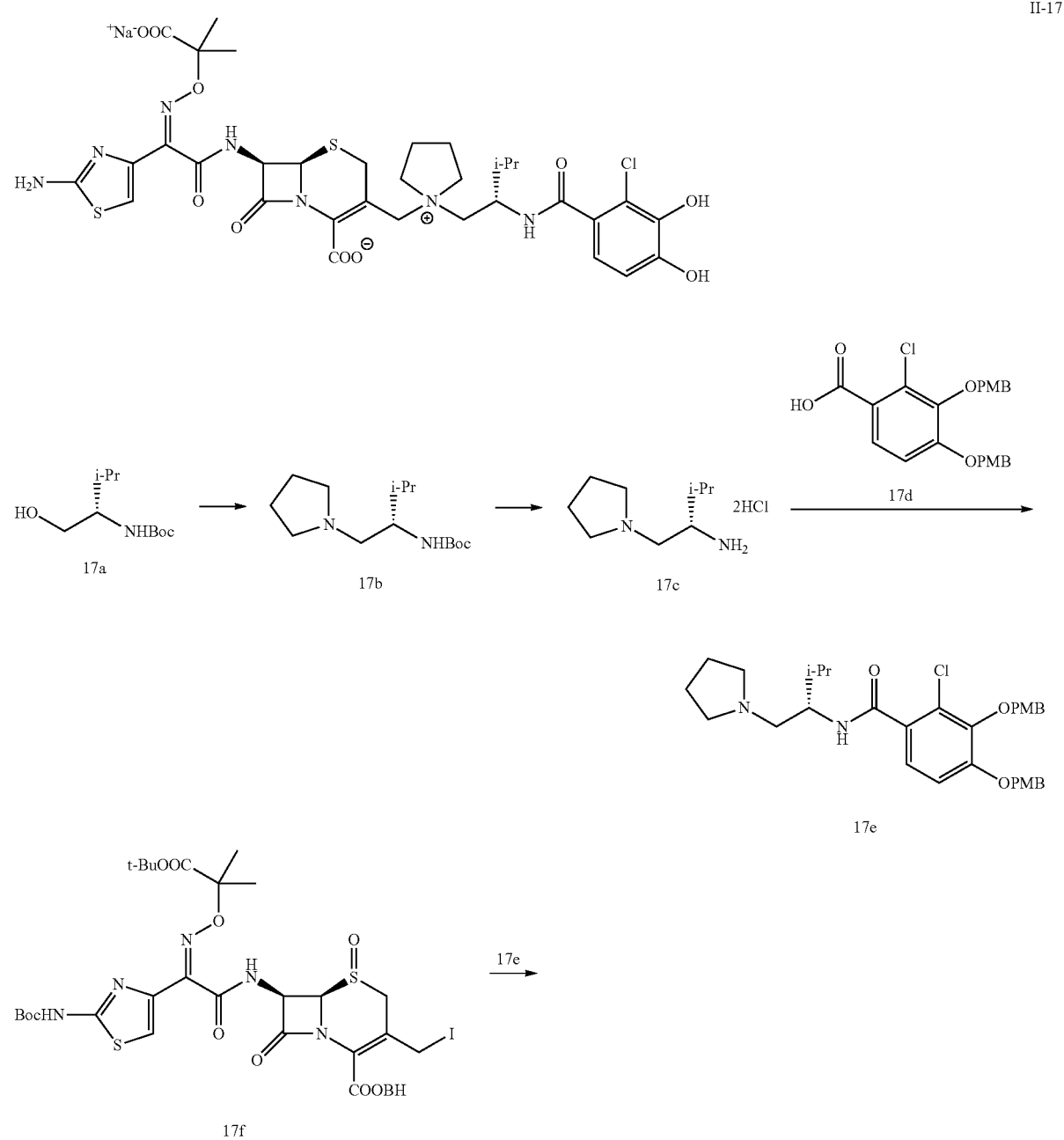

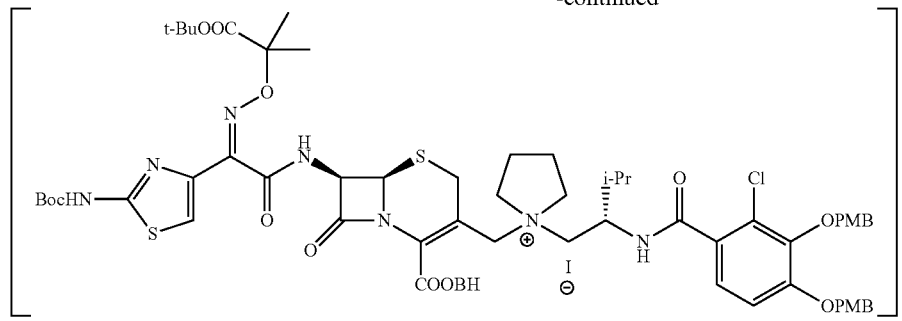

17g

Step (1): Compound 17a→Compound 17b→Compound 17c

Compound 17a (5.0 g, 24.6 mmol) was dissolved in methylene chloride (40 mL), and then triethylamine (6.82 mL, 49.2 mmol) was added thereto, subsequently cooling to 0° C. Methanesulfonyl chloride (2.11 mL, 27.1 mmol) was added drop-wise to the reaction solution over 10 minutes. The reaction solution was stirred at room temperature for 1 hour, and then aqueous saturated sodium hydrogen carbonate was added thereto, followed by extraction with methylene chloride. The organic layer was dried over anhydrous magnesium sulfate, and then magnesium sulfate was removed by filtration. The solvent was then evaporated under reduced pressure. Pyrrolidine (26.4 mL, 320 mmol) was added to the resulting concentrated residue, subsequently heating to 50° C. for 2.5 hours with stirring. Excess pyrrolidine was evaporated under reduced pressure, and then ethyl acetate was added to the resulting concentrated residue, followed by extraction with aqueous 1 N hydrochloric acid solution. To the aqueous layer was added aqueous 2 N sodium hydroxide solution until the solution had a pH of 7-8, followed by extraction with methylene chloride. The organic layer was washed with water, and then dried over anhydrous magnesium sulfate. Magnesium sulfate was removed by filtration, and then concentrated in vacuo to yield Compound 17b as a white solid. The obtained Compound 17b was used for the next reaction without purification.

The whole amount of Compound 17b obtained was dissolved in methylene chloride (22 mL), and then trifluoroacetic acid (22.0 mL, 285 mmol) was added, subsequently stirring at room temperature overnight. The solvent was evaporated under reduced pressure, and then ethyl acetate was added to the concentrated residue, followed by cooling to 0° C. 4 N hydrochloric acid/ethyl acetate solution (40 mL) was then added to the solution, subsequently stirring at 0° C. for 15 minutes. The resulting solid was filtrated, and then dried in vacuo to yield Compound 17c as a white solid (3.50 g, 62%).

$^1$H-NMR (DMSO-$d_6$) δ (delta): 0.97 (6H, dd, J=3.3, 6.9 Hz), 1.87-2.13 (5H, m), 2.93-3.15 (2H, m), 3.45-3.59 (4H, m), 3.76 (1H, br), 5.75 (2H, br).

Step (2): Compound 17c→Compound 17e

Compound 17d (6.43 g, 15 mmol) was dissolved in dimethylformamide (70 mL), subsequently cooling to 0° C., and then hydrochloric acid salt (3.16 g, 16.5 mmol) of N-(3-dimethylaminopropyl)-N'-ethylcarbodiimide, and 1-hydroxybenzotriazole (2.53 g, 16.5 mmol) were added thereto in turn, followed by stirring at room temperature for 1.5 hours. The reaction solution was cooled to 0° C. again, and then Compound 17c (3.44 g, 15 mmol) and triethylamine (10.4 mL, 75 mmol) were added, subsequently stirring at 0° C. for 2 hours and further left standing at room temperature overnight. Water and tetrahydrofuran were added to the reaction mixture, followed by extraction with ethyl acetate. The organic layer was washed with aqueous saturated sodium hydrogen carbonate, washed with saturated brine, and then dried over anhydrous magnesium sulfate. Magnesium sulfate was removed by filtration, and then the solvent was concentrated in vacuo. Diisopropyl ether was then added to the resulting residue. The resulting solid was filtrated, and then dried in vacuo to yield Compound 17e as a white solid (6.21 g, 73%).

$^1$H-NMR (DMSO-$d_6$) δ (delta): 0.89 (6H, dd, J=6.9, 16.2 Hz), 1.66 (4H, br), 1.84 (1H, td, J=7.2, 18.6 Hz), 2.39-2.51 (6H, m), 3.75 (1H, s), 3.76 (1H, s), 3.94 (1H, m), 4.87 (2H, s), 5.15 (2H, s), 6.87 (2H, d, J=8.7 Hz), 6.96 (2H, d, J=8.7 Hz), 7.05 (1H, d, J=8.7 Hz), 7.18 (1H, d, J=8.7 Hz), 7.32 (2H, d, J=8.7 Hz), 7.42 (2H, d, J=8.7 Hz), 7.97 (2H, d, J=9.0 Hz).

Step (3): Compound 17e+Compound 17f→Compound 17g→Compound (II-17)

Compound 17e (1.20 g, 2.0 mmol) was dissolved in a mixed solvent of dimethylformamide (6 mL) and tetrahydrofuran (2 mL), and then Compound 17f (2.12 g, 2.0 mmol) and sodium hydrogen carbonate (0.34 g, 4.0 mmol) were added thereto, subsequently stirring at room temperature for 2 hours. The reaction solution was cooled to −40° C., and then phosphorus tribromide (0.377 mL, 4 mmol) was added, followed by stirring at 0° C. for 1 hour. Ice-cold water was then added to the reaction mixture, followed by extraction with ethyl acetate. The organic layer was washed with water, washed with saturated brine, and then dried over anhydrous magnesium sulfate. Magnesium sulfate was removed by filtration, and then the solvent was evaporated under reduced pressure to yield Compound 17g as a brown formed solid. The obtained Compound 17g was used for the next reaction without purification.

Then the whole amount of Compound 17g obtained was dissolved in methylene chloride (30 mL), and then anisole (2.19 mL, 20 mmol) and 2M-aluminum chloride/nitromethane solution (10 mL, 20 mmol) were added at −40° C. in turn, subsequently stirring at 0° C. for 1.5 hours. To the reaction solution was added 2 N hydrochloric acid, acetonitrile, and diisopropyl ether that had been cooled to 0° C., followed by stirring to completely dissolve insolubles. The aqueous layer was then separated. H920-SS resin was added to the aqueous layer, and then acetonitrile was concentrated in vacuo. The resulting concentrated solution was purified by ODS column chromatography. An aqueous 0.2 N sodium hydroxide solution was added to the solution of the resulting desired compound until the solution had pH=6.0. Excess sodium hydroxide was then neutralized by adding one piece of dry ice. The obtained solution was concentrated in vacuo, and then lyophilized to yield Compound (II-17) as a white powder (823 mg, 50%).

$^1$H-NMR (D$_2$O) δ (delta): 0.95-1.05 (5H, m), 1.49 (3H, s), 1.51 (3H, s), 2.07 (1H, br), 2.19 (4H, br), 3.43-3.69 (8H, m), 3.99 (1H, d, J=16.8 Hz), 4.18 (1H, d, J=13.8 Hz), 4.54 (1H, m), 5.37 (1H, d, J=5.4 Hz), 5.90 (1H, d, J=5.1 Hz), 6.73 (2H, m), 6.98 (1H, s).

Elementary analysis for: C$_{33}$H$_{39}$ClN$_7$O$_{10}$S$_2$Na.0.2NaHCO$_3$.4.0H$_2$O Calcd.: C, 44.05; H, 5.26; Cl, 3.92; N, 10.83; S, 7.09(%).
Found: C, 44.07; H, 5.30; Cl, 4.14; N, 10.72; S, 6.93(%).

EXAMPLE 60

Synthesis of Compound (II-18)

[Formula 134]

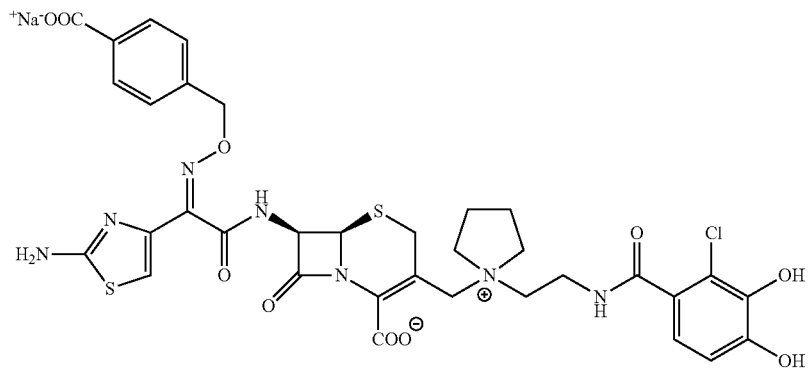

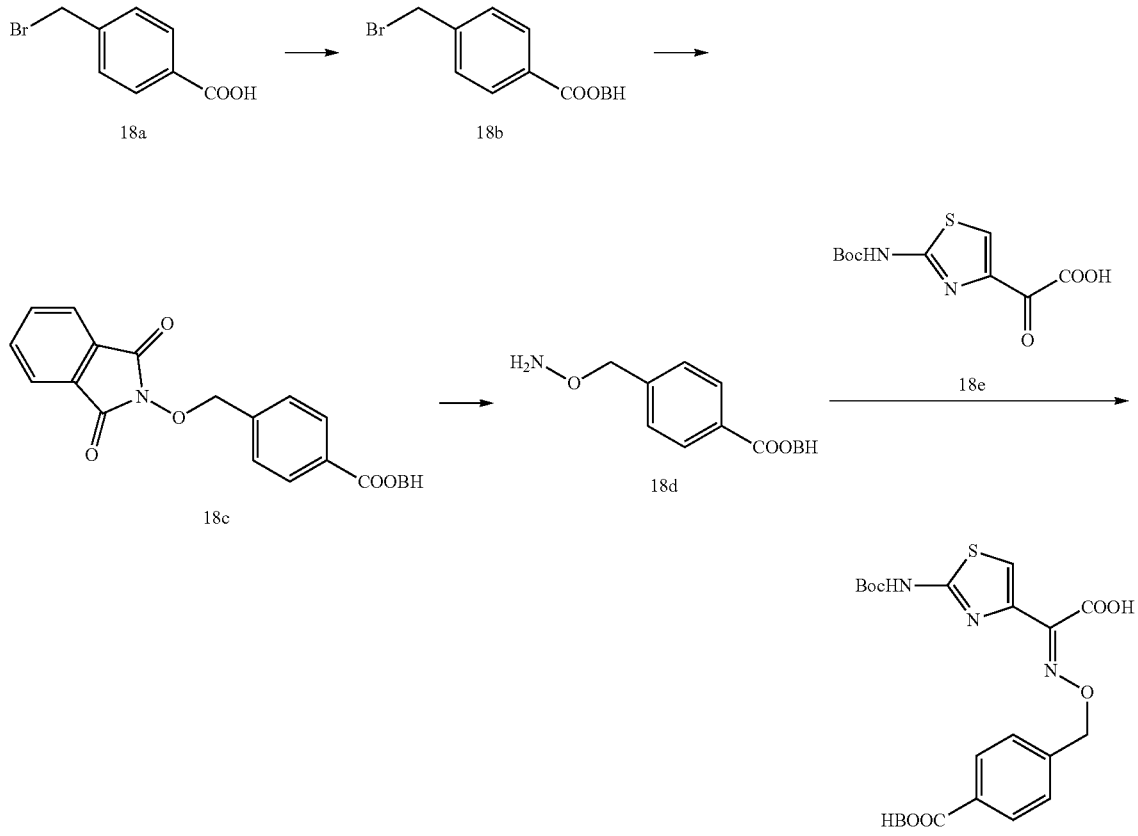

-continued

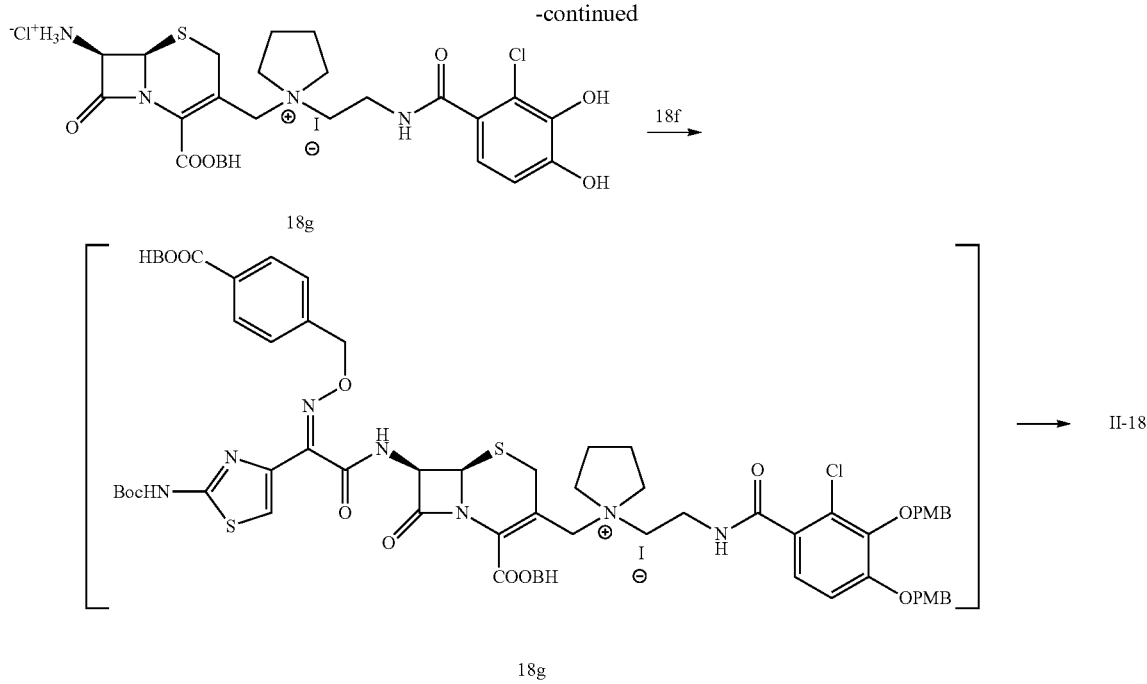

Step (1): Compound 18a→Compound 18b

Compound 18a (6.45 g, 30 mmol) was dissolved in tetrahydrofuran (70 mL), and then diphenyldiazomethane (6.99 g, 36 mmol) was added thereto. The reaction solution was then stirred at room temperature for 1 hour, subsequently heating at reflux for 2 hours. The reaction mixture was concentrated in vacuo, and then Methanol was added to the residue. The resulting solid was filtrated, and then dried in vacuo to yield Compound 18b as a white solid (9.01 g, 79%).

$^1$H-NMR (CDCl$_3$) δ (delta): 4.50 (2H, s), 7.11 (1H, s), 7.25-7.49 (12H, m), 8.11 (2H, d, J=8.1 Hz).

Step (2): Compound 18b→Compound 18c

Compound 18b (9.0 g, 23.6 mmol) and N-hydroxyphthalimide (4.62 g, 28.3 mmol) were dissolved in dimethylformamide (90 mL), and then triethylamine (3.93 mL, 28.3 mmol) was added thereto, subsequently heating to 50° C. for 1 hour with stirring. Ice-cold water and tetrahydrofuran were then added to the reaction solution, followed by extraction with ethyl acetate. The organic layer was washed with aqueous saturated sodium hydrogen carbonate, washed with saturated brine, and dried over anhydrous magnesium sulfate. Magnesium sulfate was removed by filtration, and then the solvent was concentrated in vacuo. n-Hexane was then added to the resulting residue. The resulting solid was filtrated, and then dried in vacuo to yield Compound 18c as a white solid (9.28 g, 85%).

$^1$H-NMR (CDCl$_3$) δ (delta): 5.27 (2H, s), 7.10 (1H, s), 7.25-7.44 (10H, m), 7.63 (2H, d, J=8.4 Hz), 7.71-7.82 (4H, m), 8.14 (2H, d, J=8.4 Hz)

Step (3): Compound 18c→Compound 18d→Compound 18f

Compound 18c (6.95 g, 15 mmol) was dissolved in methylene chloride (70 mL), subsequently cooling to 0° C., and then methylhydrazine (0.88 mL, 16.5 mmol) was added in one portion, followed by stirring at 0° C. for 1.5 hours. The resulting solid was then removed by filtration. The solvent was evaporated under reduced pressure, and further dried in vacuo to yield Compound 18d as a pale yellow solid. The obtained Compound 18d was used for the next reaction without purification.

Then a solution of Compound 18e (4.08 g, 15 mmol) in methanol (40 mL) was cooled to 0° C. To this solution was added a methylene chloride (20 mL) solution of the whole amount of Compound 18c obtained as described above, followed by stirring at 0° C. for 1 hour and further at room temperature for 1 hour. The reaction solution was concentrated in vacuo, and then water was added to the residue, followed by extraction with ethyl acetate. The organic layer was washed with water, washed with saturated brine, and then dried over anhydrous magnesium sulfate. Magnesium sulfate was removed by filtration, and then the solvent was concentrated in vacuo. After methanol was added to the resulting residue, the resulting solid was filtrated, and then dried in vacuo to yield Compound 18f as a white solid (6.23 g, 71%).

$^1$H-NMR (DMSO-d$_6$) δ (delta): 1.46 (9H, s), 5.31 (2H, s), 7.04 (1H, s), 7.27-7.43 (7H, m), 7.52-7.55 (6H, m), 8.11 (2H, d, J=8.4 Hz).

Step (4): Compound 18f+Compound 18g→Compound 18h→Compound (II-18)

Compound 18g (2.37 g, 2.22 mmol) was dissolved in methylene chloride (30 mL), subsequently cooling to −10° C. Then Compound 18f (1.18 g, 2.0 mmol), hydrochloric acid salt (0.51 g, 2.67 mmol) of N-(3-dimethylaminopropyl)-N'-ethylcarbodiimide, and pyridine (0.233 mL, 2.89 mmol) were added thereto in turn, subsequently stirring at −10° C. for 1.5 hours. Aqueous 2 N hydrochloric acid solution (2 mL) was added to the reaction mixture, and then concentrated in vacuo. Water was then added thereto, followed by extraction with ethyl acetate. The organic layer was washed with water, washed with saturated brine, and then dried over anhydrous magnesium sulfate. After magnesium sulfate was removed by filtration, the solvent was evaporated under reduced pressure, and further dried in vacuo to yield Compound 18h as a brown formed solid. The obtained Compound 18h was used for the next reaction without purification.

The whole amount of Compound 18h obtained was dissolved in methylene chloride (15 mL), subsequently cooling to −40° C., and then anisole (1.97 mL, 18 mmol) and trifluoroacetic acid (30 mL) were added thereto in turn, followed by stirring at 0° C. for 1 hour. The solvent was evaporated under reduced pressure, and then ice-cold water, acetonitrile, and diisopropyl ether were added thereto. After the aqueous layer was separated, HP20-SS resin was added thereto, acetonitrile was concentrated in vacuo. The resulting mixed solution was purified by ODS column chromatography. An aqueous 0.2 N sodium hydroxide solution was added to the obtained solution of the desired compound until the solution had pH=6.0, and then excess sodium hydroxide was neutralized by adding one piece of dry ice. The resulting solution was concentrated in vacuo, and then lyophilized to yield Compound (II-18) as a white powder (138 mg, 7%).

$^1$H-NMR (D$_2$O) δ (delta): 2.20 (4H, br), 3.24 (1H, d, J=17.4 Hz), 3.41-3.91 (10H, m), 4.08 (1H, d, J=14.1 Hz), 5.22 (1H, d, J=5.1 Hz), 5.26 (2H, s), 5.76 (1H, d, J=4.8 Hz), 6.80 (1H, d, J=8.1 Hz), 6.89 (1H, d, J=8.4 Hz), 6.93 (1H, s), 7.46 (2H, d, J=8.1 Hz), 7.81 (2H, d, J=8.1 Hz).

Elementary analysis for: C$_{34}$H$_{33}$ClN$_7$O$_{10}$S$_2$Na.0.2NaHCO$_3$.5.6H$_2$O Calcd.: C, 43.70; H, 4.76; Cl, 3.77; N, 10.43; S, 6.82(%).

Found: C, 43.67; H, 4.70; Cl, 3.80; N, 10.44; S, 7.05(%).

EXAMPLE 61

Synthesis of Compound (II-19)

[Formula 135]

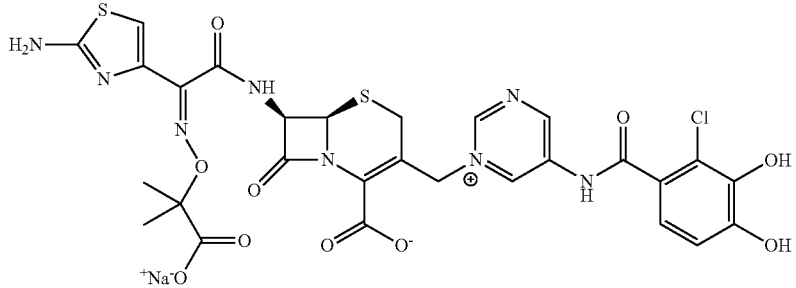

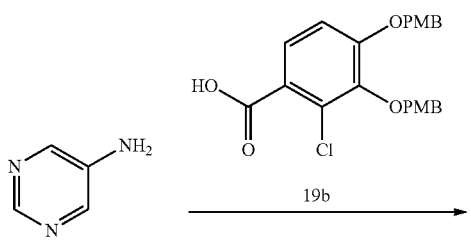

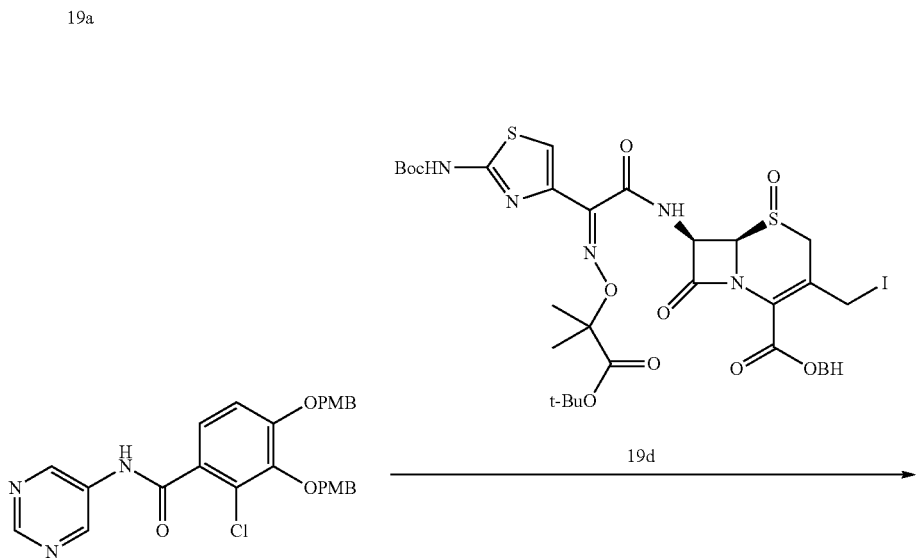

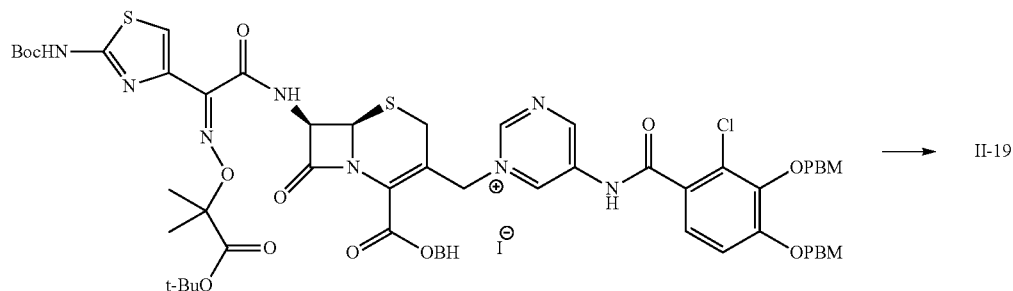

19e

Step (1): Compound 19a+Compound 19b→Compound 19c

5-Aminopyridine 19a (0.951 g, 10 mmol), Compound 19b (4.72 g, 11.00 mmol), 1-hydroxybenzotriazole (1.486 g, 11.00 mmol), and hydrochloric acid salt (2.109 g, 11.00 mmol) of N-(3-dimethylaminopropyl)-N'-ethylcarbodiimide were dissolved in dimethylacetamide (19.5 mL), subsequently stirring at 70° C. for 8.5 hours. Distilled water was added to the reaction solution, and then the precipitated solid was filtrated. The filtrated residue was washed with aqueous saturated sodium hydrogen carbonate, washed with distilled water, and then washed with diisopropyl ether. The residue was dissolved in methanol, followed by stirring for 3.5 hours under reflux. The reaction solution was filtrated, and then the filtrated residue was washed with methanol. The residue was dried in vacuo to yield Compound 19c as a white solid (1.41 g, 28%).

$^1$H-NMR (DMSO-$d_6$) δ (delta): 10.80 (1H, s), 9.09 (2H, s), 8.93 (1H, s), 7.48-7.26 (6H, m), 6.99 (2H, d, J=8.5 Hz), 6.88 (2H, d, J=8.5 Hz), 5.21 (2H, s), 4.93 (2H, s), 3.77 (3H, s), 3.75 (3H, s).

Step (2): Compound 19c+Compound 19d→Compound 19e

Compound 19c (0.506 g, 1.00 mmol) and Compound 19d (0.940 g, 1.00 mmol) were dissolved in dimethylacetamide (3 mL), subsequently stirring at room temperature for 6 hours.

Dimethylformamide (30 mL) was added to the reaction solution, followed by cooling to −40° C., and then phosphorus tribromide (0.19 mL, 2.00 mmol) was added thereto. The reaction solution was stirred at −40° C. for 3 hours, and then ethyl acetate and ice water were added thereto. The organic layer was extracted with operation of separation, then washed with saturated brine, and further dried over anhydrous magnesium sulfate. Magnesium sulfate was filtrated, the solvent was evaporated under reduced pressure to Compound 19e as a formed solid. The obtained 19e was used for the next reaction without purification.

Step (3): Compound 19e→Compound (II-19)

The whole amount of the crude Compound 19e obtained by the previous reaction was dissolved in methylene chloride (15 mL), subsequently cooling to −40° C. Anisole (1.09 mL, 10.0 mmol) and 2M-aluminum chloride/nitromethane solution (5.00 mL, 10.0 mmol) were added thereto in turn, followed by stirring at 0° C. for 2 hours. To the reaction solution was added distilled water, acetonitrile, diisopropyl ether, and aqueous 2 N hydrochloric acid solution, and then stirred. Because precipitation appeared, the supernatant was separated by decantation. The aqueous layer was separated from the supernatant by operation of separation. The aqueous layer was combined with the decantation residue, and then aqueous 2 N hydrochloric acid solution and acetonitrile were added to make a homogeneous solution. HP-20SS resin was added to the solution, concentrated, subjected into column chromatography connecting HP20SS column and subsequent ODS column, and then purified. The resulting solution of the desired compound was concentrated in vacuo, and then lyophilized to yield Compound (II-19) as a white powder (58 mg, 8%).

$^1$H-NMR (D$_2$O) δ (delta): 8.34 (1H, s), 7.18 (1H, d, J=8.5 Hz), 6.86 (1H, d, J=8.5 Hz), 6.58 (1H, s), 6.35 (1H, d, J=2.2 Hz), 5.79 (1H, d, J=4.7 Hz), 5.46 (1H, d, J=4.7 Hz), 5.12 (1H, d, J=10.6 Hz), 5.03-4.66 (3H, m), 4.48 (1H, d, J=10.6 Hz), 1.32 (6H, s).

MS (m+1)=733

Elementary analysis for $C_{23}H_{24}ClN_8O_{10}S_2Na$ (NaHCO$_3$)$_{1.5}$(H$_2$O)$_{6.1}$ Calcd.: C, 35.75; H, 3.83; Cl, 3.58; N, 11.31; S, 6.47; Na, 5.80(%).

Found: C, 35.53; H, 3.63; Cl, 5.26; N, 11.80; S, 6.59; Na, 3.04(%).

EXAMPLE 62

Synthesis of Compound (II-20)

[Formula 136]

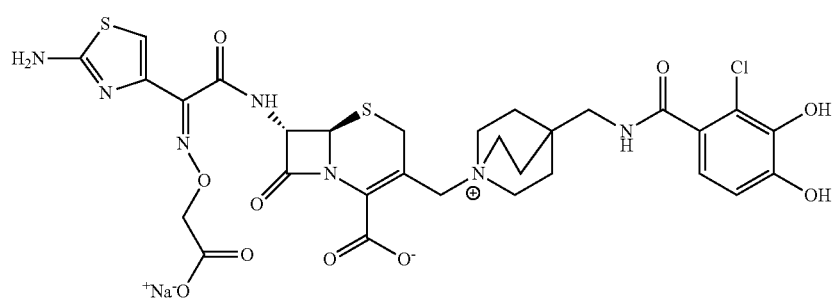

II-20

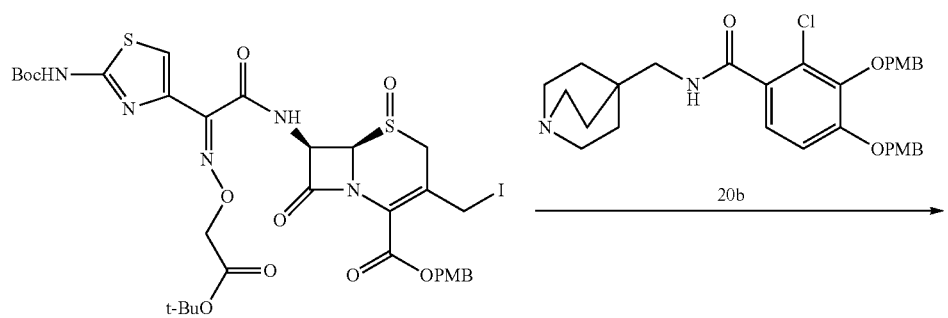

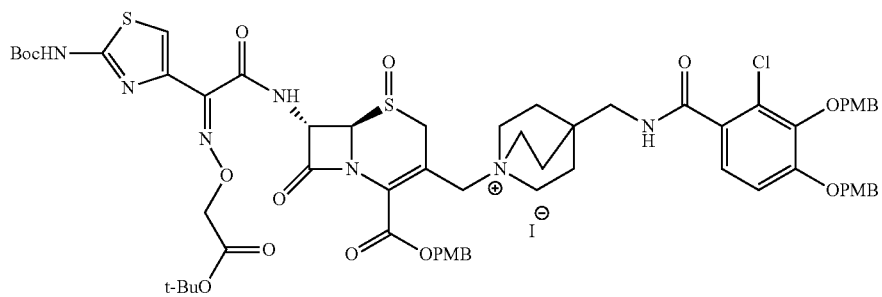

Step (1): Compound 20a+Compound 20b→Compound 20c

Compound 20a (1.00 g, 1.16 mmol) and Compound 20b (0.606 g, 1.10 mmol) were dissolved in dimethylformamide (3.5 mL), subsequently stirring at room temperature for 3 hours. Ethyl acetate and aqueous 0.2 N hydrochloric acid solution were then added to the reaction solution. The organic layer was separated, washed with aqueous 0.2 N hydrochloric acid solution, washed with saturated brine, and then dried over anhydrous magnesium sulfate. Magnesium sulfate was filtrated, and then the solvent was evaporated under reduced pressure to yield 20c as a formed solid. The obtained Compound 20c was used for the next reaction without purification.

Step (2): Compound 20c→Compound (II-20)

The whole amount of the crude Compound 20c obtained by the previous reaction was treated similarly as described above to yield Compound (II-20) as a white powder (83 mg, 10%).

$^1$H-NMR (D$_2$O) δ (delta): 7.00 (1H, s), 6.93 (1H, d, J=8.5 Hz), 6.88 (1H, d, J=8.5 Hz), 5.23 (1H, d, J=2.6 Hz), 5.13 (1H, d, J=2.6 Hz), 4.94-4.56 (3H, m), 4.33 (1H, d, J=13.6 Hz), 3.97-3.85 (2H, m), 3.53-3.33 (8H, m), 1.98-1.91 (6H, m).

MS (m+1)=751

Elementary analysis for C$_{30}$H$_{31}$ClN$_7$NaO$_{10}$S$_2$ (NaHCO$_3$)$_{0.5}$(H$_2$O)$_{4.5}$ Calcd.: C, 40.92; H, 4.56; Cl, 3.96; N, 10.95; S, 7.16; Na, 3.85(%).

Found: C, 40.76; H, 4.63; Cl, 4.09; N, 10.89; S, 7.34; Na, 2.77(%).

EXAMPLE 63
Synthesis of Compound (II-21)
[Formula 137]
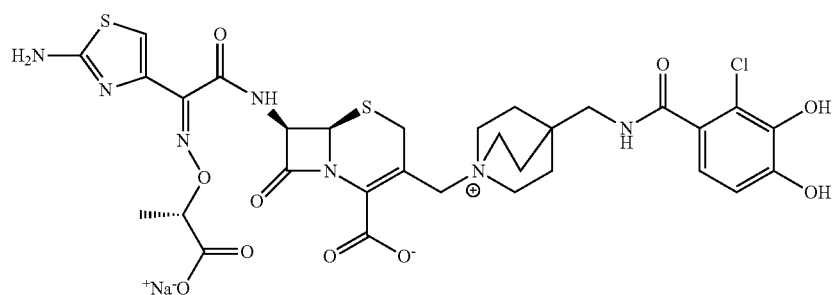
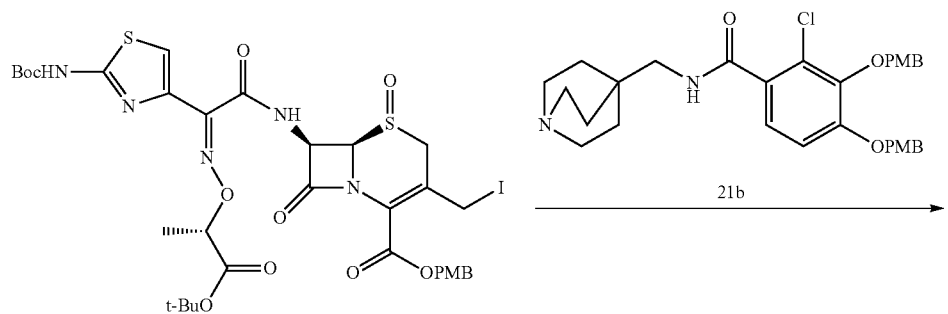
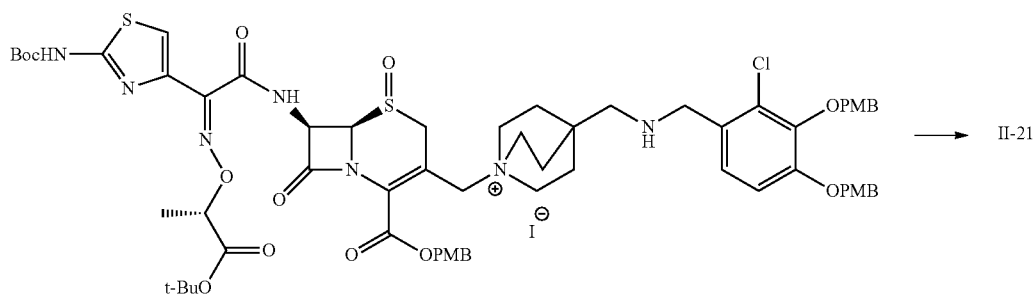

Step (1): Compound 21a+Compound 21b→Compound 21c

Treatment similar to that described above yielded Compound 20c as a formed solid. The obtained 20c was used for the next reaction without purification.

Step (2): Compound 21c→Compound (II-21)

The whole amount of the crude Compound 21c obtained by the previous reaction was treated similarly to that described above to yield Compound (II-21) as a white powder (406 mg, 48%).

$^1$H-NMR (D$_2$O) δ (delta): 6.98 (1H, s), 6.92 (1H, d, J=8.4 Hz), 6.87 (1H, d, J=8.4 Hz), 5.85 (1H, d, J=5.0 Hz), 5.32 (1H, d, J=5.0 Hz), 3.88-3.80 (2H, m), 4.86-4.55 (3H, m), 3.53-3.27 (8H, m), 1.94-1.88 (6H, m), 1.47 (3H, d, J=7.1 Hz).

MS (m+1)=765

Elementary analysis for C$_{31}$H$_{33}$ClN$_7$NaO$_{10}$S$_2$ (NaHCO$_3$)$_{0.5}$(H$_2$O)$_{4.5}$ Calcd.: C, 41.61; H, 4.71; Cl, 3.90; N, 10.78; S, 7.05; Na, 3.79(%).

Found: C, 41.78; H, 4.87; Cl, 4.01; N, 10.77; S, 7.07; Na, 2.74(%).

EXAMPLE 64

Synthesis of Compound (II-22)

Step (1): Compound 22a+Compound 22b→Compound 22c

According a method similar to that described in *Bioorg. Med. Chem.* 2007, 15, 6716, the obtained Compound 22a (892 mg, 1 mmol) and Compound 22b (525 mg, 0.99 mmol) were dissolved in dimethylacetamide (3 mL), and then potassium iodide (450 mg, 3 mmol) was added to the reaction solution in a water bath, subsequently stirring at room temperature for 100 minutes. Dimethylformamide (6 mL) was added to the reaction solution, followed by cooling to 0° C., potassium iodide (1.33 g, 8 mmol) and acetyl chloride (0.43 mL, 6 mmol) were added thereto in turn, subsequently stirring at the same temperature for one hour. The reaction solution was then diluted with ethyl acetate. An aqueous 10% sodium hydrogen sulfite solution was added thereto, and then the organic layer was separated. The organic layer was washed with saturated brine, and then dried over magnesium sulfate. Magnesium sulfate was filtrated, and then concentrated in vacuo to yield Compound 22c. Compound 22c was used for the next reaction without purification.

Step (2): Compound 22c→Compound (II-22)

The whole amount of the crude Compound 22c described above was dissolved in methylene chloride (8 mL) and anisole (1.1 mL, 10 mmol), and then cooled to −40° C. 2M-aluminum chloride/nitromethane solution (5 mL, 10 mmol) was

[Formula 138]

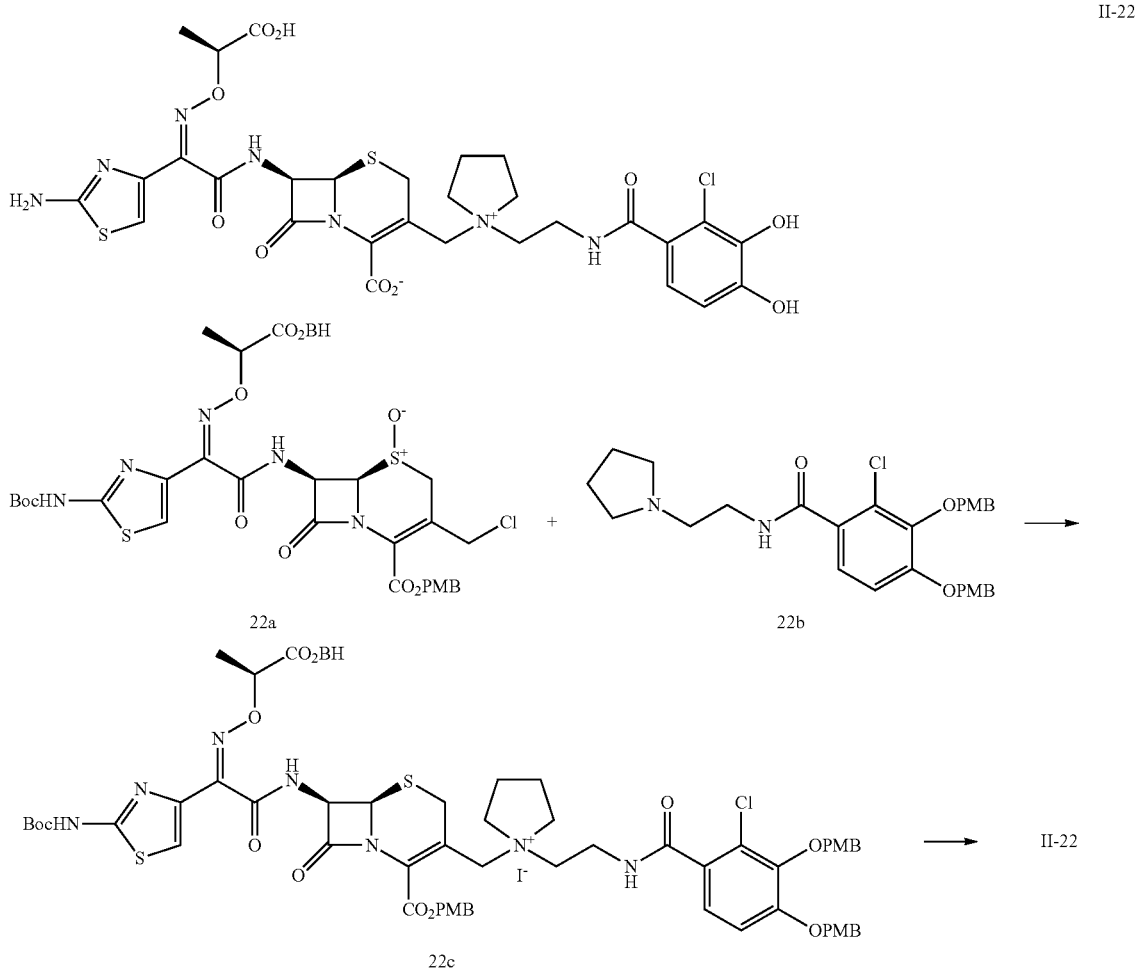

then added thereto, subsequently stirring for one hour in an ice bath. The reaction solution was solved into a mixed solution of aqueous 1 N hydrochloric acid solution and acetonitrile, and then diisopropyl ether was added thereto. After the aqueous layer was separated, HP-20SS resin was added, and then concentrated in vacuo. The concentrated solution was subjected to ODS column chromatography eluting with water-acetonitrile. Fractions containing the desired compound were concentrated in vacuo, and then lyophilized to yield Compound (II-22) (338.3 mg, 46%) as a powder.

MS: 738.03 (M+H)

$^1$H-NMR (DMSO-$d_6$) δ (delta): 9.60 (1H, d, J=8.52 Hz), 8.48 (1H, t, J=5.8 Hz), 7.28 (2H, br s), 6.88-6.78 (3H, m), 5.78 (1H, dd, J=8.2, 5.2 Hz), 5.19 (1H, d, J=5.2 Hz), 5.08 (1H, d, J=13.5 Hz), 4.63 (1H, q, J=7.2 Hz), 3.96 (1H, d, J=13.2 Hz), 3.87 (1H, d, J=16.5 Hz), 3.60-3.55 (9H, m), 2.17-2.01 (4H, m), 1.45 (3H, d, J=7.2 Hz).

Elementary analysis for $C_{29}H_{32}ClN_7O_{10}S_2 \cdot 5.1(H_2O)$

Calcd.: C, 41.96; H, 5.12; N, 11.81; S, 7.73; Cl, 4.27(%).

Found: C, 41.91; H, 4.92; N, 12.07; S, 7.78; Cl, 4.08(%).

EXAMPLE 65

Synthesis of Compound (II-23)

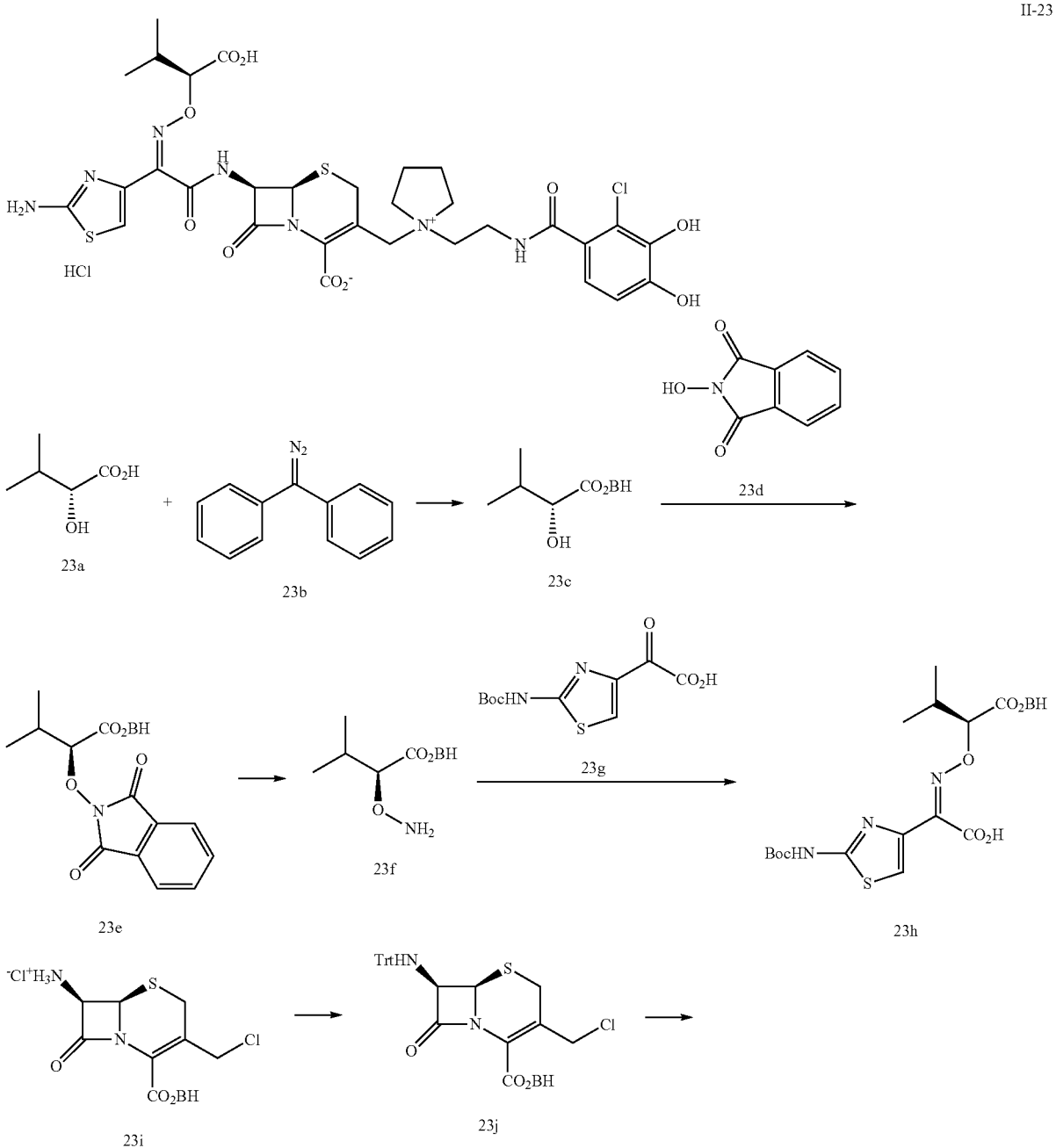

-continued

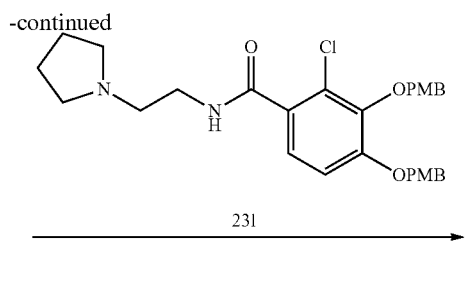

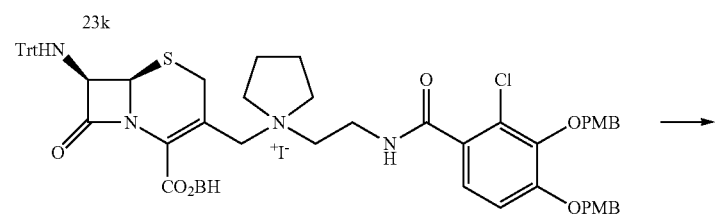

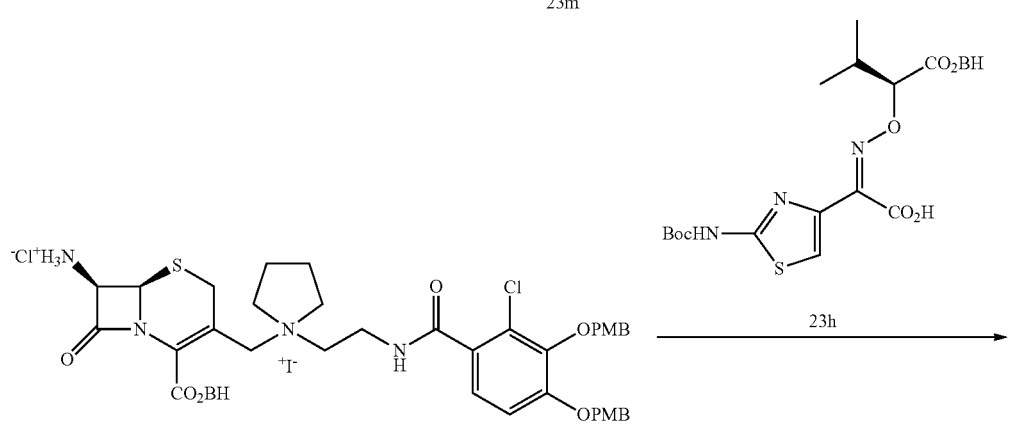

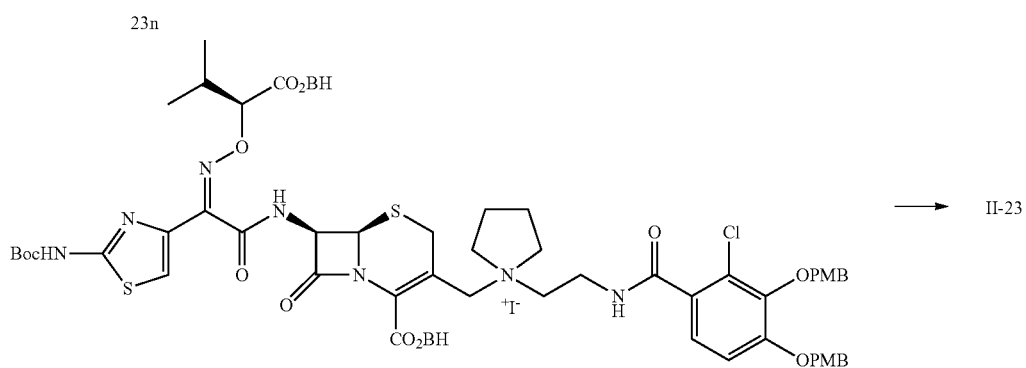

Step (1): Compound 23a+Compound 23b→Compound 23c

Compound 23a (4 g, 33.9 mmol) was dissolved in tetrahydrofuran (50 mL). While stirring, a tetrahydrofuran solution (30 mL) of diphenyldiazomethane 23b (6.91 g, 35.6 mmol) was added drop-wise thereto. After the reaction solution was stirred at room temperature for two hours, the solvent was evaporated under reduced pressure. n-Hexane (100 mL) was then added to the residue. The resulting solid was filtrated, and then washed with n-hexane to yield Compound 23c (8.25 g, 86%) as a solid.

$^1$H-NMR (CDCl$_3$) δ (delta): 7.36-7.29 (10H, m), 6.96 (1H, s), 4.16 (1H, d, J=3.2 Hz), 2.67 (1H, br s), 2.23-2.13 (1H, m), 1.02 (3H, d, J=7.0 Hz), 0.77 (3H, d, J=7.0 Hz).

Step (2): Compound 23c+Compound 23d→Compound 23e

Compound 23c (8.17 g, 28.7 mmol) was dissolved in tetrahydrofuran (80 mL), and then triphenylphosphine (8.29 g, 31.6 mmol), Compound 23d (5.16 g, 31.6 mmol), and diisopropyl azodicarboxylate (6.15 mL, 31.6 mmol) were added thereto in turn. After stirring at room temperature for three hours, triphenylphosphine (1.51 g, 5.74 mmol), Compound 23d (0.93 g, 5.74 mmol), and diisopropyl azodicarboxylate (1.1 mL, 5.74 mmol) were added thereto in turn, followed by further stirring for 45 minutes. The solvent was evaporated under reduced pressure, and then methanol (120 mL) was added. The resulting solid was filtrated, and then washed with methanol to yield Compound 23e (7.46 g, 60%) as a solid.

$^1$H-NMR (CDCl$_3$) δ (delta): 7.79-7.72 (4H, m), 7.38-7.20 (10H, m), 6.98 (1H, s), 4.65 (1H, d, J=7.14 Hz), 2.45-2.34 (1H, m), 1.18 (3H, d, J=6.73 Hz), 1.00 (3H, d, J=6.73 Hz).

Step (3): Compound 23e→Compound 23f→Compound 23h

Compound 23e (3.01 g, 7 mmol) was dissolved in methylene chloride (30 mL), and then methylhydrazine (0.39 mL, 7.35 mmol) was added thereto under ice-cooling, subsequently stirring at the same temperature for one hour. The resulting solid was then removed by filtration. Methanol (15 mL) was added to the filtrate, and then Compound 23g (2.00 g, 7.35 mmol) was added thereto under ice-cooling, subsequently stirring at the same temperature for three hours. The solvent was then evaporated under reduced pressure. Ethyl acetate and water were added thereto, and then the organic layer was separated. The organic layer was washed with saturated brine, and then dried over anhydrous magnesium sulfate. Magnesium sulfate was filtrated, and then the solvent was evaporated under reduced pressure. After evaporation, ethyl acetate was added to the resulting solid to yield Compound 23h (1.66 g, 44%) as a solid.

$^1$H-NMR (CDCl$_3$) δ (delta): 7.38-7.26 (10H, m), 6.94 (1H, s), 4.96 (1H, d, J=3.7 Hz), 2.41-2.30 (1H, m), 1.07 (3H, d, J=7.0 Hz), 0.85 (3H, d, J=7.0 Hz).

MS: 552.22 (M–H).

Step (4): Compound 23i→Compound 23j

Compound 23i (45.1 g, 100 mmol) was suspended in methylene chloride (750 mL), and then 2,6-lutidine (24.5 mL, 210 mmol) and trityl chloride (30.7 g, 110 mmol) were added under ice-cooling in turn, subsequently stirring at room temperature for 3 hours. 2,6-Lutidine (5.8 mL, 50 mmol) was added to the reaction solution, followed by stirring 165 minutes, and then trityl chloride (8.37 g, 30 mmol) was added thereto, subsequently stirring for 30 minutes. 2,6-Lutidine (5.8 mL, 50 mmol) was further added to the reaction solution, and then left standing at room temperature overnight. An aqueous 1 N hydrochloric acid solution was added to the reaction solution, and then the organic layer was separated. The organic layer was washed with water, washed with saturated brine, and then dried over anhydrous magnesium sulfate. Magnesium sulfate was removed by filtration, and then evaporation yielded Compound 23j (84.7 g).

$^1$H-NMR (CDCl$_3$) δ (delta): 7.51-7.24 (25H, m), 6.98 (1H, s), 4.80 (1H, dd, J=9.8, 4.8 Hz), 4.28-4.43 (3H, m), 3.49 (1H, d, J=18.1 Hz), 3.35 (1H, d, J=18.1 Hz), 3.00 (1H, d, J=9.9 Hz).

Step (5): Compound 23j→Compound 23k

The crude Compound 23j (84.7 g) obtained as described above was dissolved in methylene chloride, and then a solution of m-chloroperbenzoic acid (75%, 23g, 100 mmol) in methylene chloride (200 mL) was added thereto under ice-cooling, subsequently stirring at the same temperature for 30 minutes. m-Chloroperbenzoic acid (75%, 6.90 g, 30 mmol) was further added, followed by stirring for 30 minutes under ice-cooling. An aqueous sodium hydrogen carbonate solution was added to the reaction solution, and then the organic layer was separated. The organic layer was washed with aqueous 5% sodium sulfite solution, washed with water, washed with saturated brine, and then dried over anhydrous magnesium sulfate. Magnesium sulfate was removed by filtration, and then the solvent was evaporated under reduced pressure. The resulting residue was dissolved in a small amount of methylene chloride, and then diisopropyl ether was added. After the resulting solid was filtrated, the filtrated residue was washed with diisopropyl ether, and then dried in vacuo to yield Compound 23k (59.8 g, 89%) as a solid.

$^1$H-NMR (CDCl$_3$) δ (delta): 7.57-7.28 (25H, m), 6.92 (1H, s), 4.89-4.84 (2H, m), 4.04 (1H, d, J=12.2 Hz), 3.46-3.56 (3H, m), 3.05 (1H, d, J=18.5 Hz).

Step (6): Compound 23k+Compound 23l→Compound 23m

Compound 23k (13.5 g, 20 mmol) and Compound 23l (10.5 g, 20 mmol) was dissolved in dimethylacetamide (60 mL), and then was degassed in a water bath. While the reaction solution was stirred, potassium iodide (8.99 g, 60 mml) was added thereto, followed by stirring at room temperature for 90 minutes. Dimethylformamide (100 mL) was added to the reaction solution under ice-cooling, followed by degassing, and then potassium iodide (26.6 g, 160 mmol) and acetyl chloride (8.56 mL, 120 mL) were added thereto in turn, subsequently stirring at the same temperature for one hour. The reaction solution was then poured into a solution of sodium hydrogen sulfite (68 g) dissolved in brine (1200 mL). The resulting solid was filtrated, and then washed with water. The filtrated residue was dissolved in methylene chloride, washed with water, and then washed with saturated brine. The organic layer was then dried over anhydrous magnesium sulfate. Magnesium sulfate was removed by filtration, and then the solvent was evaporated under reduced pressure to yield Compound 23m (27.3 g).

Step (7): Compound 23m→Compound 23n

The crude Compound 23m (27.3 g) obtained as described above was dissolved in acetone (130 mL), and then aqueous 6 N hydrochloric acid solution (4.93 mL, 29.6 mmol) was added thereto at room temperature for 3.5 hours. Methylene chloride (500 mL) was added to the reaction solution to dilute, and then dried over anhydrous magnesium sulfate. Magnesium sulfate was removed by filtration, and then the solvent was evaporated under reduced pressure to yield 23n (26.6 g).

MS: 903.35 (M+H).

Step (8): Compound 23n+Compound 23h→Compound 23o

Compound 23n (1.18 g, 1.1 mmol), Compound 23h (554 mg, 1 mmol), and hydrochloric acid salt (253 mg, 1.32 mmol) of N-(3-dimethylaminopropyl)-N'-ethylcarbodiimide were dissolved in methylene chloride (15 mL), and then cooled to 0° C. Pyridine (0.12 mL, 1.43 mmol) was added to the reaction solution, followed by stirring for one hour under ice-cooling. Aqueous 2 N hydrochloric acid solution (1 mL), ethyl acetate, and water were added to the reaction solution, and then the organic layer was separated. The organic layer was washed with saturated brine, and then dried over anhydrous magnesium sulfate. Magnesium sulfate was removed by filtration, and then the solvent was evaporated under reduced pressure to yield Compound 23o (1.52 g).

MS: 1438.58 (M+H)

Step (9): Compound 23o→Compound (II-23)

The crude Compound 23o (1.52 g) obtained as described above was dissolved in methylene chloride (8 mL) and anisole (1.1 mL, mmol), and then cooled to −40° C. 2M aluminum chloride/nitromethane solution (5 mL, 10 mmol) was added thereto, followed by stirring at a temperature between −10° C. and −5° C. for one hour. The reaction solution was dissolved into aqueous 1 N hydrochloric acid solution and acetonitrile, and then the aqueous layer was separated. After the aqueous layer was washed with diisopropyl ether, HP-20SS resin was added thereto, and then concentrated in vacuo. The concentrated solution was subjected to ODS column chromatography, eluting with aqueous hydrochloric acid solution-acetonitrile. Fractions containing the desired compound was concentrated in vacuo, and then lyophilized to yield Compound (II-23) (195.9 mg, 26%) as a powder.
MS: 766.07 (M+H).
$^1$H-NMR (DMSO-$d_6$) δ (delta): 9.67 (1H, d, J=8.0 Hz), 8.53 (1H, t, J=5.2 Hz), 6.82 (1H, s), 6.78-6.75 (2H, m), 5.93 (1H, dd, J=8.0, 5.2 Hz), 5.31 (1H, d, J=5.0 Hz), 4.66 (1H, d, J=13.9 Hz), 4.36 (1H, d, J=5.1 Hz), 4.29 (2H, d, J=14.6 Hz), 3.99 (3H, d, J=17.1 Hz), 3.62-3.40 (9H, m), 2.15-1.89 (5H, m), 0.96 (6H, dd, J=5.1, 6.7 Hz).
Elementary analysis for $C_{31}H_{36}ClN_7O_{10}S_2 \cdot 4.2(H_2O) \cdot 1.9$ (HCl)
Calcd.: C, 40.86; H, 5.12; N, 10.76; S, 7.04; Cl, 11.28(%).
Found: C, 40.86; H, 5.03; N, 10.72; S, 6.99; Cl, 11.20(%).
EXAMPLE 66
Synthesis of Compound (II-24)
[Formula 140]
II-24
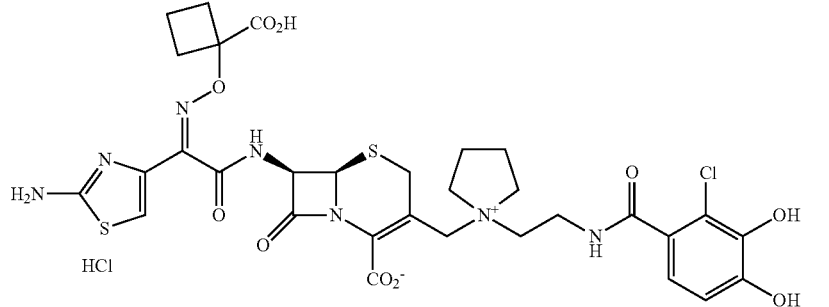
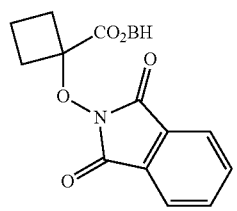
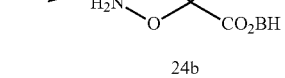
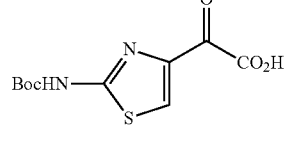
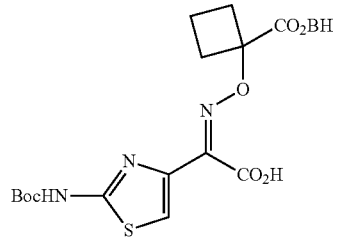
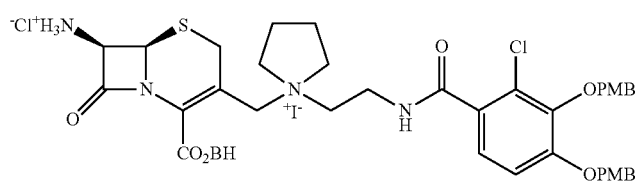
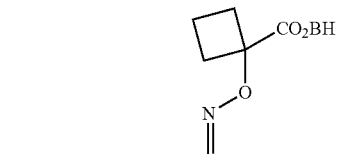

-continued

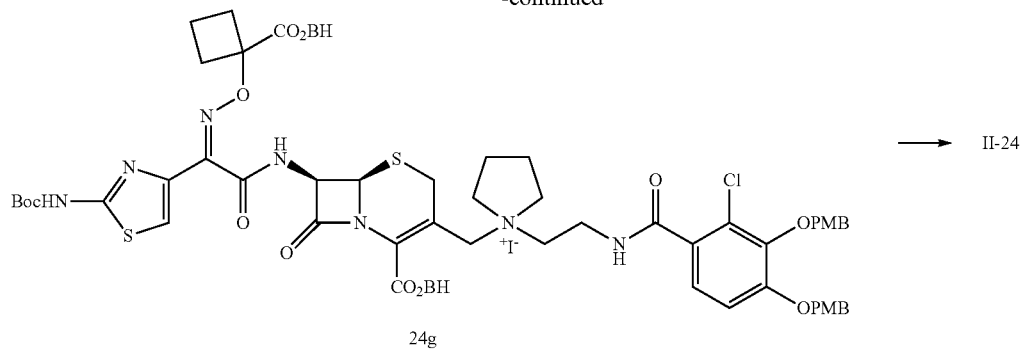

24g

→ II-24

Step (1): Compound 24a→Compound 24b→Compound 24d

Compound 24a (2.99 g, 7 mmol), synthesized similarly by a method described in *Bioorg. Med. Chem.* 2007, 15, 6716, was dissolved in methylene chloride (30 mL). Methylhydrazine (0.37 mL, 7 mmol) was then added thereto under ice-cooling, subsequently stirring at the same temperature for one hour. The solid which appeared during the reaction was then removed by filtration. Methanol (15 mL) was added to the filtrate, and then Compound 24c (1.91 g, 7 mmol) was added thereto under ice-cooling, followed by stirring at the same temperature for one hour. After stirring at room temperature for another three hours, ethyl acetate and aqueous 0.1 N hydrochloric acid solution were added thereto. The organic layer was separated, washed with water, washed with saturated brine, and then dried over anhydrous magnesium sulfate. After magnesium sulfate was removed by filtration, the solvent was concentrated in vacuo, and then diisopropyl ether was added to the residue. The resulting solid was filtrated, and then washed with diisopropyl ether to yield Compound 24d (2.29 g, 59%) as a solid.

MS: 552.05 (M+H).

$^1$H-NMR (CDCl$_3$) δ (delta): 7.37-7.23 (10H, m), 6.92 (1H, s), 2.64-2.51 (4H, m), 2.06-2.03 (2H, m), 1.55 (9H, s).

Step (2): Compound 24e+Compound 24f→Compound 24g→Compound (II-24)

Compound 24e (1.18 g, 1.1 mmol) and Compound 24f (546 mg, 0.99 mmol) were used, and Compound 24g and Compound (II-24) were obtained according to a procedure similar to that described above.

Compound 24g (1.67 g). MS: 1437.59 (M+H).

Compound (II-24) (251.7 mg, 33%)

MS: 764.04 (M+H)

$^1$H-NMR (DMSO-d$_6$) δ (delta): 9.75 (1H, d, J=8.2 Hz), 8.55 (1H, br s), 6.86-6.78 (2H, m), 5.97 (1H, dd, J=8.2, 5.2 Hz), 5.35 (1H, d, J=5.2 Hz), 4.68 (1H, d, J=14.6 Hz), 4.31 (1H, d, J=13.7 Hz), 4.02 (1H, d, J=17.1 Hz), 3.66-3.10 (9H, m), 2.78-2.67 (2H, m), 2.46-1.84 (10H, m).

Elementary analysis for C$_{31}$H$_{34}$ClN$_7$O$_{10}$S$_2$.3.9(H$_2$O).1.7 (HCl)

Calcd.: C, 41.53; H, 4.89; N, 10.94; S, 7.15; Cl, 10.68(%).
Found: C, 41.33; H, 4.85; N, 11.66; S, 6.89; Cl, 10.75(%).

EXAMPLE 67

Synthesis of Compound (II-25)

[Formula 141]

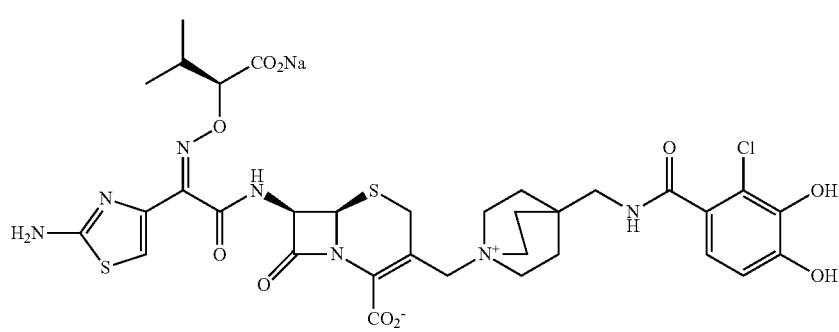

II-25

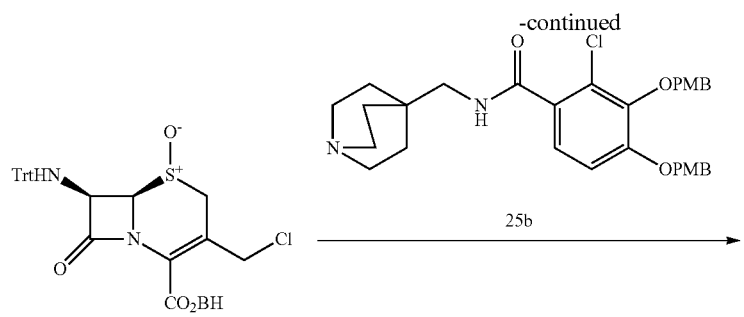

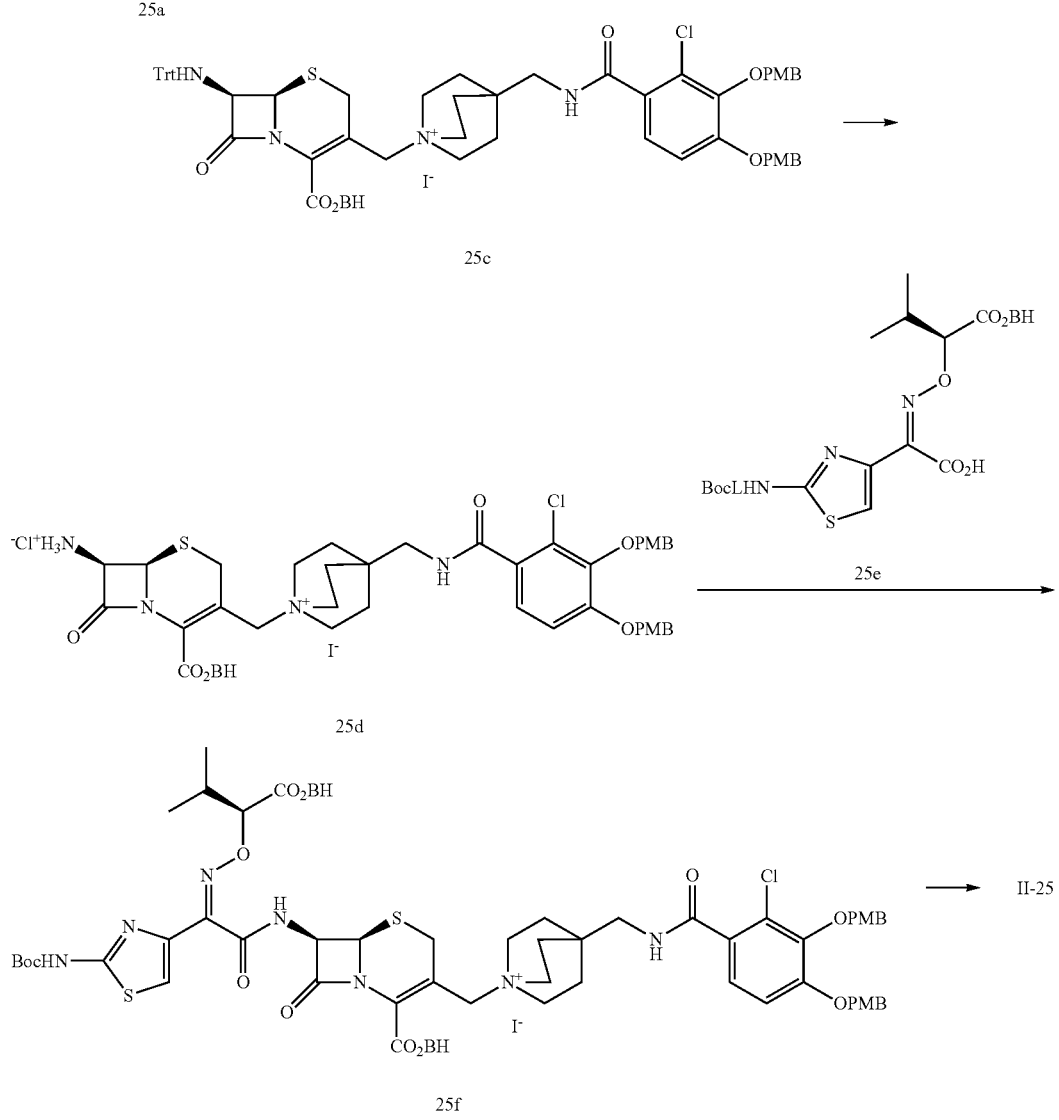

Step (1): Compound 25a+Compound 25b→Compound 25c

Compound 25a (1.91 g, 2.83 mmol) and Compound 25b (1.56 g, 2.83 mmol) were dissolved in dimethylacetamide (9 mL), and then degassed in a water bath. While the reaction solution was stirred, potassium iodide (1.27 g, 8.49 mmol) was added thereto, followed by stirring at room temperature for 40 minutes. Dimethylformamide (15 mL) was added to the reaction solution under ice-cooling, followed by degassing, and then potassium iodide (3.76 g, 22.6 mmol) and acetyl chloride (1.21 mL, 17.0 mmol) were added thereto in turn, subsequently stirring at the same temperature for one hour. The reaction solution was then poured into a solution of sodium hydrogen sulfite (8.5 g) dissolved in brine (150 mL). The resulting solid was filtrated, and then washed with water. The obtained solid was dissolved in methylene chloride, washed with water, and then saturated brine. The organic layer was then dried over anhydrous magnesium sulfate. Magnesium sulfate was removed by filtration, and then the solvent was evaporated under reduced pressure to yield Compound 25c (3.56 g).

MS: 1171.44 (M+H).

Step (2): Compound 25c→Compound 25d

The crude Compound 25c (3.56 g) obtained as described above was dissolved in acetone (20 mL), and then aqueous 6 N hydrochloric acid solution (0.68 mL, 4.06 mmol) was added thereto, subsequently stirring at room temperature for 5 hours. Methylene chloride and methanol were added to the reaction solution to dilute, and then dried over anhydrous magnesium sulfate. Magnesium sulfate was removed by filtration, and then the solvent was evaporated under reduced pressure to yield 25d (3.83 g).

MS: 929.56 (M+H).

Step (3): Compound 25d+Compound 25e→Compound 25f

Compound 25d (1.20 g, 1.1 mmol) and Compound 25e (554 mg, 1 mmol) were used, and Compound 25f (1.34 g) was obtained according to a procedure similar to that described above.

MS: 1464.89 (M+H)

Step (4): Compound 25f→Compound (II-25)

The whole amount of 25f obtained as described above was dissolved in methylene chloride (2 mL) and anisole (0.83 mL, 7.63 mmol), and then ice-cooled. Trifluoroacetic acid (8.5 mL, 110 mmol) was then added thereto, subsequently stirring under ice-cooling for one hour. Trifluoroacetic acid (2 mL) was further added thereto, followed by stirring at room temperature for 30 minutes. After the solvent was evaporated under reduced pressure, diisopropyl ether was added thereto, and then the resulting solid was filtrated. The obtained solid was then dissolved in acetonitrile and aqueous 1 N hydrochloric acid solution. HP-20SS resin was added thereto, and then concentrated in vacuo. The concentrated solution was then subjected to ODS column chromatography, eluting with water-acetonitrile. An aqueous 0.2 N sodium hydroxide solution was then added to fractions containing the desired compound to obtain a sodium salt. The solvent was concentrated in vacuo, and then lyophilized to yield Compound (II-25) (201.2 mg, 29%) as a powder.

MS: 792.21 (M+H)

$^1$H-NMR (D$_2$O) δ (delta): 6.97 (1H, s), 6.90-6.83 (2H, m), 5.85 (1H, d, J=4.8 Hz), 5.34 (1H, d, J=4.8 Hz), 4.58 (1H, d, J=14.5 Hz), 4.34 (1H, d, J=5.2 Hz), 3.89-3.83 (2H, m), 3.50-3.33 (9H, m), 2.15-2.13 (1H, m), 1.98-1.84 (6H, m), 0.99 (6H, t, J=6.9 Hz).

Elementary analysis for $C_{33}H_{37}ClN_7O_{10}S_2Na \cdot 4.8(H_2O) \cdot 0.1(NaHCO_3)$ Calcd.: C, 43.73; H, 5.18; N, 10.78; S, 7.05; Cl, 3.90; Na, 2.78(%).

Found: C, 43.87; H, 5.17; N, 10.72; S, 6.63; Cl, 3.94; Na, 2.88(%).

EXAMPLE 68

Synthesis of Compound (II-26)

[Formula 142]

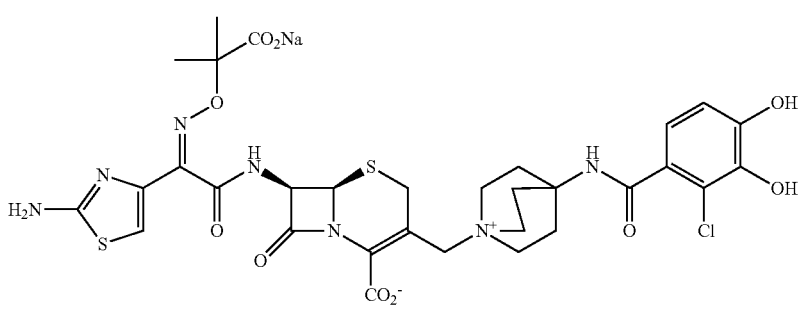

II-26

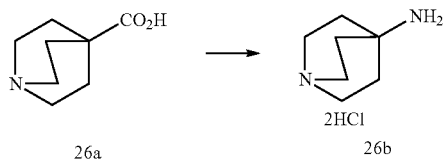

26a → 26b (2HCl)

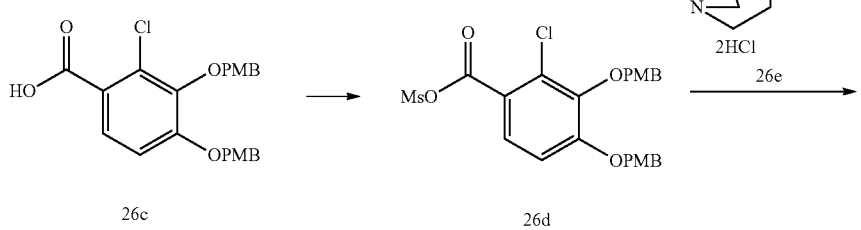

26c → 26d → (26e, 2HCl)

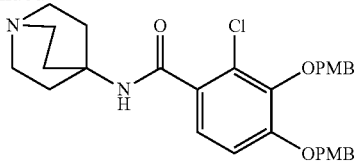

26f

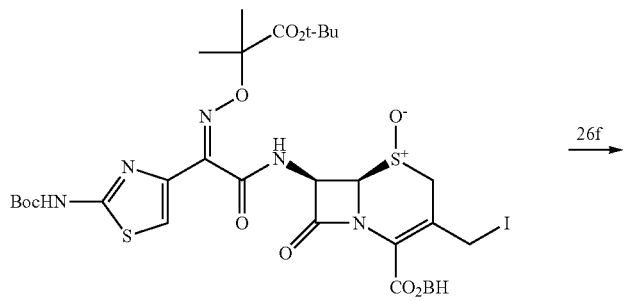

26g

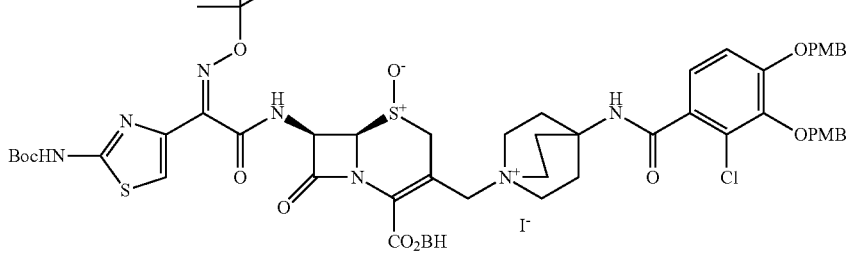

26h

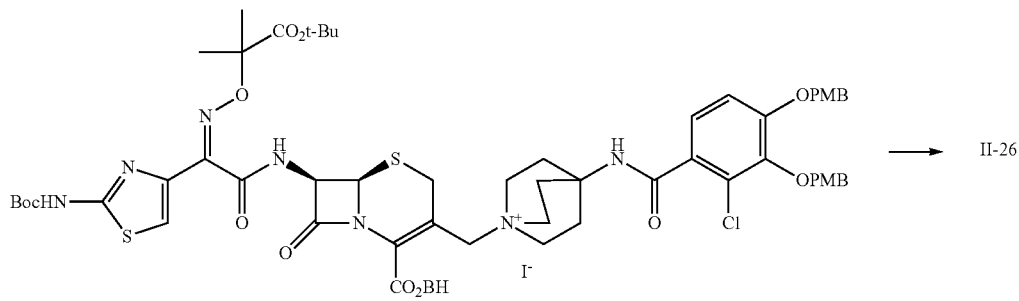

26i

→ II-26

Step (1): Compound 26a→Compound 26b

To Compound 26a (1 g, 6.44 mmol), synthesized similarly by a method described in *Helv. Chim. Acta.* 1954, 37, 1672, was added thionyl chloride (7 mL), subsequently heating at reflux for two hours. After thionyl chloride was evaporated under reduced pressure, xylene was added thereto, and then concentrated in vacuo again. The concentrated solution was cooled to 0° C., and then an aqueous solution (25 mL) of sodium azide (1.67 g, 25.7 mmol) was added thereto with stirring, followed by stirring at the same temperature for 10 minutes. Potassium carbonate was then added to the reaction solution until effervescence ceased. After extraction with toluene, the organic layer was washed with anhydrous magnesium sulfate, and then magnesium sulfate was removed by filtration. The resulting solution was then heated at reflux for 45 minutes. After extraction with aqueous 6 N hydrochloric acid solution, the separated aqueous layer was further heated at reflux for 150 minutes. The reaction solution was cooled to room temperature, and then concentrated in vacuo. After isopropanol was added to the residue, the resulting solid was filtrated, washed with isopropanol, and then dried in vacuo to yield Compound 26b (655.9 mg, 51%).

$^1$H-NMR (D$_2$O) δ (delta): 3.57 (6H, t, J=7.6 Hz), 2.26 (6H, t, J=7.6 Hz).

MS: 127.11 (M+H).

Step (2): Compound 26c→Compound 26d+Compound 26b→Compound 26e

Compound 26c (858 mg, 2 mmol) was dissolved in dimethylacetamide (9 mL), and then cooled to −15° C. Triethylamine (0.33 mL, 2.4 mmol) was added to the solution, and then methanesulfonyl chloride (0.20 mL, 2.6 mmol) was added thereto, followed by stirring for 30 minutes at temperature between −10° C. and −5° C. The reaction solution was cooled to −15° C., and then triethylamine (0.92 mL, 7.2 mmol) and Compound 26b (478 mg, 2.4 mmol) were added thereto in turn, subsequently stirring for 90 minutes under ice-cooling. An aqueous 0.2 N sodium hydroxide solution was added to the reaction solution, followed by extraction with ethyl acetate. The organic layer was washed with water, washed with saturated brine, and then dried over anhydrous magnesium sulfate. Magnesium sulfate was removed by filtration, and then the solvent was concentrated in vacuo. The concentrated solution was subjected to silica gel column chromatography, eluting with chloroform/methanol. Fractions containing the desired compound were concentrated in vacuo to yield Compound 26e (459.5 mg, 43%).

MS: 537.19 (M+H).

$^1$H-NMR (CDCl$_3$) δ (delta): 7.37-7.34 (4H, m), 6.91 (2H, dd, J=8.5, 2.1 Hz), 6.83 (2H, d, J=8.5 Hz), 5.85 (1H, br s), 5.08 (2H, s), 4.94 (2H, s), 3.83 (3H, s), 3.81 (3H, s), 3.01 (6H, t, J=7.6 Hz), 1.98 (6H, t, J=7.6 Hz).

Step (3): Compound 26f+Compound 26e→Compound 26g

Compound 26f (450 mg, 0.84 mmol) was dissolved in dimethylformamide (3 mL), and then degassed. Compound 26e (783 mg, 0.84 mmol) was then added thereto, followed by stirring at room temperature for 40 minutes. After the reaction solution was diluted with ethyl acetate, aqueous 10% sodium hydrogen sulfite solution was added, and then the organic layer was separated. The organic layer was washed with water, and then washed with saturated brine. The organic layer was dried over magnesium sulfate, and then magnesium sulfate was filtrated. The solvent was evaporated under reduced pressure to yield Compound 26g (1.04 g).

MS: 1343.92 (M+H).

Step (4): Compound 26g→Compound 26h

The whole amount (1.04 g) of the crude Compound 26g obtained as described above was dissolved in dimethylformamide (6 mL), and then cooled to −40° C. Phosphorus tribromide (0.10 mL, 1.06 mmol) was added to the reaction solution, followed by stirring at the same temperature for 40 minutes. Ethyl acetate was added to the reaction solution to dilute, and then the organic layer was separated. The organic layer was washed with water, and then washed with saturated brine. After the organic layer was dried over anhydrous magnesium sulfate, magnesium sulfate was filtrated, and then the solvent was evaporated under reduced pressure to yield Compound 26h (931 mg).

MS: 1327.87 (M+H)

Step (4): Compound 26h→Compound (II-26)

The whole amount (931 mg) of the crude Compound 26h obtained as described above was used, and treated according to a procedure similar to that described above, and thus Compound (II-26) (292.7 mg, 59%) was obtained as a powder.

MS: 764.28 (M+H).

$^1$H-NMR (D$_2$O) δ (delta): 6.99 (1.0H, s), 6.89 (2H, dd, J=8.1, 14.5 Hz), 5.89 (1H, d, J=5.0 Hz), 5.37 (1H, d, J=5.0 Hz), 4.63 (1H, d, J=13.1 Hz), 3.92 (2H, dd, J=15.0, 10.4 Hz), 3.49-3.79 (6H, m), 3.43 (1H, d, J=17.5 Hz), 2.34-2.56 (6H, m), 1.52 (6H, d, J=4.6 Hz).

Elementary analysis for C$_{31}$H$_{33}$ClN$_7$O$_{10}$S$_2$Na.6.6(H$_2$O).0.2(NaHCO$_3$)

Calcd.: C, 40.65; H, 5.07; N, 10.64; S, 6.96; Cl, 3.85; Na, 2.99(%).

Found: C, 40.54; H, 4.85; N, 10.81; S, 7.26; Cl, 3.79; Na, 3.05(%).

EXAMPLE 69

Synthesis of Compound (II-27)

[Formula 143]

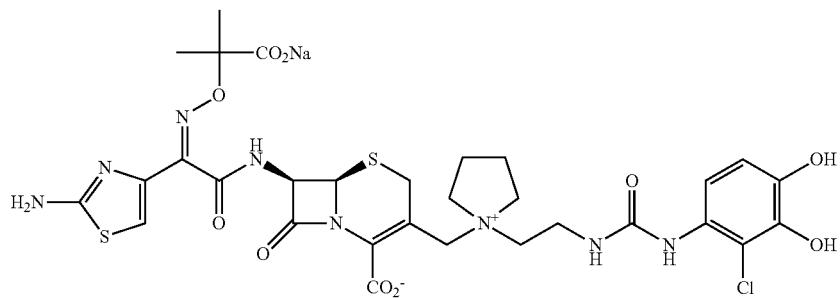

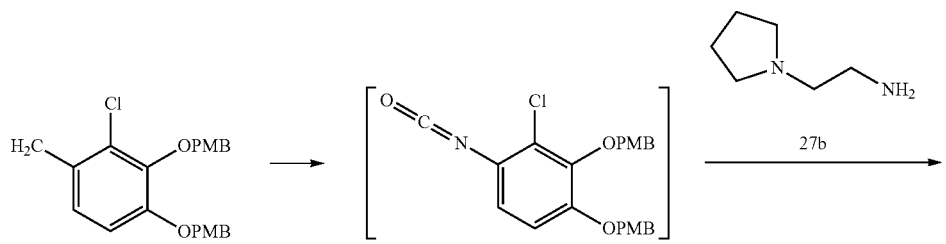

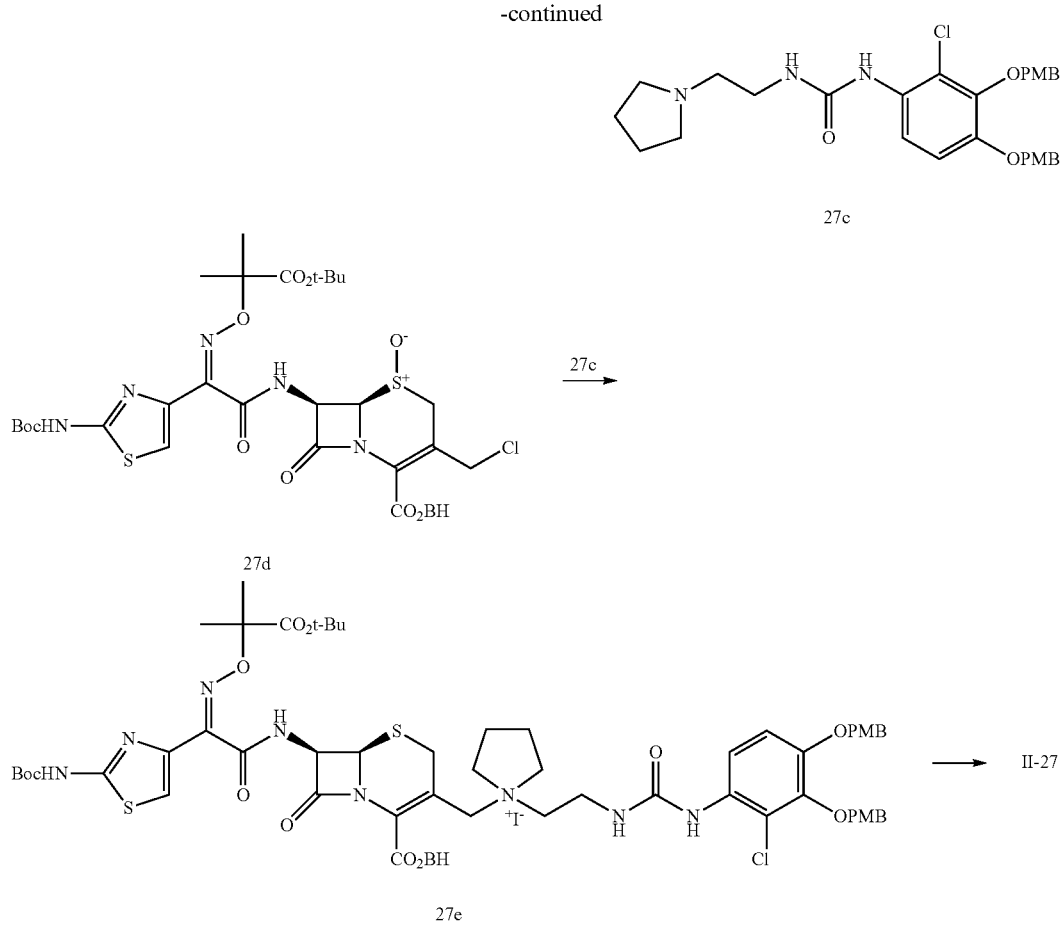

Step (1): Compound 27a+Compound 27b→Compound 27c

Compound 27a (2.14 g, 5 mmol) was suspended in toluene (25 mL), and then triethylamine (0.83 mL, 6 mmol) and diphenylphosphoryl azide (1.29 mL, 6 mmol) were added thereto in turn, followed by heating at reflux for one hour. Compound 27b (0.86 g, 7.5 mmol) was then added, subsequently heating at reflux for another two hours. The reaction solution was cooled to room temperature, and then the solvent was evaporated under reduced pressure. Water was added to the residue, followed by extraction with ethyl acetate and tetrahydrofuran, and then the organic layer was concentrated in vacuo. Isopropanol was added to the resulting residue, and then the resulting solid was filtrated to yield 27c (1.84 g, 68%).

$^1$H-NMR (DMSO-$d_6$) δ (delta): 8.65 (1H, br s), 7.91 (1H, br s), 7.67 (1H, dd, J=14.9, 9.6 Hz), 7.39 (2H, d, J=7.3 Hz), 7.29 (2H, d, J=7.6 Hz), 7.09 (1H, dd, J=18.4, 8.9 Hz), 6.95 (2H, d, J=7.6 Hz), 6.86 (2H, d, J=7.8 Hz), 5.06 (2H, s), 4.89 (2H, s), 3.76 (3H, s), 3.74 (3H, s), 3.29-3.10 (2H, m), 2.48-2.42 (6H, m), 1.70-1.67 (4H, m).

MS: 540.36 (M+H).

Step (2): Compound 27d+Compound 27c→Compound 27e

Compound 27d (1011 mg, 1.2 mmol) was dissolved in dimethylacetamide (5 mL), and then degassed in a water bath. Potassium iodide (540 mg, 3.6 mmol) was then added thereto, followed by stirring at room temperature for 20 minutes. Compound 27c (648 mg, 1.2 mmol) was added to the reaction solution, subsequently stirring at room temperature for one hour. Ethyl acetate and water were added to the reaction solution, and insolubles were removed by filtration. The organic layer separated from the filtrate was washed with aqueous 10% sodium hydrogen sulfite solution, washed with water, washed with saturated brine, and then dried over anhydrous magnesium sulfate. Magnesium sulfate was removed by filtration, and then the solvent was concentrated in vacuo. The concentrated residue was dissolved in dimethylformamide (12 mL), and then cooled to –40° C. Phosphorus tribromide (0.17 mL, 1.84 mmol) was added thereto, followed by stirring at the same temperature for 90 minutes. Ethyl acetate was added to the reaction solution to dilute, and then water was added thereto. The organic layer was separated, and then dried over anhydrous magnesium sulfate. Magnesium sulfate was filtrated, and then the solvent was evaporated under reduced pressure to yield Compound 27e (1.05 g).

MS: 1330.11 (M+H)

Step (3): Compound 27e→Compound (II-27)

The whole amount (1.05 g) of the crude Compound 27e obtained as described above was used, and treated according to a procedure similar to that described above, and thus Compound (II-27) (90.7 mg, 16%) was obtained as a powder.

MS: 767.37 (M+H).

$^1$H-NMR (D$_2$O) δ (delta): 6.99 (1H, s), 6.88 (2H, s), 5.87 (1H, d, J=4.9 Hz), 5.35 (1H, d, J=4.9 Hz), 4.78 (1H, d, J=14.0 Hz), 4.08 (1H, d, J=14.0 Hz), 3.91 (1H, d, J=16.9 Hz), 3.76-3.33 (9H, m), 2.25-2.15 (4H, m), 1.50 (6H, d, J=4.1 Hz).

Elementary analysis for $C_{30}H_{34}ClN_8O_{10}S_2Na \cdot 5.7(H_2O)$

Calcd.: C, 40.40; H, 5.13; N, 12.56; S, 7.19; Cl, 3.98; Na, 2.58(%).

Found: C, 40.37; H, 5.00; N, 12.48; S, 7.48; Cl, 3.83; Na, 2.36(%).

EXAMPLE 70
Synthesis of Compound (II-28)
[Formula 144]
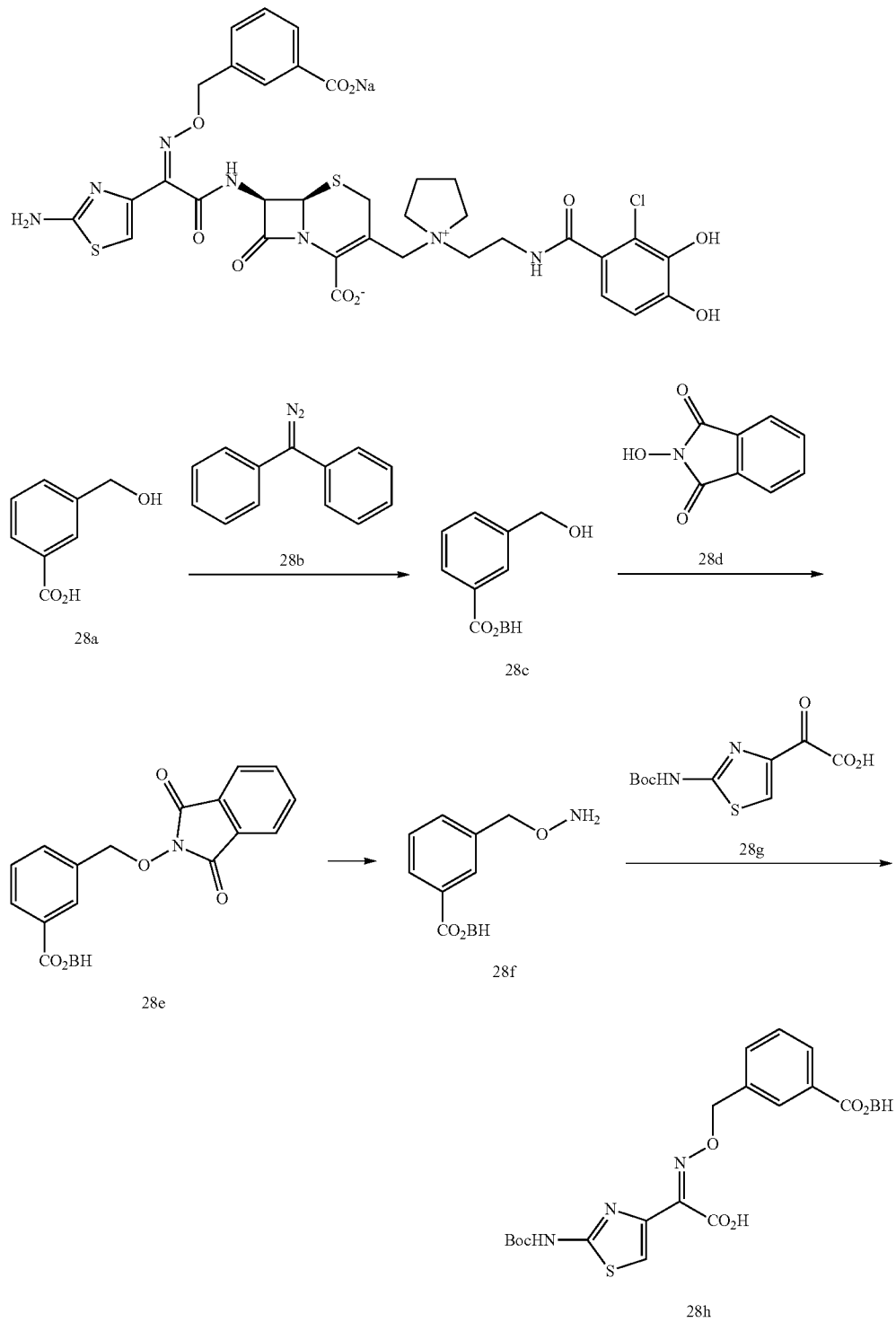

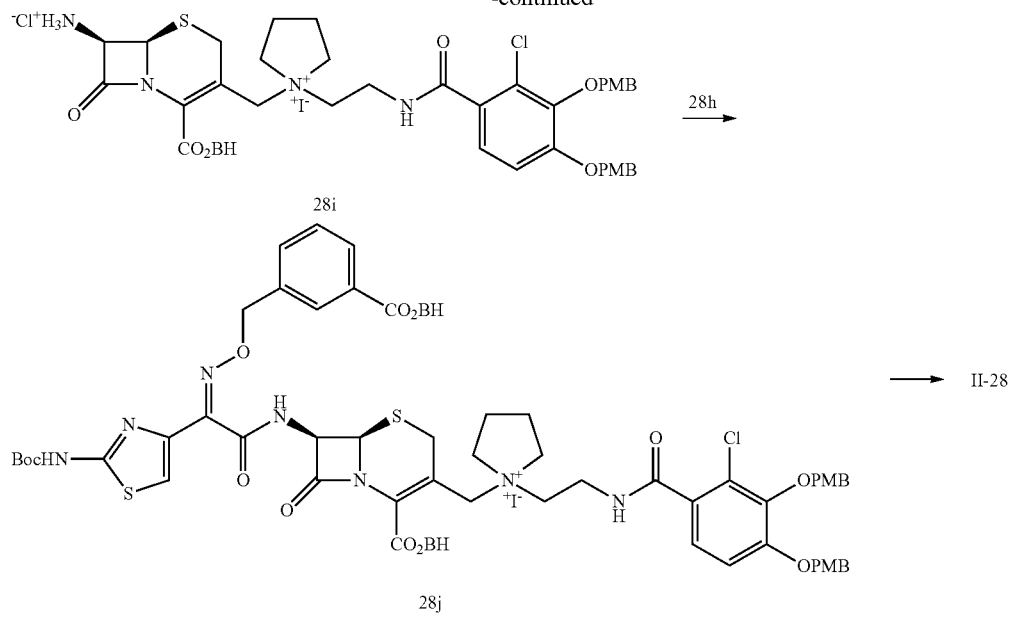

Step (1): Compound 28a+Compound 28b→Compound 28c

Compound 28a (4.29 g, 28.2 mmol), synthesized similarly by a method described in *J. Org. Chem.* 1993, 58, 6372, was dissolved in tetrahydrofuran (40 mL), and then diphenyldiazomethane 28b (8.21 g, 42.3 mmol) was added, followed by heating at reflux for 20 hours. The solvent was evaporated under reduced pressure, and then subjected to silica gel column chromatography, eluting with ethyl acetate-hexane. Fractions containing the desired compound were concentrated in vacuo to yield Compound 28c (7.95 g, 89%).

$^1$H-NMR (CDCl$_3$) δ (delta): 8.11 (1H, s), 8.07 (1H, d, J=7.7 Hz), 7.59 (1H, d, J=7.7 Hz), 7.48-7.26 (9H, m), 7.12 (1H, s), 4.76 (2H, d, J=5.7 Hz), 1.78 (1H, t, J=5.7 Hz).

Step (2): Compound 28c+Compound 28d→Compound 28e

To Compound 28c (7.95 g, 25.0 mmol) was added tetrahydrofuran (140 mL), and then N-hydroxyphthalimide 28d (4.89 g, 30 mmol) and triphenylphosphine (7.86 g, 30 mmol) were added thereto in turn, subsequently cooling to 0° C. Diisopropyl azodicarboxylate (7.28 mL, 37.5 mmol) was then added to the reaction solution, followed by stirring at room temperature for two hours. The solvent was evaporated under reduced pressure. After methanol was added to the resulting residue under ice-cooling, the resulting solid was filtrated, and then dried in vacuo to yield Compound 28e (7.84 g, 68%).

$^1$H-NMR (CDCl$_3$) δ (delta): 8.24 (1H, s), 8.15 (1H, d, J=7.9 Hz), 7.85-7.78 (3H, m), 7.75-7.68 (2H, m), 7.51 (1H, t, J=7.7 Hz), 7.43 (4H, dd, J=7.9, 1.4 Hz), 7.38-7.26 (6H, m), 7.10 (1H, s), 5.27 (2H, s).

Step (3): Compound 28e→Compound 28f→Compound 28h

To Compound 28e (5.56 g, 12 mmol) was added methylene chloride (25 mL), and then methylhydrazine (0.64 mL, 12 mmol) was added thereto under ice-cooling, followed by stirring at the same temperature for one hour. The solvent was evaporated under reduced pressure, and then methanol (45 mL) was added. Under ice-cooling, Compound 28g (3.27 g, 12 mmol) was then added, subsequently stirring for three hours. The solvent was evaporated under reduced pressure, and then ethyl acetate, tetrahydrofuran, and saturated brine were added thereto. The organic layer was separated, and then the solvent was evaporated under reduced pressure to yield Compound 28h (7.49 g, 97%).

$^1$H-NMR (CDCl$_3$) δ (delta): 8.11 (1H, s), 8.04 (1H, d, J=8.1 Hz), 7.56 (1H, d, J=7.6 Hz), 7.46-7.24 (12H, m), 7.12 (1H, s), 5.26 (2H, s).

Step (4): Compound 28i+Compound 28h→Compound 28j

Compound 28i (1.60 g, 1.5 mmol) and Compound 28h (793 mg, 1.35 mmol) were used, and Compound 28j (1.68 g) was obtained according to a procedure similar to that described above.

MS: 1472.84 (M+H).

Step (5): Compound 28j→Compound (II-28)

The whole amount of the crude Compound 28j obtained as described above was dissolved in methylene chloride (3 mL) and anisole (1.07 mL, 9.78 mmol), and then cooled to 0° C. Trifluoroacetic acid (12 mL, 110 mmol) was then added to the reaction solution, followed by stirring for 30 minutes under ice-cooling. Trifluoroacetic acid (4 mL) was further added to the reaction solution, subsequently stirring at room temperature for 90 minutes. After the solvent was evaporated under reduced pressure, diisopropyl ether was added, and then the resulting solid was filtrated. The solid was dissolved in acetonitrile and aqueous 1 N hydrochloric acid solution, and then HP-20SS resin was added. The solvent was concentrated in vacuo, subjected to ODS column chromatography, eluting with water-acetonitrile. An aqueous 0.2 N sodium hydroxide solution was used for fractions containing the desired compound to obtain a sodium salt. The fractions were concentrated in vacuo, and then lyophilized to yield Compound (II-28) (204.6 mg, 23%) as a powder.

MS: 800.24 (M+H)

$^1$H-NMR (D$_2$O) δ (delta): 7.90 (1H, s), 7.79 (1H, d, J=7.63 Hz), 7.55 (1H, d, J=7.17 Hz), 7.41 (1H, t, J=7.93 Hz), 6.97-6.92 (2H, m), 6.82 (1H, d, J=8.08 Hz), 5.75 (1H, d, J=4.88 Hz), 5.26 (2H, s), 5.21, 4.73 (1H, d, J=4.88 Hz) (1H, d, J=4.88 Hz), 4.10 (1H, d, J=14.64 Hz), 3.93-3.47 (9H, m), 3.27 (1H, d, J=16.62 Hz), 2.12-2.26 (4H, m).

Elementary analysis for C$_{34}$H$_{33}$ClN$_7$O$_{10}$S$_2$Na.5.2(H$_2$O) .0.1(NaHCO$_3$)

Calcd.: C, 44.31; H, 4.74; N, 10.61; S, 6.94; Cl, 3.84; Na, 2.74(%).
Found: C, 44.16; H, 4.62; N, 10.77; S, 7.12; Cl, 4.07; Na, 2.86(%).
EXAMPLE 71
Synthesis of Compound (II-29)
[Formula 145]
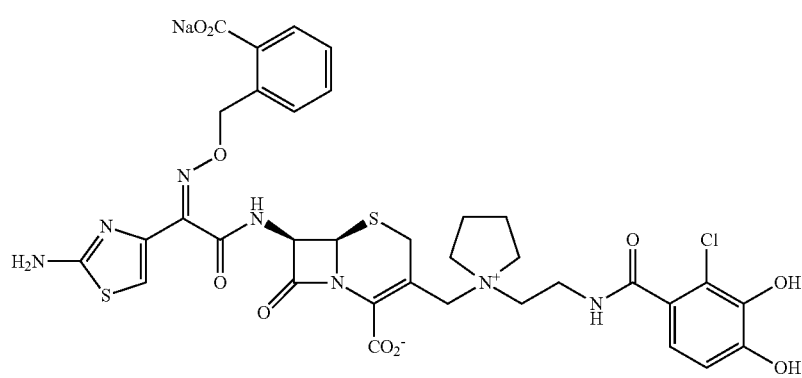
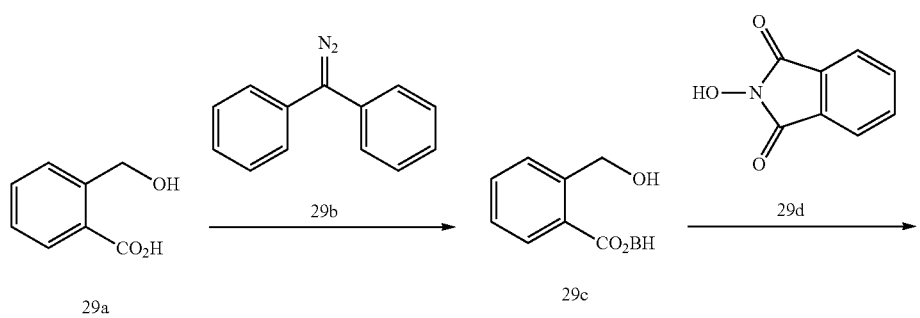
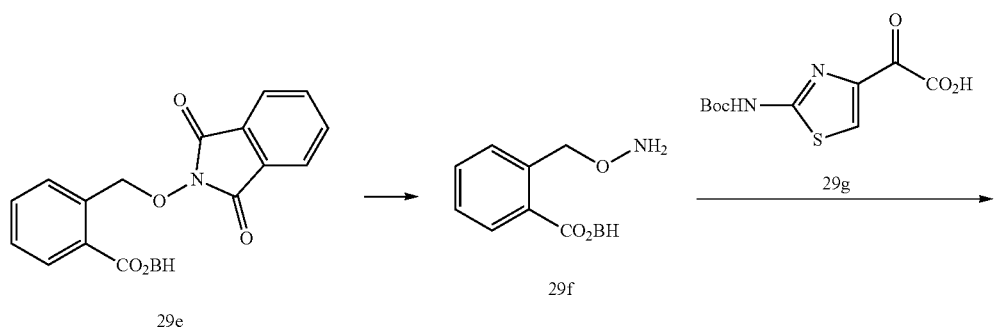
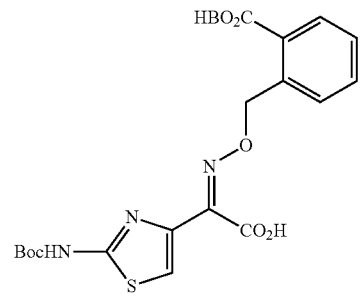

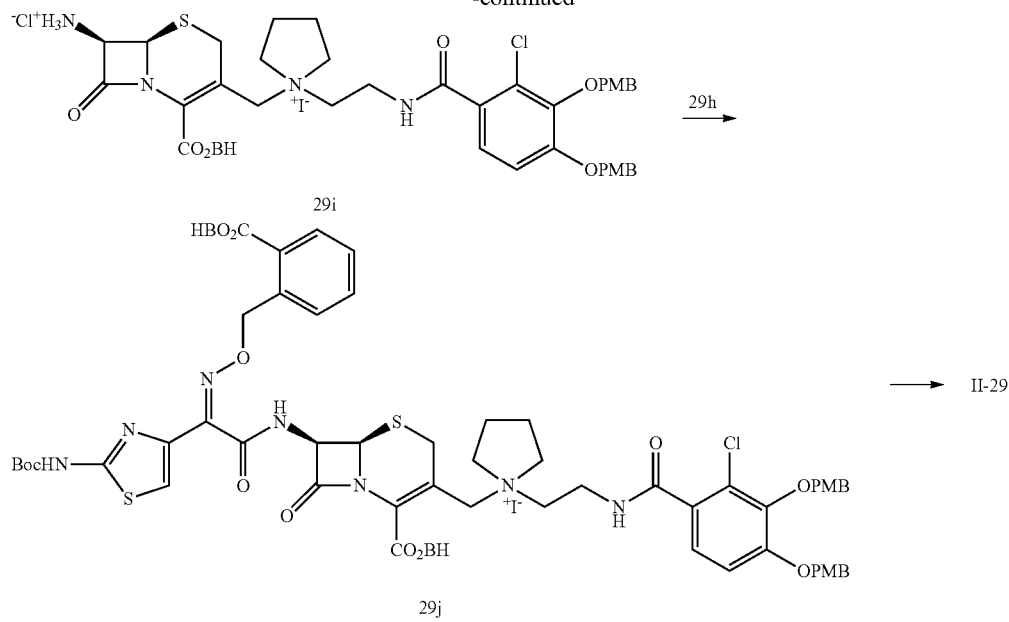

Step (1): Compound 29a→Compound 29h

Compound 29a, synthesized similarly by a method described in *J. Am. Chem. Soc.* 2001, 123, 1856, was used, and Compound 29h was obtained according to a procedure similar to that described above.

Compound 29c (7.75 g, 107%)

$^1$H-NMR (CDCl$_3$) δ (delta): 8.18 (1H, dd, J=8.5, 1.1 Hz), 7.55 (1H, td, J=7.5, 1.2 Hz), 7.47-7.25 (12H, m), 7.11 (1H, s), 4.76 (2H, d, J=7.4 Hz), 3.72 (1H, t, J=7.4 Hz).

Compound 29e (10.2 g, 90%)

$^1$H-NMR (CDCl$_3$) δ (delta): 8.16 (1H, d, J=7.6 Hz), 7.86-7.70 (5H, m), 7.59 (1H, t, J=7.5 Hz), 7.46-7.24 (11H, m), 7.05 (1H, s), 5.66 (2H, s).

Compound 29h (4.03 g, 69%)

$^1$H-NMR (CDCl$_3$) δ (delta): 8.08 (1H, d, J=7.5 Hz), 7.59 (1H, d, J=7.6 Hz), 7.52-7.24 (13H, m), 7.06 (1H, s), 5.66 (2H, s).

MS: 588.20 (M+H).

Step (2): Compound 29i+Compound 29h→Compound 29j→Compound (II-29)

Compound 29i (793 mg, 1.35 mmol) and Compound 29h (793 mg, 1.35 mmol) were used, and Compound (II-29) was obtained according to a procedure similar to that described above.

Compound 29j (1.78 g)

MS: 1473.89 (M+H).

Compound (II-29) (157.3 mg, 17%)

MS: 800.23 (M+H)

$^1$H-NMR (D$_2$O) δ (delta): 7.52-7.44 (2H, m), 7.40-7.30 (2H, m), 6.95 (1H, s), 6.90 (1H, d, J=8.24 Hz), 6.82 (1H, d, J=8.24 Hz), 5.80 (1H, d, J=4.73 Hz), 5.44 (2H, s), 5.28 (1H, d, J=5.03 Hz), 4.83 (1H, d, J=14.18 Hz), 4.10 (1H, d, J=14.18 Hz), 3.92-3.36 (10H, m), 2.21-2.18 (4H, m).

Elementary analysis for C$_{34}$H$_{33}$ClN$_7$O$_{10}$S$_2$Na.4.6(H$_2$O).0.2(NaHCO$_3$)

Calcd.: C, 44.56; H, 4.64; N, 10.64; S, 6.96; Cl, 3.85; Na, 2.99(%).

Found: C, 44.51; H, 4.60; N, 10.71; S, 6.85; Cl, 3.74; Na, 2.98(%).

EXAMPLE 73

Synthesis of Compound (II-31)

[Formula 146]

II-31

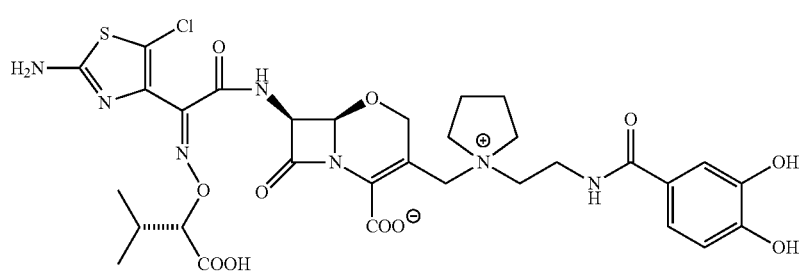

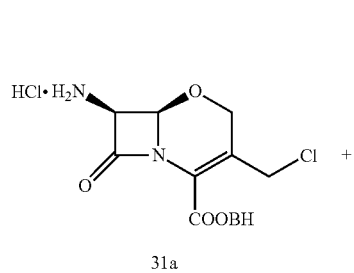

31a

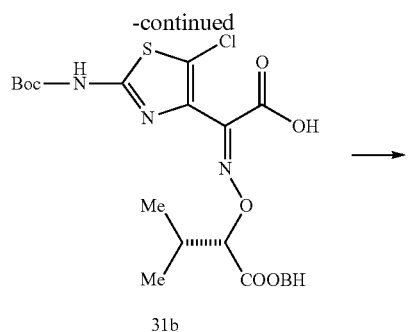

31b

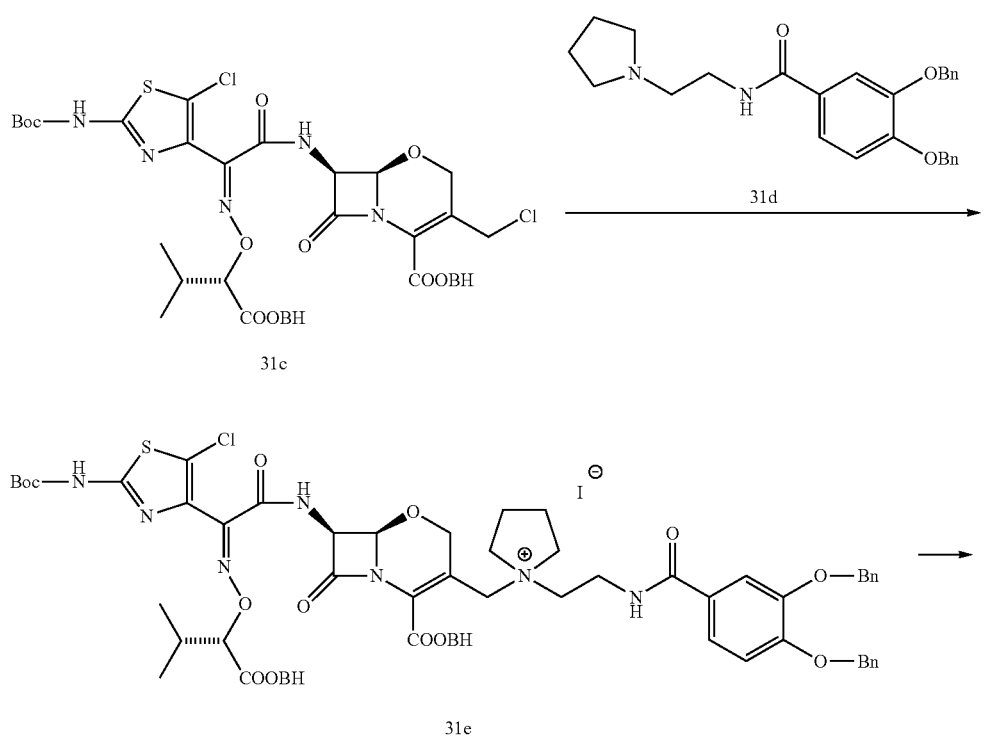

Step (1): Compound 31a+Compound 31b→Compound 31c

Compound 31a (2.18 g, 5 mmol) and Compound 31b (2.94 g, 5 mmol) was suspended in methylene chloride (20 mL). Pyridine (0.48 mL) and hydrochloric acid salt (1.05 g) of N-(3-dimethylaminopropyl)-N'-ethylcarbodiimide were then added thereto under ice-cooling, followed by stirring for 30 minutes. The reaction solution was diluted with ethyl acetate and water, and then the organic layer was separated. The organic layer was washed with water, dried over anhydrous magnesium sulfate, and then concentrated in vacuo. The residue was purified by silica gel column chromatography to yield Compound 31c (3.82 g).

$^1$H-NMR (CDCl$_3$) δ (delta): 0.93 (3H, d, J=3.9 Hz), 0.95 (3H, d, J=4.8 Hz), 1.47 (9H, s), 2.15-2.20 (1H, m), 4.40-4.66 (5H, m), 5.33 (1H, d, J=3.0 Hz), 5.82 (1H, dd, J=3.0, 7.0 Hz), 6.89 (1H, s), 6.94 (11H, s), 7.12-7.63 (21H, m), 9.39 (1H, d, J=6 Hz).

Step (2): Compound 31c+Compound 31d→Compound 31e→Compound (II-31)

Compound 31c was dissolved in DMF (5-fold volume), and then potassium iodide (1.5 equivalents) and Compound 31d (equivalent mole) were added thereto, followed by stirring at room temperature for 2 hours. The solution was slowly added to stirred 5% brine (50-fold volume), and then the precipitated deposits were filtrated. The filtrated solid was washed with water, suspended in water, and then lyophilized to yield the crude product 31e (100%). The crude product 31e was dissolved in methylene chloride (20-fold volume) and nitromethane (10-fold volume). Anisole (10 equivalents) followed by 2M aluminum chloride/nitromethane solution (10 equivalents) were then added at room temperature, subsequently stirring for 1 hour. After reacting, the reaction solution was poured into cold 1N hydrochloric acid/acetonitrile/diisopropyl ether (3/1/5). The aqueous layer was separated, and then subjected to HP-20 column chromatography to purify it. After eluting with acetonitrile/water, eluates were concentrated in vacuo, and then lyophilized to yield Compound (II-31).

LC/MS (ES+): 750 (M+H$^+$)

IR (KBr) cm$^{-1}$: 3309, 1784, 1667, 1608, 1532

Elementary analysis for $C_{31}H_{36}ClN_7O_{11}S \cdot 3.6H_2O$

Calcd.: C, 45.68; H, 5.34; N, 12.03; Cl, 4.35; S, 3.93(%).

Found: C, 45.56; H, 5.02; N, 12.25; Cl, 4.56; S, 4.06(%).

EXAMPLE 74

Synthesis of Compound (II-32)

[Formula 147]

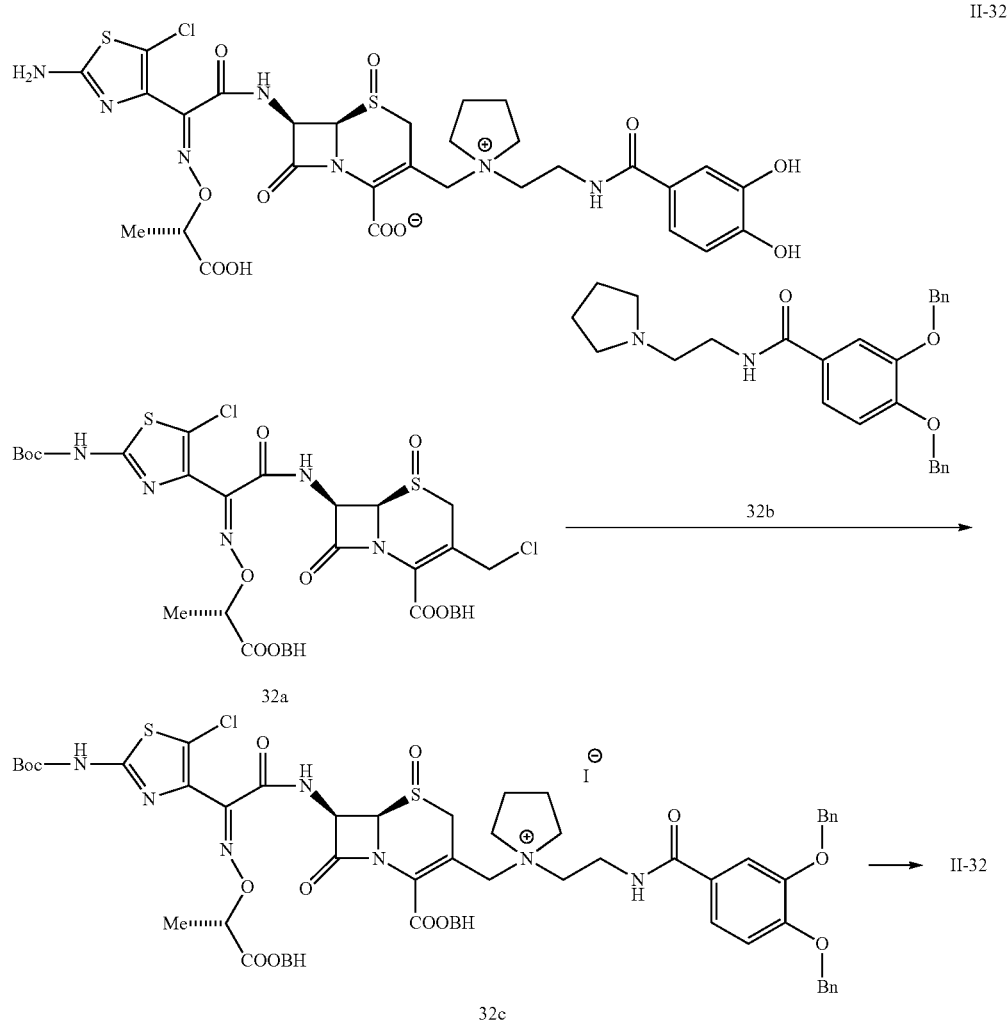

Step (1): Compound 32a+Compound 32b→Compound 32c→Compound (II-32)

Compound 32a (a mixture of α(alpha), β(beta)-sulfoxide=7:2) (0.68 g, 0.7 mmol) and Compound 32b were dissolved in dimethylformamide (6 mL), and then potassium iodide (0.21 g, 2 equivalents) was added thereto, followed by stirring at room temperature for 1.5 hours. The solution was slowly added to stirred 5% brine (50-fold volume), and then the precipitated deposits were filtrated. The filtrated solid was washed with water, suspended in water, and then lyophilized to yield the crude product 32c (1.07 g). The crude product 32c was dissolved in methylene chloride (20-fold volume) and nitromethane (10-fold volume). Anisole (10 equivalents) followed by 2M aluminum chloride/nitromethane solution (10 equivalents) were added at room temperature, subsequently stirring for 1 hour. After reacting, the reaction solution was poured into cold 1N hydrochloric acid/acetonitrile/diisopropyl ether (3/1/5). The aqueous layer was separated, and then subjected to HP-20 column chromatography to purify it. After eluting with acetonitrile/water, eluates were concentrated in vacuo, and then lyophilized to yield Compound (a mixture of α (alpha), β (beta)-sulfoxide=80:15) (II-32).

LC/MS (ES+): 755 (M+H$^+$)
IR (KBr) cm$^{-1}$: 3297, 1790, 1611, 1530,
Elementary analysis for $C_{291}H_{32}ClN_7O_{11}S_2.3.4H_2O$
Calcd.: C, 42.71; H, 4.80; N, 12.02; Cl, 4.35; S, 7.86(%).
Found: C, 42.67; H, 4.68; N, 12.17; Cl, 4.30; S, 7.71(%).

Test Example 1

Compound (I) of the present invention was investigated for the antimicrobial activity thereof.
(Test Methods)
(Microbe/Strain Species Nos. 1-14):
Measurement of Minimum Inhibitory Concentration (MIC, microg/ml) was conducted according to the standard method of the Japan Society for Chemotherapy, and the amount of bacteria for inoculation was 1000 cfu/spot, and sensitive disc medium was used as the test medium, and conducted using agar plate incubation.

(Microbe/Strain Species Nos. 15-17):

Measurement of Minimum Inhibitory Concentration (MIC, microg/ml) was conducted according to the CLSI (Clinical and Laboratory Standards Institute) and the amount of bacteria for inoculation was 10000 cfu/spot, and Mueller-Hinton agar medium was used as the test medium, and conducted using agar plate incubation.

Test results are shown in Tables 1-6. In the tables, a unit of the values of inhibitory activity is microg/ml (μg/ml).

TABLE 1

| Bacteria Strain No. | Bacteria Species | Strain Name | Comparative Compound 1 | Compound (I-1) | Compound (I-2) | Compound (I-3) |
|---|---|---|---|---|---|---|
| 1 | Klebsiella pneumoniae | ATCC 700603 | 16 | 0.5 | 0.25 | 0.125 |
| 2 | Pseudomonas aeruginosa | SR24 | 4 | 0.063 | 0.063 | 0.031 |
| 3 | Pseudomonas aeruginosa | SR27060 | 32 | 0.25 | 0.125 | 0.125 |
| 4 | Acinetobacter baumannii | SR24396 | 64 | 0.125 | 0.25 | 0.125 |
| 5 | Stenotrophomonas maltophilia | SR21970 | 16 | 0.5 | | |

TABLE 2

| Bacteria Strain No. | Bacteria Species | Strain Name | Compound (I-8) | Compound (I-12) | Compound (I-15) | Compound (I-17) |
|---|---|---|---|---|---|---|
| 1 | Klebsiella pneumoniae | ATCC 700603 | 0.125 | 0.25 | 0.125 | 0.25 |
| 2 | Pseudomonas aeruginosa | SR24 | 0.031 | 0.063 | 0.063 | 0.063 |
| 3 | Pseudomonas aeruginosa | SR27060 | 0.125 | 0.125 | 0.125 | 0.125 |
| 4 | Acinetobacter baumannii | SR24396 | 0.25 | 0.25 | 0.25 | 0.5 |
| 5 | Stenotrophomonas maltophilia | SR21970 | | 0.5 | 4 | 0.5 |

TABLE 3

| Bacteria Strain No. | Bacteria Species | Strain Name | Compound (I-18) | Compound (I-19) | Compound (I-22) | Compound (I-23) |
|---|---|---|---|---|---|---|
| 1 | Klebsiella pneumoniae | ATCC 700603 | 0.125 | 0.125 | 0.125 | 0.031 |
| 2 | Pseudomonas aeruginosa | SR24 | 0.063 | 0.063 | 0.063 | 0.031 |
| 3 | Pseudomonas aeruginosa | SR27060 | 0.25 | 0.125 | 0.125 | 0.125 |
| 4 | Acinetobacter baumannii | SR24396 | 0.25 | 0.125 | 0.25 | 0.125 |
| 5 | Stenotrophomonas maltophilia | SR21970 | 0.5 | 0.25 | 4 | |

TABLE 4

| Bacteria Strain No. | Bacteria Species | Strain Name | Compound (I-25) | Compound (I-26) | Compound (II-1) | Compound (II-2) | Compound (II-3) |
|---|---|---|---|---|---|---|---|
| 1 | Klebsiella pneumoniae | ATCC 700603 | 0.5 | 0.5 | 0.5 | 0.5 | 0.125 |
| 2 | Pseudomonas aeruginosa | SR24 | 0.125 | 0.125 | 0.125 | 0.125 | 0.125 |
| 3 | Pseudomonas aeruginosa | SR27060 | 0.25 | 0.5 | 0.25 | 0.25 | 0.5 |
| 4 | Acinetobacter baumannii | SR24396 | 0.5 | 1 | 0.125 | 0.125 | 0.25 |
| 5 | Stenotrophomonas maltophilla | SR21970 | | | 2 | 0.5 | 1 |

TABLE 5

| Bacteria Strain No. | Bacteria Species | Strain Name | Compound (II-4) | Compound (II-10) | Compound (II-12) | Compound (II-13) | Compound (II-16) |
|---|---|---|---|---|---|---|---|
| 1 | Klebsiella pneumoniae | ATCC 700603 | 0.5 | 0.5 | 0.25 | 0.25 | 0.125 |
| 2 | Pseudomonas aeruginosa | SR24 | 0.125 | 0.125 | 0.063 | 0.063 | 0.125 |
| 3 | Pseudomonas aeruginosa | SR27060 | 0.25 | 0.25 | 0.25 | 0.5 | 0.25 |
| 4 | Acinetobacter baumannii | SR24396 | 0.25 | 0.25 | 0.25 | 0.25 | 0.5 |
| 5 | Stenotrophomonas maltophilia | SR21970 | 1 | 1 | 1 | 1 | 1 |

TABLE 6

| Bacteria Strain No. | Bacteria Species | Strain Name | Compound (II-17) | Compound (II-22) | Compound (II-23) | Compound (II-24) | Compound (II-25) |
|---|---|---|---|---|---|---|---|
| 1 | Klebsiella pneumoniae | ATCC 700603 | 0.25 | 0.5 | 0.125 | 0.125 | 0.25 |
| 2 | Pseudomonas aeruginosa | SR24 | 0.063 | 0.125 | 0.125 | 0.063 | 0.063 |
| 3 | Pseudomonas aeruginosa | SR27060 | 0.25 | 0.25 | 0.25 | 0.5 | 0.25 |
| 4 | Acinetobacter baumannii | SR24396 | 0.5 | 0.125 | 0.25 | 0.125 | 0.25 |
| 5 | Stenotrophomonas maltophilia | SR21970 | 1 | 2 | 0.5 | 0.5 | 1 |

Bacterial strains described in the above tables and enzyme (beta-lactamase) produced thereby are explained in Table 7.

TABLE 7

| Bacteria Species | Strain Name | Enzyme Produced | Strain Type |
|---|---|---|---|
| K. pneumoniae | ATCC700603 | SHV-18 | ESBL producer strain |
| P. aeruginosa | SR24 | None | Ceftazidime sensitive strain |
| P. aeruginosa | SR27060 | IMP-1 | MBL producer strain (carbapenem resistant strain) |
| A. baumannii | SR24396 | None | |
| S. maltophilia | SR21970 | L-1 | MBL producer strain (carbapenem resistant strain) |

[Formula 148]

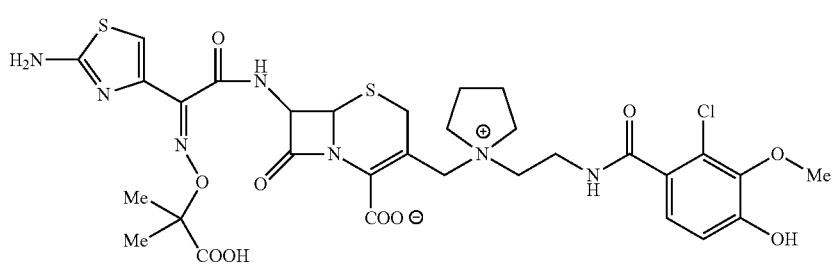

Comparative Compound 1

As shown in the above results, the compounds of the present invention were shown to have a wide antimicrobial spectrum, in particular, potent antimicrobial spectrum against Gram negative bacteria, and/or effectiveness against multi-drug resistant bacteria, and exhibited high stability against beta-lactamase producing Gram negative bacteria. In comparison to Comparative Compound 1 having no catechol group, it was shown that the compounds of the present invention have more potent antimicrobial activity.

Formulation Example 1

Powder of a compound of the present invention is loaded to prepare an injection agent.

INDUSTRIAL APPLICABILITY

The compounds of the present invention have a wide antimicrobial spectrum, and are effective as an antimicrobial drug having high stability against beta-lactamase producing Gram negative bacteria. Moreover, the compounds have good bioavailability, and high water solubility, and thus particularly effective as an injection agent.

The invention claimed is:
1. A compound of the formula:

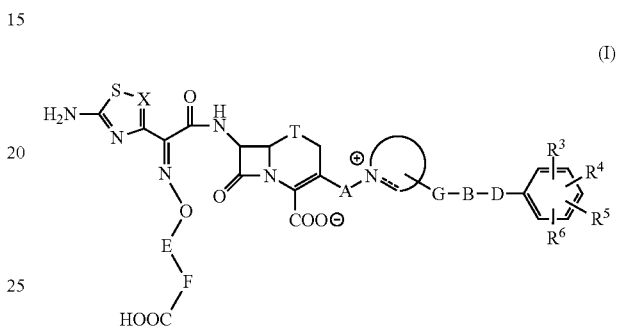

(I)

wherein,

X is N, CH or C—Cl;

T is S, S=O, $CH_2$ or O;

A is lower alkylene, lower alkenylene or lower alkynylene;

G is optionally present, and when present is, —$CH_2$—CH($CH_3$)—, —$CH_2$—CH($^i$Pr)—, lower alkylene optionally substituted with a carbocyclic group, lower alkenylene, or lower alkynylene;

B is optionally present, and when present B is a 5- or 6-membered heterocyclic group containing at least 1 N atom(s);

D is optionally present, and when present D is, —CO—, —O—CO—, —CO—O—, —$NR^7$—, —$NR^7$—CO—, —CO—$NR^7$—, —$NR^7$—CO—$NR^7$—, —O—, —S—, —SO—, —$SO_2$—$NR^7$—, —$NR^7$—$SO_2$—, —$CH_2$—$NR^7$—CO— or —$SO_2$—;

E is of the formula:

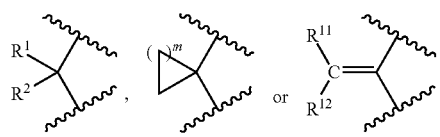

wherein $R^1$ and $R^2$ are each independently hydrogen, halogen, lower alkyl optionally substituted with carbamoyl, lower alkylthio, or phenyl, $R^{11}$ and $R^{12}$ are each independently hydrogen, lower alkyl optionally substituted with carbamoyl or carboxyl, carboxyl, or a carbamoyl, and m refers to an integer of 1 to 5;
F is optionally present, and when present F is phenylene;
$R^3$ and $R^4$ are —$OR^8$;
$R^5$ and $R^6$ each is independently hydrogen, halogen, nitrile, or —$OR^8$;
$R^7$ each is independently hydrogen or lower alkyl;
$R^8$ each is independently hydrogen, lower alkyl, halo(lower)alkyl, lower alkylcarbonyl or carbamoyl;
the formula:

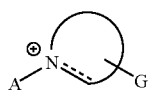

is an optionally substituted, saturated or unsaturated, monocyclic or condensed cyclic quaternary ammonium group containing one or more N atom(s);
wherein the substituents are at least one selected from the group consisting of halogen, hydroxy, lower alkyl, halo(lower)alkyl, lower alkoxy, and halo(lower)alkoxy;
the broken line represents the presence or absence of a bond between the cationic N atom and a ring-forming atom;
provided that
when G bonds to the cationic N atom, the broken line is absent;
when G does not bond to the cationic N atom, the broken line represents a single bond between the cationic N atom and a neighboring atom or represents lower alkylene between the cationic N atom and a ring-forming atom other than the neighboring atom; and
when G and B are not present, and D is —NH—CO— or —S—, then a group of the formula:

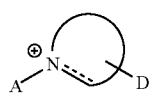

is not a group of the formula:

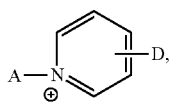

wherein a hydrogen atom(s) on the quaternary ring is(are) optionally substituted;
or an ester at the carboxyl at the 7-position side chain or at the 4-position, a protected compound at the amino on the ring in the 7-side chain, a pharmaceutically acceptable salt, or a solvate thereof.

2. The compound, or an ester at the carboxyl at the 7-position side chain or at the 4-position, a protected compound at the amino on the ring in the 7-side chain, a pharmaceutically acceptable salt, or a solvate thereof according to claim 1, wherein said formula

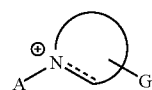

is the following formula:

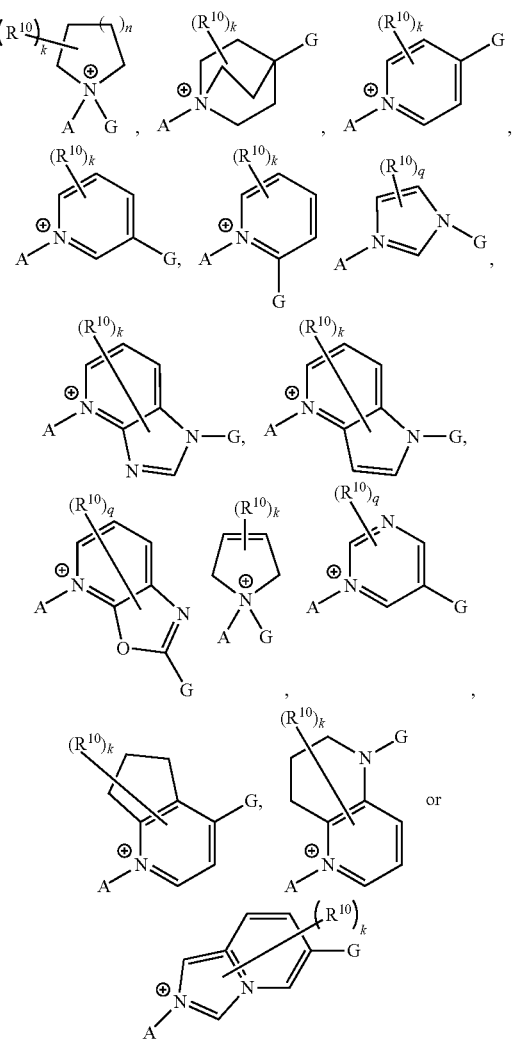

wherein n is an integer from 0 to 5, k is an integer from 0 to 5, q is an integer from 0 to 3, $R^{10}$ is halogen, hydroxy, lower alkyl, halo(lower)alkyl, lower alkoxy, or halo(lower)alkoxy, provided that $R^{10}$ may be identical or different at k or q occurrences, and A and G are as defined in claim 1.

3. The compound, or an ester at the carboxyl at the 7-position side chain or at the 4-position, a protected compound at the amino on the ring in the 7-side chain, a pharmaceutically acceptable salt, or a solvate thereof according to claim 1, wherein said formula is the formula:

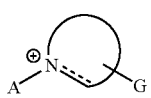

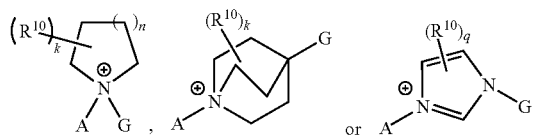

wherein n, k, q and $R^{10}$ are as defined in claim 2, and A and G are as defined in claim 1.

4. The compound, or an ester at the carboxyl at the 7-position side chain or at the 4-position, a protected compound at the amino on the ring in the 7-side chain, a pharmaceutically acceptable salt, or a solvate thereof according to claim 1, wherein the formula

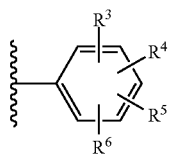

is the formula:

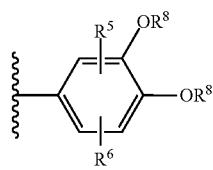

wherein $R^5$, $R^6$ and $R^8$ are as defined in claim 1.

5. The compound, or an ester at the carboxyl at the 7-position side chain or at the 4-position, a protected compound at the amino on the ring in the 7-side chain, a pharmaceutically acceptable salt, or a solvate thereof according to claim 1, wherein the formula:

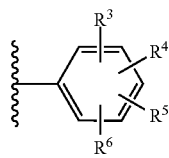

is the formula

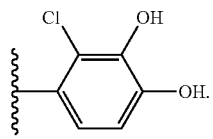 [SMILES: *c1ccc(O)c(O)c1Cl]

6. The compound, or an ester at the carboxyl at the 7-position side chain or at the 4-position, a protected compound at the amino on the ring in the 7-side chain, a pharmaceutically acceptable salt, or a solvate thereof according to claim 1, wherein A is —$CH_2$—, —$CH_2$—$CH_2$—, —$CH_2$—$CH_2$—$CH_2$—$CH$=$CH$—, —$CH$=$CH$—$CH_2$— or —$CH_2$—$CH$=$CH$—.

7. The compound, or an ester at the carboxyl at the 7-position side chain or at the 4-position, a protected compound at the amino on the ring in the 7-side chain, a pharmaceutically acceptable salt, or a solvate thereof according to claim 1, wherein G is optionally present, and when present is —$CH$=$CH$—, —$CH$=$CH$—$CH_2$—, —$CH_2$—$CH$=$CH$—, —$CH_2$—$CH(CH_3)$—, —$CH_2$—$CH(^iPr)$— or —$CH_2$—$CH$(Ph)-, wherein iPr refers to isopropyl group, and Ph refers to a phenyl group.

8. The compound, or an ester at the carboxyl at the 7-position side chain or at the 4-position, a protected compound at the amino on the ring in the 7-side chain, a pharmaceutically acceptable salt, or a solvate thereof according to claim 1, wherein B is optionally present, and when present is the formula:

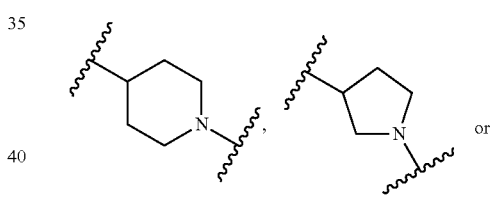

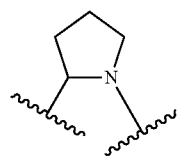

9. The compound, or an ester at the carboxyl at the 7-position side chain or at the 4-position, a protected compound at the amino on the ring in the 7-side chain, a pharmaceutically acceptable salt, or a solvate thereof according to claim 1, wherein D is absent, —CO—, —O—CO—, —CO—O—, —$NR^7$—, —$NR^7$—CO—$NR^7$—, —$NR^7$—CO— or —CO—$NR^7$—, wherein $R^7$ is as defined in claim 1.

10. The compound, or an ester at the carboxyl at the 7-position side chain or at the 4-position, a protected compound at the amino on the ring in the 7-side chain, a pharmaceutically acceptable salt, or a solvate thereof according to claim 1, wherein D is optionally present, and when present is —CO—, —NR$^7$—CO—NR$^7$—, —NR$^7$—CO— or —CO—NR$^7$—, wherein R$^7$ is as defined in claim 1.

11. The compound, or an ester at the carboxyl at the 7-position side chain or at the 4-position, a protected compound at the amino on the ring in the 7-side chain, a pharmaceutically acceptable salt, or a solvate thereof according to claim 1, wherein R$^8$ is hydrogen or a lower alkyl.

12. The compound, or an ester at the carboxyl at the 7-position side chain or at the 4-position, a protected compound at the amino on the ring in the 7-side chain, a pharmaceutically acceptable salt, or a solvate thereof according to claim 1, wherein X is N.

13. The compound, or an ester at the carboxyl at the 7-position side chain or at the 4-position, a protected compound at the amino on the ring in the 7-side chain, a pharmaceutically acceptable salt, or a solvate thereof according to claim 1, wherein X is CH or C—Cl.

14. The compound, or an ester at the carboxyl at the 7-position side chain or at the 4-position, a protected compound at the amino on the ring in the 7-side chain, a pharmaceutically acceptable salt, or a solvate thereof according to claim 1, wherein T is S.

15. The compound, or an ester at the carboxyl at the 7-position side chain or at the 4-position, a protected compound at the amino on the ring in the 7-side chain, a pharmaceutically acceptable salt, or a solvate thereof according to claim 1, wherein
X is N, CH or C—Cl;
T is S;
A is a lower alkylene;
G is optionally present, and when present is a lower alkylene;
the formula:

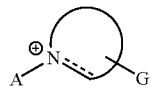

is the formula:

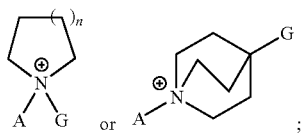

B is absent;
n is an integer of 0-3;
D is —NH—CO— or —CO—NH—;
E is the formula:

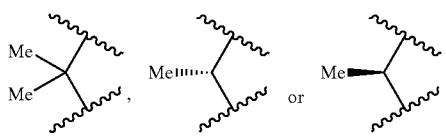

wherein Me refers to a methyl group;
F is absent;
R$^3$ and R$^4$ are —OH, and R$^5$ is hydrogen or Cl, and R$^6$ is hydrogen.

16. A pharmaceutical composition comprising the compound, or an ester at the carboxyl at the 7-position side chain or at the 4-position, a protected compound at the amino on the ring in the 7-side chain, a pharmaceutically acceptable salt, or a solvate thereof according to claim 1.

17. The pharmaceutical composition according to claim 16, which has an antimicrobial activity.

18. The compound according to claim 1, which is selected from the group consisting of:

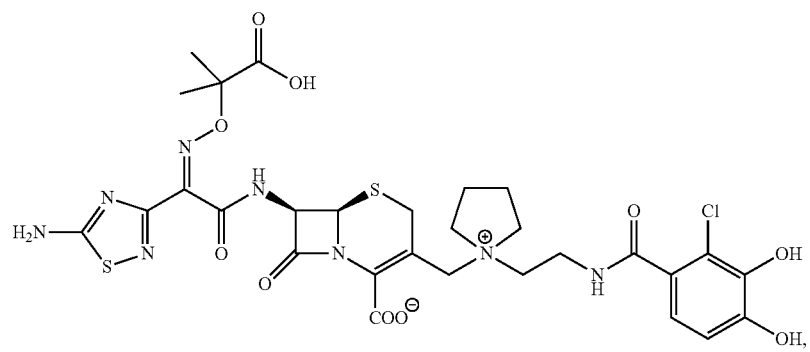

I-1

-continued
I-2
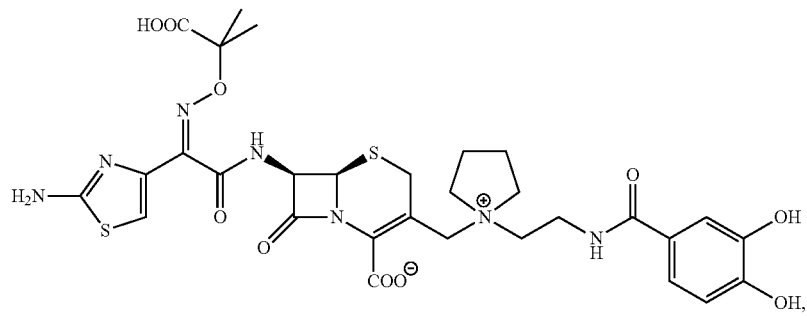
I-3
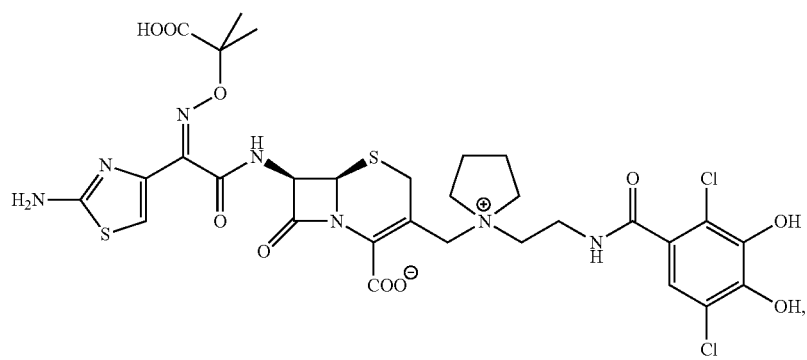
I-4
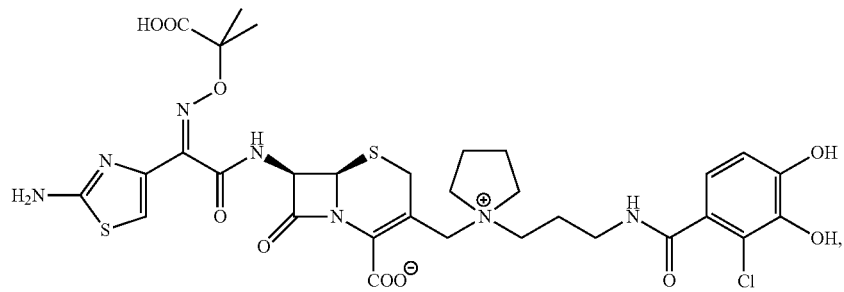
I-8
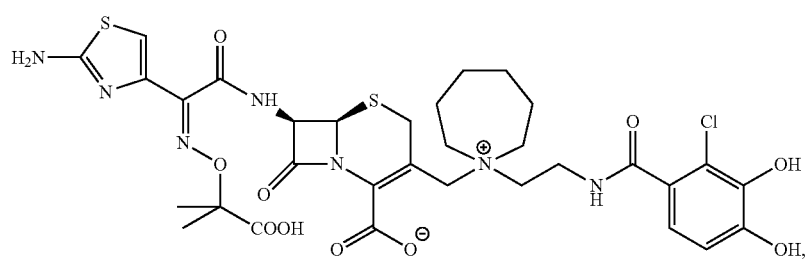
I-12
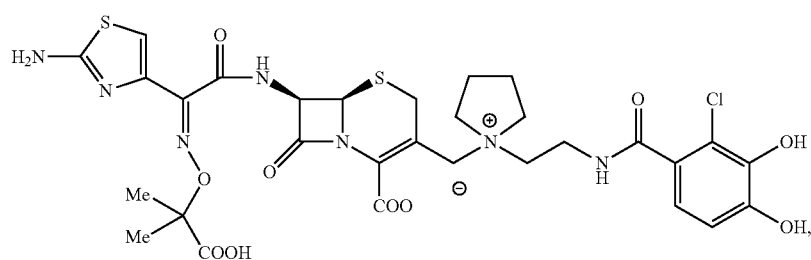

-continued
I-15
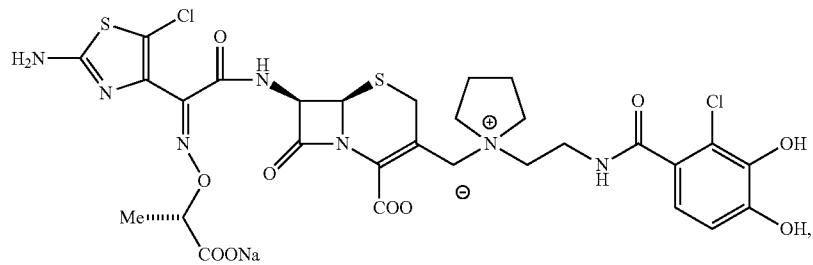
I-17
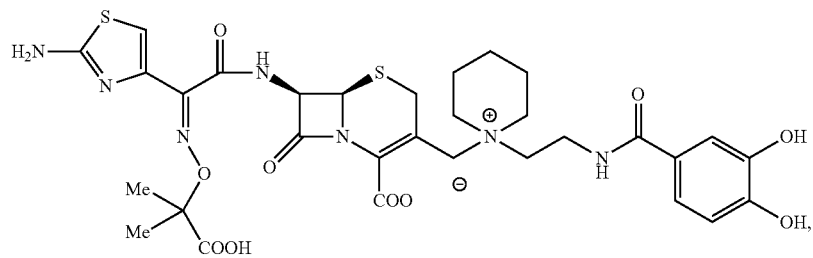
I-18
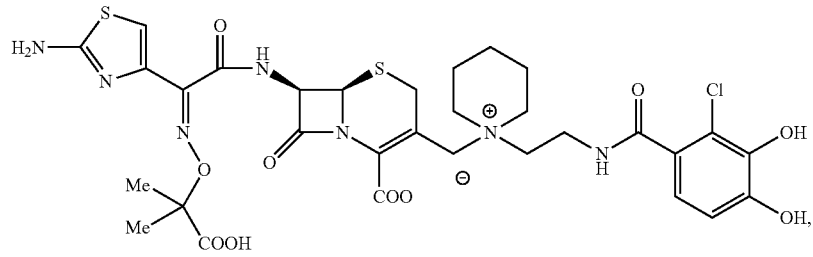
I-19
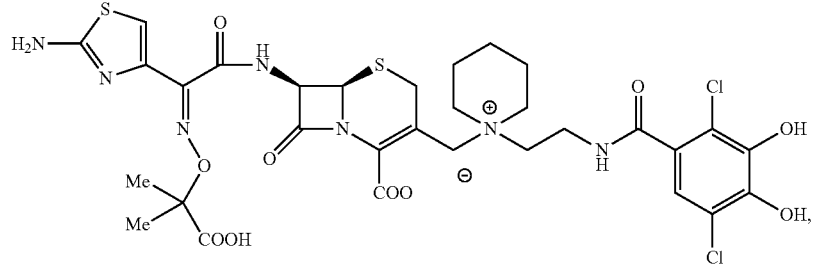
I-22
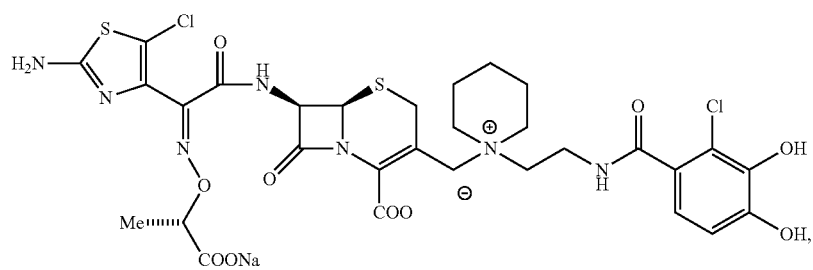
I-23
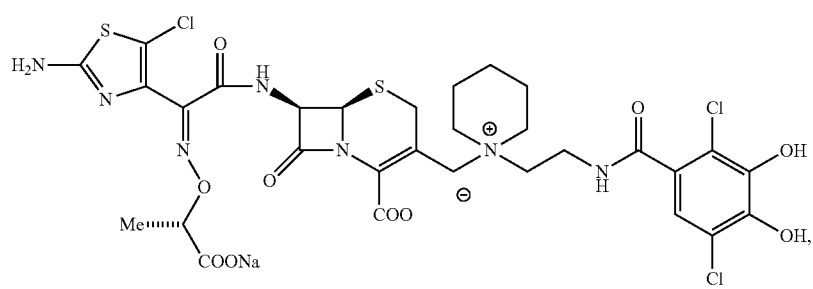

-continued
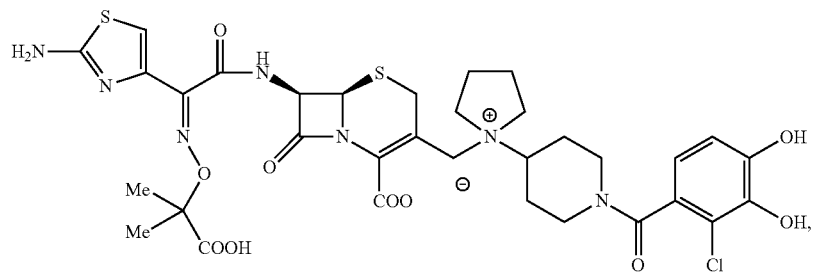
I-29
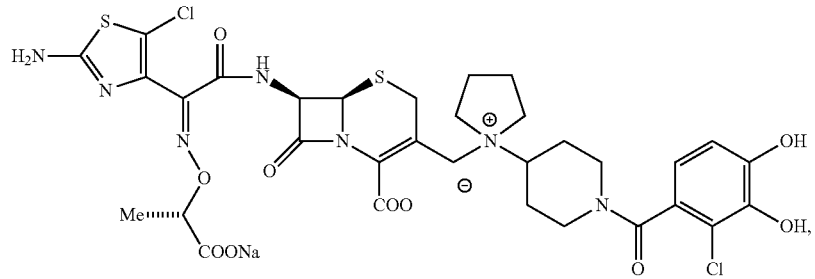
I-32
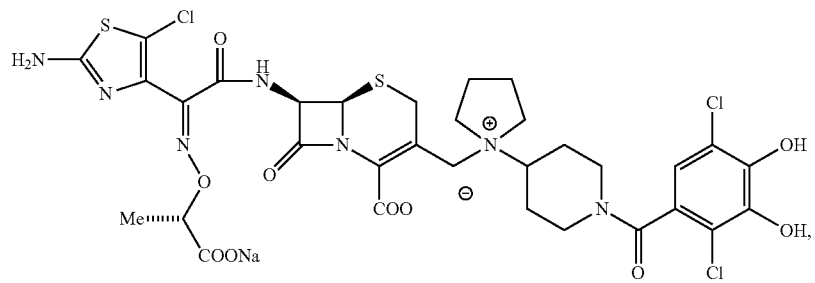
I-33
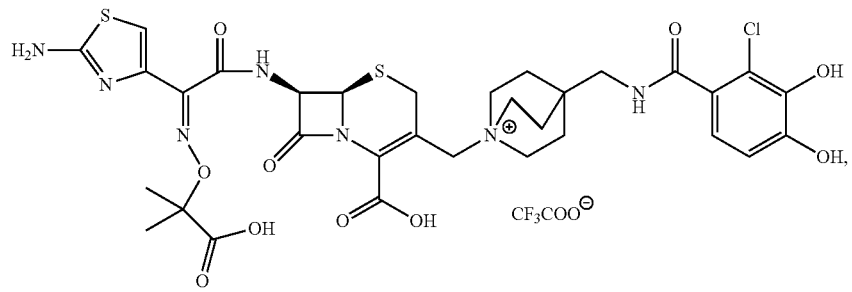
I-37
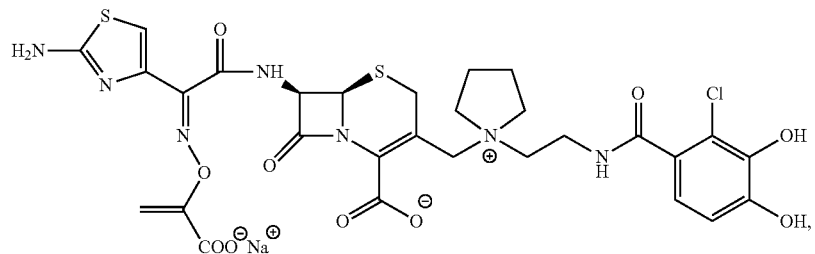
II-1

-continued
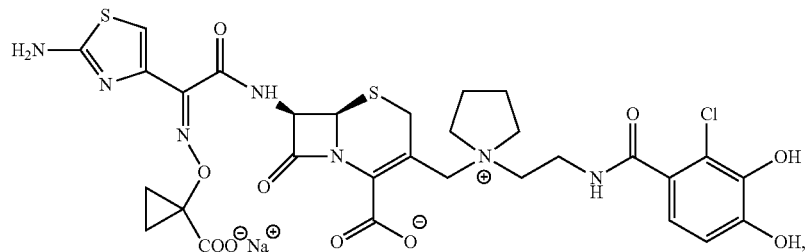
II-2
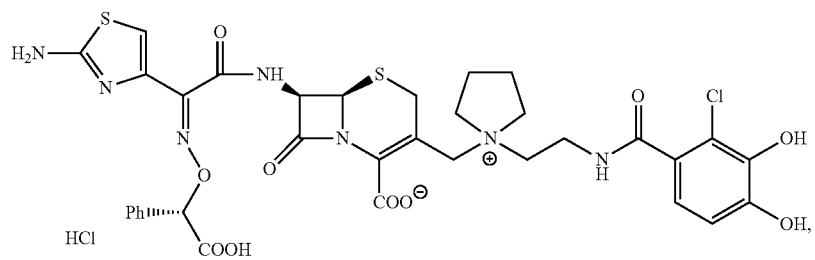
II-3
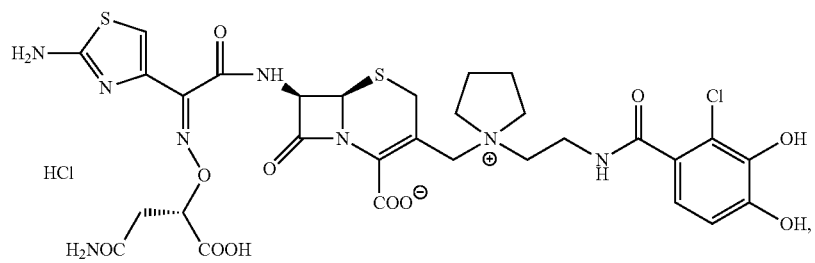
II-4
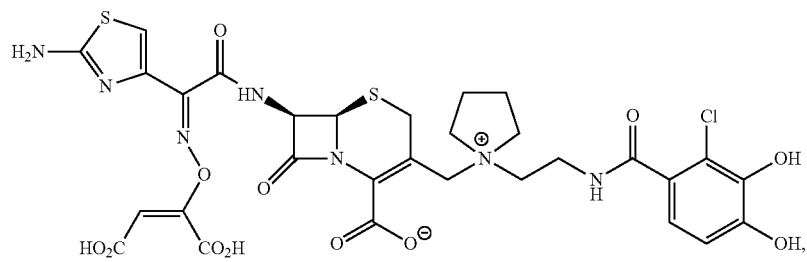
II-10
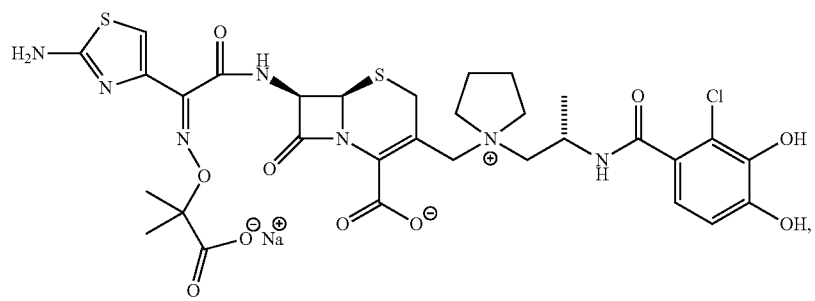
II-12

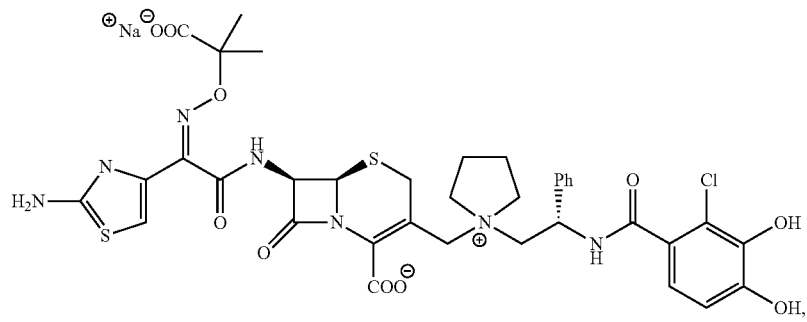
II-16
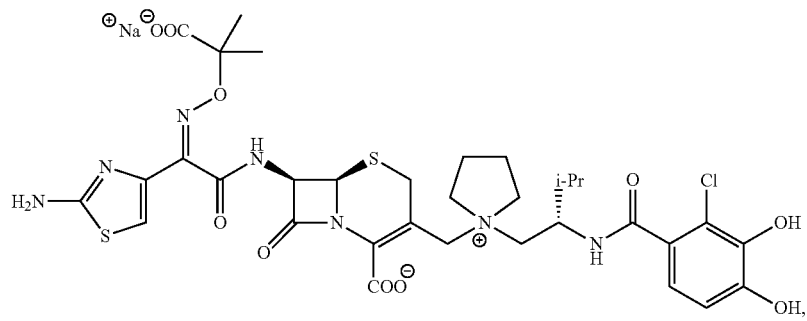
II-17
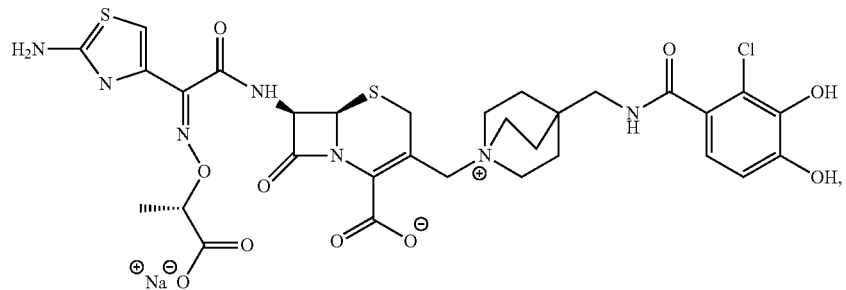
II-21
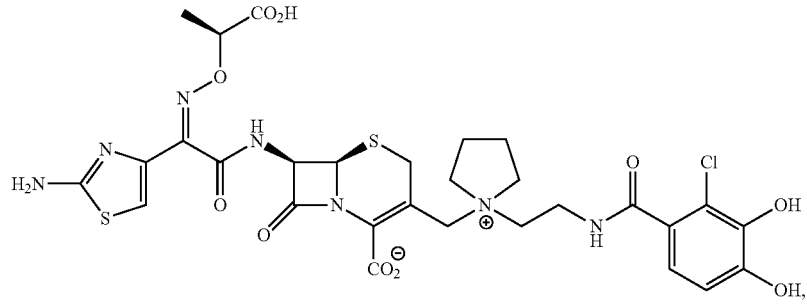
II-22
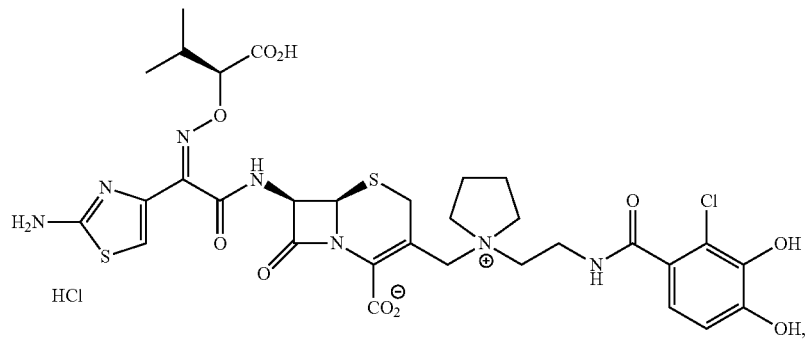
II-23

II-24

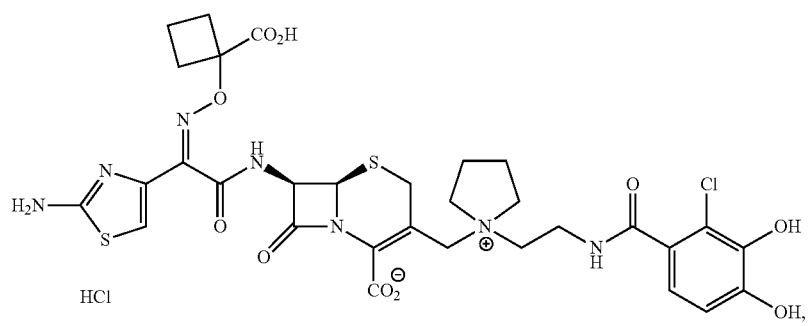

II-25

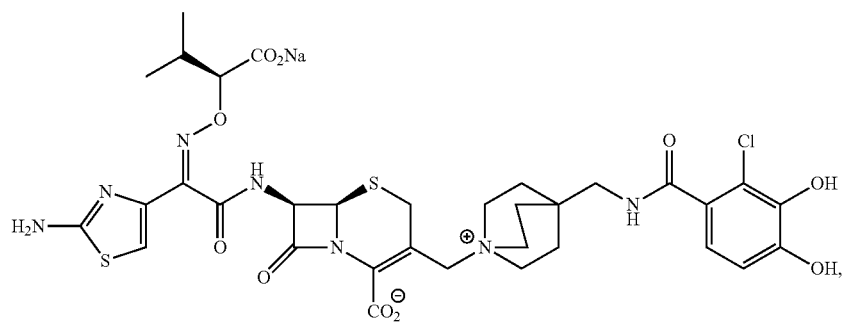

and

II-26

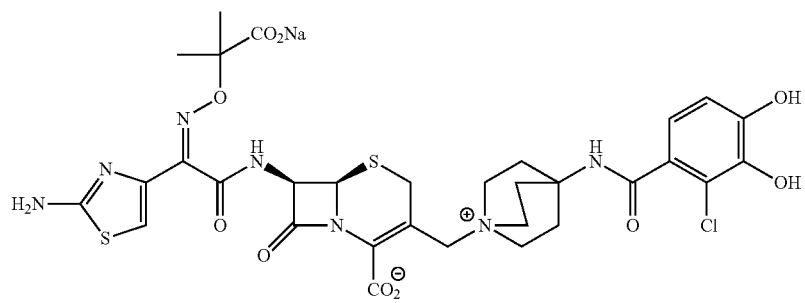

or an ester at the carboxyl at the 7-position side chain or at the 4-position, a protected compound at the amino on the ring in the 7-side chain, a pharmaceutically acceptable salt, or a solvate thereof.

19. The compound according to claim 1, which is of the formula:

I-12

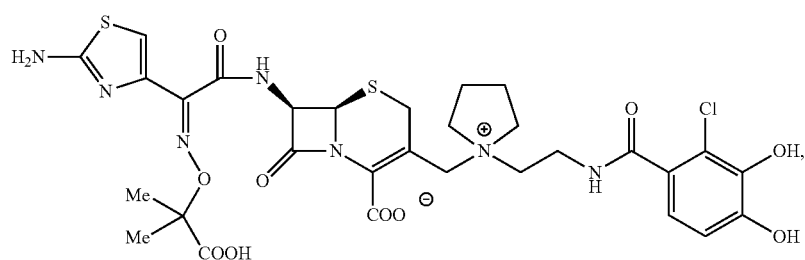

or an ester at the carboxyl at the 7-position side chain or at the 4-position, a protected compound at the amino on the ring in the 7-side chain, a pharmaceutically acceptable salt, or a solvate thereof.

20. The compound according to claim 1, which is of the formula:

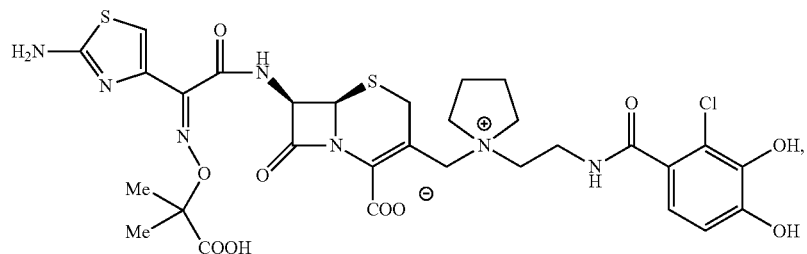

I-12 or a pharmaceutically acceptable salt, or a solvate thereof.

21. A method for treating a bacterial infection, comprising administering to a subject in need thereof the compound, or an ester at the carboxyl at the 7-position side chain or at the 4-position, a protected compound at the amino on the ring in the 7-side chain, a pharmaceutically acceptable salt, or a solvate thereof according to claim 1.

* * * * *